US009974867B2

(12) United States Patent
Chari et al.

(10) Patent No.: US 9,974,867 B2
(45) Date of Patent: *May 22, 2018

(54) CYTOTOXIC BENZODIAZEPINE DERIVATIVES

(71) Applicant: IMMUNOGEN, INC., Waltham, MA (US)

(72) Inventors: Ravi V. J. Chari, Newton, MA (US); Michael Louis Miller, Framingham, MA (US); Manami Shizuka, Belmont, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/476,770

(22) Filed: Mar. 31, 2017

(65) Prior Publication Data
US 2017/0340749 A1    Nov. 30, 2017

Related U.S. Application Data

(63) Continuation of application No. 15/170,428, filed on Jun. 1, 2016, which is a continuation of application No. 14/843,604, filed on Sep. 2, 2015, now Pat. No. 9,381,256.

(60) Provisional application No. 62/164,352, filed on May 20, 2015, provisional application No. 62/149,409, filed on Apr. 17, 2015, provisional application No. 62/087,065, filed on Dec. 3, 2014, provisional application No. 62/045,236, filed on Sep. 3, 2014.

(51) Int. Cl.
| A61K 47/68 | (2017.01) |
| C07D 487/04 | (2006.01) |
| C07D 519/00 | (2006.01) |
| A61K 45/06 | (2006.01) |
| C07K 16/28 | (2006.01) |
| A61K 39/00 | (2006.01) |

(52) U.S. Cl.
CPC ......... *A61K 47/6803* (2017.08); *A61K 45/06* (2013.01); *A61K 47/6845* (2017.08); *A61K 47/6849* (2017.08); *A61K 47/6851* (2017.08); *C07D 487/04* (2013.01); *C07D 519/00* (2013.01); *C07K 16/28* (2013.01); *C07K 16/2866* (2013.01); *A61K 2039/505* (2013.01); *C07K 2317/21* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| 8,426,402 B2 | 4/2013 | Li et al. |
| 8,557,966 B2 | 10/2013 | Ab et al. |
| 8,765,740 B2 | 7/2014 | Li et al. |
| 8,802,667 B2 | 8/2014 | Li et al. |
| 8,809,320 B2 | 8/2014 | Li et al. |
| 8,889,669 B2 | 11/2014 | Li et al. |
| 9,133,275 B2 | 9/2015 | Ab et al. |
| 9,169,272 B2 | 10/2015 | Li et al. |
| 9,381,256 B2 | 7/2016 | Chari et al. |
| 9,598,490 B2 | 3/2017 | Ab et al. |
| 9,657,100 B2 | 5/2017 | Ab et al. |
| 9,670,278 B2 | 6/2017 | Ab et al. |
| 9,670,279 B2 | 6/2017 | Ab et al. |
| 9,670,280 B2 | 6/2017 | Ab et al. |
| 2012/0238731 A1 | 9/2012 | Fishkin et al. |
| 2015/0030616 A1 | 1/2015 | Li et al. |
| 2015/0315193 A1 | 11/2015 | Li et al. |
| 2016/0367698 A1 | 12/2016 | Chari et al. |

*Primary Examiner* — Michael Barker
(74) *Attorney, Agent, or Firm* — McCarter & English, LLP; Yu Lu; Xin Zhang

(57) ABSTRACT

The invention relates to novel benzodiazepine derivatives with antiproliferative activity and more specifically to novel benzodiazepine compounds of formula (I)-(VII). The invention also provides conjugates of the benzodiazepine compounds linked to a cell-binding agent. The invention further provides compositions and methods useful for inhibiting abnormal cell growth or treating a proliferative disorder in a mammal using the compounds or conjugates of the invention.

20 Claims, 19 Drawing Sheets

FIG. 1
MS for deglycosylated huMov19-sulfo-SPDB-1d Conjugate
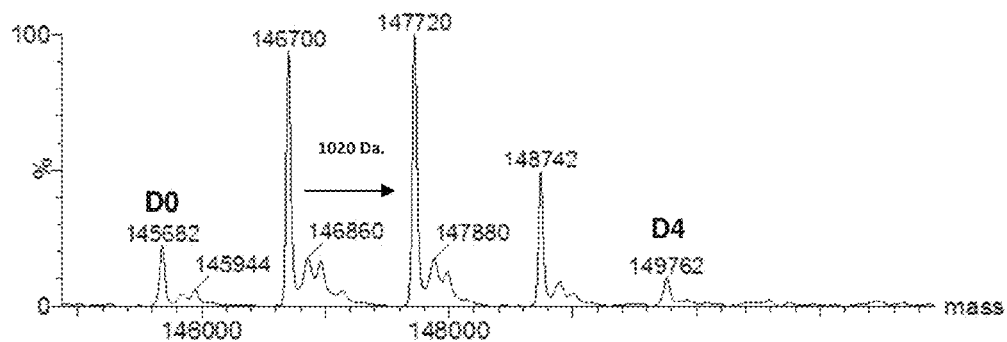
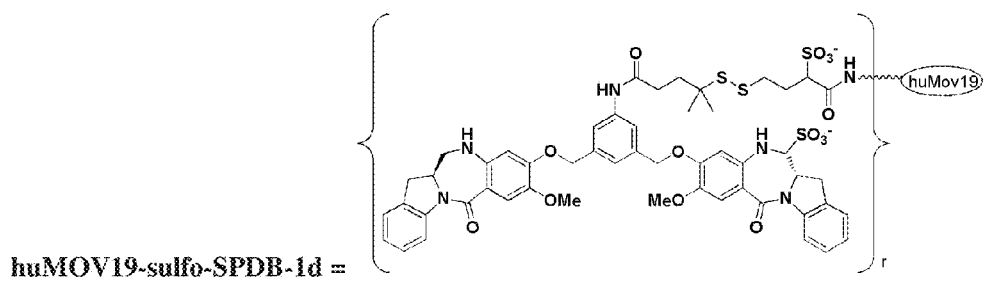
huMOV19-sulfo-SPDB-1d =

Anti-Tumor Activity (Median Tumor Volume, mm$^3$) of huMOV19-sulfo-SPDB-1d in SCID Mice Bearing NCI-H2110 Xenografts

| Treatment Group | | Dose (ug/kg) | T/C (Day 23) | Regressions | | Result |
|---|---|---|---|---|---|---|
| | | | | PR | CR | |
| A | Control | - | - | - | - | - |
| B | huMov19-sulfo-SPDB-1d | 5 | 0% | 6/6 | 6/6 | Highly Active |
| C | huMov19-sulfo-SPDB-1d | 25 | 0% | 6/6 | 6/6 | Highly Active |

MS for deglycosylated huML66-sulfo-SPDB-1d Conjugate huMOV19-sulfo-SPDB-1d

Anti-Tumor Activity (Median Tumor Volume, mm³) of huMov19-sulfo-SPDB-1d in SCID Mice Bearing NCI-H2110 Xenografts

| | Treatment Group | Dose (μg/kg) | T/C (Day 28) | Regressions | | Result |
|---|---|---|---|---|---|---|
| | | | | PR | CR | |
| A | Control | - | - | - | - | - |
| B | huMov19-sulfo-SPDB-1d | 1 | 116% | 0/6 | 0/6 | Inactive |
| C | huMov19-sulfo-SPDB-1d | 3 | 12% | 0/6 | 0/6 | Active |
| D | huMov19-sulfo-SPDB-1d | 5 | 1% | 6/6 | 3/6 | Highly Active |

Anti-Tumor Activity (Median Tumor Volume, mm³) of huML66-sulfo-SPDB-1d Conjugate in SCID Mice Bearing NCI-H1703 Xenografts

| Agent | Compound 1d dose (µg/kg) | Ab dose (mg/kg) | T/C (%) | CR | Results |
|---|---|---|---|---|---|
| huML66-sulfo-SPDB-1d | 5 | 0.3 | 74 | 0/6 | inactive |
| | 20 | 1.2 | 5 | 3/6 | highly active |
| | 50 | 2.9 | 0 | 6/6 | highly active |

FIG. 14A    Ishikawa cells
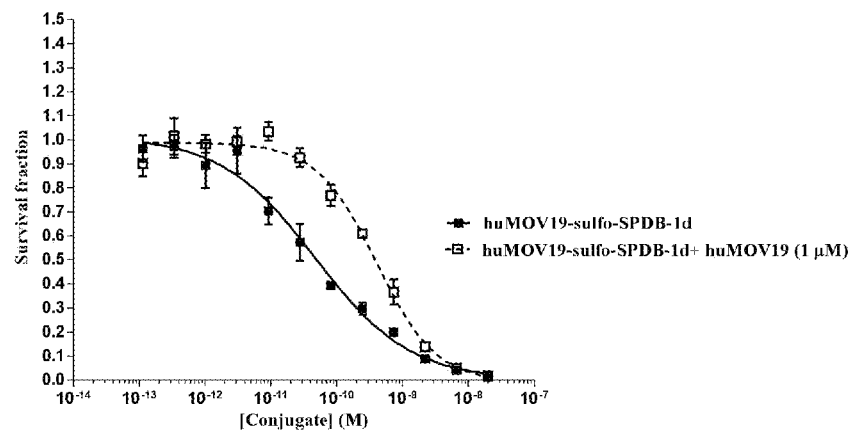
FIG. 14B    KB cells
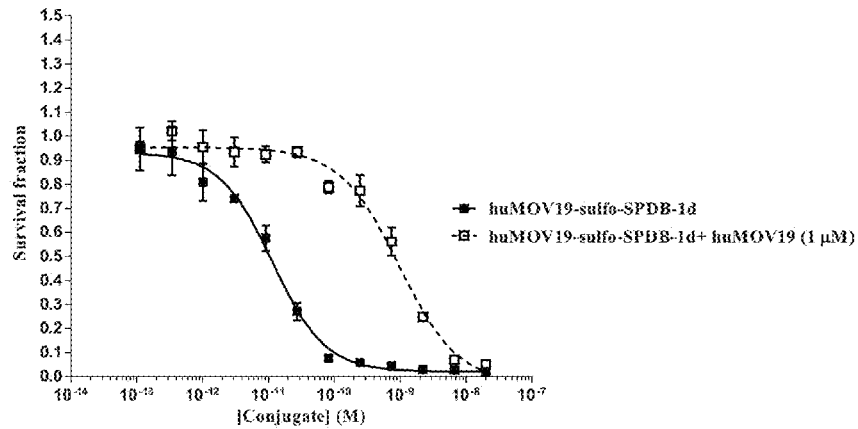

FIG. 14C   NCI-H2110 cells
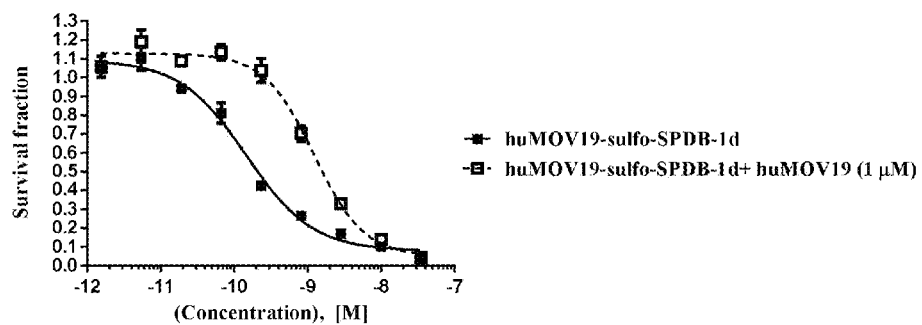
FIG. 14D   T47D cells
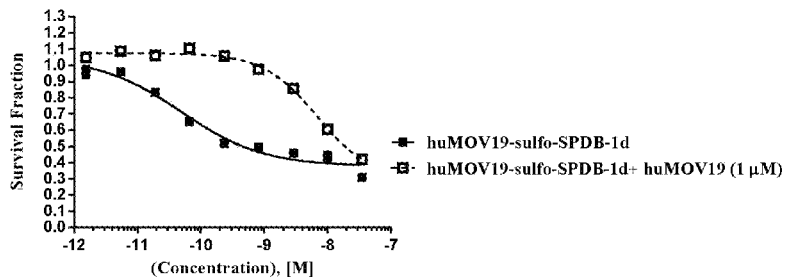

| | Treatment Group | Dose (μg/kg) | T/C (Day 24) | Regressions | | Result |
|---|---|---|---|---|---|---|
| | | | | PR | CR | |
| A | Vehicle Control | - | - | - | - | - |
| B | huMov19-sulfo-SPDB-1d | 1 | 127% | 0/6 | 0/6 | Inactive |
| C | huMov19-sulfo-SPDB-1d | 3 | 12% | 0/6 | 0/6 | Active |
| D | huMov19-sulfo-SPDB-1d | 5 | 4% | 6/6 | 3/6 | Highly Active |

| | Treatment Group | Dose (μg/kg) | T/C (Day 33) | Regressions | | Result |
|---|---|---|---|---|---|---|
| | | | | PR | CR | |
| A | Vehicle Control | - | - | - | - | - |
| B | huMov19-sulfo-SPDB-1d | 10 | 22% | 0/6 | 0/6 | Active |
| C | huMov19-sulfo-SPDB-1d | 30 | 13% | 1/6 | 1/6 | Active |
| D | chKTI-sulfo-SPDB-1d | 30 | 44% | 0/6 | 0/6 | Inactive |

CYTOTOXIC BENZODIAZEPINE DERIVATIVES

REFERENCE TO RELATED APPLICATIONS

This application is a continuation application of U.S. patent application Ser. No. 14/843,604, filed Sep. 2, 2015, which claims the benefit of the filing date under 35 U.S.C. § 119(e), of U.S. Provisional Application No. 62/045,236, filed on Sep. 3, 2014, U.S. Provisional Application No. 62/087,065, filed on Dec. 3, 2014, U.S. Provisional Application No. 62/149,409, filed on Apr. 17, 2015, and U.S. Provisional Application No. 62/164,352, filed on May 20, 2015, the entire contents of each of which, including all drawings, formulae, specifications, and claims, are incorporated herein by reference.

FIELD OF THE INVENTION

The present invention relates to novel cytotoxic compounds, and cytotoxic conjugates comprising these cytotoxic compounds and cell-binding agents. More specifically, this invention relates to novel benzodiazepine compounds, derivatives thereof, intermediates thereof, conjugates thereof, and pharmaceutically acceptable salts thereof, which are useful as medicaments, in particular as antiproliferative agents.

BACKGROUND OF THE INVENTION

Benzodiazepine derivatives are useful compounds for treating various disorders, and include medicaments such as, antiepileptics (imidazo [2,1-b][1,3,5] benzothiadiazepines, U.S. Pat. No. 4,444,688; U.S. Pat. No. 4,062,852), antibacterials (pyrimido[1,2-c][1,3,5]benzothiadiazepines, GB 1476684), diuretics and hypotensives (pyrrolo(1,2-b)[1,2,5] benzothiadiazepine 5,5 dioxide, U.S. Pat. No. 3,506,646), hypolipidemics (WO 03091232), anti-depressants (U.S. Pat. No. 3,453,266), osteoporosis (JP 2138272).

It has been shown in animal tumor models that benzodiazepine derivatives, such as pyrrolobenzodiazepines (PBDs), act as anti-tumor agents (N-2-imidazolyl alkyl substituted 1,2,5-benzothiadiazepine-1,1-dioxide, U.S. Pat. No. 6,156,746), benzo-pyrido or dipyrido thiadiazepine (WO 2004/069843), pyrrolo [1,2-b] [1,2,5] benzothiadiazepines and pyrrolo[1,2-b][1,2,5] benzodiazepine derivatives (WO2007/015280), tomaymycin derivatives (e.g., pyrrolo [1,4]benzodiazepines), such as those described in WO 00/12508, WO2005/085260, WO2007/085930, and EP 2019104. Benzodiazepines are also known to affect cell growth and differentiation (Kamal A., et al., Bioorg Med Chem. 2008 Aug. 15; 16(16):7804-10 (and references cited therein); Kumar R, Mini Rev Med Chem. 2003 June; 3(4):323-39 (and references cited therein); Bednarski J J, et al., 2004; Sutter A. P, et al., 2002; Blatt N B, et al., 2002), Kamal A. et al., Current Med. Chem., 2002; 2; 215-254, Wang J-J., J. Med. Chem., 2206; 49:1442-1449, Alley M. C. et al., Cancer Res. 2004; 64:6700-6706, Pepper C. J., Cancer Res 2004; 74:6750-6755, Thurston D. E. and Bose D. S., Chem Rev 1994; 94:433-465; and Tozuka, Z., et al., Journal of Antibiotics, (1983) 36; 1699-1708. General structure of PBDs is described in US Publication Number 20070072846. The PBDs differ in the number, type and position of substituents, in both their aromatic A rings and pyrrolo C rings, and in the degree of saturation of the C ring. Their ability to form an adduct in the minor groove and crosslink DNA enables them to interfere with DNA processing, hence their potential for use as antiproliferative agents.

The first pyrrolobenzodiazepine to enter the clinic, SJG-136 (NSC 694501) is a potent cytotoxic agent that causes DNA inter-strand crosslinks (S. G Gregson et al., 2001, *J. Med. Chem.*, 44: 737-748; M. C. Alley et al., 2004, *Cancer Res.*, 64: 6700-6706; J. A. Hartley et al., 2004, *Cancer Res.*, 64: 6693-6699; C. Martin et al., 2005, *Biochemistry.*, 44: 4135-4147; S. Arnould et al., 2006, *Mol. Cancer Ther.*, 5: 1602-1509). Results from a Phase I clinical evaluation of SJG-136 revealed that this drug was toxic at extremely low doses (maximum tolerated dose of 45 µg/m$^2$, and several adverse effects were noted, including vascular leak syndrome, peripheral edema, liver toxicity and fatigue. DNA damage was noted at all doses in circulating lymphocytes (D. Hochhauser et al., 2009, *Clin. Cancer Res.*, 15: 2140-2147). Thus, there exists a need for improved benzodiazepine derivatives that are less toxic and still therapeutically active for treating a variety of proliferative disease states, such as cancer.

SUMMARY OF THE INVENTION

The novel cytotoxic benzodiazepine dimer compounds described herein and conjugates thereof have unexpectedly higher therapeutic index (ratio of maximum tolerated dose to minimum effective dose) in vivo compared to benzodiazepine derivatives and conjugates thereof described in the art.

Thus, provided herein are novel cytotoxic benzodiazepine dimer compounds represented by any one of the following formulas:

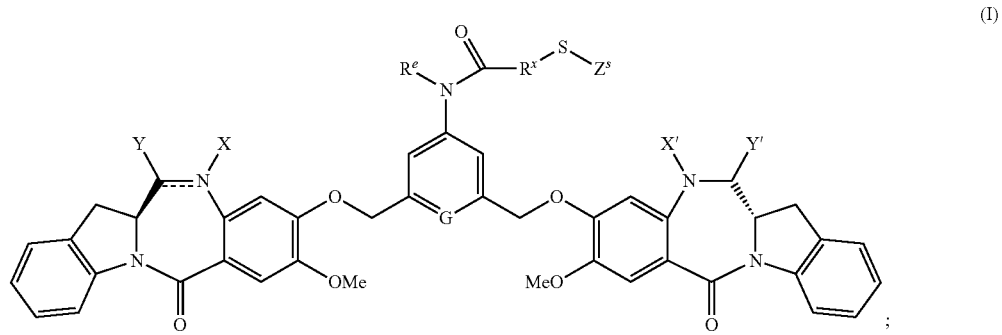

(I)

-continued
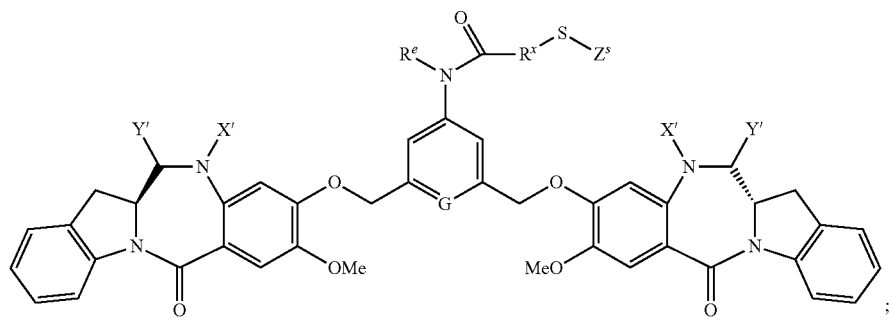
(II);
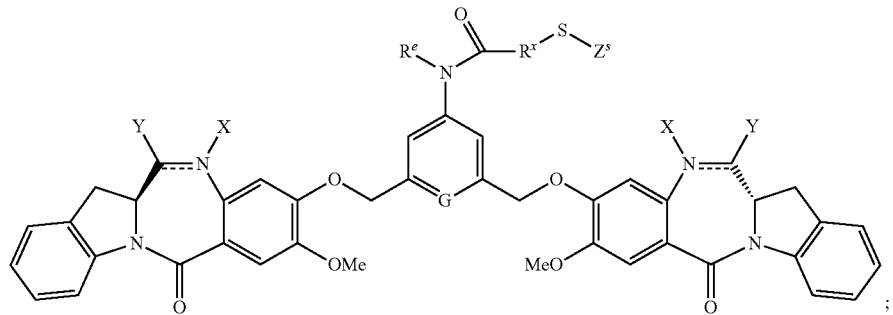
(III);
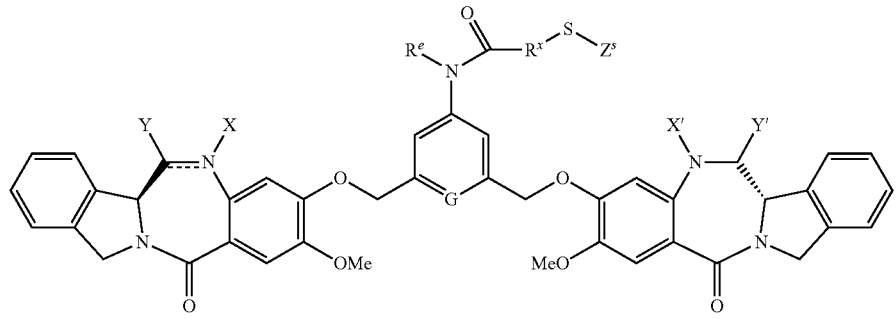
(IV);
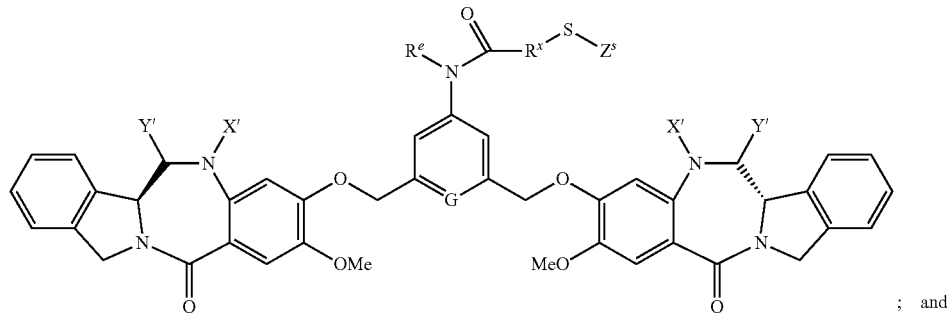
(V); and
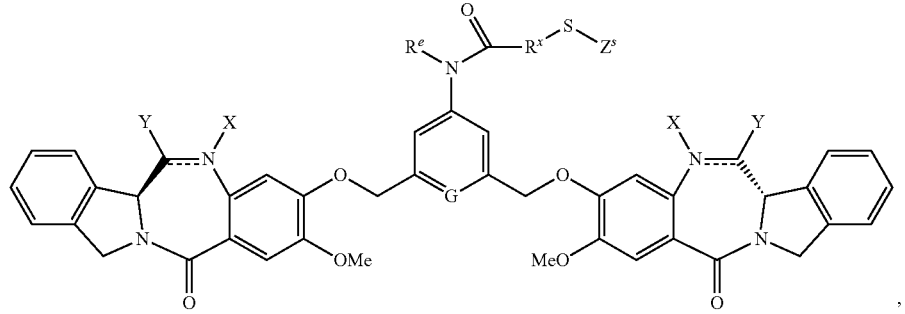
(VI), or a pharmaceutically acceptable salt thereof, wherein:

the double line == between N and C represents a single bond or a double bond, provided that when it is a double bond, X is absent and Y is —H, and when it is a single bond, X is selected from —H, or an amine protecting group;

Y is selected from —H, —OR, —OCOR', —SR, —NR'R", —SO$_3$M, —SO$_2$M or —OSO$_3$M, wherein M is —H or a cation;

R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24, and R$^c$ is a linear or branched alkyl having 1 to 4 carbon atoms;

R' and R" are the same or different, and are selected from —H, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R$^c$;

X' is selected from the group consisting of —H, —OH, an optionally substituted linear, branched or cyclic alkyl, alkenyl or alkynyl having from 1 to 10 carbon atoms, phenyl, and an amine-protecting group;

Y' is selected from the group consisting of —H, an oxo group, an optionally substituted linear, branched or cyclic alkyl, alkenyl or alkynyl having from 1 to 10 carbon atoms;

R$^x$ is a linear or branched alkylene having 1 to 6 carbon atoms, optionally substituted with a charged substituent or an ionizable group Q;

R$^e$ is —H or a linear or branched alkyl having 1 to 6 carbon atoms;

G is selected from —CH— or —N—;

Z$^s$ is —H, —SR$^d$, —COR$^{d'}$ or is selected from any one of the following formulas:

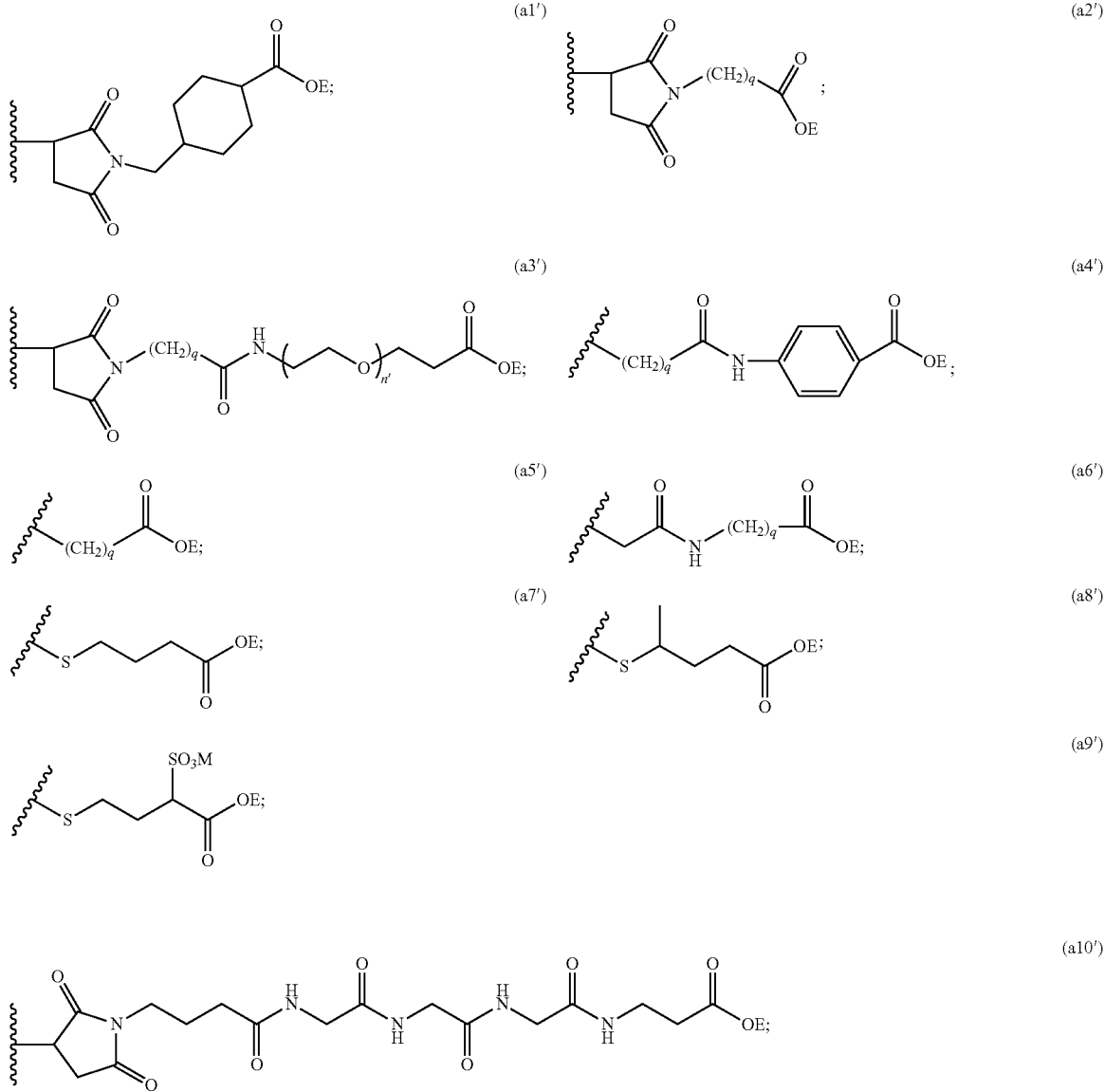

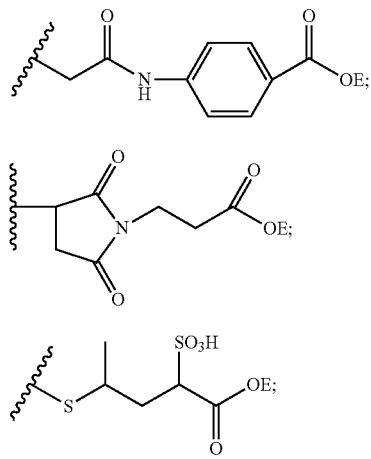

wherein:
q is an integer from 1 to 5;
$R^d$ is a linear or branched alkyl having 1 to 6 carbon atoms or is selected from phenyl, nitrophenyl, dinitrophenyl, carboxynitrophenyl, pyridyl and nitropyridyl;

$R^{d'}$ is a linear or branched alkyl having 1 to 6 carbon atoms;
n' is an integer from 2 to 6;
—C(=O)OE represents a reactive ester group; and
M is H⁺ or a cation, provided that the compound is not

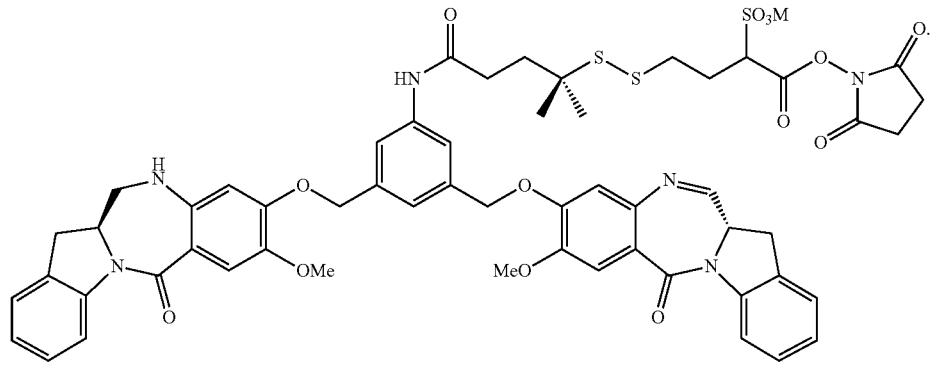

In one embodiment, the reactive ester group represented by —C(=O)OE is selected from N-hydroxysuccinimide ester, N-hydroxysulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester.

In one embodiment, for compounds of structural formulas (I), (II), (III), (IV), (V) and (VI), $Z^s$ is represented by the following structural formulas:

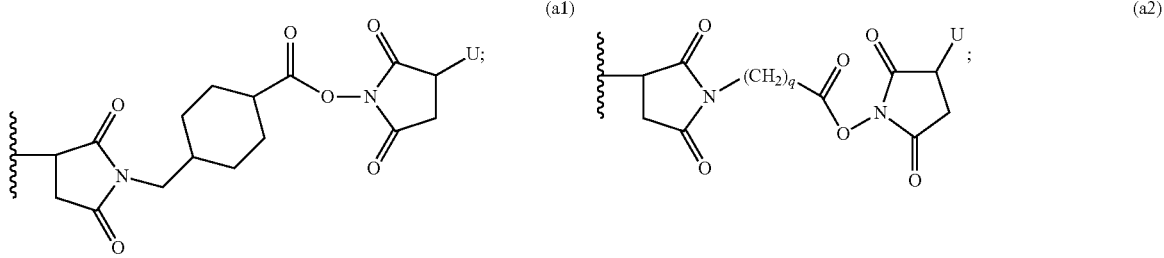

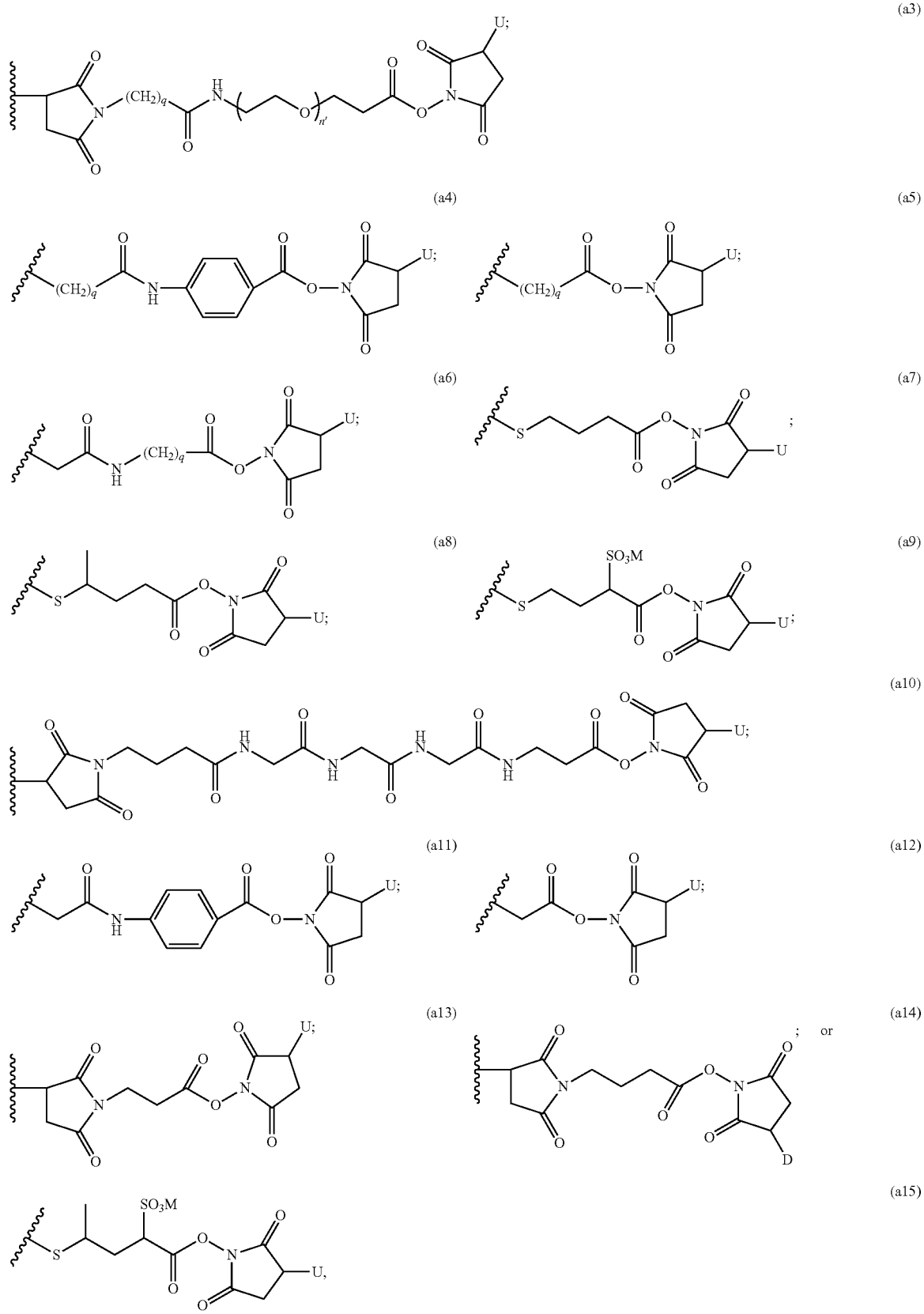

wherein U is —H or —SO₃M; and the remaining variables are as described above for (a1')-(a15').

In one embodiment, for compound of structural formula (I) or a pharmaceutically acceptable salt thereof, $Z^s$ is selected from formulas (a1')-(a8') and (a10')-(a15'); or is selected from formulas (a1)-(a8) and (a10)-(a15).

A second object of the invention is to provide conjugates of cell binding agents with the novel benzodiazepine compounds or derivatives thereof of the present invention. These conjugates are useful as therapeutic agents, which are delivered specifically to target cells and are cytotoxic.

Specifically, a conjugate of the invention can comprise: a cytotoxic compound and a cell binding agent (CBA), wherein the cytotoxic compound is covalently linked to the CBA, and wherein the cytotoxic compound is represented by any one of the following formulas:

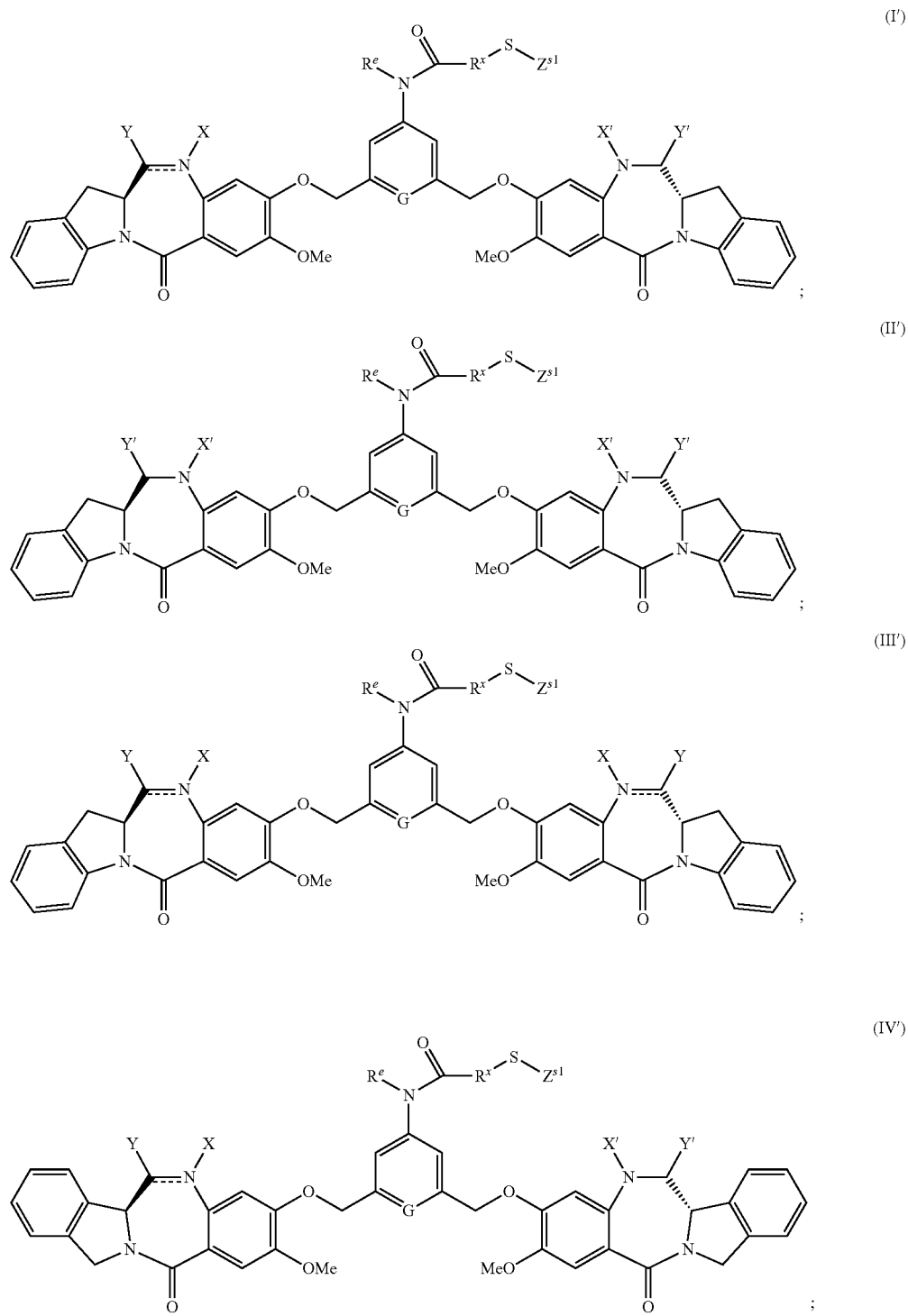

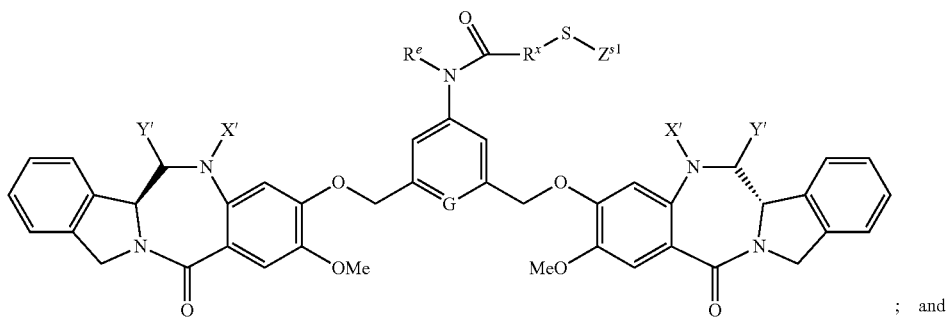

(V')

; and

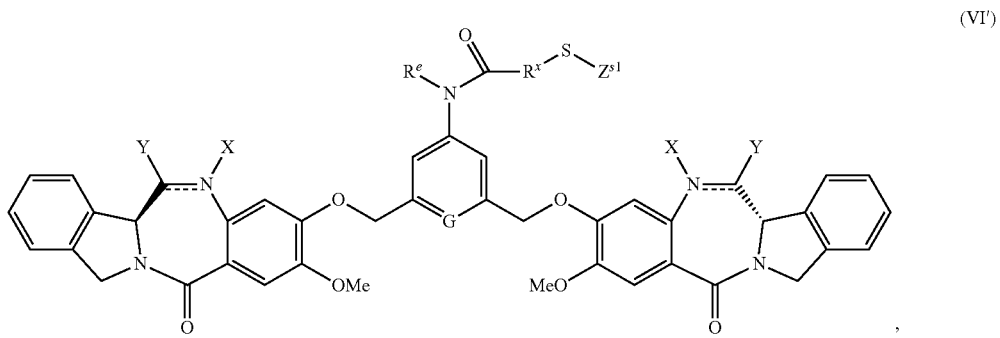

(VI')

, or a pharmaceutically acceptable salt thereof, wherein:

the double line == between N and C represents a single bond or a double bond, provided that when it is a double bond, X is absent and Y is —H, and when it is a single bond, X is selected from —H, or an amine protecting group;

Y is selected from —H, —OR, —OCOR', —SR, —NR'R", —SO$_3$M, —SO$_2$M or —OSO$_3$M, wherein M is —H or a cation;

R is —H, an optionally substituted linear, branched or cyclic alkyl, alkenyl or alkynyl having from 1 to 10 carbon atoms or a PEG group —(CH$_2$CH$_2$O)$_n$—R$^c$, wherein n is an integer from 1 to 24, and R$^c$ is a linear or branched alkyl having 1 to 4 carbon atoms;

R' and R" are the same or different, and are selected from —H, —OR, —NRR$^{g'}$, —COR, an optionally substituted linear, branched or cyclic alkyl, alkenyl or alkynyl having from 1 to 10 carbon atoms, an optionally substituted aryl having from 6 to 18 carbon atoms, an optionally substituted 3- to 18-membered heterocyclic ring having 1 to 6 heteroatoms selected from O, S, N and P, a PEG group —(CH$_2$CH$_2$O)$_n$—R$^c$, wherein n is an integer from 1 to 24, preferably n is 2, 4 or 8; and R$^{g'}$ is —H, an optionally substituted linear, branched or cyclic alkyl, alkenyl or alkynyl having from 1 to 10 carbon atoms or a PEG group —(CH$_2$CH$_2$O)$_n$—R$^c$;

X' is selected from the group consisting of —H, —OH, an optionally substituted linear, branched or cyclic alkyl, alkenyl or alkynyl having from 1 to 10 carbon atoms, phenyl, and an amine-protecting group;

Y' is selected from the group consisting of —H, an oxo group, an optionally substituted linear, branched or cyclic alkyl, alkenyl or alkynyl having from 1 to 10 carbon atoms;

R$^x$ is a linear or branched alkylene having 1 to 6 carbon atoms, optionally substituted with a charged substituent or an ionizable group Q;

R$^e$ is —H or a linear or branched alkyl having 1 to 6 carbon atoms;

G is selected from —CH— or —N—;

Z$^{s1}$ is selected from any one of the following formulas:

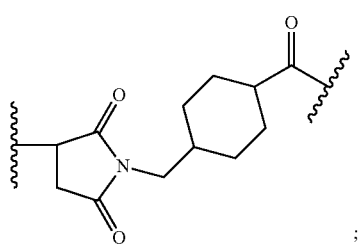

(b1)

;

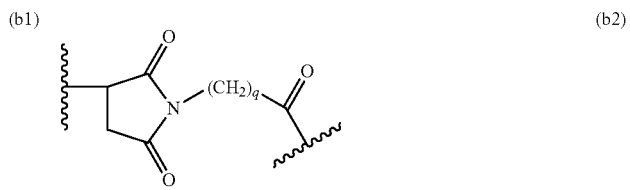

(b2)

;

-continued

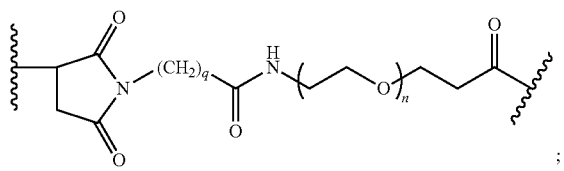

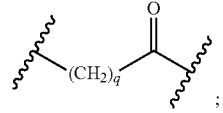

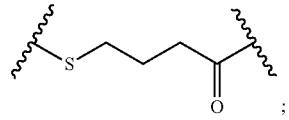

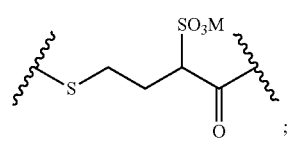

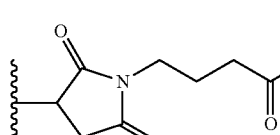

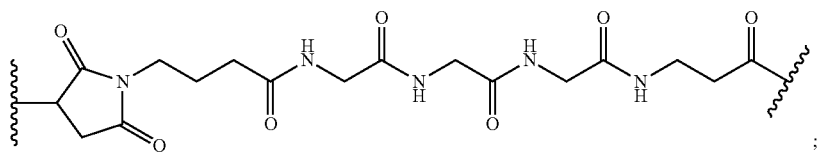

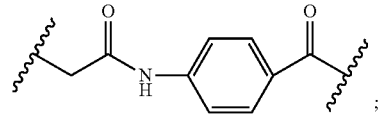

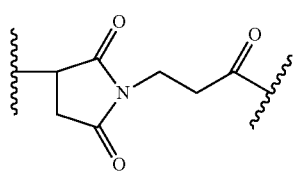

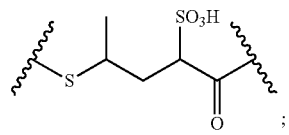

wherein:

q is an integer from 1 to 5;

$R^d$ is a linear or branched alkyl having 1 to 6 carbon atoms or is selected from phenyl, nitrophenyl, dinitrophenyl, carboxynitrophenyl, pyridyl and nitropyridyl;

n is an integer from 2 to 6; and

M is $H^+$ or a cation.

In one embodiment, for conjugates of the present invention, the cell-binding agent is an anti-folate receptor antibody or an antibody fragment thereof. More specifically, the anti-folate receptor antibody is huMOV19 antibody.

In yet another embodiment, for conjugates of the present invention, the cell-binding agent is an anti-EGFR antibody or an antibody fragment thereof. In one embodiment, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66. More specifically, the anti-EGFR antibody is huML66.

The present invention also includes a composition (e.g., a pharmaceutical composition) comprising novel benzodiazepine compounds, derivatives thereof, or conjugates thereof, (and/or solvates, hydrates and/or salts thereof) and a carrier (a pharmaceutically acceptable carrier). The present invention additionally includes a composition (e.g., a pharmaceutical composition) comprising novel benzodiazepine compounds, derivatives thereof, or conjugates thereof (and/or solvates, hydrates and/or salts thereof), and a carrier (a pharmaceutically acceptable carrier), further comprising a second therapeutic agent. The present compositions are useful for inhibiting abnormal cell growth or treating a proliferative disorder in a mammal (e.g., human) The present compositions are useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds, derivatives thereof, or conjugates thereof, (and/or solvates and salts thereof) or a composition thereof, alone or in combination with a second therapeutic agent. The present invention includes a method of synthesizing and using novel benzodiazepine compounds, derivatives thereof, and conjugates thereof for in vitro, in situ, and in vivo diagnosis or treatment of mammalian cells, organisms, or associated pathological conditions.

The compounds of this invention, derivatives thereof, or conjugates thereof, and compositions comprising them, are useful for treating or lessening the severity of disorders, such as, characterized by abnormal growth of cells (e.g., cancer). Other applications for compounds and conjugates of this invention include, but are not limited to, treating conditions such as cancer, rheumatoid arthritis, multiple sclerosis, graft versus host disease (GVHD), transplant rejection, lupus, myositis, infection, immune deficiency such as AIDS and inflammatory diseases in a mammal (e.g., human).

BRIEF DESCRIPTION OF THE FIGURES

FIG. 1 shows MS spectrometry data for huMov19-sulfo-SPDB-1d conjugate.

FIGS. 14A, 14B, 14C and 14D shows in vitro cytotoxicity of huMOV19-sulfo-SPDB-1d conjugate against various cancer cell lines.

DETAILED DESCRIPTION OF THE INVENTION

Figure 2:
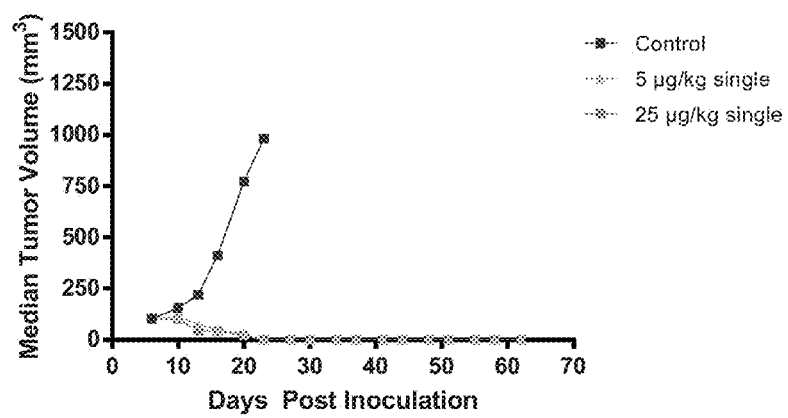
FIG. 2 shows in vivo efficacy of huMov19-sulfo-SPDB-1d conjugate in NCI-H2110 tumor bearing SCID mice.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents that can be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, compound-linker molecules, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

As used herein, the term "cell-binding agent" or "CBA" refers to a compound that can bind a cell (e.g., on a cell-surface ligand) or bind a ligand associated with or proximate to the cell, preferably in a specific manner. In certain embodiments, binding to the cell or a ligand on or near the cell is specific. The CBA may include peptides and non-peptides.

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like. Preferably, the alkenyl has two to ten carbon atoms. More preferably, the alkyl has two to four carbon atoms.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6], or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle can be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups can be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclyl include the oxidized forms such as NO, SO, and $SO_2$.

The term "halo" or "halogen" refers to F, Cl, Br or I.

The alkyl, alkenyl, alkynyl, cyclic alkyl, cyclic alkenyl, cyclic alkynyl, carbocyclyl, aryl, heterocyclyl and heteroaryl described above can be optionally substituted with one more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated).

If a substituent is described as being "optionally substituted," the substituent can be either (1) not substituted, or (2) substituted. If a carbon of a substituent is described as being optionally substituted with one or more of a list of substituents, one or more of the hydrogens on the carbon (to the extent there are any) can separately and/or together be replaced with an independently selected optional substituent. If a nitrogen of a substituent is described as being optionally substituted with one or more of a list of substituents, one or more of the hydrogens on the nitrogen (to the extent there are any) can each be replaced with an independently selected optional substituent. One exemplary substituent can be depicted as —NR'R", wherein R' and R" together with the nitrogen atom to which they are attached, can form a heterocyclic ring. The heterocyclic ring formed from R' and R" together with the nitrogen atom to which they are attached can be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group can include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent can be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocycyclyl, halogen, guanidinium [—NH(C=NH)NH$_2$], —OR$^{100}$, NR$^{101}$R$^{102}$, —NO$_2$, NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)—R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyciyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocycycl, —SR$^{101}$, —SOR$^{101}$, —SO$_2$R$^{101}$ and —SO$_3$M.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "linkable to a cell binding agent" as used herein refers to the compounds described herein or derivates thereof comprising at least one linking group or a precursor thereof suitable to bond these compounds or derivatives thereof to a cell binding agent.

The term "precursor" of a given group refers to any group that can lead to that group by any deprotection, a chemical modification, or a coupling reaction.

The term "linked to a cell binding agent" refers to a conjugate molecule comprising at least one of the compounds described herein (e.g., compounds of formula (I)-(IV) and (VIII)-(XI) and drug-linker compounds describe herein), or derivative thereof bound to a cell binding agent via a suitable linking group or a precursor thereof.

The term "chiral" refers to molecules that have the property of non-superimposability of the mirror image partner, while the term "achiral" refers to molecules that are superimposable on their mirror image partner.

The term "stereoisomer" refers to compounds that have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as crystallization, electrophoresis and chromatography.

"Enantiomers" refer to two stereoisomers of a compound that are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies that are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs can only become active upon such reaction under biological conditions, or they can have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs."

One preferred form of prodrug of the invention includes compounds (with or without any linker groups) and conjugates of the invention comprising an adduct formed between an imine bond of the compounds/conjugates and an imine reactive reagent. Another preferred form of prodrug of the invention includes compounds such as those of formula (I)-(IV), wherein when the double line == between N and C represents a single bond, X is H or an amine protecting group, and the compound becomes a prodrug. A prodrug of the invention can contain one or both forms of prodrugs described herein (e.g., containing an adduct formed between an imine bond of the compounds/conjugates and an imine reactive reagent, and/or containing a Y leaving group when X is —H).

The term "imine reactive reagent" refers to a reagent that is capable of reacting with an imine group. Examples of imine reactive reagent includes, but is not limited to, sulfites (H$_2$SO$_3$, H$_2$SO$_2$ or a salt of HSO$_3^-$, SO$_3^{2-}$ or HSO$_2^-$ formed with a cation), metabisulfite (H$_2$S$_2$O$_5$ or a salt of S$_2$O$_5^{2-}$ formed with a cation), mono, di, tri, and tetra-thiophosphates (PO$_3$SH$_3$, PO$_2$S$_2$H$_3$, POS$_3$H$_3$, PS$_4$H$_3$ or a salt of PO$_3$S$^{3-}$, PO$_2$S$_2^{3-}$, POS$_3^{3-}$ or PS$_4^{3-}$ formed with a cation), thio phosphate esters ((R$^i$O)$_2$PS(OR$^i$), R$^i$SH, R$^i$SOH, R$^i$SO$_2$H, R$^i$SO$_3$H), various amines (hydroxyl amine (e.g., NH$_2$OH), hydrazine (e.g., NH$_2$NH$_2$), NH$_2$O—R$^i$, R$^{i'}$NH—R$^i$, NH$_2$—R$^i$), NH$_2$—CO—NH$_2$, NH$_2$—C(=S)—NH$_2$, thiosulfate (H$_2$S$_2$O$_3$ or a salt of S$_2$O$_3^{2-}$ formed with a cation), dithionite (H$_2$S$_2$O$_4$ or a salt of S$_2$O$_4^{2-}$ formed with a cation), phosphorodithioate (P(=S)(OR$^k$)(SH)(OH) or a salt thereof formed with a cation), hydroxamic acid (R$^k$C(=O)NHOH or a salt formed with a cation), hydrazide (R$^k$CONHNH$_2$), formaldehyde sulfoxylate (HOCH$_2$SO$_2$H or a salt of HOCH$_2$SO$_2^-$ formed with a cation, such as HOCH$_2$SO$_2$Na$^+$), glycated nucleotide (such as GDP-mannose), fludarabine or a mixture thereof, wherein R$^i$ and R$^{i'}$ are each independently a linear or branched alkyl having 1 to 10 carbon atoms and are substituted with at least one substituent selected from —N(R$^j$)$_2$, —CO$_2$H, —SO$_3$H, and —PO$_3$H; R$^i$ and R$^{i'}$ can be further optionally substituted with a substituent for an alkyl described herein; R$^j$ is a linear or branched alkyl having 1 to 6 carbon atoms; and R$^k$ is a linear, branched or cyclic alkyl, alkenyl or alkynyl having 1 to 10 carbon atoms, aryl, heterocyclyl or heteroaryl (preferably, R$^k$ is a linear or branched alkyl having 1 to 4 carbon atoms; more preferably, R$^k$ is methyl, ethyl or propyl). Preferably, the cation is a monovalent cation, such as Na$^+$ or K$^+$. Preferably, the imine reactive reagent is selected from sulfites, hydroxyl amine, urea and hydrazine. More preferably, the imine reactive reagent is NaHSO$_3$ or KHSO$_3$.

As used herein and unless otherwise indicated, the terms "biohydrolyzable amide," "biohydrolyzable ester," "biohydrolyzable carbamate," "biohydrolyzable carbonate," "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines. Particularly favored prodrugs and prodrug salts are those that increase the bioavailability of the compounds of this invention when such compounds are administered to a mammal.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylenebis-(2-hydroxy-3-naphthoate)) salts, alkali metal (e.g., sodium and potassium) salts, alkaline earth metal (e.g., magnesium) salts, and ammonium salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure. Instances where multiple charged atoms are part of the pharmaceutically acceptable salt can have multiple counter ions. Hence, a pharmaceutically acceptable salt can have one or more charged atoms and/or one or more counter ions.

If the compound of the invention is a base, the desired pharmaceutically acceptable salt can be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound that further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or pre-cancerous cells.

A "therapeutic agent" encompasses both a biological agent such as an antibody, a peptide, a protein, an enzyme or a chemotherapeutic agent.

A "chemotherapeutic agent" is a chemical compound useful in the treatment of cancer.

A "metabolite" is a product produced through metabolism in the body of a specified compound, a derivative thereof, or a conjugate thereof, or salt thereof. Metabolites of a compound, a derivative thereof, or a conjugate thereof, can be identified using routine techniques known in the art and their activities determined using tests such as those described herein. Such products can result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent can comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

In one embodiment, the linking group with a reactive group attached at one end, such as a reactive ester, is selected from the following:

—O(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X",

—O(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X",

—O(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$(piperazino)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$(pyrrolo)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(piperazino)$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(pyrrolo)$_t$(CR$_{22}$R$_{23}$)$_n$(OCH$_2$CH$_2$)$_p$(CR$_{40}$R$_{41}$)$_{p''}$Y" (CR$_{24}$R$_{25}$)$_q$(CO)$_t$X", —S(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_n$(CO)$_t$X", —NR$_{33}$(C=O)$_{p''}$(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(alkynyl)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$—(CO)$_t$X", —NR$_{33}$(C=O)$_{p''}$(CR$_{20}$R$_{21}$)$_m$(piperazino)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$—(CO)$_t$X", —NR$_{33}$(C=O)$_{p''}$(CR$_{20}$R$_{21}$)$_m$(pyrrolo)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$—(CO)$_t$X", —NR$_{33}$(C=O)$_{p''}$(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_t$(CO)$_t$X", —(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(alkynyl)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(piperazino)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n'}$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n'}$(alkynyl)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n''}$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", wherein:

m, n, p, q, m', n', t' are integer from 1 to 10, or are optionally 0;

t, m", n", and p" are 0 or 1;

X" is selected from OR$_{36}$, SR$_{37}$, NR$_{38}$R$_{39}$, wherein R$_{36}$, R$_{37}$, R$_{38}$, R$_{39}$ are H, or linear, branched or cyclic alkyl, alkenyl or alkynyl having from 1 to 20 carbon atoms and, or, a polyethylene glycol unit —(OCH$_2$CH$_2$)$_n$, R$_{37}$, optionally, is a thiol protecting group when t=1, COX" forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;

Y" is absent or is selected from O, S, S—S or NR$_{32}$, wherein R$_{32}$ has the same definition as given above for R; or when Y" is not S—S and t=0, X" is selected from a maleimido group, a haloacetyl group or SR$_{37}$, wherein R$_{37}$ has the same definition as above;

A" is a residue of an amino acid or a polypeptide containing between 2 to 20 amino acid units;

R$_{20}$, R$_{21}$, R$_{22}$, R$_{23}$, R$_{24}$, R$_{25}$, R$_{26}$, and R$_{27}$ are the same or different, and are —H or a linear or branched alkyl having from 1 to 5 carbon atoms;

R$_{29}$ and R$_{30}$ are the same or different, and are —H or alkyl from 1 to 5 carbon atoms;

R$_{33}$ is —H or linear, branched or cyclic alkyl, alkenyl or alkynyl having from 1 to 12 carbon atoms, a polyethylene glycol unit R—(OCH$_2$CH$_2$)$_n$—, or R$_{33}$ is —COR$_{34}$, —CSR$_{34}$, —SOR$_{34}$, or —SO$_2$R$_{34}$, wherein R$_{34}$ is H or linear, branched or cyclic alkyl, alkenyl or alkynyl having from 1 to 20 carbon atoms or, a polyethylene glycol unit —(OCH$_2$CH$_2$)$_n$; and one of R$_{40}$ and R$_{41}$ is optionally a negatively or positively charged functional group and the other is H or alkyl, alkenyl, alkynyl having 1 to 4 carbon atoms.

Any of the above linking groups can be present in any of the compounds, drug-linker compounds, or conjugates of the invention, including replacing the linking groups of any of the formulas described herein.

The term "amino acid" refers to naturally occurring amino acids or non-naturally occurring amino acid. In one embodiment, the amino acid is represented by NH$_2$—C(R$^{aa'}$R$^{aa}$)—C(=O)OH, wherein R$^{aa}$ and R$^{aa'}$ are each independently H, an optionally substituted linear, branched or cyclic alkyl, alkenyl or alkynyl having 1 to 10 carbon atoms, aryl, heteroaryl or heterocyclyl or R$^{aa}$ and the N-terminal nitrogen atom can together form a heteroycyclic ring (e.g., as in proline). The term "amino acid residue" refers to the corresponding residue when one hydrogen atom is removed from the amine and/or carboxy end of the amino acid, such as —NH—C(R$^{aa'}$R$^{aa}$)—C(=O)O—.

The term "cation" refers to an ion with positive charge. The cation can be monovalent (e.g., Na$^+$, K$^+$, etc.), bi-valent (e.g., Ca$^{2+}$, Mg$^{2+}$, etc.) or multi-valent (e.g., Al$^{3+}$ etc.). Preferably, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Cytotoxic Compounds

In a first embodiment, the present invention is directed to cytotoxic compounds described herein (e.g., compounds of formulas (I), (II), (III), (IV), (V), and (VI) describe above or a pharmaceutically acceptable salt thereof).

In one embodiment, the cytotoxic dimer is a compound of formula (I):

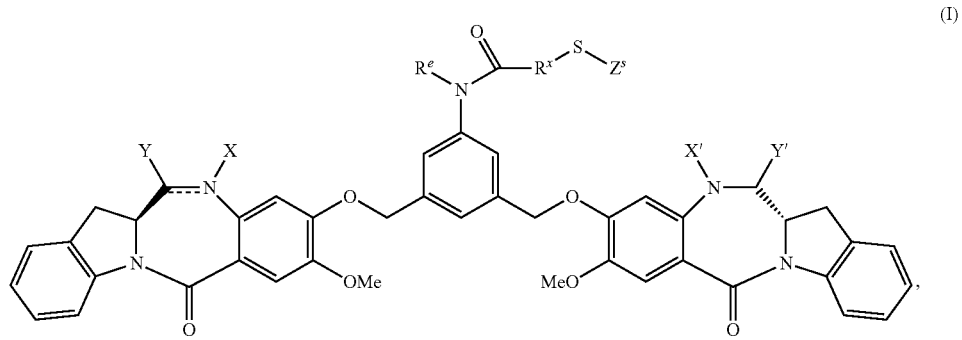

or a pharmaceutically acceptable salt thereof.

In a 1$^{st}$ specific embodiment, $Z^s$ is represented by either one of the following formulas:

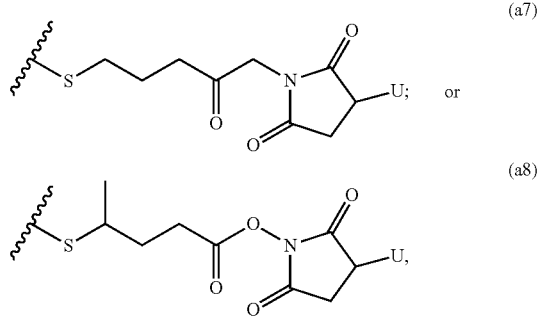

and the remaining variables are as described above in the first embodiment.

In a 2$^{nd}$ specific embodiment, $Z^s$ is —H or —SR$^d$; and the remaining variables are as described above the first embodiment.

In one embodiment, $Z^s$ is —H; and the remaining variables are as described above in the 2$^{nd}$ specific embodiment.

In another embodiments, $Z^s$ is —SR$^d$; R$^d$ is -Me or pyridyl; and the remaining variables are as described above in the 2$^{nd}$ specific embodiment.

In a 3$^{rd}$ specific embodiment, R$^e$ is H or Me; and the remaining variables are as described above in the first embodiment or the 1$^{st}$ or 2$^{nd}$ specific embodiment.

In a 4$^{th}$ specific embodiment, R$^x$ is —(CH$_2$)$_p$—(CR$^f$R$^g$)—, wherein R$^f$ and R$^g$ are each independently selected from H or a linear or branched alkyl having 1 to 4 carbon atoms; p is 0, 1, 2 or 3; and the remaining variables are as described above in the first embodiment or the 1$^{st}$, 2$^{nd}$ or 3$^{rd}$ embodiment.

In one embodiment, R$^f$ and R$^g$ are the same or different, and are selected from —H and -Me; and the remaining variables are as described above in the 4$^{th}$ specific embodiment. More specifically, R$^f$ and R$^g$ are both -Me; and p is 2.

In a 5$^{th}$ specific embodiment, R$^x$ is a linear or branched alkylene having 1 to 4 carbon atoms substituted with a charged substituent or an ionizable group Q; and the remaining variables are as described above in the first embodiment or the 1$^{st}$, 2$^{nd}$ or 3$^{rd}$ embodiment.

In one embodiment, Q is i) —$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a pharmaceutically acceptable salt thereof; or, ii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; R$_{14}$ to R$_{16}$ are each independently an optionally substituted alkyl; X$^-$ is a pharmaceutically acceptable anion; and the remaining variables are as described above as in the 5$^{th}$ specific embodiment. More specifically, Q is SO$_3$H or a pharmaceutically acceptable salt thereof.

In a 6$^{th}$ specific embodiment, the double line == between N and C represents a double bond; and the remaining variables are as described above in the first embodiment, or the 1$^{st}$, 2$^{nd}$, 3$^{rd}$, 4$^{th}$, or 5$^{th}$ specific embodiment.

In a 7$^{th}$ embodiment, the double line == between N and C represents a single bond; X is —H or an amine protecting group; Y is selected from —H, —SO$_3$M, —OH, —OMe, —OEt or —NHOH Y is selected from —H, —SO$_3$M, —OH, —OMe, —OEt or —NHOH; and the remaining variables are as described above in the first embodiment, or the 1$^{st}$, 2$^{nd}$, 3$^{rd}$, 4$^{th}$ or 5$^{th}$ specific embodiment.

In one embodiment, Y is —H, —SO$_3$M or —OH; and the remaining variables are as described above in the 7$^{th}$ specific embodiment. More specifically, M is H$^+$, Na$^+$ or K$^+$.

In a 8$^{th}$ specific embodiment, X' is —H, —OH or -Me; and the remaining variables are as described above in the first embodiment, or the 1$^{st}$, 2$^{nd}$, 3$^{rd}$, 4$^{th}$, 5$^{th}$, 6$^{th}$ or 7$^{th}$ specific embodiment. More specifically, X' is —H.

In a 9$^{th}$ specific embodiment, Y' is —H or oxo; and the remaining variables are as described above in the first embodiment, or the 1$^{st}$, 2$^{nd}$, 3$^{rd}$, 4$^{th}$, 5$^{th}$, 6$^{th}$, 7$^{th}$ or 8$^{th}$ specific embodiment. More specifically, Y' is —H.

In a 10$^{th}$ specific embodiment, for the compounds of formula (I), (II), (III), (IV), (V), and (VI), the double line == between N and C represents a single bond or a double bond, provided that when it is a double bond X is absent and Y is —H, and when it is a single bond, X is —H; Y is —OH or —SO$_3$M;

M is —H or a pharmaceutically acceptable cation;
X' and Y' are both —H; and
G is C; the remaining variables are as described above in the first embodiment, or the 1st, 2nd, 3rd, 4th or 5th specific embodiment.

In one embodiment, Y is —SO₃M and M is H⁺, Na⁺ or K⁺; and the remaining variables are as described above in the 10th specific embodiment.

In a 11th specific embodiment, the compound is any one of the following:

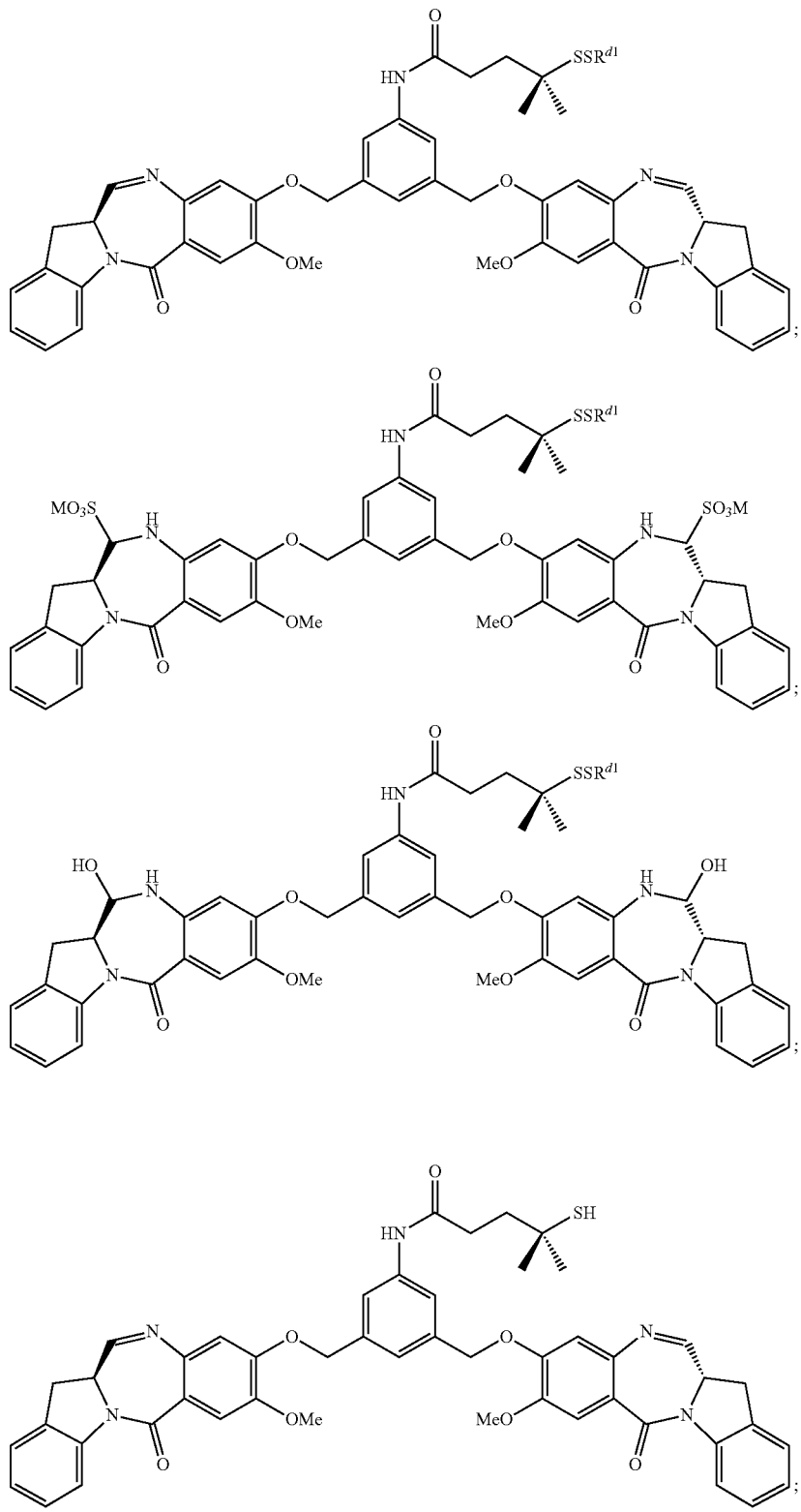

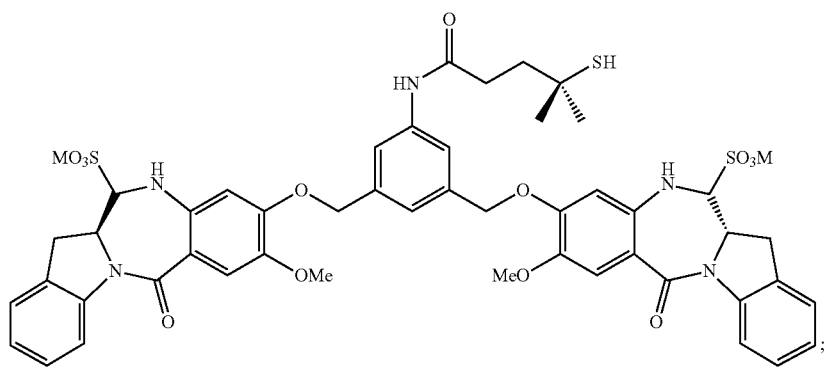
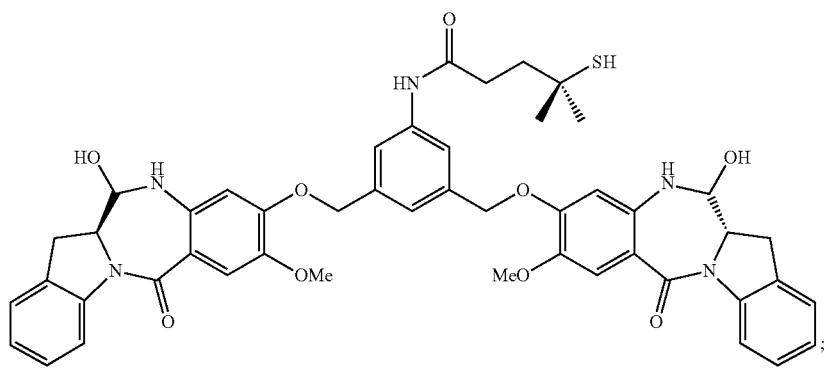
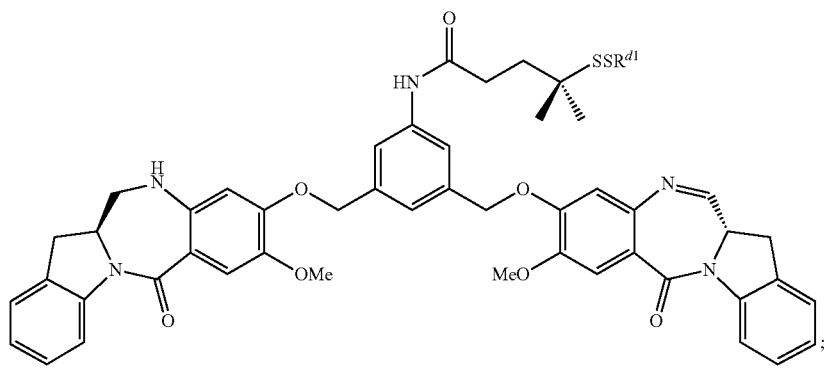
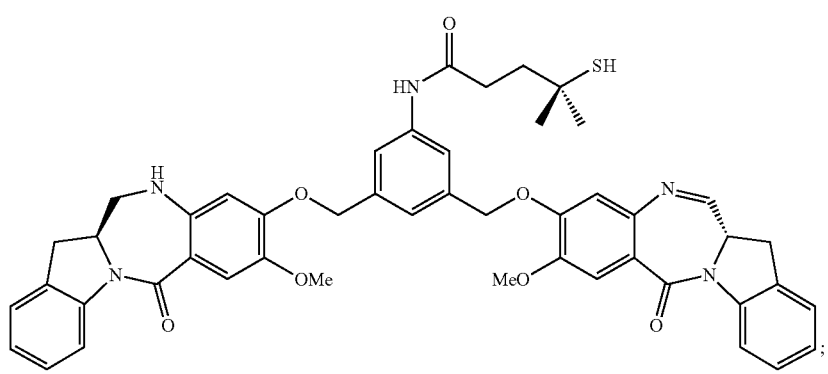

-continued
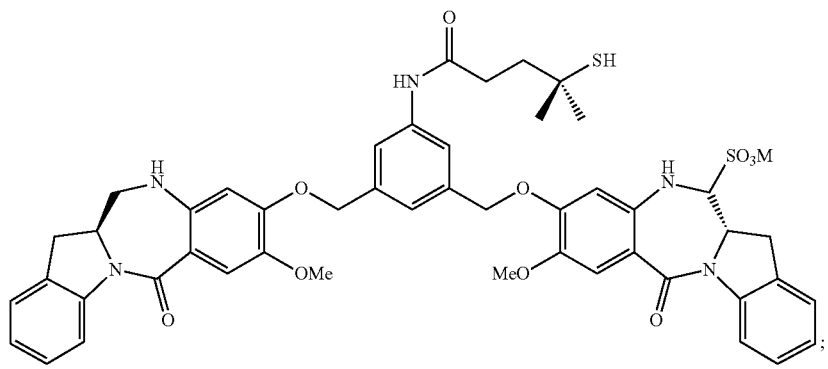
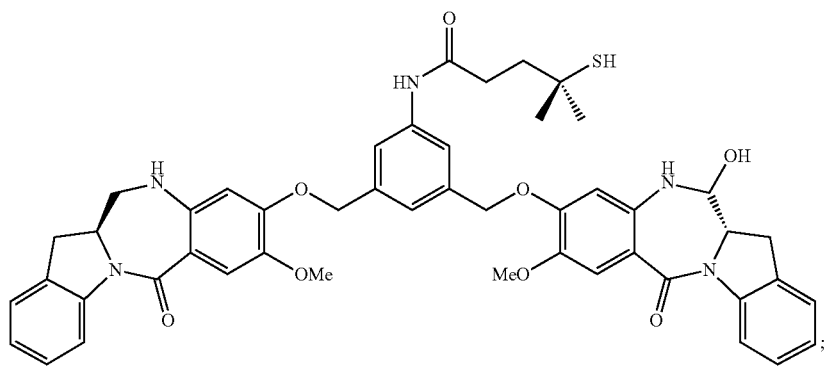
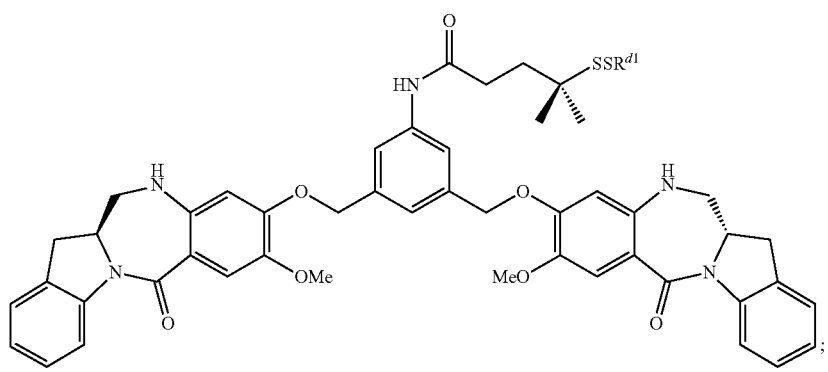
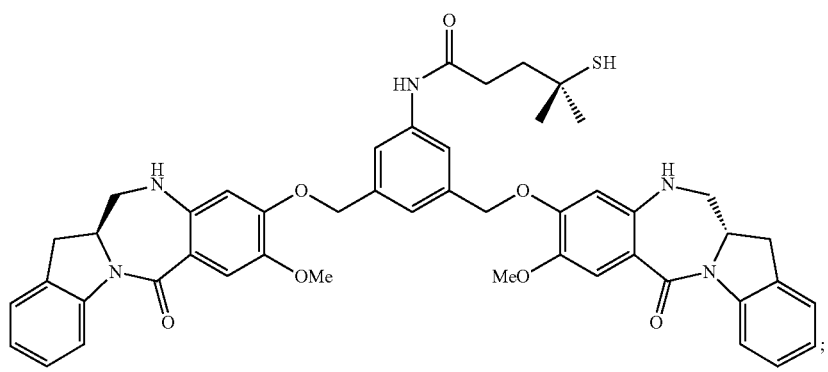

-continued
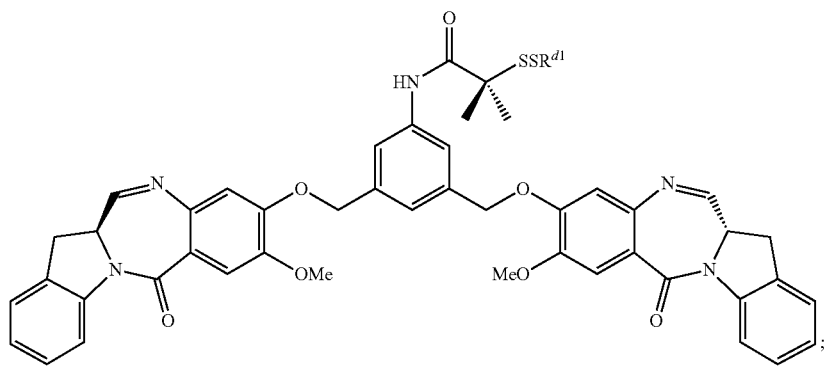
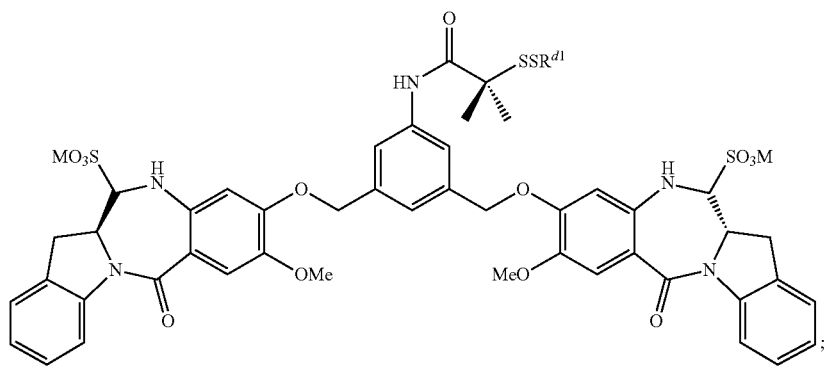
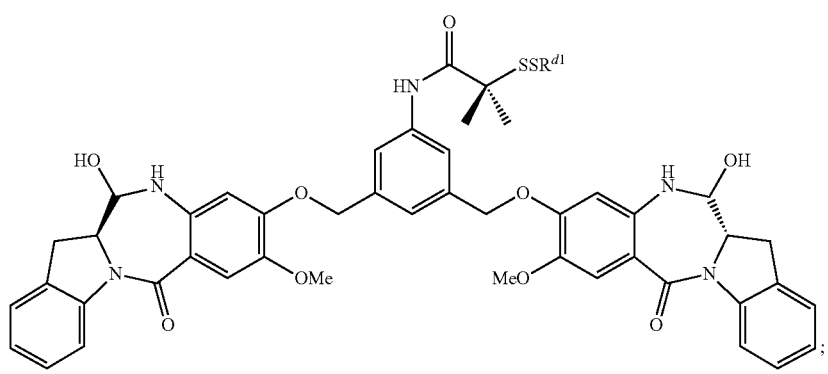
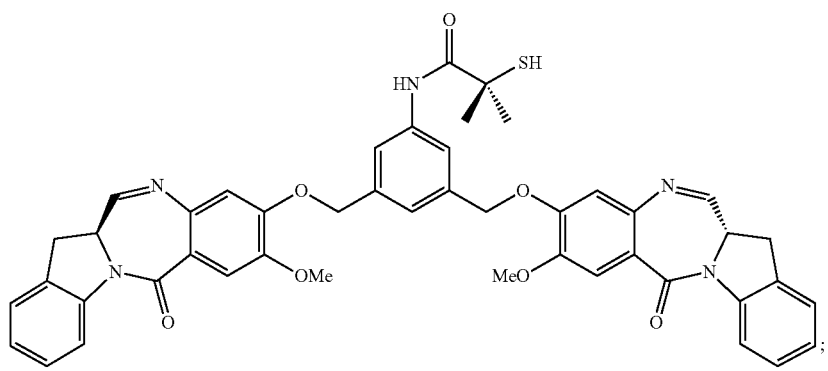

-continued
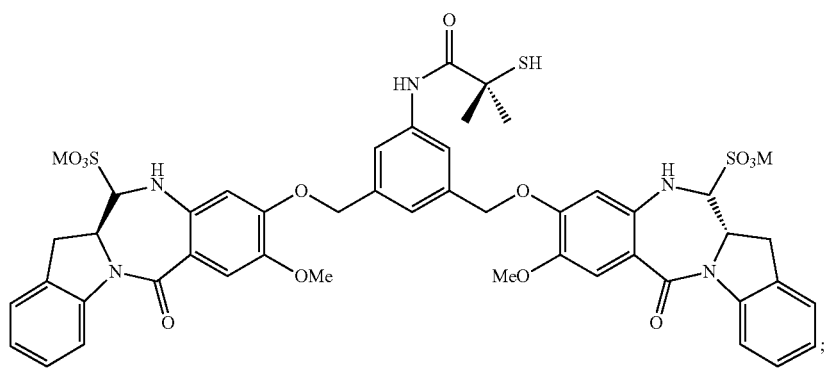
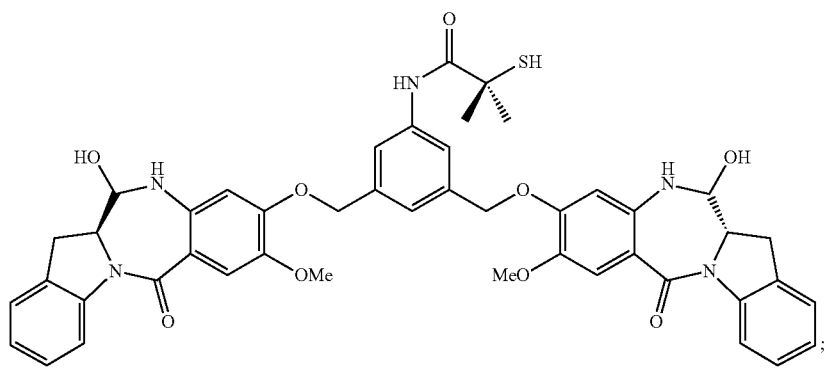
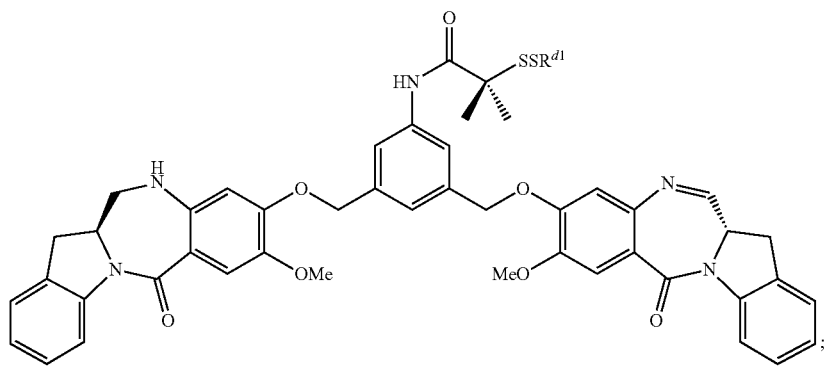
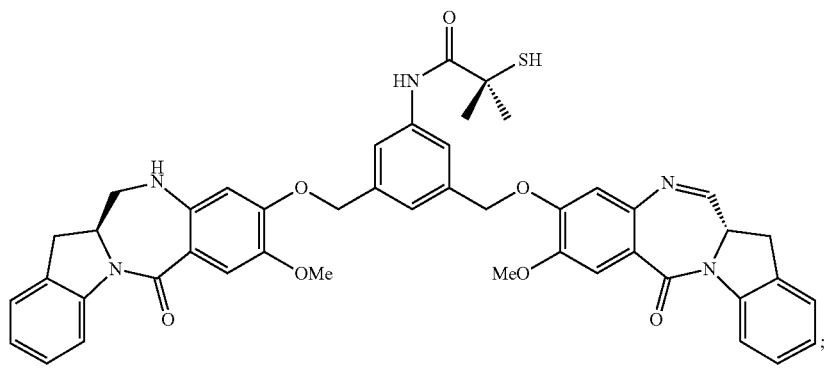

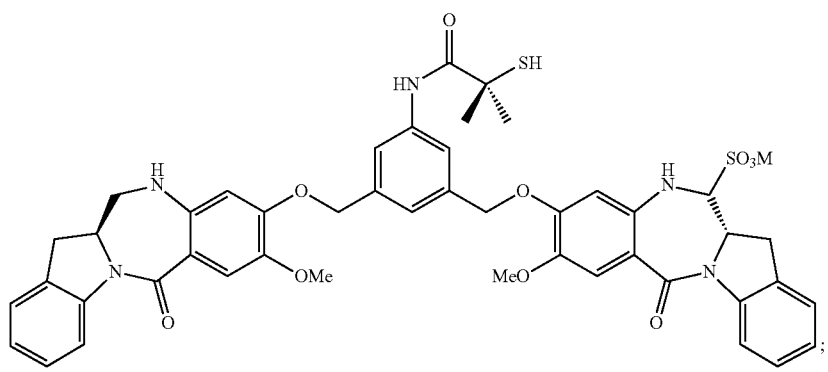
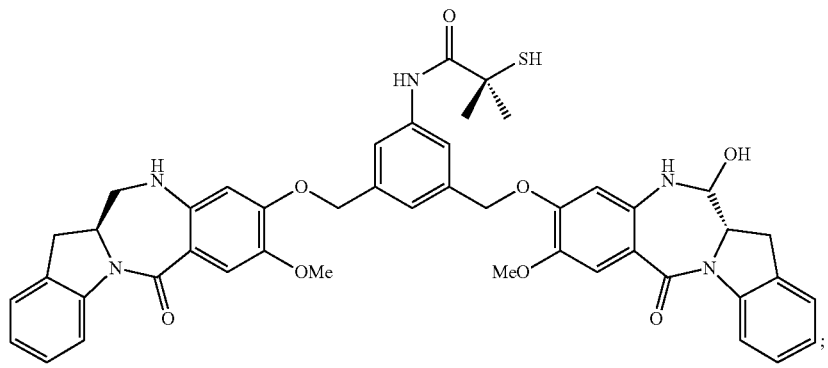
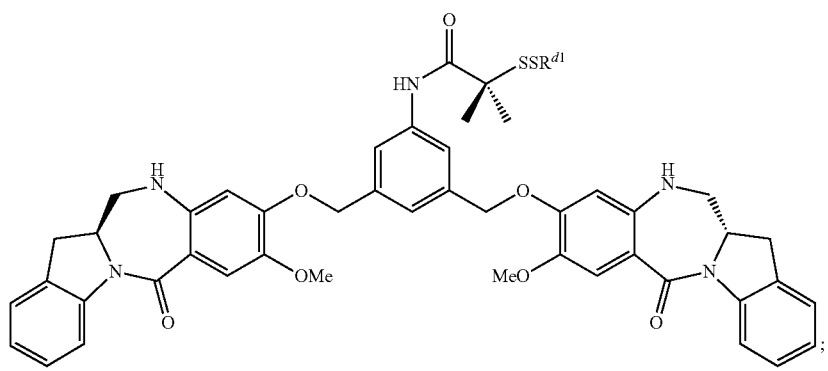
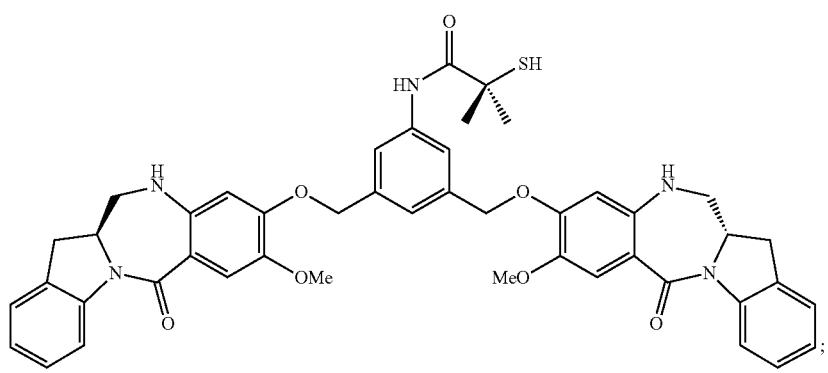

-continued
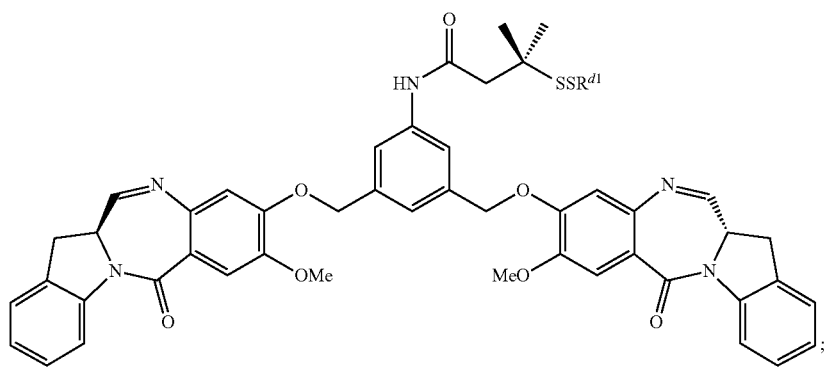
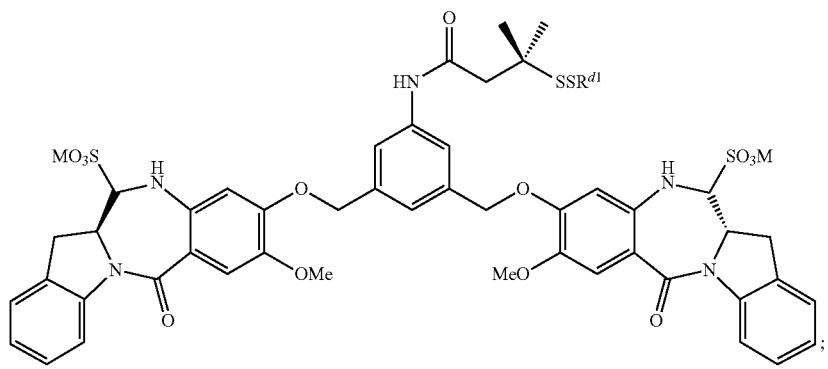
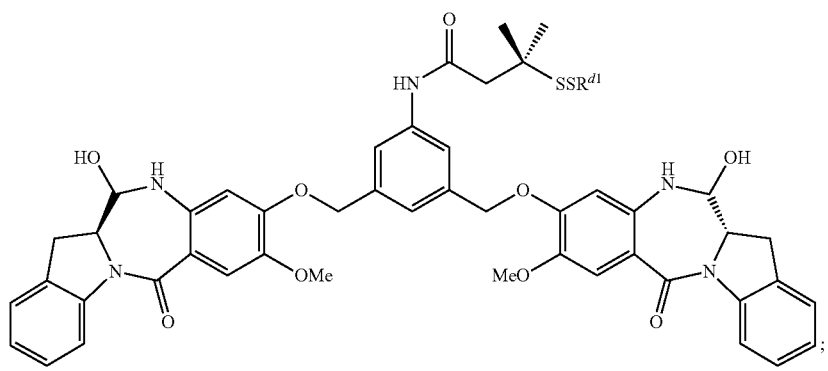
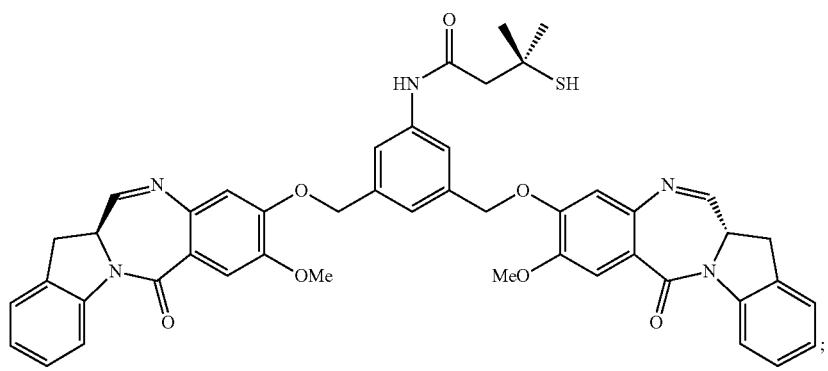

-continued
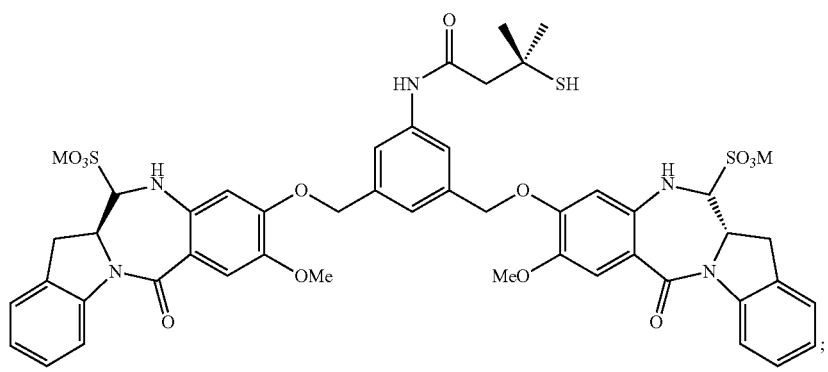
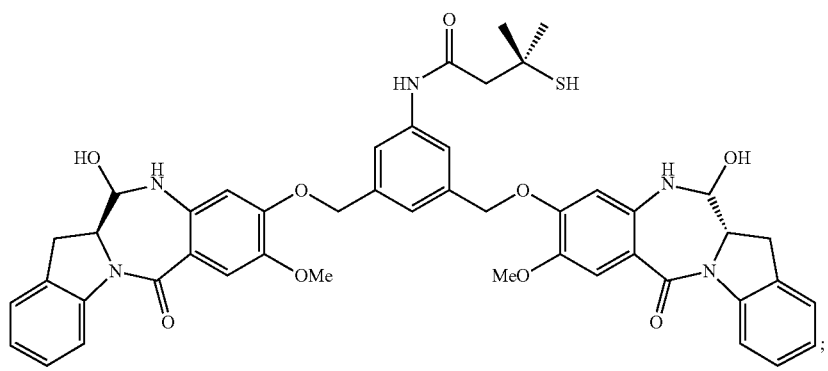
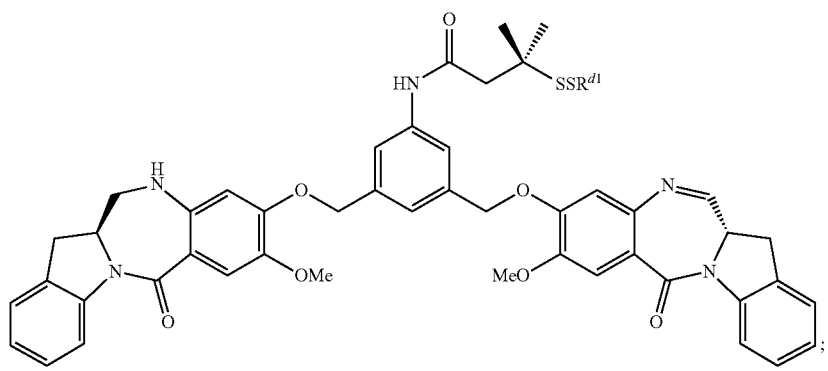
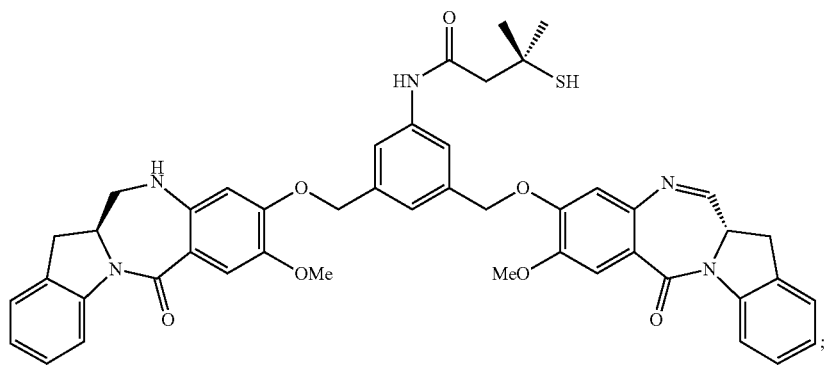

-continued
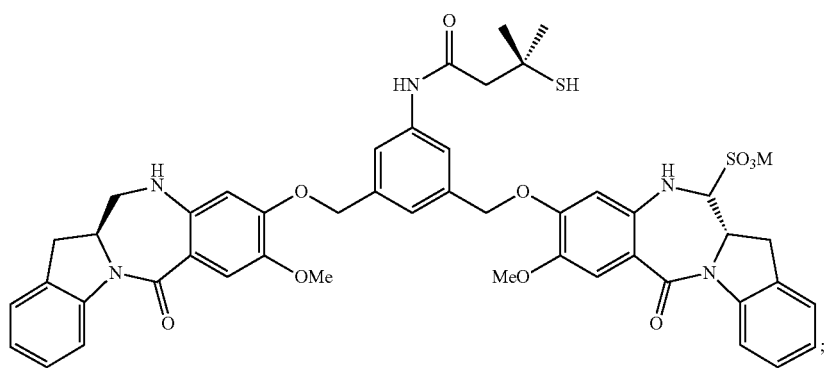
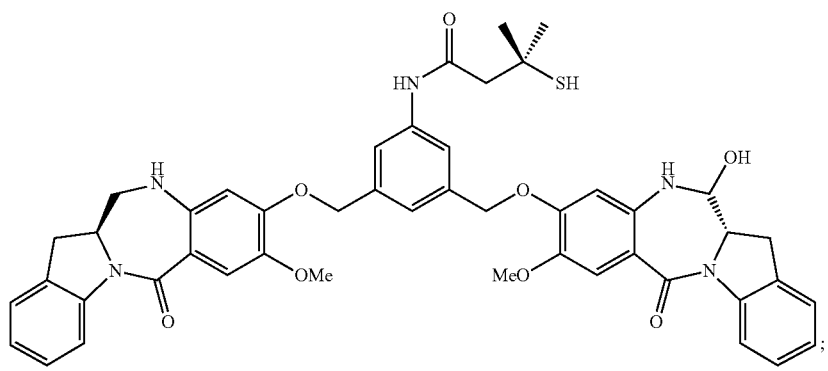
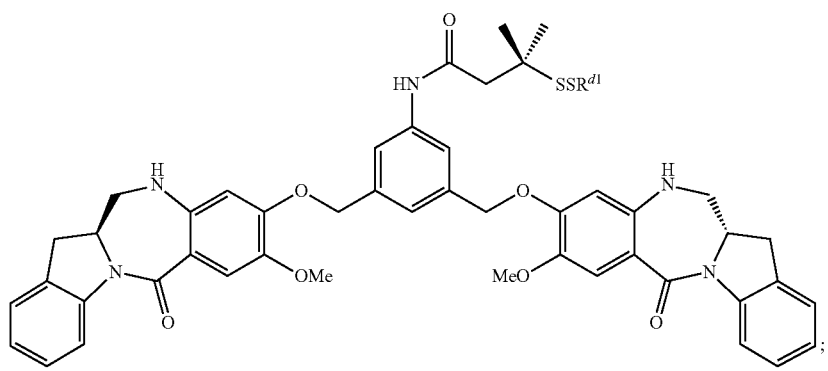
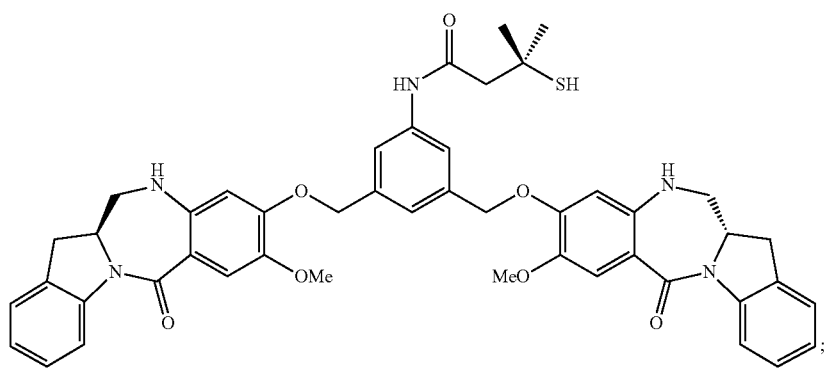

-continued
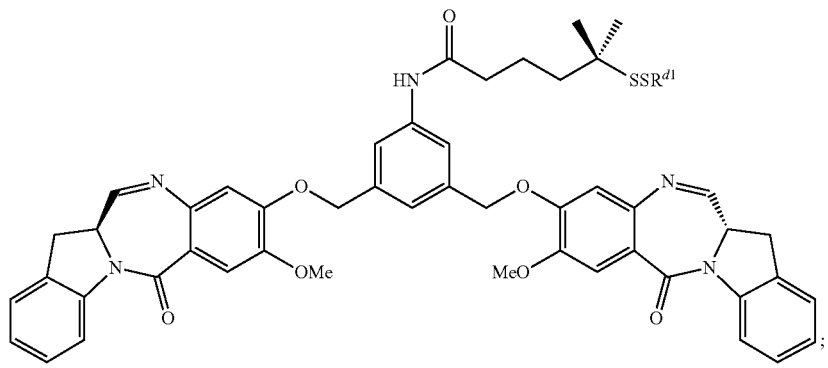
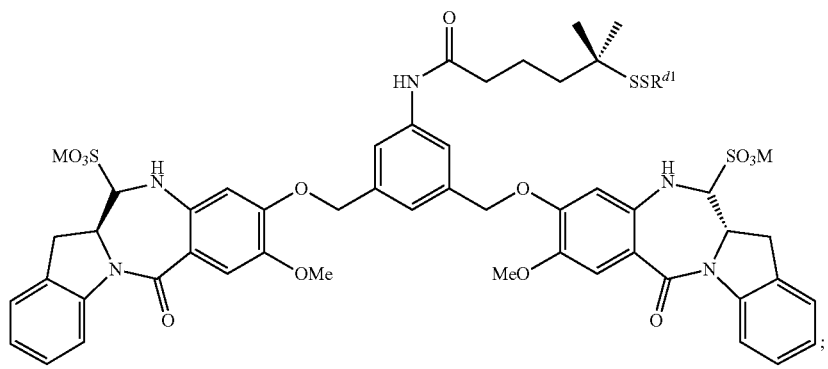
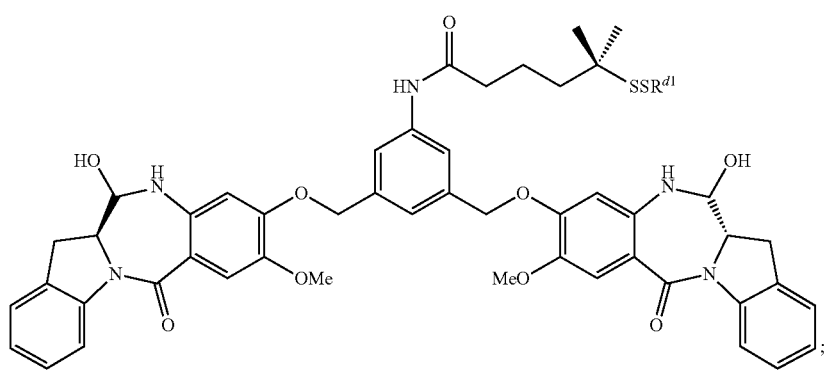
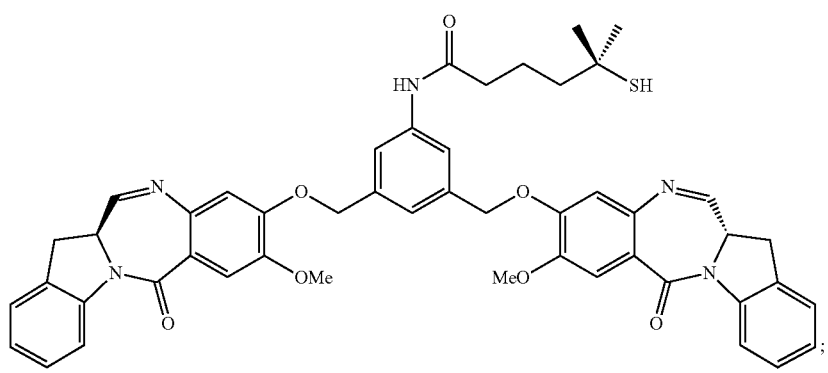

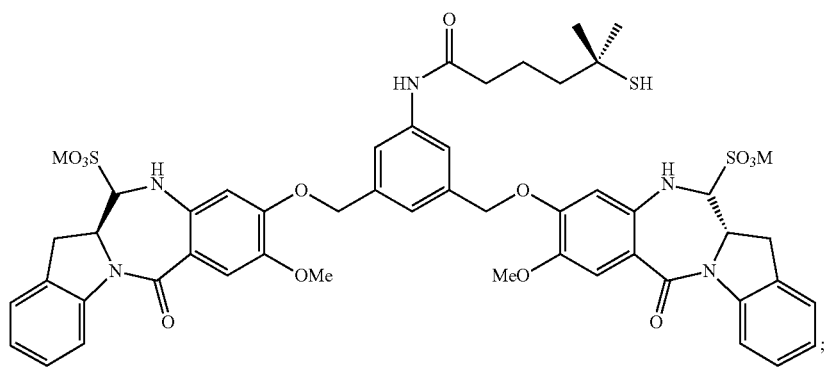
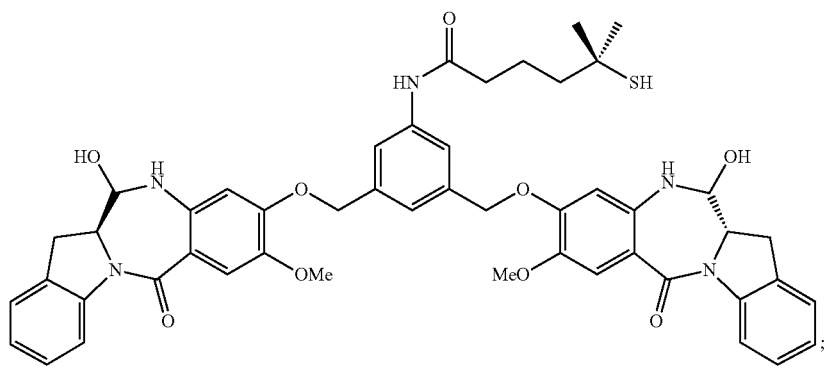
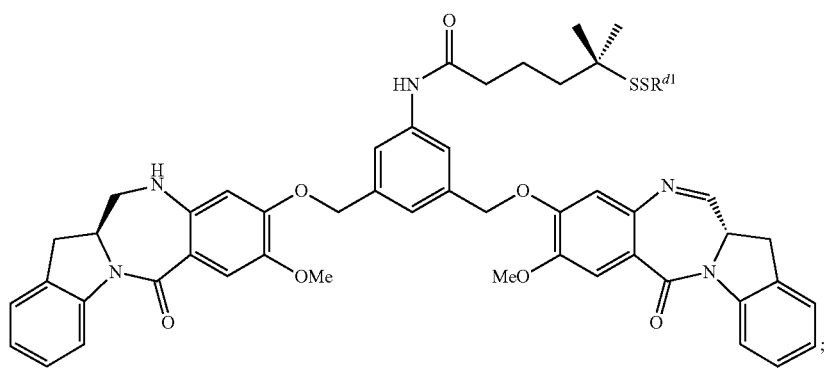
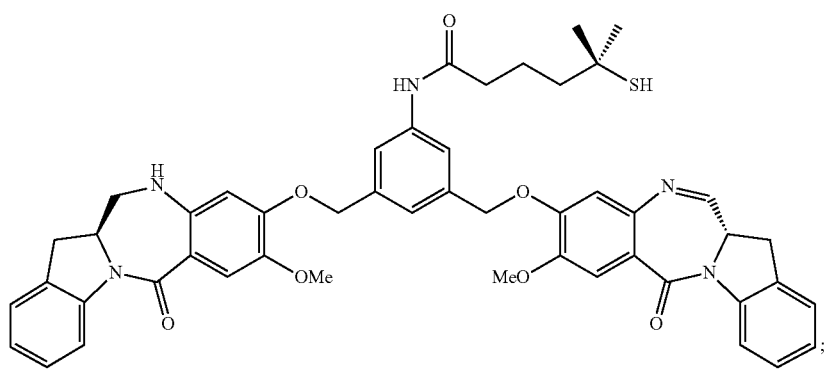

-continued
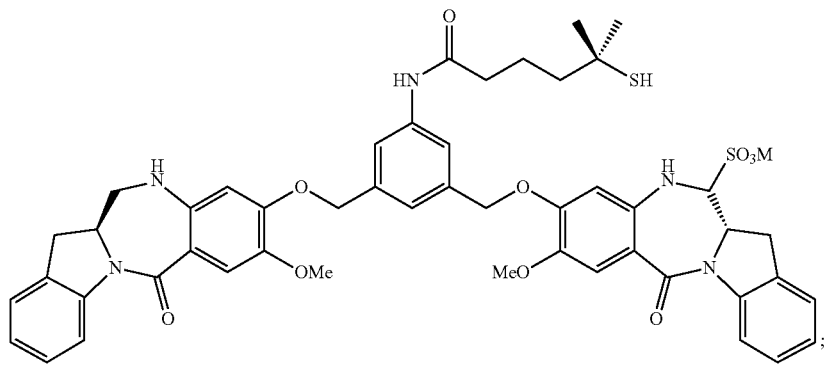
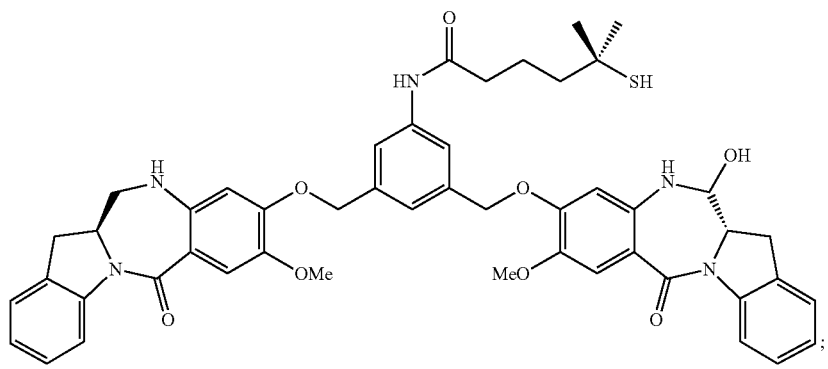
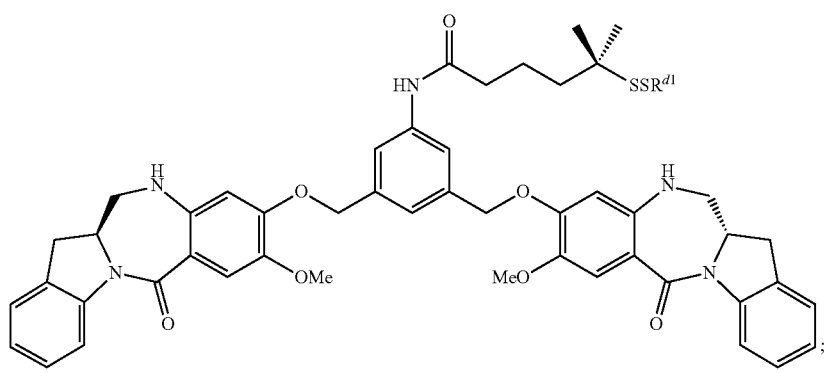
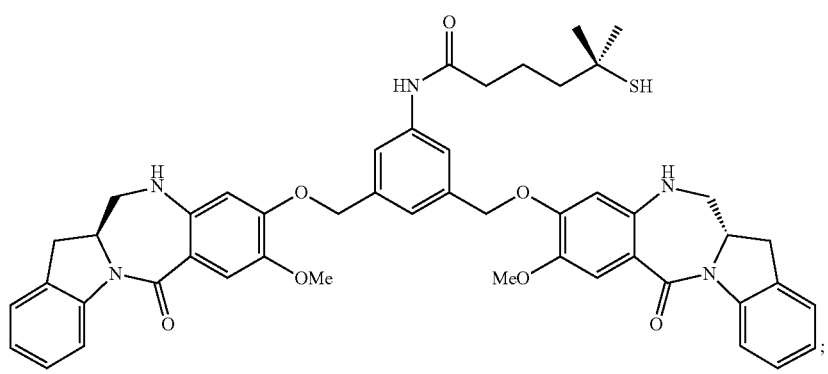

-continued
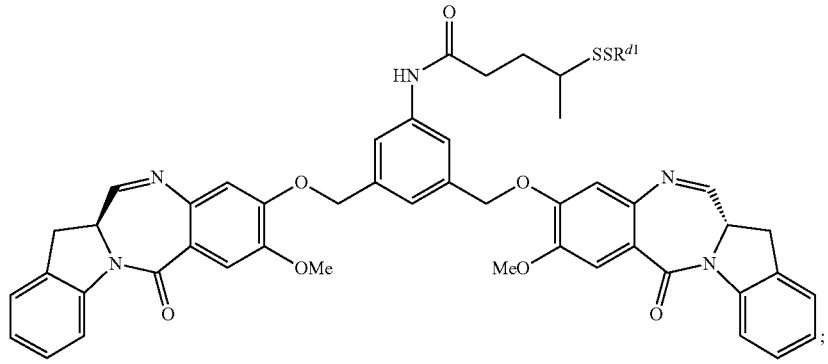
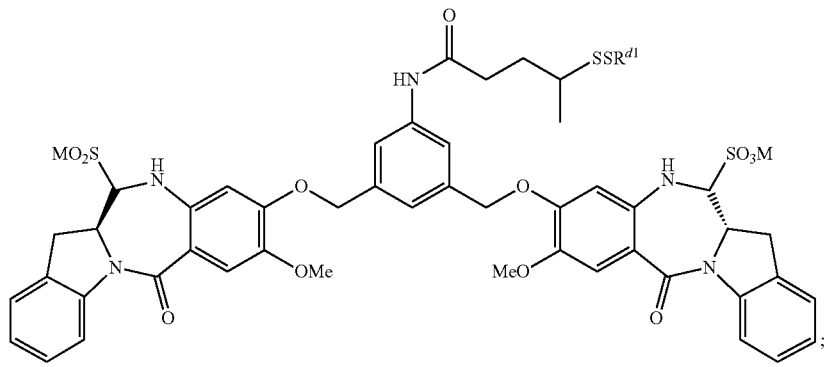
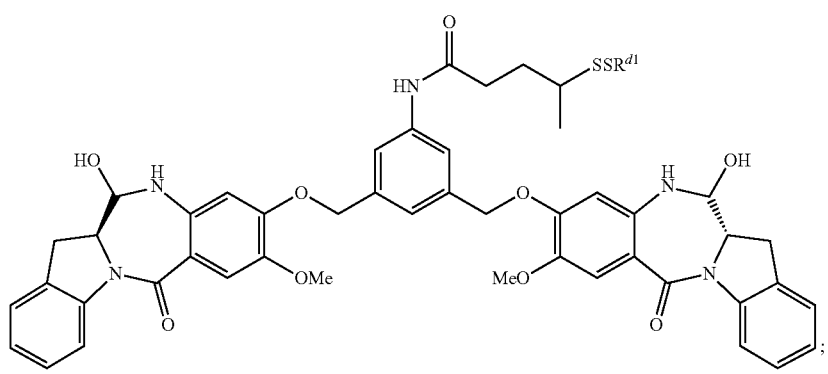
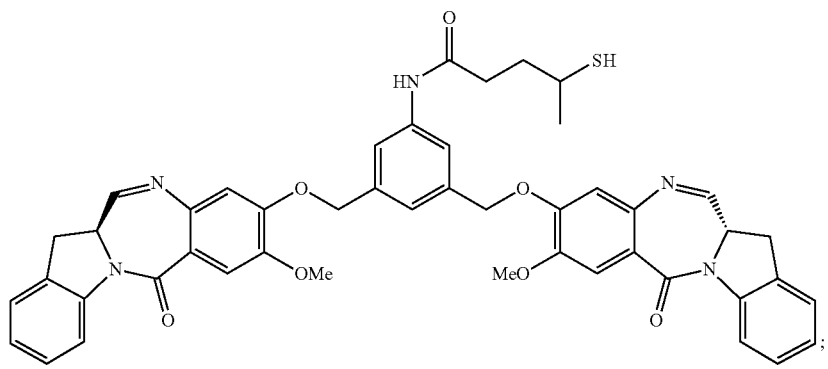

-continued
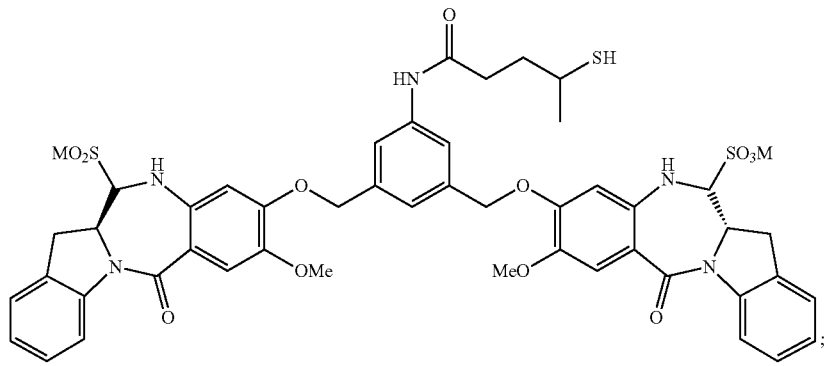
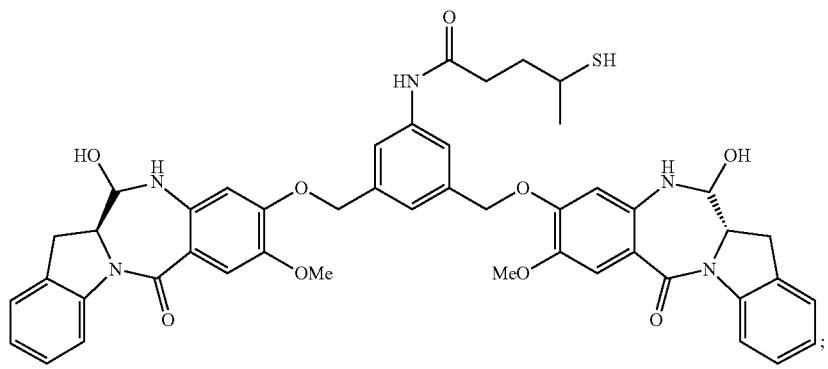
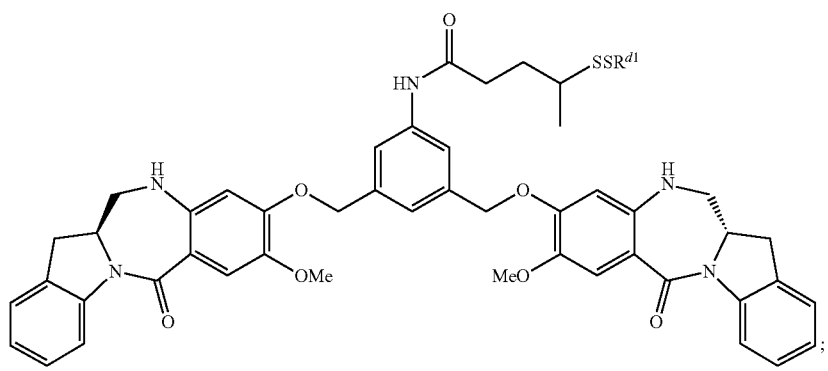
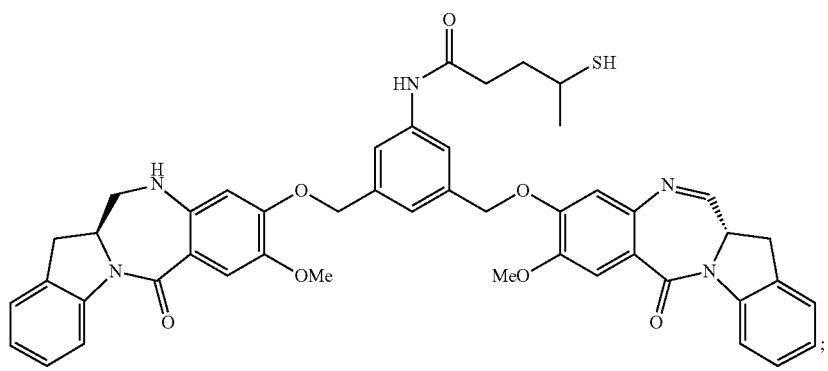

-continued
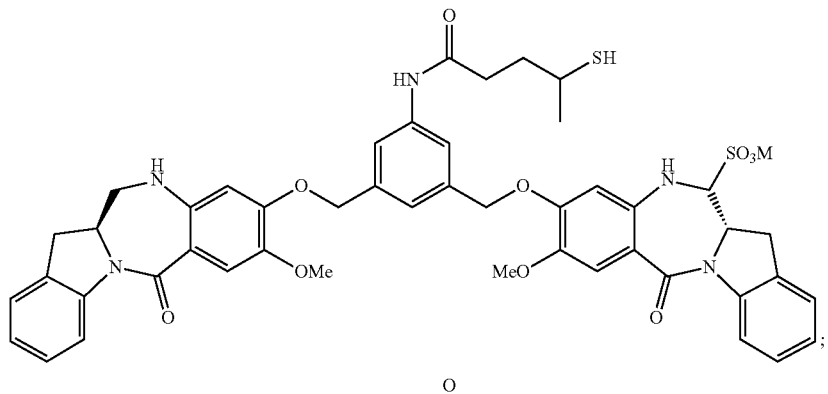
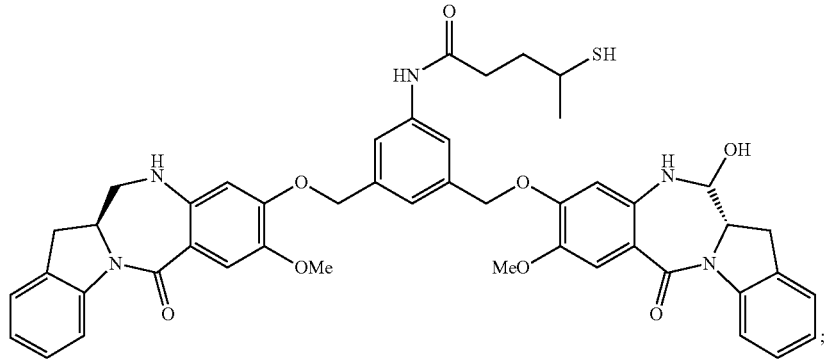
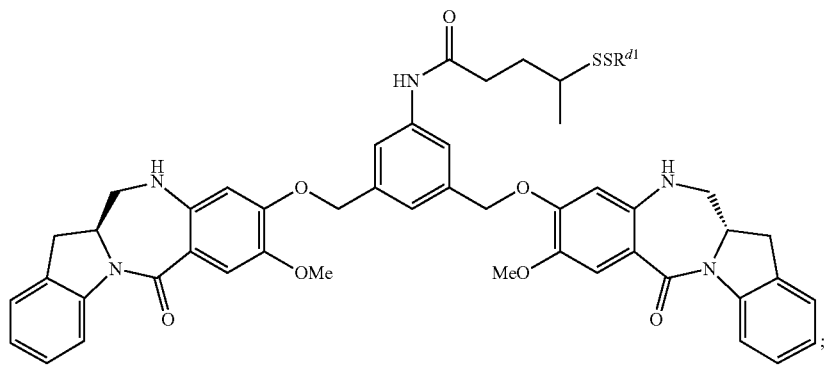
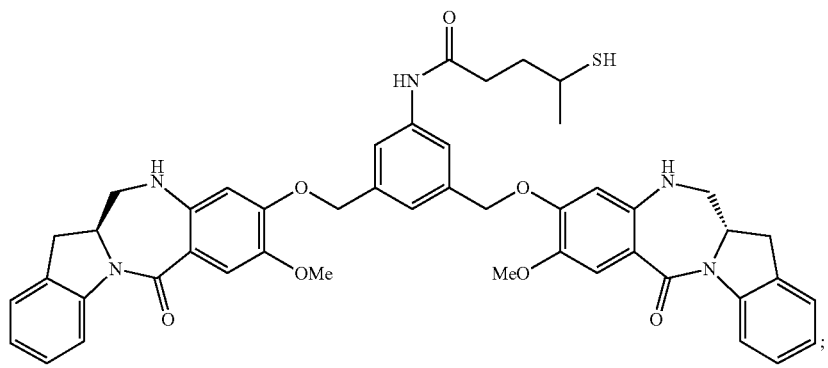

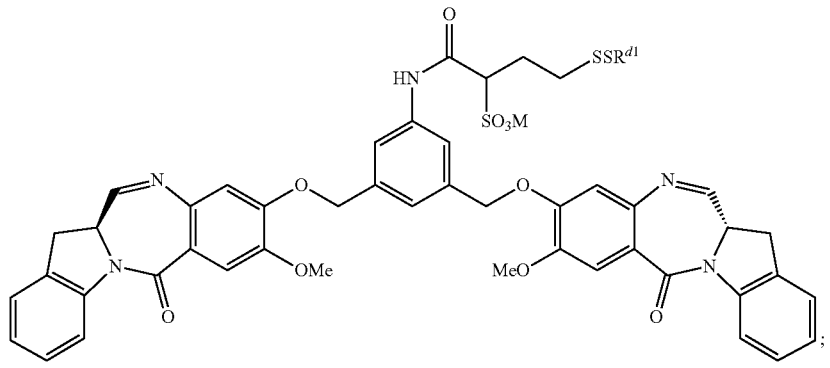
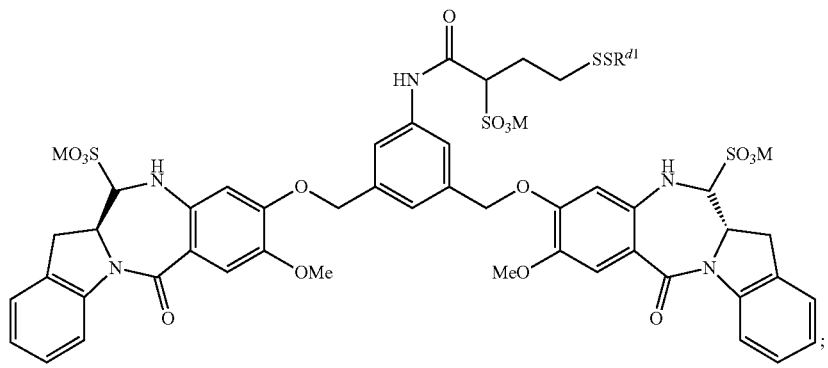
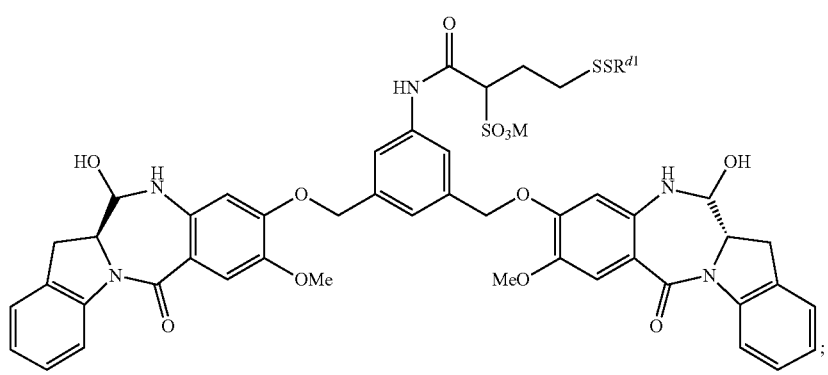
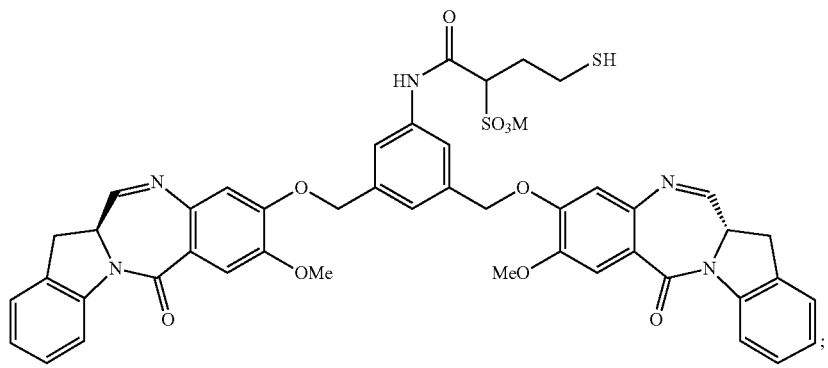

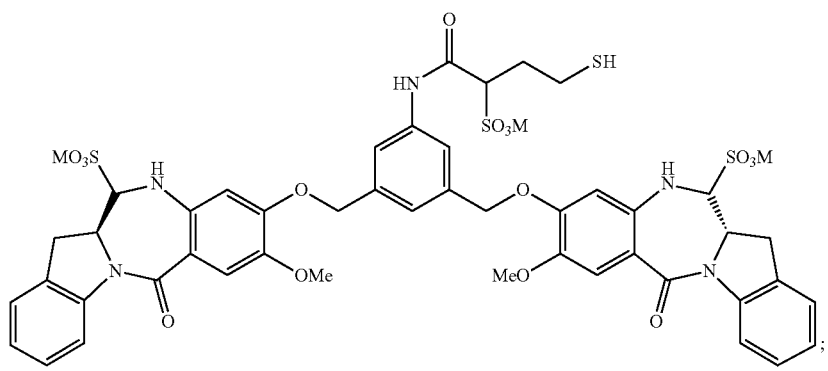
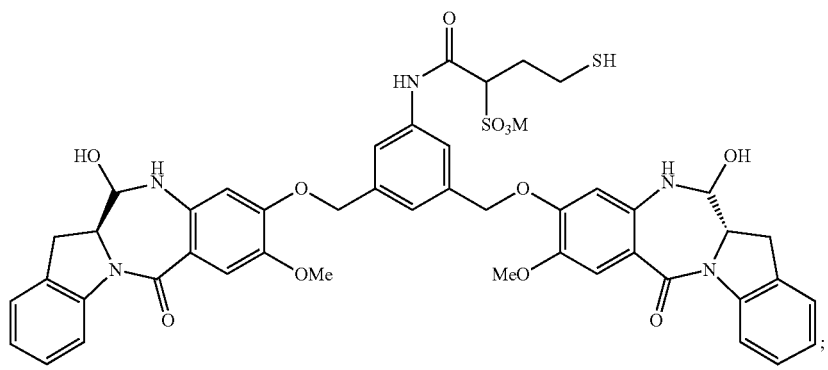
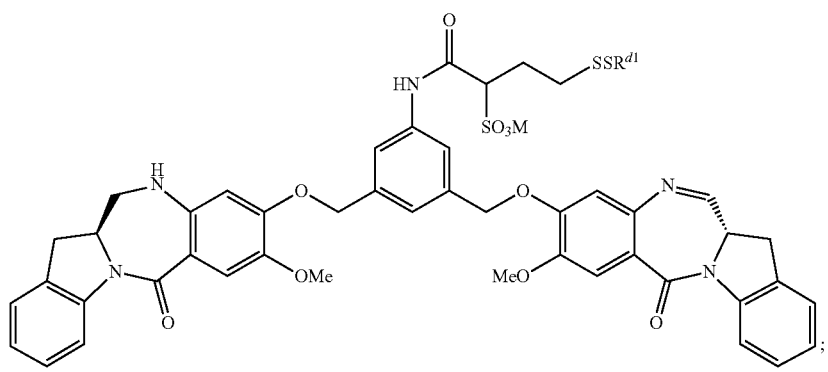
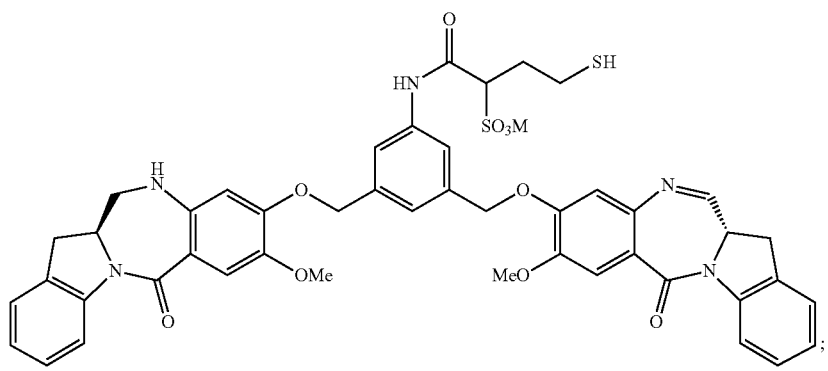

-continued
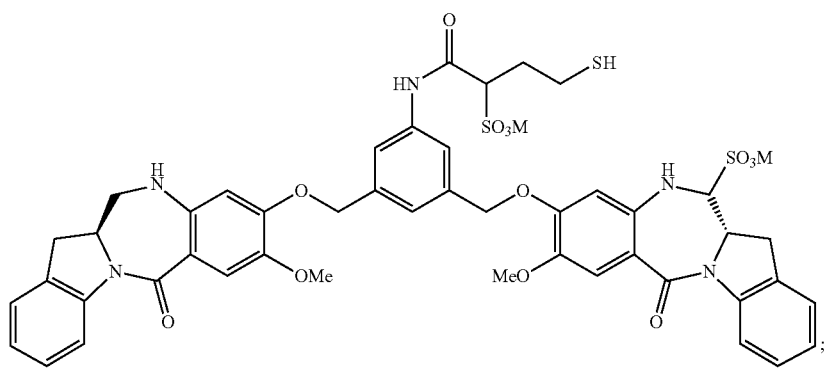
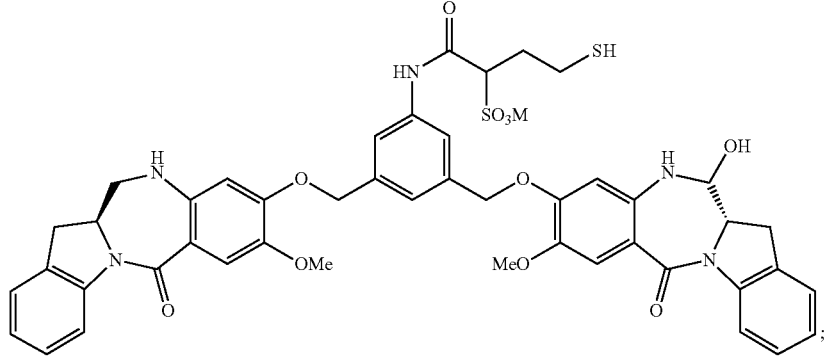
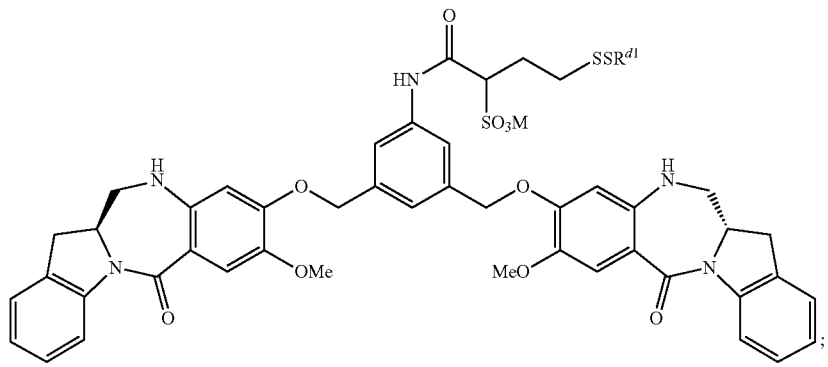
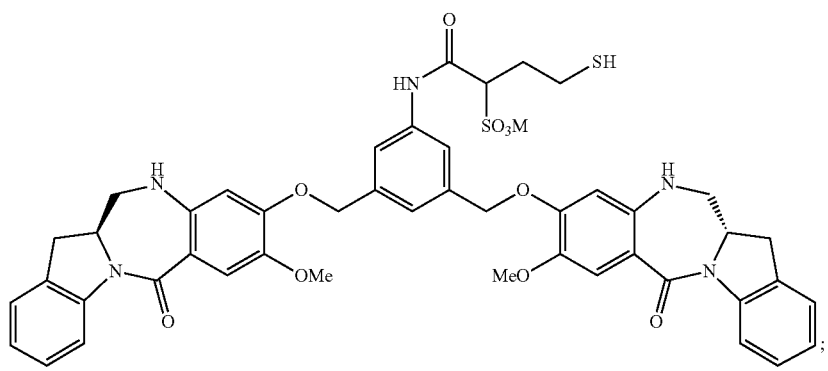

-continued
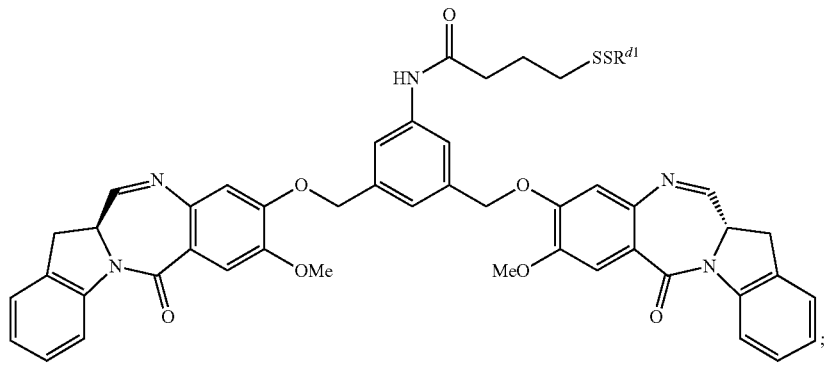
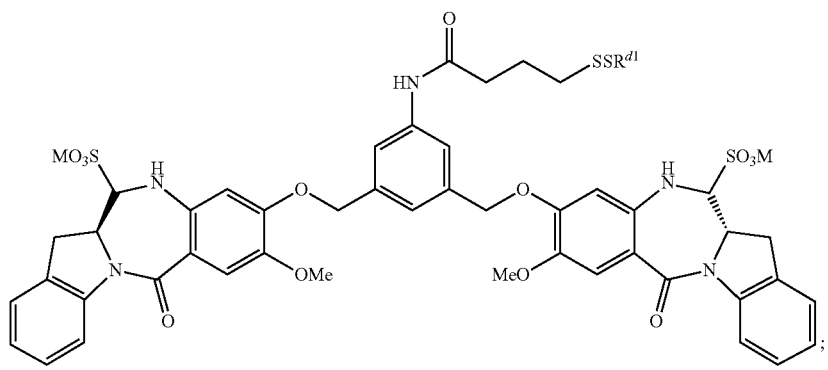
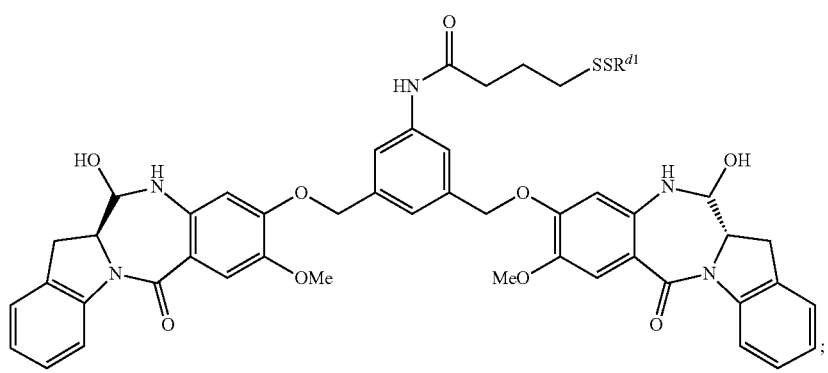
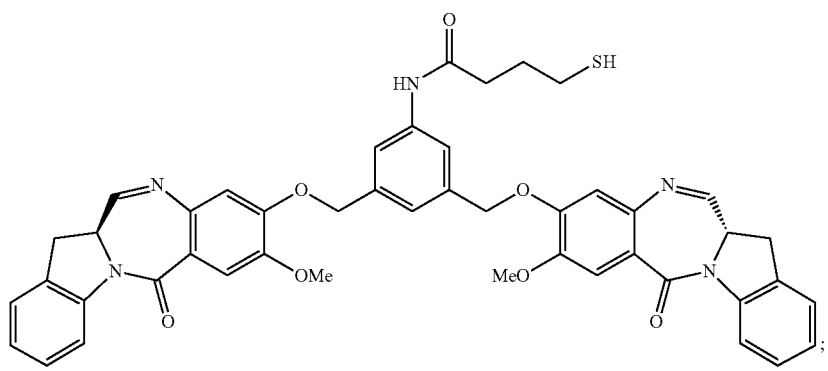

-continued
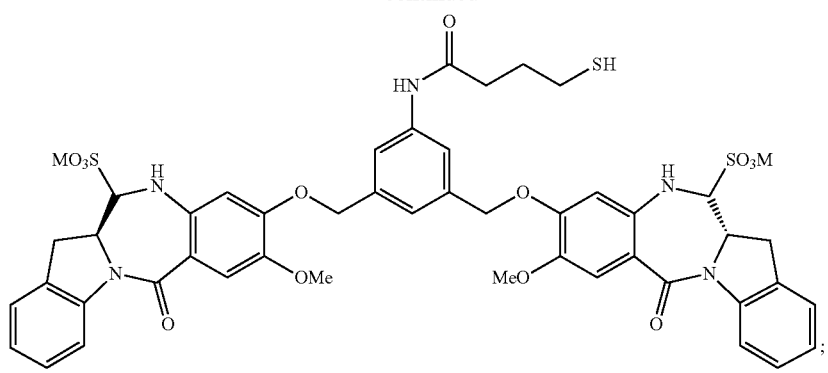
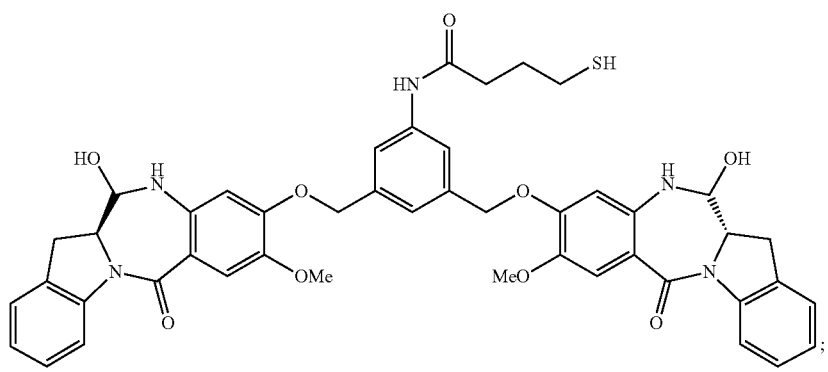
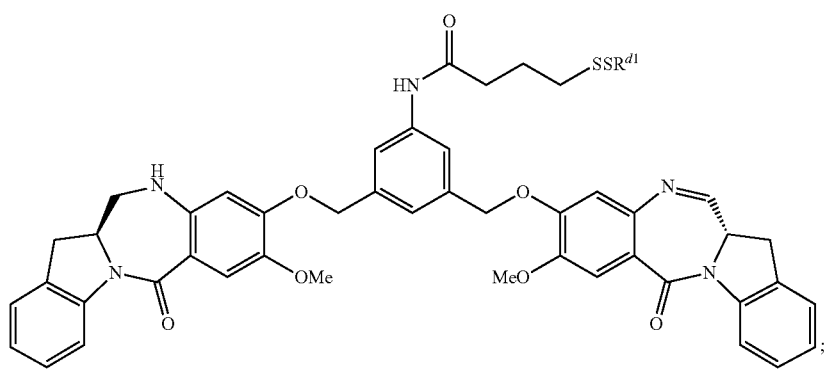
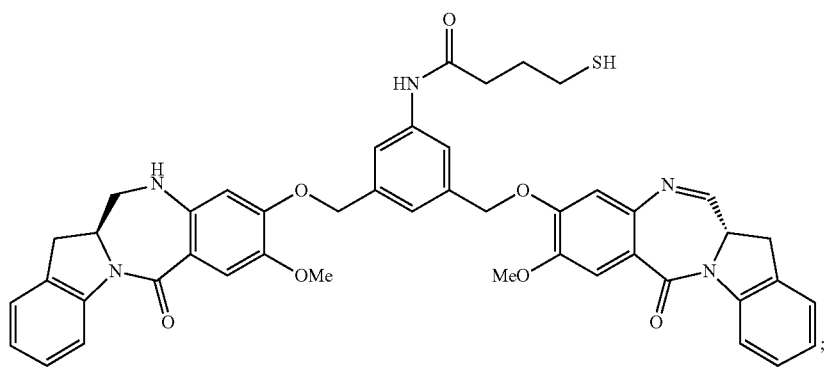

-continued
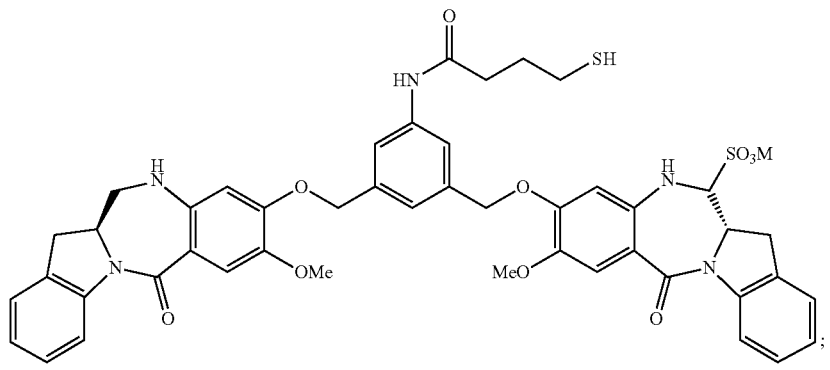
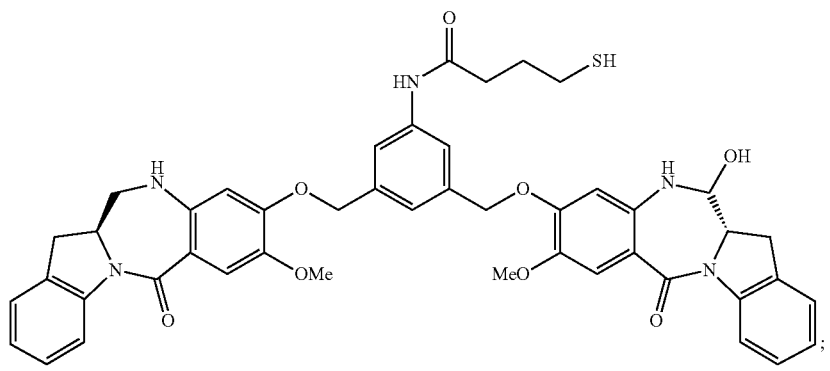
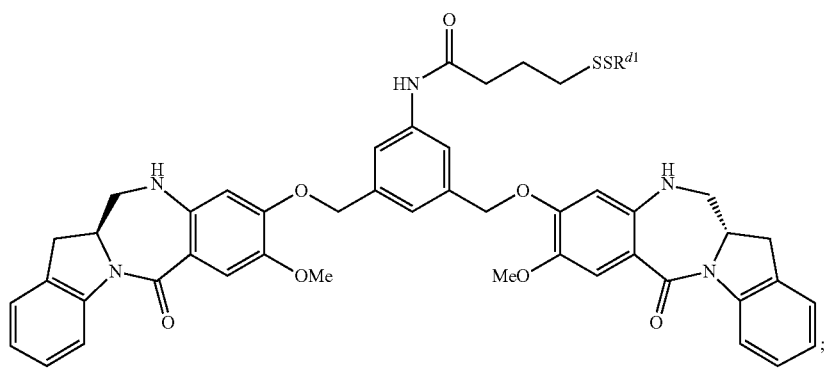
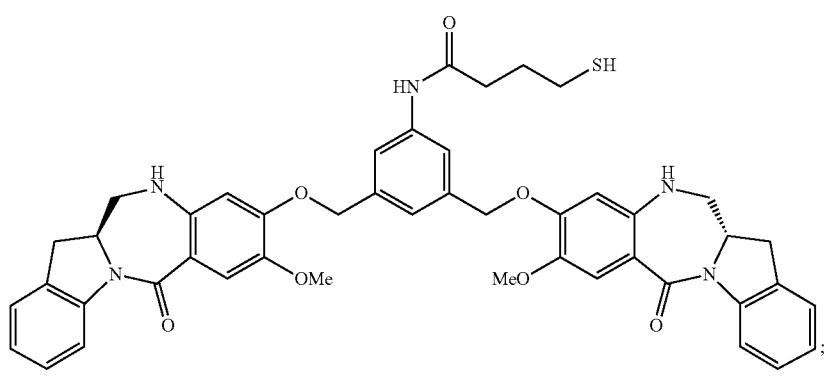

-continued
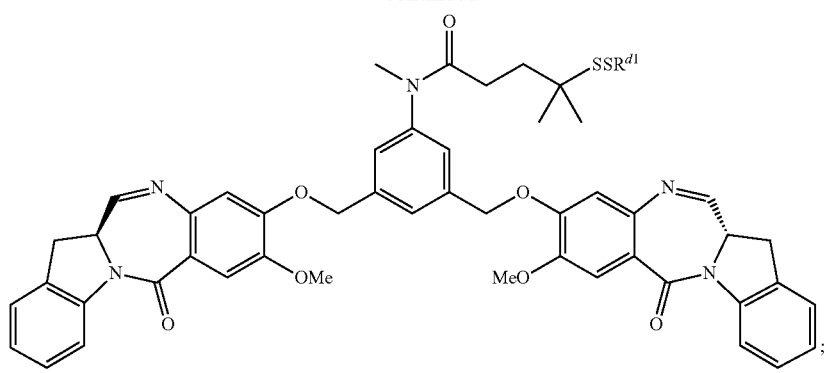
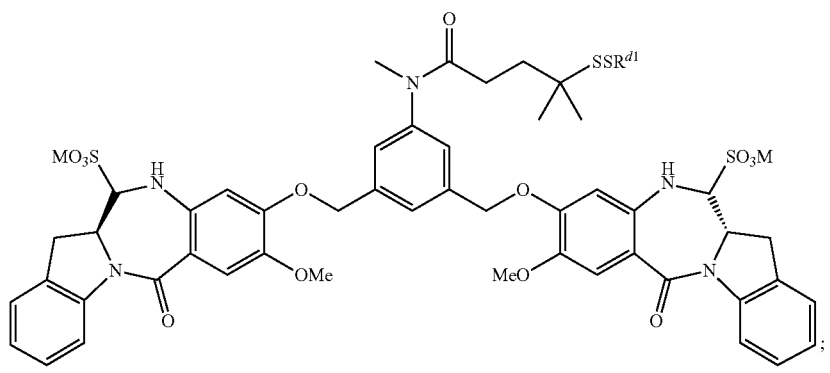
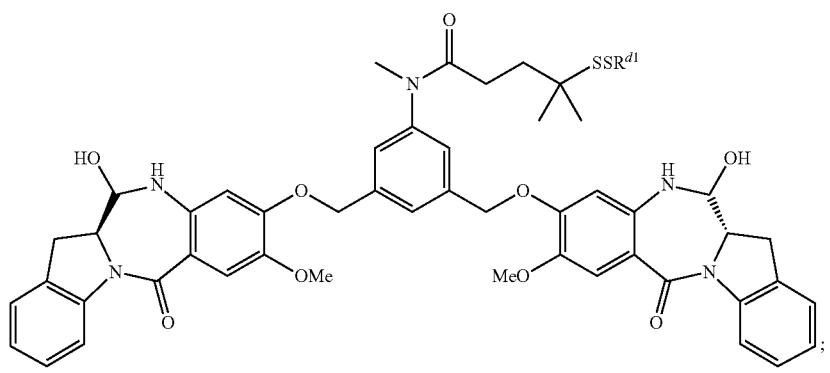
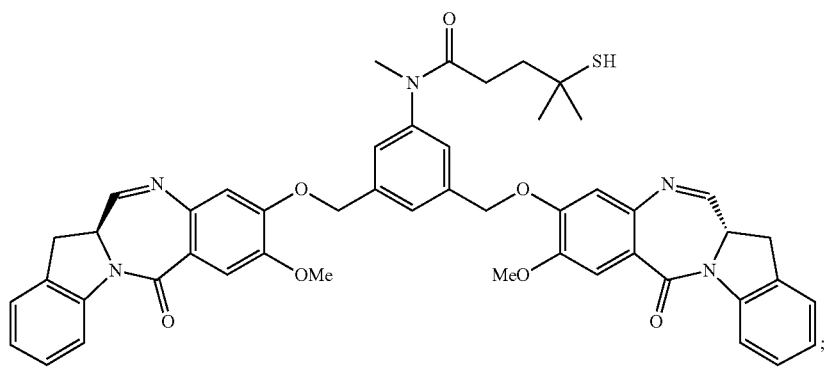

-continued
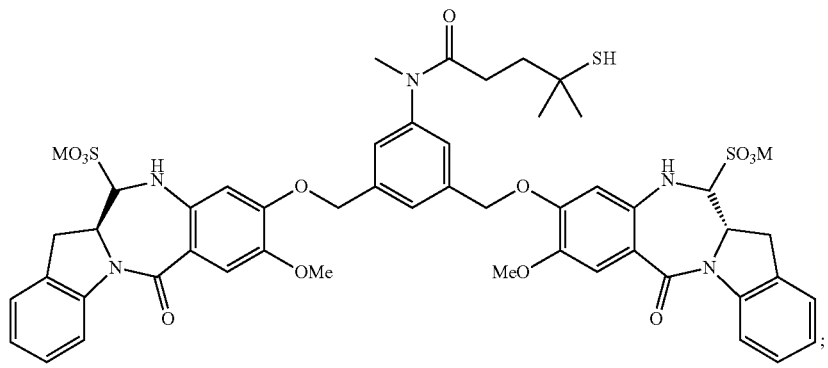
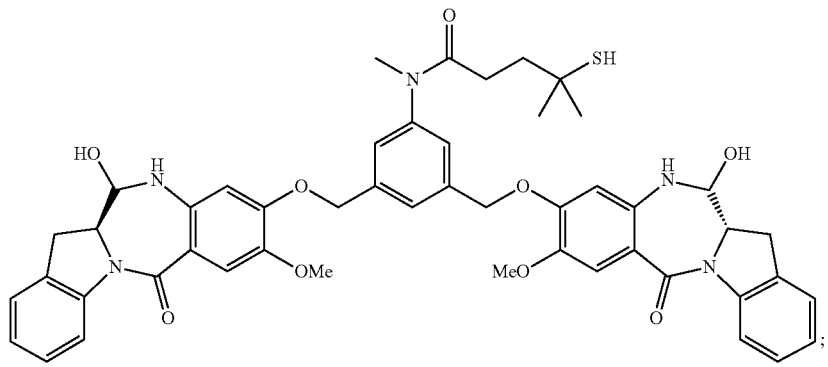
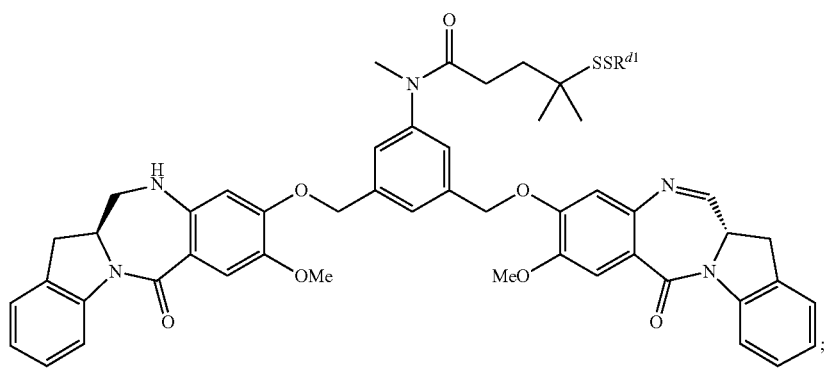
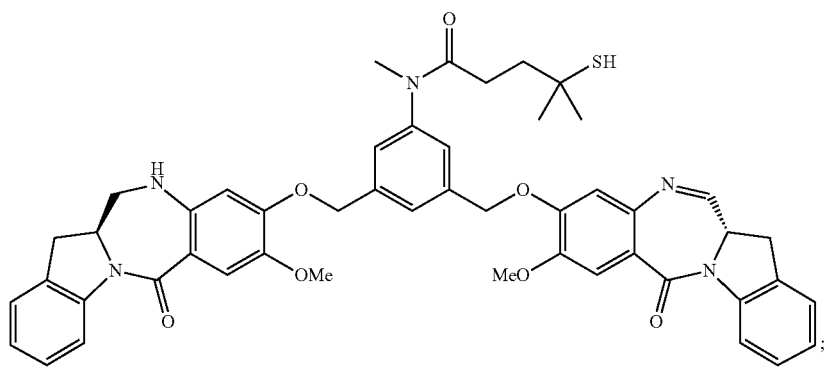

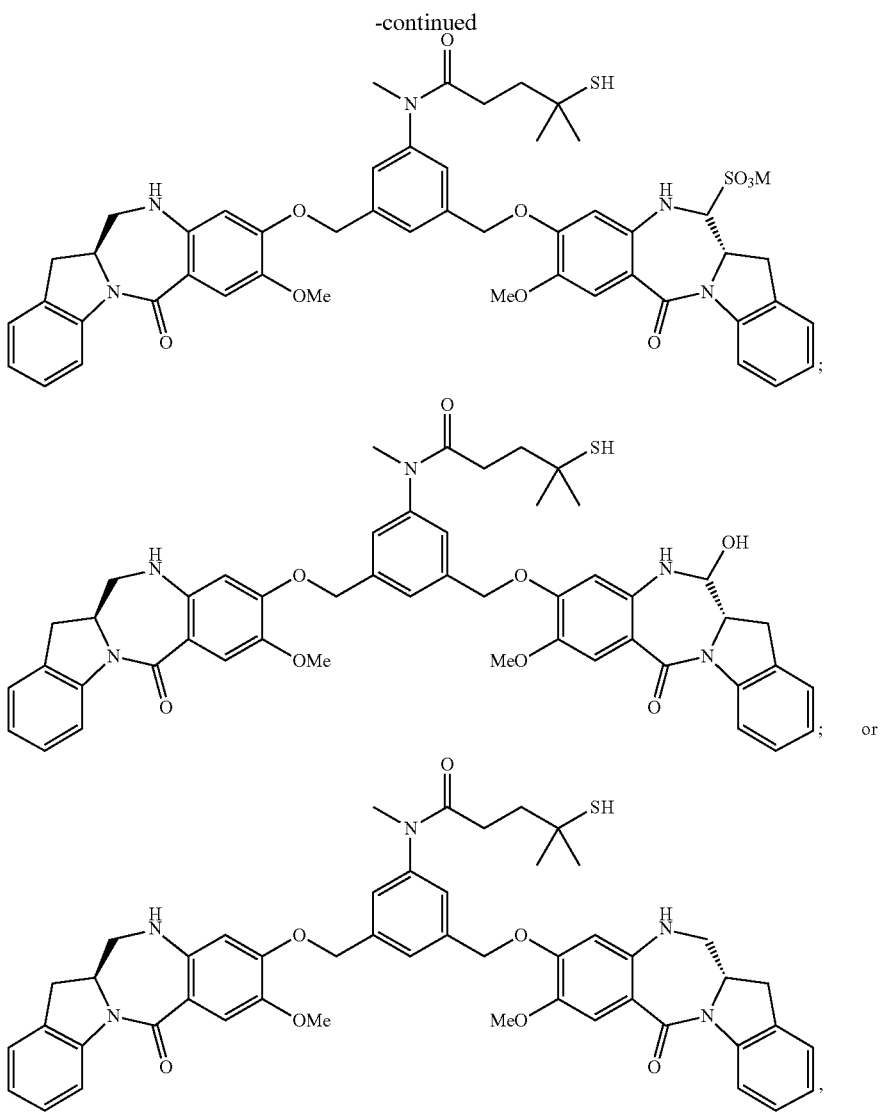

or a pharmaceutically acceptable salt thereof, wherein $R^{d1}$ is Me or Py; and M is a pharmaceutically acceptable cation. In one embodiment, M is $H^+$, $Na^+$ or $K^+$.

Drug Compounds & Drug-Linker Compounds

Certain cytotoxic compounds described above (e.g., compounds of formulas (I), (II), (III), (IV), (V) and (VI) or a pharmaceutically acceptable salt thereof, wherein $Z^s$ is —H, $SSR^d$, —SC(O)$R^{d1}$ or compounds described above having a free thiol —SH group) can further react with a bifunctional crosslinking reagent to form a drug-linker compound a reactive group bonded thereto, wherein the reactive group can form a covalent bond with a CBA.

The bifunctional crosslinking agents can be any bifunctional linker known in the art. For example, the bifunctional linkers can be used for making the drug-linker compounds are those that form disulfide bonds, thioether bonds, acid labile bonds, photolabile bonds, peptidase labile bonds and esterase labile bonds with the cytotoxic compounds (see for example, U.S. Pat. Nos. 5,208,020; 5,475,092; 6,441,163; 6,716,821; 6,913,748; 7,276,497; 7,276,499; 7,368,565; 7,388,026 and 7,414,073, all of which are incorporated herein by reference). Preferably, the bifunctional crosslinking agents are those that form disulfide bonds, thioether and peptidase labile bonds with the cytotoxic compounds. Other bifunctional crosslinking agents that can be used in the present invention include non-cleavable linkers, such as those described in U.S. publication number US 2005/0169933, or charged linkers or hydrophilic linkers and are described in US 2009/0274713, US 2010/01293140 and WO 2009/134976, each of which is expressly incorporated herein by reference. The bifunctional crosslinking agents that can be used for making the (drug-linker) compounds of the present invention also include those described in *Thermo Scientific Pierce Crosslinking Technical Handbook*, the entire teaching of which is incorporated herein by reference.

In one embodiment, the bifunctional crosslinking agent is N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB).

Synthesis of Cytotoxic Compounds

The cytotoxic compounds of the present invention can be prepared according to methods described in U.S. Pat. No. 8,765,740 and U.S. Application Publication No. 2012/0238731.

Representative processes for preparing the cytotoxic dimer compounds of the present invention are shown in Examples 1 and 2.

Cell-Binding Agents

The effectiveness of the conjugates of the invention as therapeutic agents depends on the careful selection of an appropriate cell-binding agent. Cell-binding agents can be of any kind presently known, or that become known, including peptides and non-peptides. Generally, these can be antibodies (such as polyclonal antibodies and monoclonal antibodies, especially monoclonal antibodies), lymphokines, hormones, growth factors, vitamins (such as folate etc., which can bind to a cell surface receptor thereof, e.g., a folate receptor), nutrient-transport molecules (such as transferrin), or any other cell-binding molecule or substance.

Selection of the appropriate cell-binding agent is a matter of choice that partly depends upon the particular cell population that is to be targeted, but in many (but not all) cases, human monoclonal antibodies are a good choice if an appropriate one is available. For example, the monoclonal antibody MY9 is a murine $IgG_1$ antibody that binds specifically to the CD33 Antigen (J. D. Griffin et al., *Leukemia Res.*, 8:521 (1984)), and can be used if the target cells express CD33 as in the disease of acute myelogenous leukemia (AML).

In certain embodiments, the cell-binding agent is not a protein. For example, in certain embodiments, the cell binding agent may be a vitamin that binds to a vitamin receptor, such as a cell-surface receptor. In this regard, vitamin A binds to retinol-binding protein (RBP) to form a complex, which complex in turn binds the STRA6 receptor with high affinity and increases vitamin A in-take. In another example, folic acid/folate/vitamin $B_9$ binds the cell-surface folate receptor (FR), for example, FRα, with high affinity. Folic acid or antibodies that bind to FRα can be used to target the folate receptor expressed on ovarian and other tumors. In addition, vitamin D and its analog bind to vitamin D receptor.

In other embodiments, the cell-binding agent is a protein or a polypeptide, or a compound comprising a protein or polypeptide, including antibody, non-antibody protein, or polypeptide. Preferably, the protein or polypeptides comprise one or more Lys residues with side chain —$NH_2$ group. The Lys side chain —$NH_2$ groups can be covalently linked to the bifunctional crosslinkers, which in turn are linked to the dimer compounds of the invention, thus conjugating the cell-binding agents to the dimer compounds of the invention. Each protein-based cell-binding agents can contain multiple Lys side chain —$NH_2$ groups available for linking the compounds of the invention through the bifunctional crosslinkers.

In one embodiment, GM-CSF, a ligand/growth factor which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Epidermal growth factor can be used to target squamous cancers, such as lung and head and neck. Somatostatin can be used to target neuroblastomas and other tumor types. Estrogen (or estrogen analogues) can be used to target breast cancer. Androgen (or androgen analogues) can be used to target testes.

In certain embodiments, the cell-binding agent can be a lymphokine, a hormone, a growth factor, a colony stimulating factor, or a nutrient-transport molecule.

In certain embodiments, the cell-binding agent is an antibody mimetic, such as an ankyrin repeat protein, a Centyrin, or an adnectin/monobody.

In other embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion") that specifically binds to a target cell, a chimeric antibody, a chimeric antibody fragment (or "antigen-binding portion") that specifically binds to the target cell, a domain antibody (e.g., sdAb), or a domain antibody fragment that specifically binds to the target cell.

In certain embodiments, the cell-binding agent is a humanized antibody, a humanized single chain antibody, or a humanized antibody fragment (or "antigen-binding portion"). In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody described in U.S. Provisional Application Nos. 61/307,797, 61/346,595, and 61/413,172 and U.S. application Ser. No. 13/033,723 (published as US 2012/0009181 A1). The teachings of all these applications are incorporated herein by reference in its entirety.

In certain embodiments, the cell-binding agent is a resurfaced antibody, a resurfaced single chain antibody, a resurfaced antibody fragment (or "antigen-binding portion"), or a bispecific antibody.

In certain embodiments, the cell-binding agent is a minibody, an avibody, a diabody, a tribody, a tetrabody, a nanobody, a probody, a domain antibody, or an unibody.

In other words, an exemplary cell binding agent may include an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a bispecific antibody, a domain antibody, a domain antibody fragment that specifically binds to the target cell, an interferon (e.g., α, β, γ), a lymphokine (e.g., IL-2, IL-3, IL-4, and IL-6), a hormone (e.g., insulin, thyrotropin releasing hormone (TRH), melanocyte-stimulating hormone (MSH), and a steroid hormone (e.g., androgen and estrogen)), a vitamin (e.g., folate), a growth factor (e.g., EGF, TGF-alpha, FGF, VEGF), a colony stimulating factor, a nutrient-transport molecule (e.g., transferrin; see O'Keefe et al. (1985) *J. Biol. Chem.* 260:932-937, incorporated herein by reference), a Centyrin (a protein scaffold based on a consensus sequence of fibronectin type III (FN3) repeats; see U.S. Patent Publication Nos. 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., *Cancer Res.* (2010) 70:1595-1605; Zahnd et al., *J. Biol. Chem.* (2006) 281(46):35167-35175; and Binz, H. K., Amstutz, P. & Pluckthun, A., *Nature Biotechnology* (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Avibody (including diabodies, triabodies, and tetrabodies; see U.S. Publication Nos. 2008/0152586 and 2012/0171115), dual receptor retargeting (DART) molecules (P. A. Moore et al., *Blood,* 2011; 117(17):4542-4551; Veri M C, et al., *Arthritis Rheum,* 2010 Mar. 30; 62(7):1933-43; Johnson S, et al. *J Mol Biol,* 2010 Apr. 9; 399(3):436-49), cell penetrating supercharged proteins (*Methods in Enzymol.* 502, 293-319 (2012), and other cell-binding molecules or substances.

In certain embodiments, the cell-binding agent may be a ligand that binds to a moiety on the target cell, such as a cell-surface receptor. For example, the ligand may be a growth factor or a fragment thereof that binds to a growth factor receptor; or may be a cytokine or a fragment thereof that binds to a cytokine receptor. In certain embodiments, the growth factor receptor or cytokine receptor is a cell-surface receptor.

In certain embodiments, wherein the cell-binding agent is an antibody or an antigen-binding portion thereof (including antibody derivatives), or certain antibody mimetics, the CBA may bind to a ligand on the target cell, such as a cell-surface ligand, including cell-surface receptors.

Specific exemplary antigens or ligands may include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; a receptor for hormones or growth factors; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-β5); insulin-like growth factor-I and -II; des(1-3)-IGF-I (brain IGF-I); an insulin-like growth factor binding protein; melanotransferrin; EpCAM; GD3; FLT3; PSMA; PSCA; MUC1; MUC16; STEAP; CEA; TENB2; an EphA receptor; an EphB receptor; a folate receptor; FOLR1; mesothelin; cripto; an alpha$_v$beta$_6$; integrins; VEGF; VEGFR; EGFR; transferrin receptor; IRTA1; IRTA2; IRTA3; IRTA4; IRTA5; CD proteins (e.g., CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD123, CD134, CD137, CD138, and CD152), one or more tumor-associated antigens or cell-surface receptors (see US Publication No. 20080171040 or US Publication No. 20080305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigens (e.g., a portion of the HIV envelope); a transport protein, a homing receptor; an addressin; a regulatory protein; an integrin (e.g., CD11a, CD11b, CD11c, CD18, an ICAM, VLA-4, and VCAM;) a tumor associated antigen (e.g., HER2, HER3 and HER4 receptor); endoglin; c-Met; c-kit; 1GF1R; PSGR; NGEP; PSMA; PSCA; TMEFF2; LGR5; B7H4; and fragments of any of the above-listed polypeptides.

As used herein, the term "antibody" includes immunoglobulin (Ig) molecules. In certain embodiments, the antibody is a full-length antibody that comprises four polypeptide chains, namely two heavy chains (HC) and two light chains (LC) inter-connected by disulfide bonds. Each heavy chain is comprised of a heavy chain variable region (HCVR or VH) and a heavy chain constant region (CH). The heavy chain constant region is comprised of three domains, CH1, CH2, and CH3. Each light chain is comprised of a light chain variable region (LCVR or VL) and a light chain constant region, which is comprised of one domain, CL. The VH and VL regions can be further subdivided into regions of hypervariability, termed complementarity determining regions (CDRs). Interspersed with such regions are the more conserved framework regions (FRs). Each VH and VL is composed of three CDRs and four FRs, arranged from amino-terminus to carboxy-terminus in the following order: FR1, CDR1, FR2, CDR2, FR3, CDR3, and FR4.

In certain embodiments, the antibody is IgG, IgA, IgE, IgD, or IgM. In certain embodiments, the antibody is IgG1, IgG2, IgG3, or IgG4; or IgA1 or IgA2.

In certain embodiments, the cell-binding agent is an "antigen-binding portion" of a monoclonal antibody, sharing sequences critical for antigen-binding with an antibody (such as huMy9-6 or its related antibodies described in U.S. Pat. Nos. 7,342,110 and 7,557,189, incorporated herein by reference).

As used herein, the term "antigen-binding portion" of an antibody (or sometimes interchaneably referred to as "antibody fragments"), include one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding portion" of an antibody include (without limitation): (i) a Fab fragment, a monovalent fragment consisting of the VL, VH, CL and CH1 domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a Fd fragment consisting of the VH and CH1 domains (i.e., that portion of the heavy chain which is included in the Fab); (iv) a Fv fragment consisting of the VL and VH domains of a single arm of an antibody, and the related disulfide linked Fv; (v) a dAb (domain antibody) or sdAb (single domain antibody) fragment (Ward et al., Nature 341:544-546, 1989), which consists of a VH domain; and (vi) an isolated complementarity determining region (CDR). In certain embodiments, the antigen-binding portion is a sdAb (single domain antibody).

In certain embodiments, antigen-binding portion also include certain engineered or recombinant derivatives (or "derivative antibodies") that also include one or more fragments of an antibody that retain the ability to specifically bind to an antigen, in addition to elements or sequences that may not be found in naturally existing antibodies.

For example, although the two domains of the Fv fragment, VL and VH, are coded for by separate genes, they can be joined, using standard recombinant methods, by a synthetic linker that enables them to be made as a single protein chain in which the VL and VH regions pair to form monovalent molecules (known as single chain Fv (scFv); see, e.g., Bird et al. Science 242:423-426, 1988: and Huston et al., Proc. Natl. Acad. Sci. USA 85:5879-5883, 1988).

In all embodiments described herein, the N-terminum of an scFv may be a VH domain (i.e., N-VH-VL-C), or a VL domain (i.e., N-VL-VH-C).

Divalent (or bivalent) single-chain variable fragments (di-scFvs, bi-scFvs) can be engineered by linking two scFvs. This produces a single peptide chain with two VH and two VL regions, yielding a tandem scFvs (tascFv). More tandem repeats, such as tri-scFv, may be similarly produced by linking three or more scFv in a head-to-tail fashion.

In certain embodiments, scFvs may be linked through linker peptides that are too short (about five amino acids) for the two variable regions to fold together, forcing scFvs to dimerize, and form diabodies (see, e.g., Holliger et al., Proc. Natl. Acad. Sci. USA 90:6444-6448, 1993; Poljak et al., Structure 2:1121-1123, 1994). Diabodies may be bi-specific or monospecific. Diabodies have been shown to have dissociation constants up to 40-fold lower than corresponding scFvs, i.e., having a much higher affinity to the target.

Still shorter linkers (one or two amino acids) lead to the formation of trimers, or so-called triabodies or tribodies. Tetrabodies have also been produced similarly They exhibit an even higher affinity to their targets than diabodies. Diabodies, triabodies, and tetrabodies are sometimes collectively called "AVIBODY™" cell binding agents (or "AVIBODY" in short). That is, AVIBODY having two, three, or four Target Binding Regions (TBRs) are commonly known as Dia-, Tria- and Tetra-bodies. See, for example, U.S. Publication Nos. 2008/0152586 and 2012/0171115 for details, the entire teachings of which are incorporated herein by reference.

All of these formats can be composed from variable fragments with specificity for two or more different antigens, in which case they are types of bi- or multi-specific antibodies. For example, certain bispecific tandem di-scFvs, are known as bi-specific T-cell engagers (BiTEs).

In certain embodiments, each scFv in the tandem scFv or diabody/triabody/tetrabody may have the same or different binding specificity, and each may independently have an N-terminal VH or N-terminal VL.

Single chain Fv (scFv) can also be fused to an Fc moiety, such as the human IgG Fc moiety to obtain IgG-like properties, but nevertheless they are still encoded by a single gene. As transient production of such scFv-Fc proteins in mammalians can easily achieve milligram amounts, this derivative antibody format is particularly suitable for many research applications.

Fcabs are antibody fragments engineered from the Fc constant region of an antibody. Fcabs can be expressed as soluble proteins, or they can be engineered back into a full-length antibody, such as IgG, to create mAb2. A mAb2 is a full-length antibody with an Fcab in place of the normal Fc region. With these additional binding sites, mAb2 bispecific monoclonal antibodies can bind two different targets at the same time.

In certain embodiments, the engineered antibody derivatives have reduced size of the antigen-binding Ig-derived recombinant proteins ("miniaturized" full-size mAbs), produced by removing domains deemed non-essential for function. One of the best examples is SMIPs.

A Small modular immunopharmaceutical, or SMIP, is an artificial protein largely built from parts of antibodies (immunoglobulins), and is intended for use as a pharmaceutical drug. SMIPs have similar biological half-life as antibodies, but are smaller than antibodies and hence may have better tissue penetration properties. SMIPs are single-chain proteins that comprise one binding region, one hinge region as a connector, and one effector domain. The binding region comprises a modified single-chain variable fragment (scFv), and the rest of the protein can be constructed from the Fc (such as CH2, and CH3 as the effector domain) and the hinge region of an antibody, such as IgG1. Genetically modified cells produce SMIPs as antibody-like dimers that are about 30% smaller than real antibodies.

Another example of such engineered miniaturized antibody is "unibody," in which the hinge region has been removed from IgG4 molecules. IgG4 molecules are unstable and can exchange light-heavy chain heterodimers with one another. Deletion of the hinge region prevents heavy chain-heavy chain pairing entirely, leaving highly specific monovalent light/heavy heterodimers, while retaining the Fc region to ensure stability and half-life in vivo.

A single-domain antibody (sdAb, including but not limited to those called nanobody by Ablynx) is an antibody fragment consisting of a single monomeric variable antibody domain Like a whole antibody, it is able to bind selectively to a specific antigen, but is much smaller due to its molecular weight of only 12-15 kDa. In certain embodiments, the single-domain antibody is engineered from heavy-chain antibodies (hcIgG). The first such sdAb was engineered based on an hcIgG found in camelids, called $V_HH$ fragments. In certain embodiments, the single-domain antibody is engineered from IgNAR ("immunoglobulin new antigen receptor," see below) using a $V_{NAR}$ fragment. Cartilaginous fishes (such as shark) have such heavy-chain IgNAR antibodies. In certain embodiments, the sdAb is engineered by splitting the dimeric variable domains from common immunoglobulin G (IgG), such as those from humans or mice, into monomers. In certain embodiments, a nanobody is derived from a heavy chain variable domain. In certain embodiments, a nanobody is derived from light chain variable domain. In certain embodiments, the sdAb is obtained by screening libraries of single domain heavy chain sequences (e.g., human single domain HCs) for binders to a target antigen.

The single variable new antigen receptor domain antibody fragments ($V_{NAR}$s, or $V_{NAR}$ domains) are derived from cartilaginous fish (e.g., shark) immunoglobulin new antigen receptor antibodies (IgNARs). Being one of the smallest known immunoglobulin-based protein scaffolds, such single domain proteins demonstrate favorable size and cryptic epitope recognition properties. Mature IgNAR antibodies consist of homodimers of one variable new antigen receptor ($V_{NAR}$) domain and five constant new antigen receptor ($C_{NAR}$) domains. This molecule is highly stable, and possesses efficient binding characteristics. Its inherent stability can likely be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

A minibody is an engineered antibody fragment comprising an scFv linked to a CH domain, such as the CH3γ1 (CH3 domain of IgG1) or CH4ε (CH4 domain of IgE). For example, an scFv specific for carcinoembryonic antigen (CEA) has been linked to the CH3γ1 to create a minibody, which has previously been demonstrated to possess excellent tumor targeting coupled with rapid clearance in vivo (Hu et al., *Cancer Res.* 56:3055-3061, 1996). The scFv may have a N-terminal VH or VL. The linkage may be a short peptide (e.g., two amino acid linker, such as ValGlu) that resultes in a non-covalent, hingeless minibody. Alternatively, the linkage may be an IgG1 hinge and a GlySer linker peptide that produces a covalent, hinge-minibody.

Natural antibodies are mono-specific, but bivalent, in that they express two identical antigen-binding domains. In contrast, in certain embodiments, certain engineered antibody derivatives are bi- or multi-specific molecules possess two or more different antigen-binding domains, each with different target specificity. Bispecific antibodies can be generated by fusing two antibody-producing cells, each with distinct specificity. These "quadromas" produced multiple molecular species, as the two distinct light chains and two distinct heavy chains were free to recombine in the quadromas in multiple configurations. Since then, bispecific Fabs, scFvs and full-size mAbs have been generated using a variety of technologies (see above).

The dual variable domain immunoglobulin (DVD-Ig) protein is a type of dual-specific IgG that simultaneously target two antigens/epitopes (DiGiammarino et al., *Methods Mol Biol.* 899:145-56, 2012). The molecule contains an Fc region and constant regions in a configuration similar to a conventional IgG. However, the DVD-Ig protein is unique in that each arm of the molecule contains two variable domains (VDs). The VDs within an arm are linked in tandem and can possess different binding specificities.

Trispecific antibody derivative molecules can also been generated by, for example, expressing bispecific antibodies with two distinct Fabs and an Fc. One exmaple is a mouse IgG2a anti-Ep-CAM, rat IgG2b anti-CD3 quadroma, called BiUII, which is thought to permit the co-localization of tumor cells expressing Ep-CAM, T-cells expressing CD3, and macrophages expressing FCγRI, thus potentiating the costimulatory and anti-tumor functions of the immune cells.

Probodies are fully recombinant, masked monoclonal antibodies that remain inert in healthy tissue, but are activated specifically in the disease microenvironment (e.g., through protease cleavage by a protease enriched or specific in a disease microenvironment). See Desnoyers et al., *Sci Transl Med* 5:207ra144, 2013. Similar masking techniques can be used for any of the antibodies or antigen-binding portions thereof described herein.

An intrabody is an antibody that has been modified for intracellular localization, for working within the cell to bind to an intracellular antigen. The intrabody may remain in the cytoplasm, or may have a nuclear localization signal, or may have a KDEL sequence for ER targeting. The intrabody may be a single-chain antibody (scFv), nodified immunoglobulin VL domains with hyperstability, selected antibody resistant to the more reducing intracellular environment, or expressed as a fusion protein with maltose binding protein or other stable intracellular proteins. Such optimizations have improved the stability and structure of intrabodies, and may have general applicability to any of the antibodies or antigen-binding portions thereof described herein.

The antigen-binding portions or derivative antibodies of the invention may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody from which they are derived/engineered. Sequences within these regions may contain conservative amino acid substitutions, including substitutions within the CDR regions. In certain embodiments, there is no more than 1, 2, 3, 4, or 5 conservative substitutions. In an alternative, the antigen-binding portions or derivative antibodies have a light chain region and/or a heavy chain region that is at least about 90%, 95%, 99% or 100% identical to an antibody from which they are derived/engineered. These antigen-binding portions or derivative antibodies may have substantially the same binding specificity and/or affinity to the target antigen compared to the antibody. In certain embodiments, the $K_d$ and/or $k_{off}$ values of the antigen-binding portions or derivative antibodies are within 10-fold (either higher or lower), 5-fold (either higher or lower), 3-fold (either higher or lower), or 2-fold (either higher or lower) of an antibody described herein.

In certain embodiments, the antigen-binding portions or derivative antibodies may be derived/engineered from fully human antibodies, humanized antibodies, or chimeric antibodies, and may be produced according to any art-recognized methods.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies.

Cell-binding agent can also be peptides derived from phage display (see, for example, Wang et al., *Proc. Natl. Acad. Sci. USA* (2011) 108(17), 6909-6914) or peptide library techniques (see, for example, Dane et al., *Mol. Cancer. Ther.* (2009) 8(5):1312-1318).

In certain embodiments, the CBA of the invention also includes an antibody mimetic, such as a DARPin, an affibody, an affilin, an affitin, an anticalin, an avimer, a Fynomer, a Kunitz domain peptide, a monobody, or a nanofitin.

As used herein, the terms "DARPin" and "(designed) ankyrin repeat protein" are used interchangeably to refer to certain genetically engineered antibody mimetic proteins typically exhibiting preferential (sometimes specific) target binding. The target may be protein, carbohydrate, or other chemical entities, and the binding affinity can be quite high. The DARPins may be derived from natural ankyrin repeat-containing proteins, and preferably consist of at least three, usually four or five ankyrin repeat motifs (typically about 33 residues in each ankyrin repeat motif) of these proteins. In certain embodiments, a DARPin contains about four- or five-repeats, and may have a molecular mass of about 14 or 18 kDa, respectively. Libraries of DARPins with randomized potential target interaction residues with diversities of over $10^{12}$ variants can be generated at the DNA level, for use in selecting DARPins that bind desired targets (e.g., acting as receptor agonists or antagonists, inverse agonists, enzyme inhibitors, or simple target protein binders) with picomolar affinity and specificity, using a variety of technologies such as ribosome display or signal recognition particle (SRP) phage display. See, for example, U.S. Patent Publication Nos. 2004/0132028, 2009/0082274, 2011/0118146, and 2011/0224100, WO 02/20565 and WO 06/083275 for DARPin preparation (the entire teachings of which are incorporated herein by reference), and also see C. Zahnd et al. (2010) Cancer Res., 70:1595-1605; Zahnd et al. (2006) J. Biol. Chem., 281(46):35167-35175; and Binz, H. K., Amstutz, P. & Pluckthun, A. (2005) Nature Biotechnology, 23:1257-1268 (all incorporated herein by reference). Also see U.S. Patent Publication No. 2007/0238667; U.S. Pat. No. 7,101,675; WO 2007/147213; and WO 2007/062466 (the entire teachings of which are incorporated herein by reference), for the related ankyrin-like repeats protein or synthetic peptide.

Affibody molecules are small proteins engineered to bind to a large number of target proteins or peptides with high affinity, thus imitating monoclonal antibodies. An Affibody consists of three alpha helices with 58 amino acids and has a molar mass of about 6 kDa. They have been shown to withstand high temperatures (90° C.) or acidic and alkaline conditions (pH 2.5 or pH 11), and binders with an affinity of down to sub-nanomolar range have been obtained from naïve library selections, and binders with picomolar affinity have been obtained following affinity maturation. In certain embodiments, affibodies are conjugated to weak electrophiles for binding to targets covalently.

Monobodies (also known as Adnectins), are genetically engineered antibody mimetic proteins capable of binding to antigens. In certain embodiments, monobodies consist of 94 amino acids and have a molecular mass of about 10 kDa. They are based on the structure of human fibronectin, more specifically on its tenth extracellular type III domain, which has a structure similar to antibody variable domains, with seven beta sheets forming a barrel and three exposed loops on each side corresponding to the three complementarity determining regions. Monobodies with specificity for different proteins can be tailored by modifying the loops BC (between the second and third beta sheets) and FG (between the sixth and seventh sheets).

A tribody is a self-assembly antibody mimetic designed based on the C-terminal coiled-coil region of mouse and human cartilage matrix protein (CMP), which self-assembles into a parallel trimeric complex. It is a highly stable trimeric targeting ligand created by fusing a specific target-binding moiety with the trimerization domain derived from CMP. The resulting fusion proteins can efficiently self-assemble into a well-defined parallel homotrimer with high stability. Surface plasmon resonance (SPR) analysis of the trimeric targeting ligands demonstrated significantly enhanced target-binding strength compared with the corresponding monomers. Cellular-binding studies confirmed that such tribodies have superior binding strength toward their respective receptors.

A Centyrin is another antibody mimetic that can be obtained using a library built upon the framework of a consensus FN3 domain sequence (Diem et al., Protein Eng Des Sel., 2014). This library employs diversified positions within the C-strand, CD-loop, F-strand and FG-loop of the FN3 domain, and high-affinity Centyrin variants can be selected against specific targets.

In one embodiment, the cell-binding agent is an anti-folate receptor antibody. More specifically, the anti-folate receptor antibody is a humanized antibody or antigen binding fragment thereof that specifically binds a human folate receptor 1 (also known as folate receptor alpha (FR-α)). The terms "human folate receptor 1," "FOLR1," or "folate receptor alpha (FR-α)", as used herein, refers to any native human FOLR1, unless otherwise indicated. Thus, all of these terms can refer to either a protein or nucleic acid sequence as indicated herein. The term "FOLR1" encompasses "full-length," unprocessed FOLR1 as well as any form of FOLR1 that results from processing within the cell. The FOLR1 antibody comprises: (a) a heavy chain CDR1 comprising GYFMN (SEQ ID NO: 1); a heavy chain CDR2 comprising RIHPYDGDTFYNQXaa$_1$FXaa$_2$Xaa$_3$ (SEQ ID NO: 2); and a heavy chain CDR3 comprising YDGSRAMDY (SEQ ID NO: 3); and (b) a light chain CDR1 comprising KASQSVSFAGTSLMH (SEQ ID NO: 4); a light chain CDR2 comprising RASNLEA (SEQ ID NO: 5); and a light chain CDR3 comprising QQSREYPYT (SEQ ID NO: 6); wherein Xaa$_i$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 7).

In another embodiment, the anti-folate receptor antibody is a humanized antibody or antigen binding fragment thereof that specifically binds the human folate receptor 1 comprising the heavy chain having the amino acid sequence of (SEQ ID NO: 8)
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK.

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or PTA-10774.

In another embodiment, the anti-folate receptor antibody is a humanized antibody or antigen binding fragment thereof that specifically binds the human folate receptor 1 comprising the light chain having the amino acid sequence of (SEQ ID NO: 9)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKRTVAAPSVFIFPPSDEQLKSGTASVVCLLNNFYPREAKV

-continued

```
QWKVDNALQSGNSQESVTEQDSKDSTYSLSSTLTLSKADYEKHKVYACEV

THQGLSSPVTKSFNRGEC;
or (SEQ ID NO: 10)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

In another embodiment the anti-folate receptor antibody is a humanized antibody or antigen binding fragment thereof that specifically binds the human folate receptor 1 comprising the heavy chain having the amino acid sequence of SEQ ID NO: 8, and the light chain having the amino acid sequence of SEQ ID NO: 9 or SEQ ID NO: 10. Preferably, the antibody comprises the heavy chain having the amino acid sequence of SEQ ID NO: 8 and the light chain having the amino acid sequence of SEQ ID NO: 10 (hu FOLR1).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1, and comprising a heavy chain variable domain at least about 90%, 95%, 99% or 100% identical to

```
                                              (SEQ ID NO: 11)
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSS,
``` and a light chain variable domain at least about 90%, 95%, 99% or 100% identical to

```
                                              (SEQ ID NO: 12)
DIVLTQSPLSLAVSLGQPAIISCKASQSVSFAGTSLMHWYHQKPGQQPRL
```

```
LIYRASNLEAGVPDRFSGSGSKTDFTLNISPVEAEDAATYYCQQSREYPY

TFGGGTKLEIKR;
or (SEQ ID NO: 13)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKR.
```

In another embodiment, the anti-folated receptor antibody is huMov19 or M9346A (see, for example, U.S. Pat. No. 8,709,432, U.S. Pat. No. 8,557,966, and WO2011106528, all incorporated herein by reference).

In another embodiment, the cell-binding agent is an anti-EGFR antibody or an antibody fragment thereof. In one embodiment, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66 or EGFR-8. More specifically, the anti-EGFR antibody is huML66.

In yet another embodiment, the anti-EGFR antibody comprising the heavy chain having the amino acid sequence of SEQ ID NO: 14, and the light chain having the amino acid sequence of SEQ ID NO: 15. As used herein, double underlined sequences represent the variable regions (i.e., heavy chain variable region or HCVR, and light chain variable region or LCVR) of the heavy or light chain sequences, while bold sequences represent the CDR regions (i.e., from N-terminal to C-terminal, CDR1, CDR2, and CDR3, respectively, of the heavy chain or light chain sequences).

| Antibody | Full-Length Heavy/Light Chain Amino Acid Sequence |
|---|---|
| huML66HC | <u>QVQLQESGPGLVKPSETLSLTCTVSGLSLASNSVSWIRQPPGKGLEWMGVIWNH GGTDYNPSIKSRLSISRDTSKSQVFLKMNSLTAADTAMYFCVRKGGIYFDYWGQ GVLVTVSS</u>ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQ KSLSLSPG (SEQ ID NO: 14) |
| huML66LC | <u>DTVLTQSPSLAVSPGERATISCRASESVSTLMHWYQQKPGQQPKLLIYLASHRES GVPARFSGSGSGTDFTLTIDPMEAEDTATYYCQQSRNDPWTFGQGTKLELKRTV</u>AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 15) |

In yet another embodiment, the anti-EGFR antibody comprises the heavy chain CDR1-CDR3 of SEQ ID NO: 14, and/or the light chain CDR1-CDR3 of SEQ ID NO: 15, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 14, and/or a light chain variable region (LCVR) sequence at least about 90%, 95%, 97%, 99%, or 100% identical to SEQ ID NO: 15, and preferably specifically binds EGFR.

In another embodiment, the anti-EGFR antibody are antibodies described in 8,790,649 and WO 2012/058588, herein incorporated by reference. In one embodiment, the anti-EGFR antibody is huEGFR-7R antiboby.

In one embodiment, the anti-EGFR antibody comprises an immunoglobulin heavy chain region having the amino acid sequence of (SEQ ID NO: 16)
QVQLVQSGAEVAKPGASVKLSCKASGYTFTSYWMQWVKQRPGQGLECIGT

IYPGDGDTTYTQKFQGKATLTADKSSSTAYMQLSSLRSEDSAVYYCARYD

APGYAMDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG and an immunoglobulin light chain region having the amino acid sequence of (SEQ ID NO: 17)
DIQMTQSPSSLSASVGDRVTITCRASQDINNYLAWYQHKPGKGPKLLIHY

TSTLHPGIPSRFSGSGSGRDYSFSISSLEPEDIATYYCLQYDNLLYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC, or an immunoglobulin light chain region having the amino acid sequence of (SEQ ID NO: 18)
DIQMTQSPSSLSASVGDRVTITCKASQDINNYLAWYQHKPGKGPKLLIHY

TSTLHPGIPSRFSGSGSGRDYSFSISSLEPEDIATYYCLQYDNLLYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In another embodiment, the anti-EGFR antibody comprises an immunoglobulin heavy chain region having the amino acid sequence set forth in SEQ ID NO:16 and an immunoglobulin light chain region having the amino acid sequence set forth in SEQ ID NO:17.

In another embodiment, the anti-EGFR antibody comprises an immunoglobulin heavy chain region having the amino acid sequence set forth in SEQ ID NO:16 and an immunoglobulin light chain region having the amino acid sequence set forth in SEQ ID NO:18.

In yet another embodiment, the anti-EGFR antibody comprises the heavy chain CDR1-CDR3 of SEQ ID NO: 16, and/or the light chain CDR1-CDR3 of SEQ ID NO: 17 or 18, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 16, and/or a light chain variable region (LCVR) sequence at least about 90%, 95%, 97%, 99%, or 100% identical to SEQ ID NO: 17 or 18, and preferably specifically binds EGFR.

In another embodiment, the cell-binding agent is an anti-CD19 antibody, such as those described in U.S. Pat. No. 8,435,528 and WO2004/103272, herein incorporated by reference. In one embodiment, the anti-CD19 antibody comprises an immunoglobulin heavy chain region having the amino acid sequence of (SEQ ID NO: 19)
QVQLVQPGAEVVKPGASVKLSCKTSGYTFTSNWMHWVKQAPGQGLEWIGE

IDPSDSYTNYNQNFQGKAKLTVDKSTSTAYMEVSSLRSDDTAVYYCARGS

NPYYYAMDYWGQGTSVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK and an immunoglobulin light chain region having the amino acid sequence of (SEQ ID NO: 20)
EIVLTQSPAIMSASPGERVTMTCSASSGVNYMHWYQQKPGTSPRRWIYDT

SKLASGVPARFSGSGSGTDYSLTISSMEPEDAATYYCCHQRGSYTFGGGTK

LEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSS

PVTKSFNRGEC.

In another embodiment, the anti-CD19 antibody is huB4 antibody.

In yet another embodiment, the anti-CD19 antibody comprises the heavy chain CDR1-CDR3 of SEQ ID NO: 19, and/or the light chain CDR1-CDR3 of SEQ ID NO: 20, and preferably specifically binds CD19.

In yet another embodiment, the anti-CD19 antibody comprises a heavy chain variable region (HCVR) sequence at least about 90%, 95%, 97%, 99%, or 100% identical to SEQ ID NO: 19, and/or a light chain variable region (LCVR) sequence at least about 90%, 95%, 97%, 99%, or 100% identical to SEQ ID NO: 20, and preferably specifically binds CD19.

In yet another embodiment, the cell-binding agent is an anti-Muc1 antibody, such as those described in U.S. Pat. No. 7,834,155, WO 2005/009369 and WO 2007/024222, herein incorporated by reference. In one embodiment, the anti-Muc1 antibody comprises an immunoglobulin heavy chain region having the amino acid sequence of (SEQ ID NO: 21)
QAQLVQSGAEVVKPGASVKMSCKASGYTFTSYNMHWVKQTPGQGLEWIG

YIYPGNGATNYNQKFQGKATLTADTSSSTAYMQISSLTSEDSAVYFCARG

DSVPFAYWGQGTLVTVSAASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK and an immunoglobulin light chain region having the amino acid sequence of (SEQ ID NO: 22)
EIVLTQSPATMSASPGERVTITCSAHSSVSFMHWFQQKPGTSPKLWIYST

SSLASGVPARFGGSGSGTSYSLTISSMEAEDAATYYCQQRSSFPLTFGAG

TKLELK<u>R</u>TVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC.

In another embodiment, the anti-Muc1 antibody is huDS6 antibody.

In yet another embodiment, the anti-Muc1 antibody comprises the heavy chain CDR1-CDR3 of SEQ ID NO: 21, and/or the light chain CDR1-CDR3 of SEQ ID NO: 22, and preferably specifically binds Muc1.

In yet another embodiment, the anti-Muc1 antibody comprises a heavy chain variable region (HCVR) sequence at least about 90%, 95%, 97%, 99%, or 100% identical to SEQ ID NO: 21, and/or a light chain variable region (LCVR) sequence at least about 90%, 95%, 97%, 99%, or 100% identical to SEQ ID NO: 22, and preferably specifically binds Muc1.

In another embodiment, the cell-binding agent is an anti-CD33 antibody or fragment thereof, such as the antibodies or fragments thereof described in U.S. Pat. Nos. 7,557,189, 7,342,110, 8,119,787 and 8,337,855 and WO2004/043344, herein incorporated by reference. In another embodiment, the anti-CD33 antibody is huMy9-6 antibody.

In one embodiment, the anti-CD33 antibody comprises an immunoglobulin heavy chain region having the amino acid sequence of (SEQ ID NO: 23)
QVQLQQPGAEVVKPGASVKMSCKASGYTFTSYYIHWIKQTPGQGLEWVGV

IYPGNDDISYNQKFQGKATLTADKSSTTAYMQLSSLTSEDSAVYYCAREV

RLRYFDVWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG, and an immunoglobulin light chain region having the amino acid sequence of (SEQ ID NO: 24)
EIVLTQSPGSLAVSPGERVTMSCKSSQSVFFSSSQKNYLAWYQQIPGQSP

RLLIYWASTRESGVPDRFTGSGSGTDFTLTISSVQPEDLAIYYCHQYLSS

RTFGQGTKLEIK<u>R</u>TVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

In yet another embodiment, the anti-CD33 antibody comprises the heavy chain CDR1-CDR3 of SEQ ID NO: 23, and/or the light chain CDR1-CDR3 of SEQ ID NO: 24, and preferably specifically binds CD33.

In yet another embodiment, the anti-CD33 antibody comprises a heavy chain variable region (HCVR) sequence at least about 90%, 95%, 97%, 99%, or 100% identical to SEQ ID NO: 23, and/or a light chain variable region (LCVR) sequence at least about 90%, 95%, 97%, 99%, or 100% identical to SEQ ID NO: 24, and preferably specifically binds CD33.

In another embodiment, the cell-binding agent is an anti-CD37 antibody or an antibody fragment thereof, such as those described in U.S. Pat. No. 8,765,917 and WO 2011/112978, herein incorporated by reference. In one embodiment, the anti-CD37 antibody is huCD37-3 antibody.

In one embodiment, the anti-CD37 antibody comprises an immunoglobulin light chain region having the amino acid sequence of (SEQ ID NO: 25)
DIQMTQSPSSLSVSVGERVTITCRASENIRSNLAWYQQKPGKSPKLLVNV

ATNLADGVPSRFSGSGSGTDYSLKINSLQPEDFGTYYCQHYWGTTWTFGQ

GTKLEIK<u>R</u>TVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC and an immunoglobulin heavy chain region having the amino acid sequence of (SEQ ID NO: 26)
QVQVQESGPGLVAPSQTLSITCTVSGFSLTTSGVSWVRQPPGKGLEWLGV

IWGDGSTNYHPSLKSRLSIKKDHSKSQVFLKLNSLTAADTATYYCAKGGY

SLAHWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG, or an immunoglobulin heavy chain region having the amino acid sequence of (SEQ ID NO: 27)
QVQVQESGPGLVAPSQTLSITCTVSGFSLTTSGVSWVRQPPGKGLEWLGV

IWGDGSTNYHSSLKSRLSIKKDHSKSQVFLKLNSLTAADTATYYCAKGGY

SLAHWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

In another embodiment, the anti-CD37 antibody comprises an immunoglobulin light chain region having the amino acid sequence set forth in SEQ ID NO:25 and an immunoglobulin heavy chain region having the amino acid sequence set forth in SEQ ID NO:26.

In yet another embodiment, the anti-CD37 antibody comprises an immunoglobulin light chain region having the amino acid sequence set forth in SEQ ID NO:25 and an immunoglobulin heavy chain region having the amino acid sequence set forth in SEQ ID NO:27.

In yet another embodiment, the anti-CD37 antibody comprises the heavy chain CDR1-CDR3 of SEQ ID NO: 26 or 27, and/or the light chain CDR1-CDR3 of SEQ ID NO: 25, and preferably specifically binds CD37.

In yet another embodiment, the anti-CD37 antibody comprises a heavy chain variable region (HCVR) sequence at least about 90%, 95%, 97%, 99%, or 100% identical to SEQ ID NO: 26 or 27, and/or a light chain variable region (LCVR) sequence at least about 90%, 95%, 97%, 99%, or 100% identical to SEQ ID NO: 25, and preferably specifically binds CD37.

In yet another embodiment, the anti-CD37 antibody comprises an immunoglobulin light chain region having the amino acid sequence of (SEQ ID NO: 28)
EIVLTQSPATMSASPGERVTMTCSATSSVTYMHWYQQKPGQSPKRWIYDT

SNLPYGVPARFSGSGSGTSYSLTISSMEAEDAATYYCQQWSDNPPTFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC and an immunoglobulin heavy chain region having the amino acid sequence of (SEQ ID NO: 29)
QVQLQESGPGLLKPSQSLSLTCTVSGYSITSGFAWHWIRQHPGNKLEWMG

YILYSGSTVYSPSLKSRISITRDTSKNHFFLQLNSVTAADTATYYCARGY

YGYGAWFAYWGQGTLVTVSAASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG.

In yet another embodiment, the anti-CD37 antibody comprises the heavy chain CDR1-CDR3 of SEQ ID NO: 29, and/or the light chain CDR1-CDR3 of SEQ ID NO: 28, and preferably specifically binds CD37.

In yet another embodiment, the anti-CD37 antibody comprises a heavy chain variable region (HCVR) sequence at least about 90%, 95%, 97%, 99%, or 100% identical to SEQ ID NO: 29, and/or a light chain variable region (LCVR) sequence at least about 90%, 95%, 97%, 99%, or 100% identical to SEQ ID NO: 28, and preferrably specifically binds CD37.

In yet another embodiment, the anti-CD37 antibody is huCD37-50 antibody.

Cell-Binding Agent-Drug Conjugates

The present invention also provides cell-binding agent-drug conjugates comprising a cell-binding agent linked to one or more cytotoxic compounds of the present invention via a variety of linkers, including, but not limited to, disulfide linkers, thioether linkers, amide bonded linkers, peptidase-labile linkers, acid-labile linkers, esterase-labile linkers.

Representative conjugates of the invention are antibody/cytotoxic compound, antibody fragment/cytotoxic compound, epidermal growth factor (EGF)/cytotoxic compound, melanocyte stimulating hormone (MSH)/cytotoxic compound, thyroid stimulating hormone (TSH)/cytotoxic compound, somatostatin/cytotoxic compound, folate/cytotoxic compound, estrogen/cytotoxic compound, estrogen analogue/cytotoxic compound, androgen/cytotoxic compound, and androgen analogue/cytotoxic compound.

In a preferred embodiment, the present invention provides conjugates comprising an indolinobenzodiazepine dimer compound (e.g., compounds of formulas (I)-(VI) or pharmaceutically acceptable salt thereof) and the cell-binding agent linked through a covalent bond. The linker can be cleaved at the site of the tumor/unwanted proliferating cells to deliver the cytotoxic agent to its target in a number of ways. The linker can be cleaved, for example, by low pH (hydrazone), reductive environment (disulfide), proteolysis (amide/peptide link), or through an enzymatic reaction (esterase/glycosidase).

Thus in a second embodiment, the invention provides a conjugate comprising: a cytotoxic compound and a cell binding agent (CBA), wherein the cytotoxic compound is covalently linked to the CBA, and wherein the cytotoxic compound is represented by any one of the following formulas (I'), (II'), (III'), (IV'), (V') or (VI') or a pharmaceutically acceptable salt thereof described above.

In certain embodiments, the conjugate comprises a CBA and a cytotoxic compound represented by the following formula:

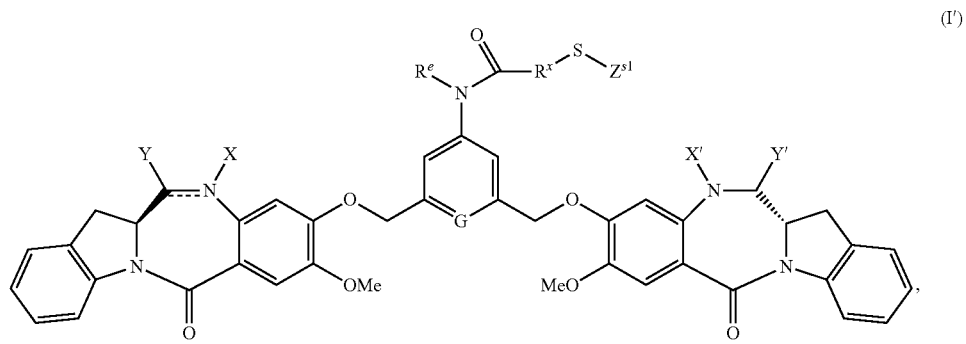

or a pharmaceutically acceptable salt thereof.

In a 1st specific embodiment, $Z^{s1}$ is represented by either one of the following formulas:

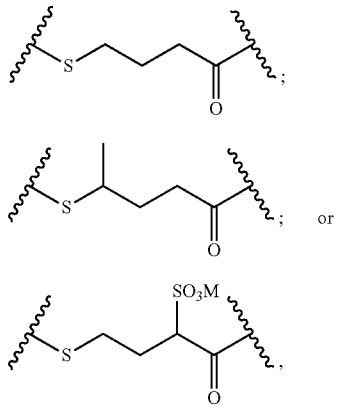

and the remaining variables are as described above in the second embodiment.

In a 2nd specific embodiment, $R^e$ is H or Me; the remaining variables are as described above in the second embodiment or the 1st specific embodiment.

In a 3rd specific embodiment, $R^x$ can be $-(CH_2)_p-(CR^fR^g)-$, wherein $R^f$ and $R^g$ are each independently selected from H or a linear or branched alkyl having 1 to 4 carbon atoms; p is 0, 1, 2 or 3; and the remaining variables are as described above in the second embodiment or the 1st or 2nd specific embodiment.

In one embodiment, $R^f$ and $R^g$ are the same or different, and are selected from —H and -Me; and the remaining variables are as described above in the 3rd specific embodiment. More specifically, $R^f$ and $R^g$ are both -Me; and p is 2.

In a 4th specific embodiment, $R^x$ is a linear or branched alkylene having 1 to 4 carbon atoms substituted with a charged substituent or an ionizable group Q; and the remaining variables are as described above in the second embodiment or the 1st or 2nd specific embodiment.

In one embodiment, Q is i) $-SO_3H$, $-Z'-SO_3H$, $-OPO_3H_2$, $-Z'-OPO_3H_2$, $-PO_3H_2$, $-Z'-PO_3H_2$, $-CO_2H$, $-Z'-CO_2H$, $-NR_{11}R_{12}$, or $-Z'-NR_{11}R_{12}$, or a pharmaceutically acceptable salt thereof; or, ii) $-N^+R_{14}R_{15}R_{16}X^-$ or $-Z'-N^+R_{14}R_{15}R_{16}X^-$; Z' is an optionally substituted alkylene, an optionally substituted cycloalkylene or an optionally substituted phenylene; $R_{14}$ to $R_{16}$ are each independently an optionally substituted alkyl; and $X^-$ is a pharmaceutically acceptable anion; and the remaining variables are as described above in the 4th specific embodiment. More specifically, Q is $SO_3H$ or a pharmaceutically acceptable salt thereof.

In a 5th specific embodiment, the double line == between N and C represents a double bond; and the remaining variables are as described above in the second embodiment or the 1st, 2nd, 3rd or 4th specific embodiment.

In a 6th specific embodiment, the double line == between N and C represents a single bond; X is —H or an amine protecting group; Y is selected from —H, $-SO_3M$, —OH, —OMe, —OEt or —NHOH; and the remaining variables are as described above in the second embodiment or the 1st, 2nd, 3rd or 4th specific embodiment.

In one embodiment, Y is —H, $-SO_3M$ or —OH; and the remaining variables are as described in the 6th specific embodiment. More specifically, M is $H^+$, $Na^+$ or $K^+$.

In a 7th embodiment, X' is —H, —OH or -Me; and the remaining variables are as described above in the second embodiment or the 1st, 2nd, 3rd, 4th, 5th or 6th specific embodiment. More specifically, X' is —H.

In a 8th specific embodiment, Y' is —H or oxo; and the remaining variables are as described above in the second embodiment or the 1st, 2nd, 3rd, 4th, 5th, 6th or 7th specific embodiment. More specifically, Y' is —H.

In a 9th specific embodiment, for formulas (I'), (II'), (III'), (IV'), (V'), and (VI'), the double line == between N and C represents a single bond or a double bond, provided that when it is a double bond X is absent and Y is —H, and when it is a single bond, X is —H; Y is —OH or $-SO_3M$;

M is —H or a pharmaceutically acceptable cation;

X' and Y' are both —H;

G is C; and the remaining variables are as described above in the second embodiment or the 1st, 2nd, 3rd or 4th specific embodiment.

In one embodiment, Y is $-SO_3M$ and M is $H^+$, $Na^+$ or $K^+$; and the remaining variables are as described above the 9th specific embodiment.

In a 10th specific embodiment, the conjugates of the invention include the following:

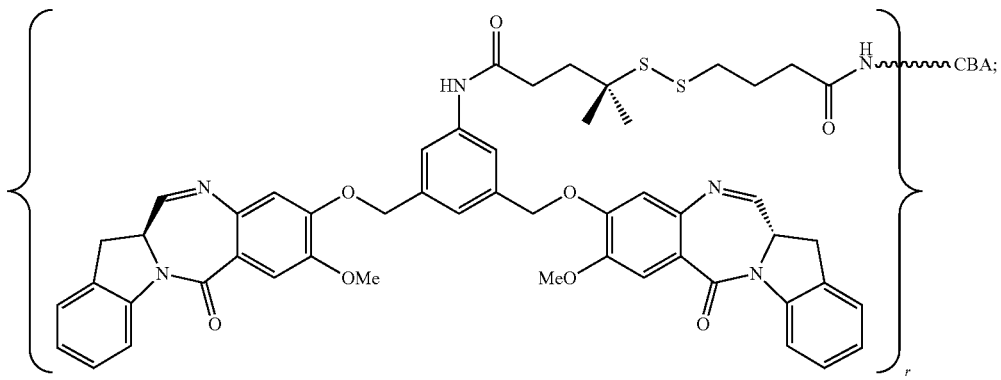

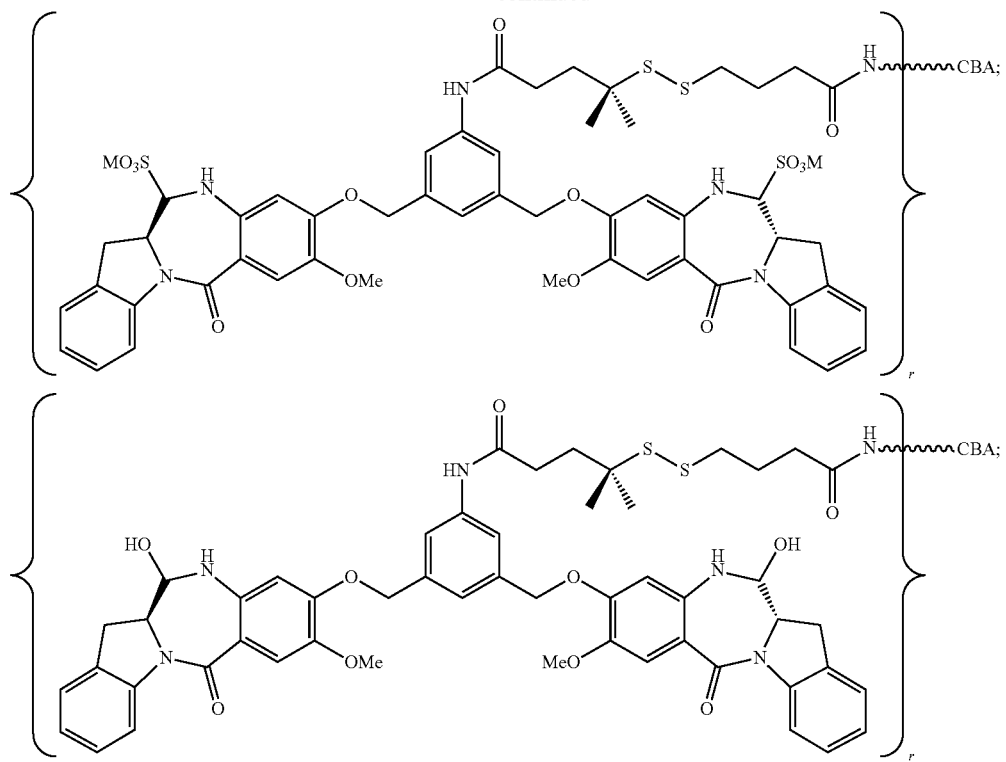
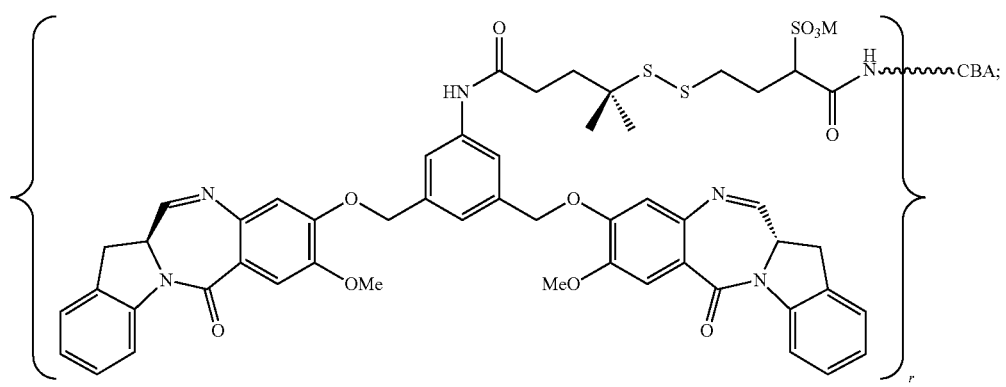
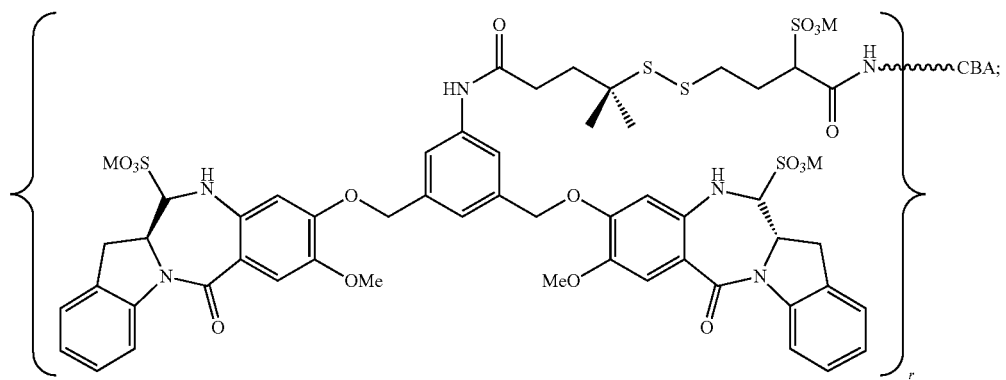

-continued
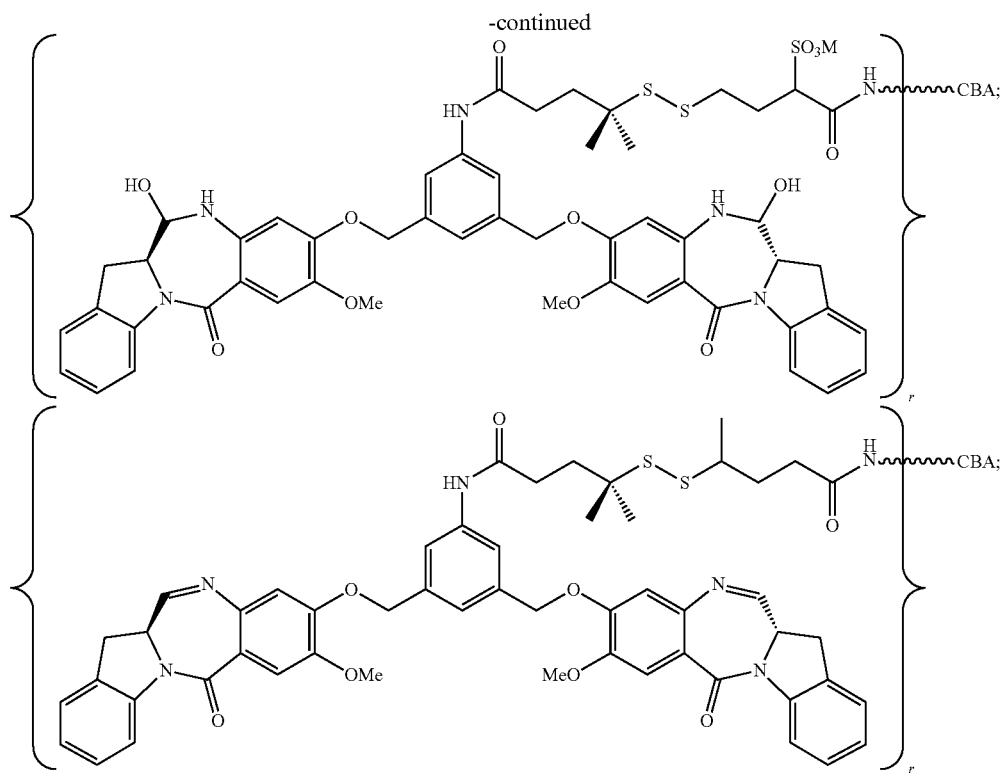
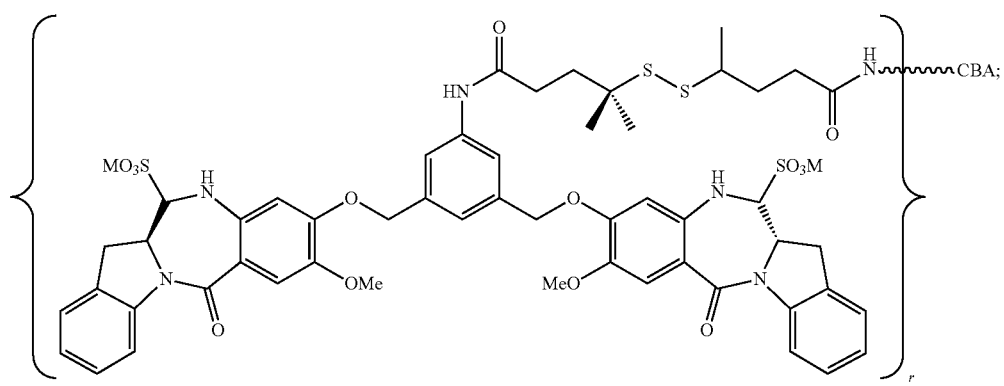
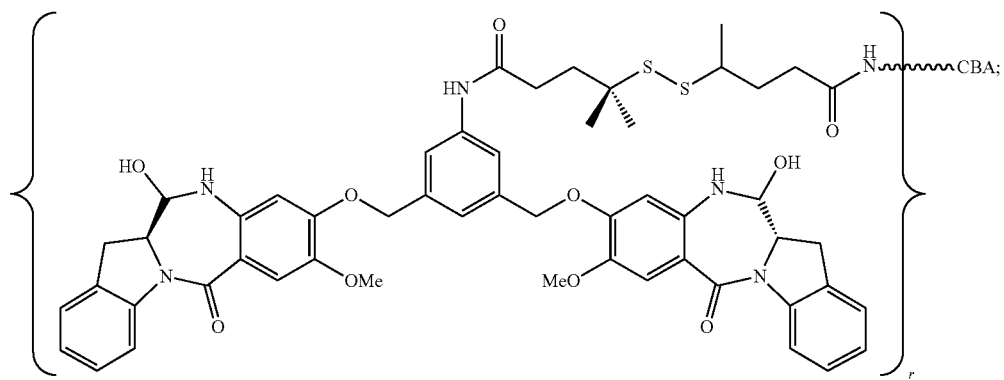

-continued
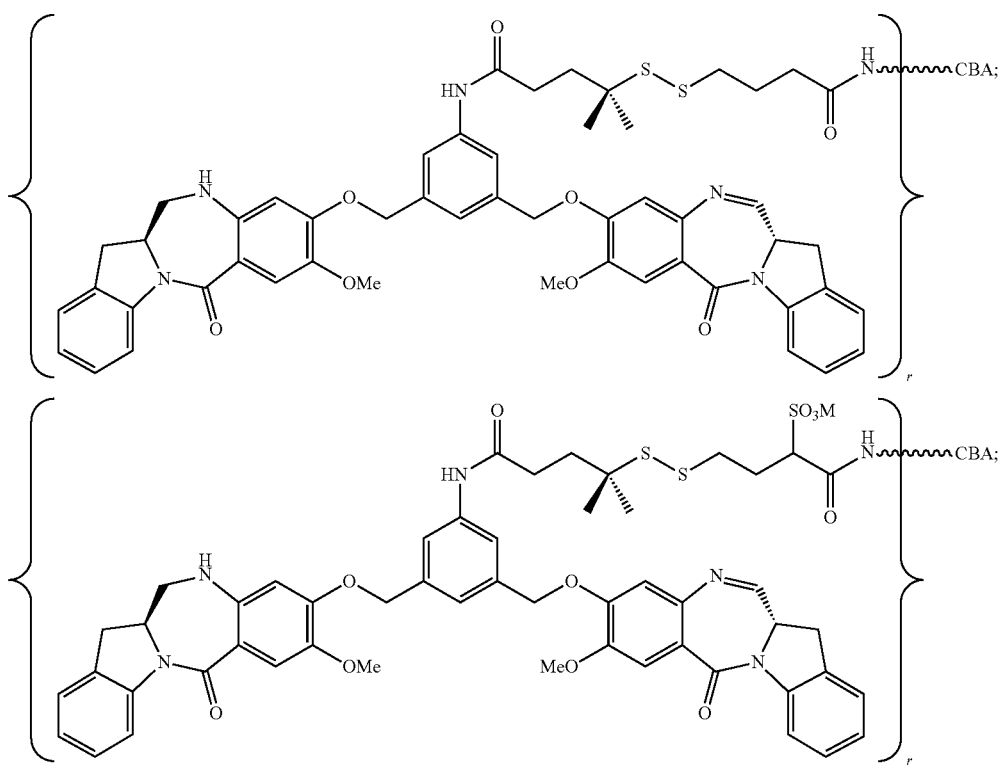
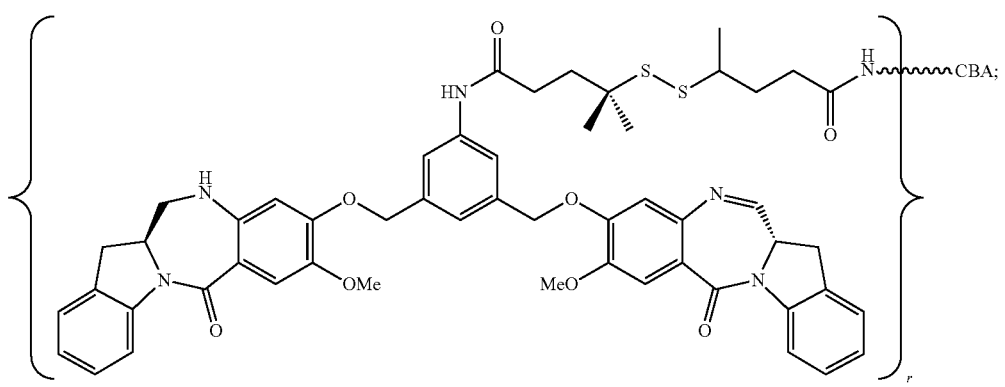
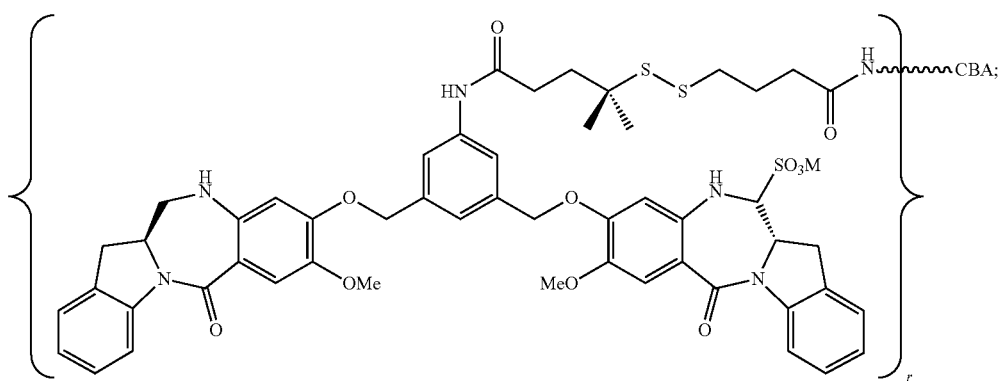

-continued
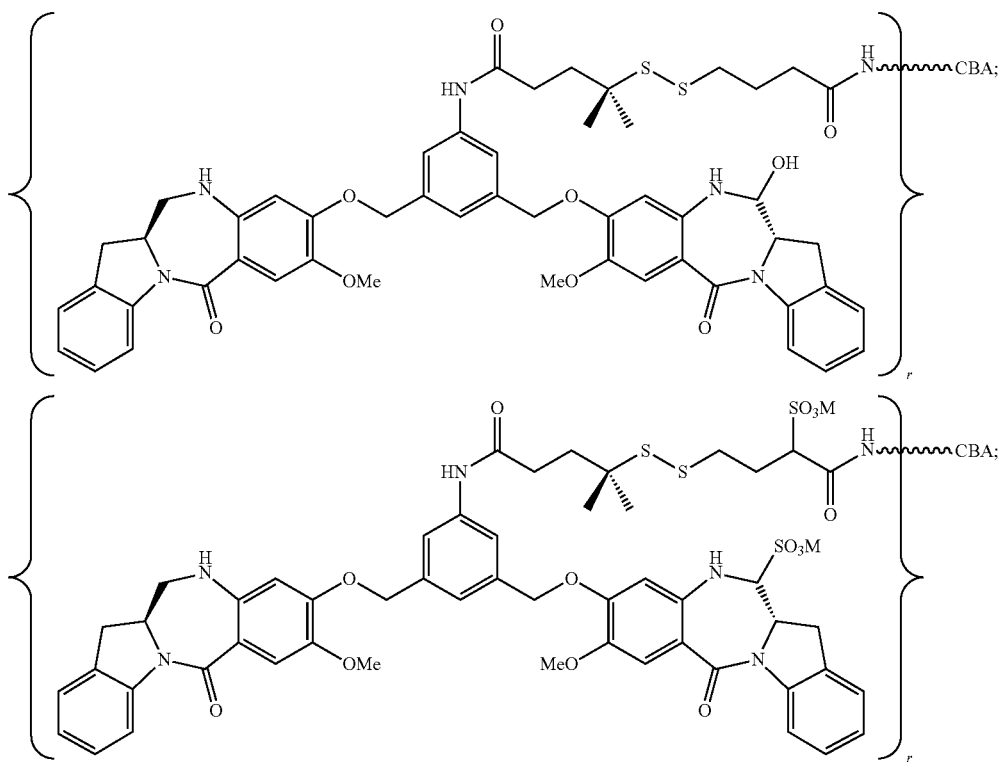
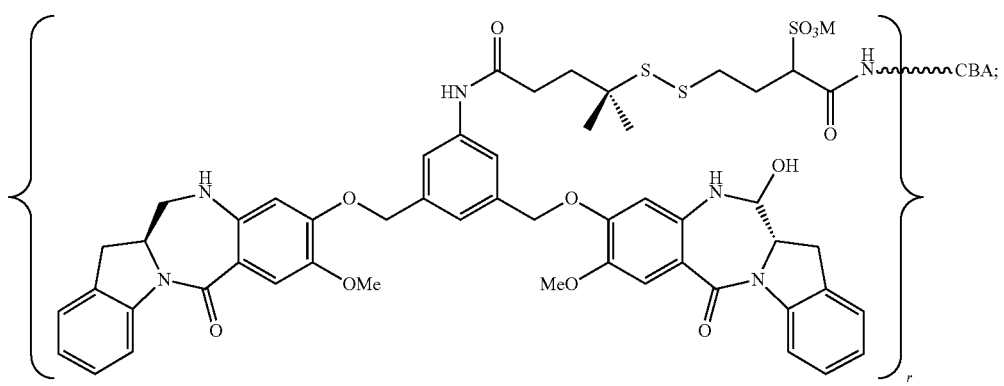
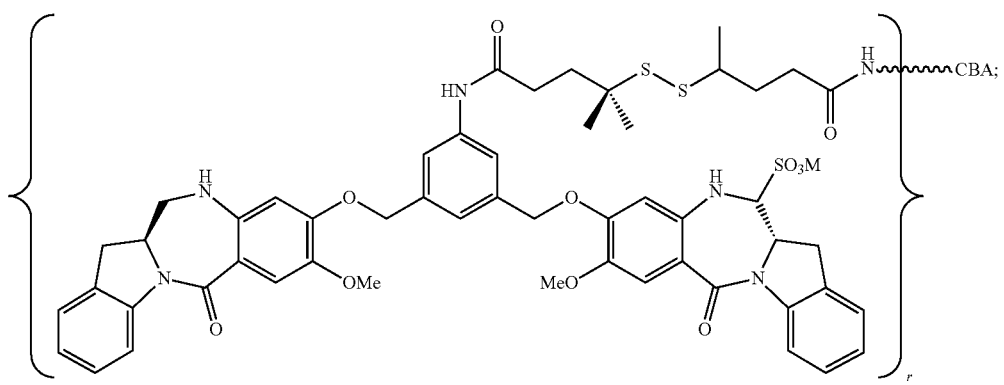

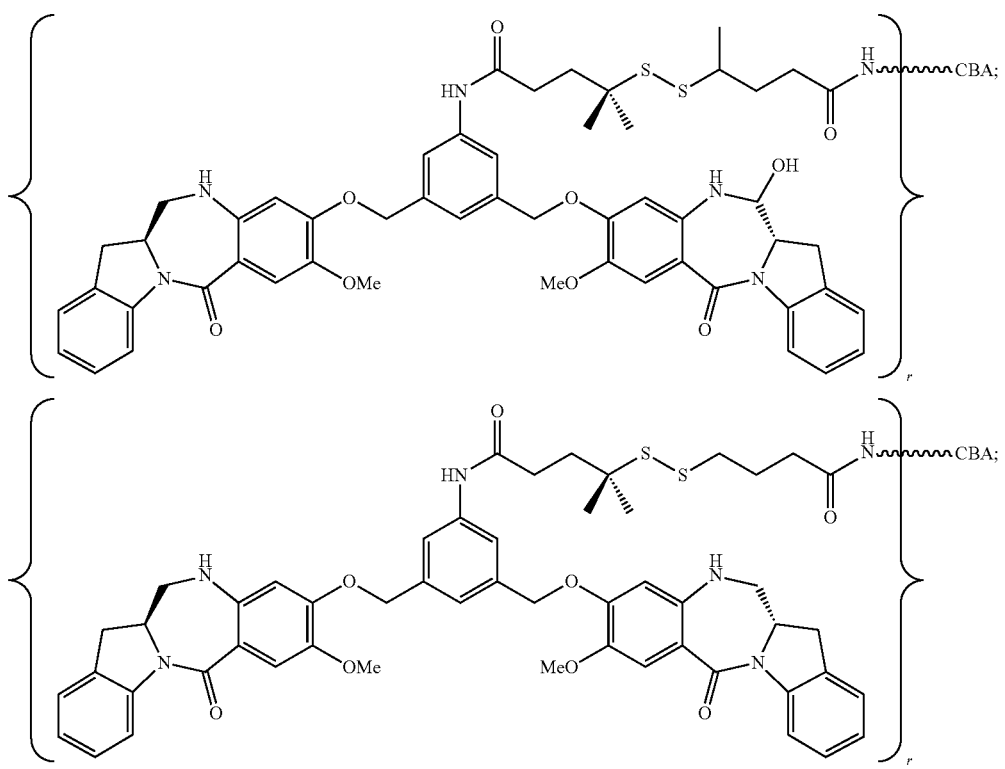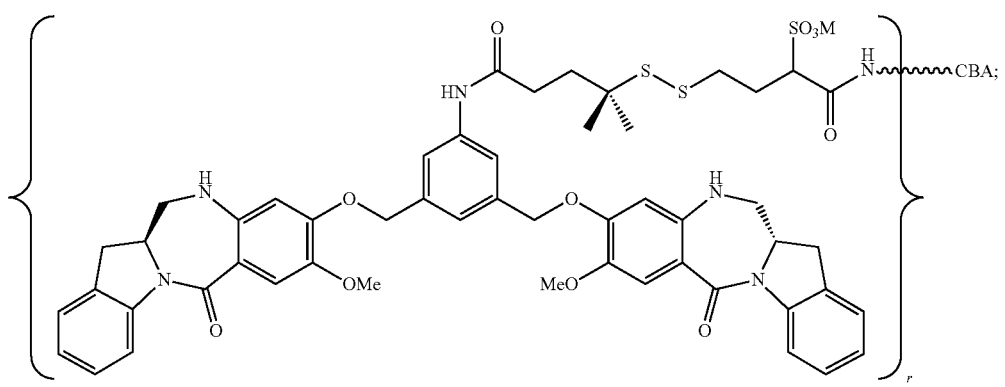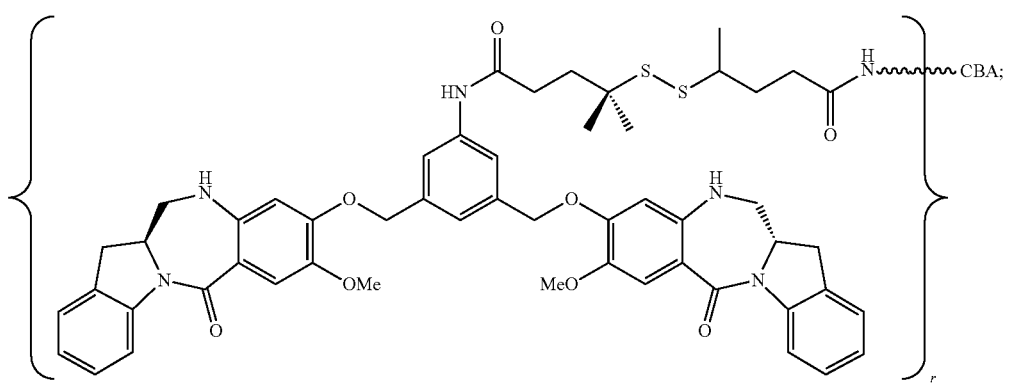

-continued
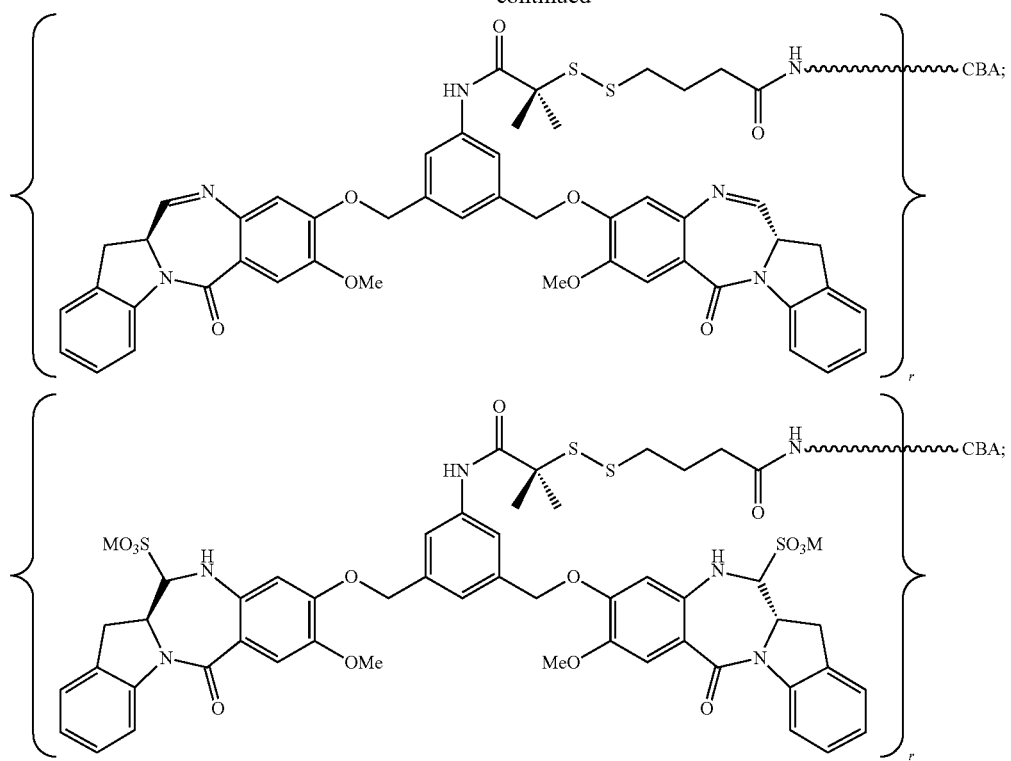
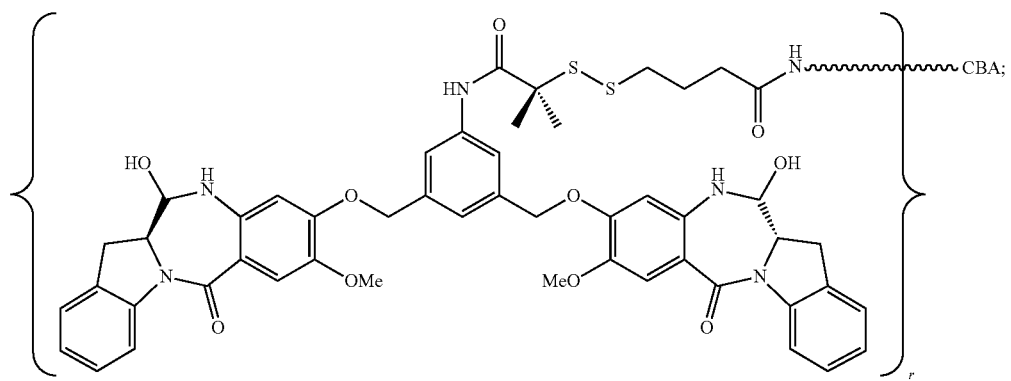
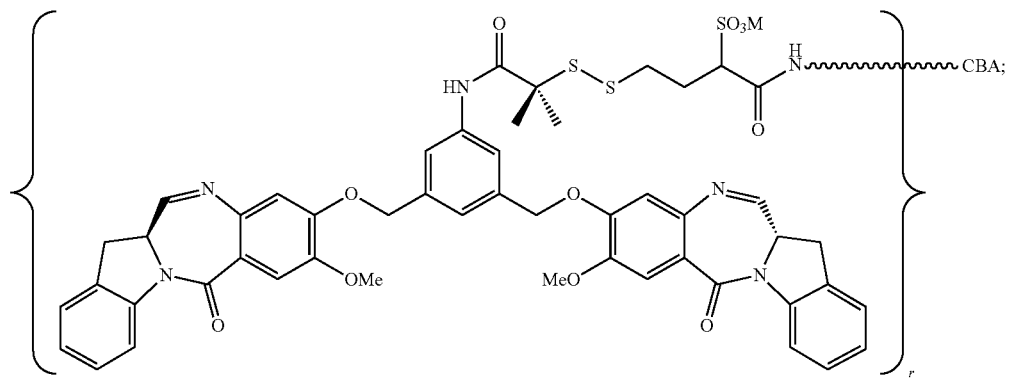

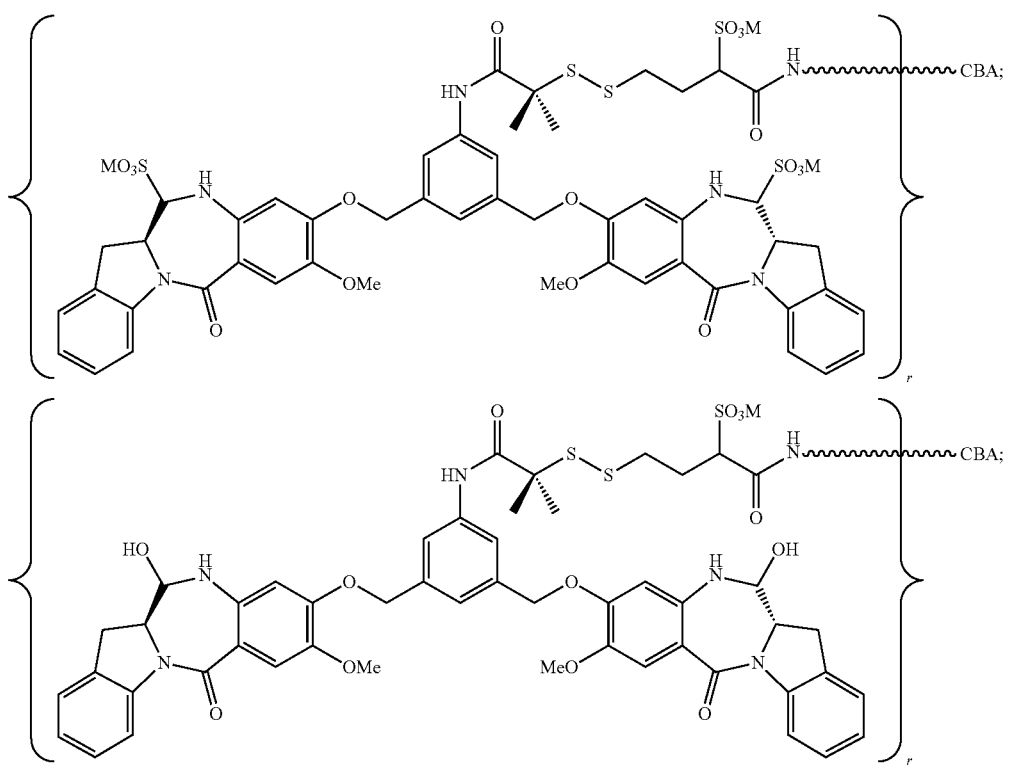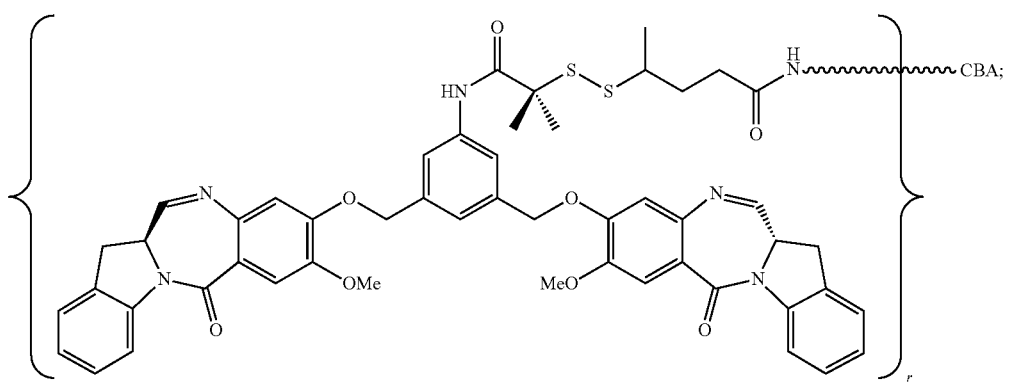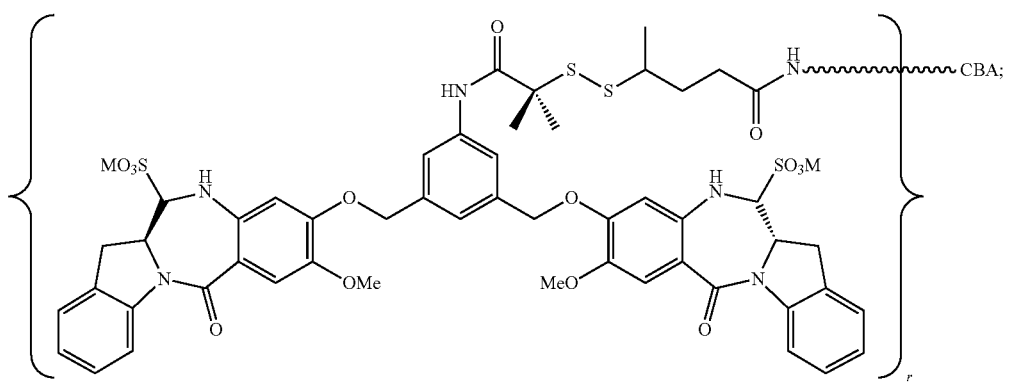

-continued
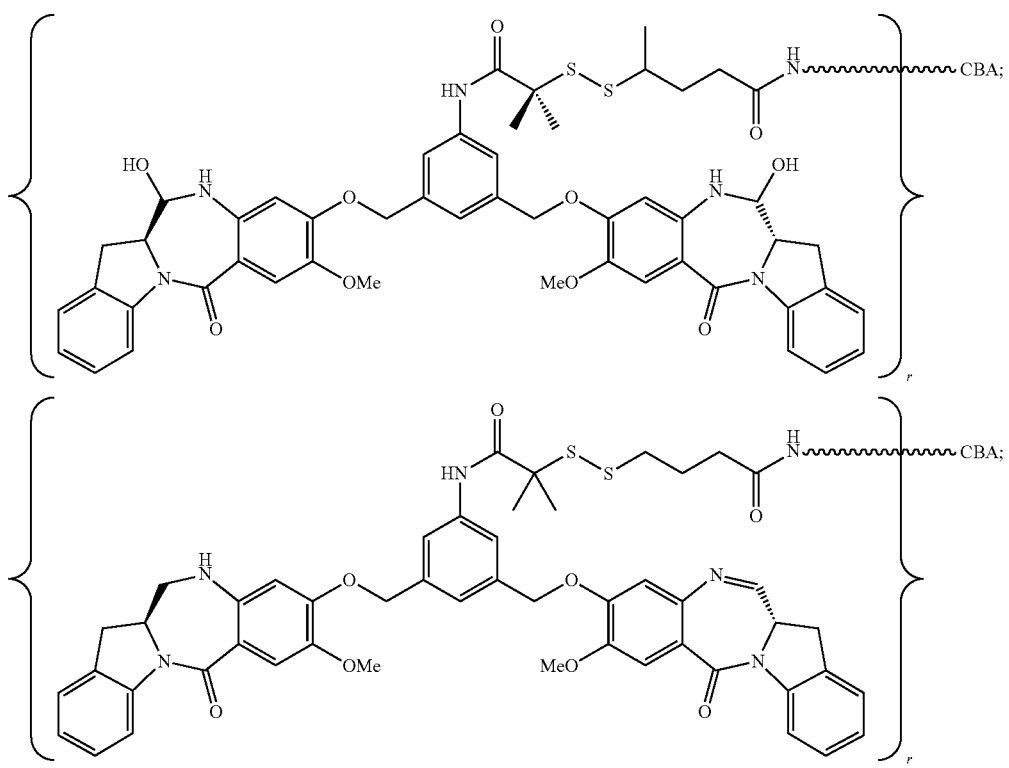
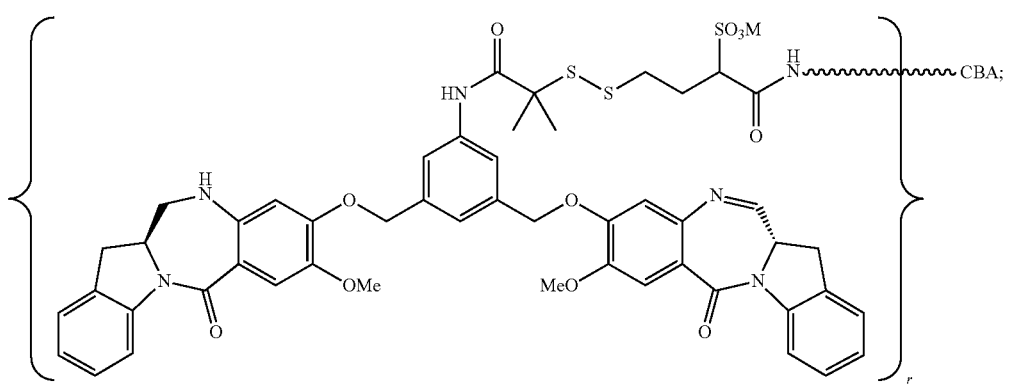
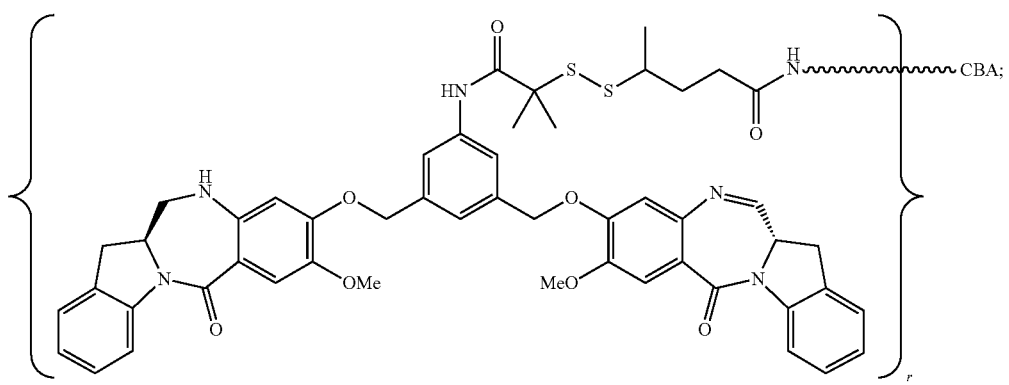

-continued
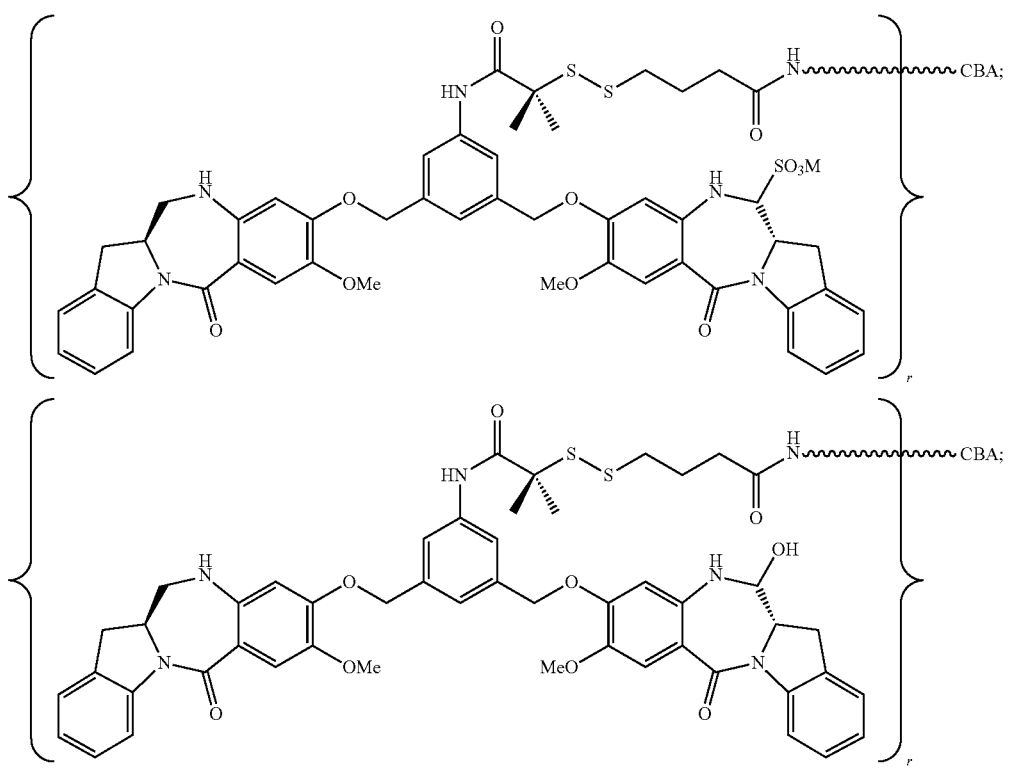
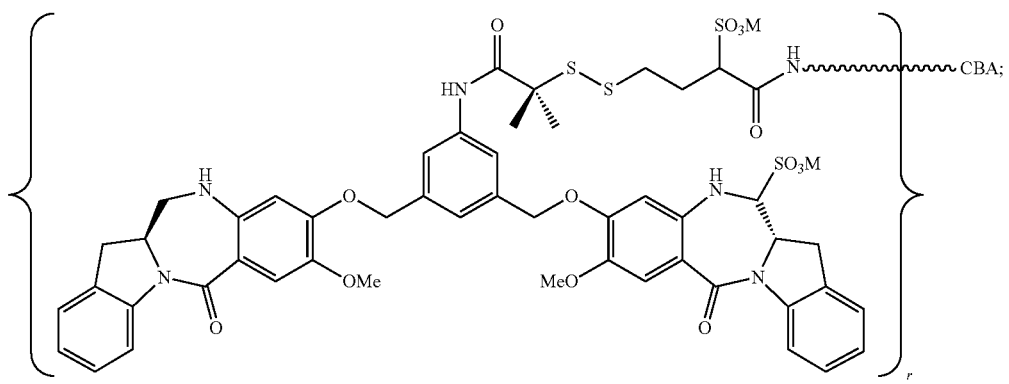
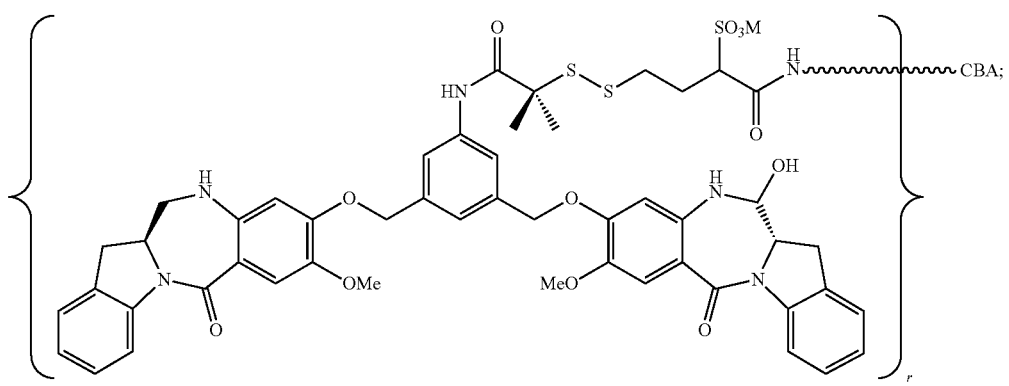

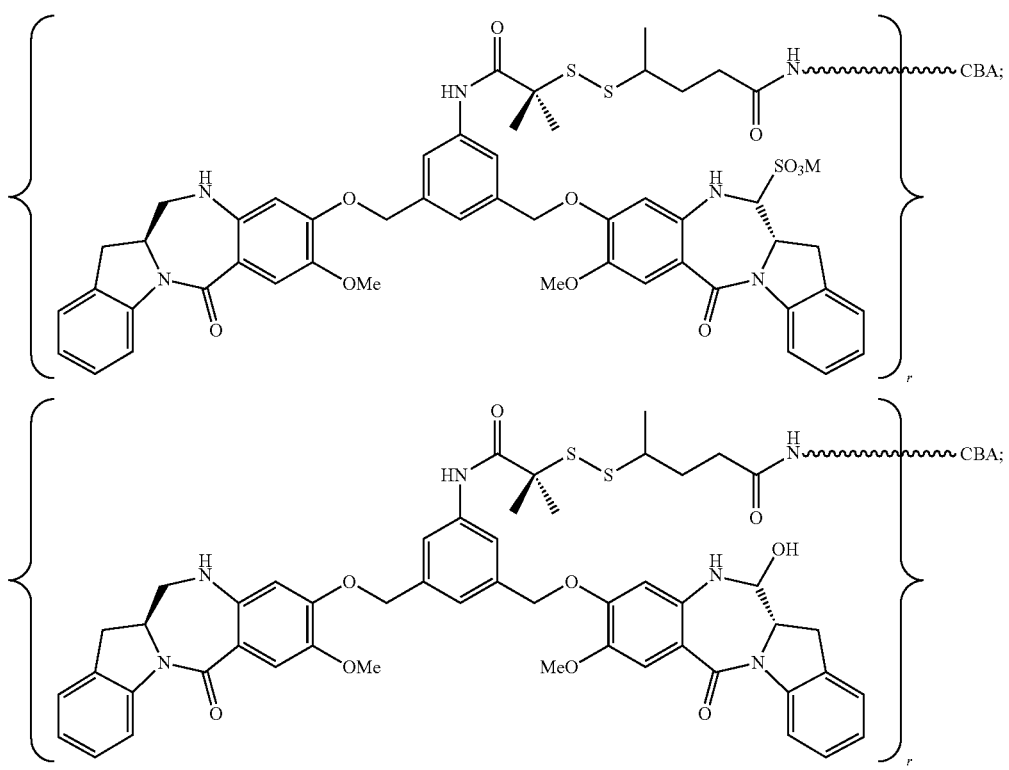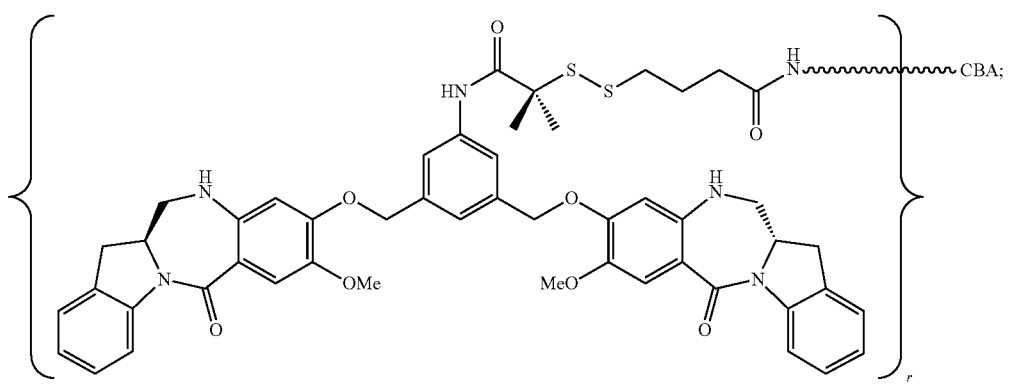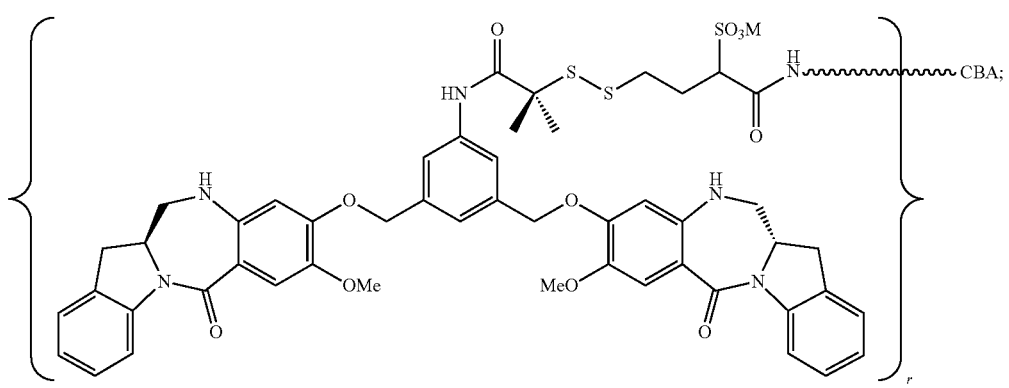

-continued
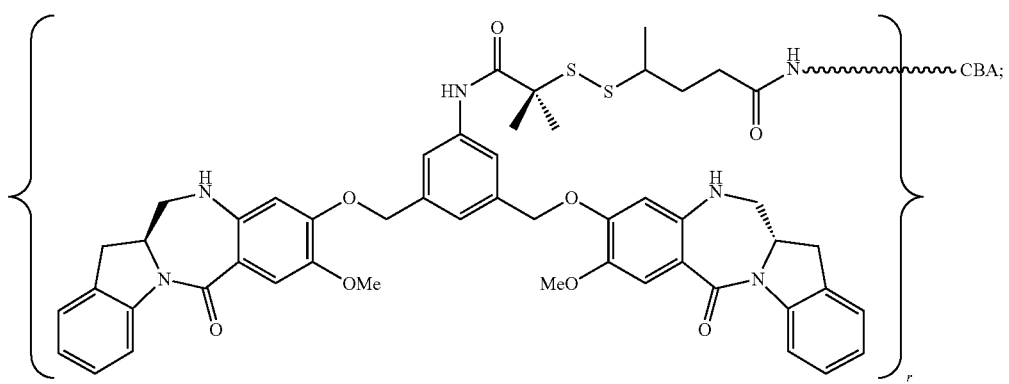
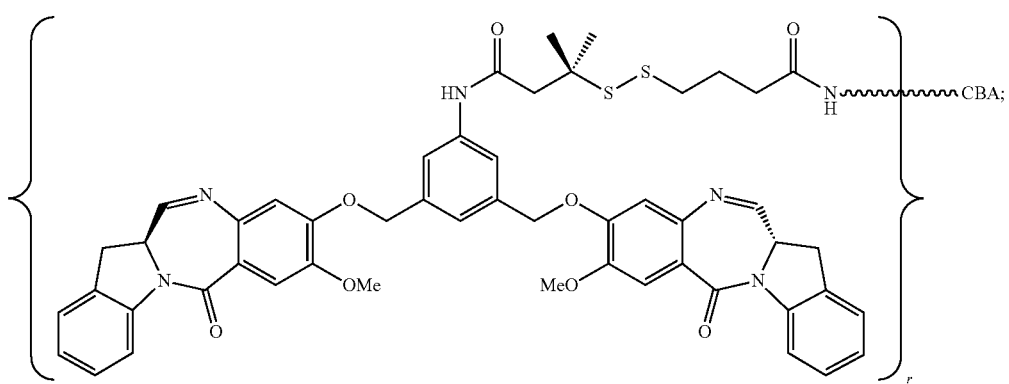
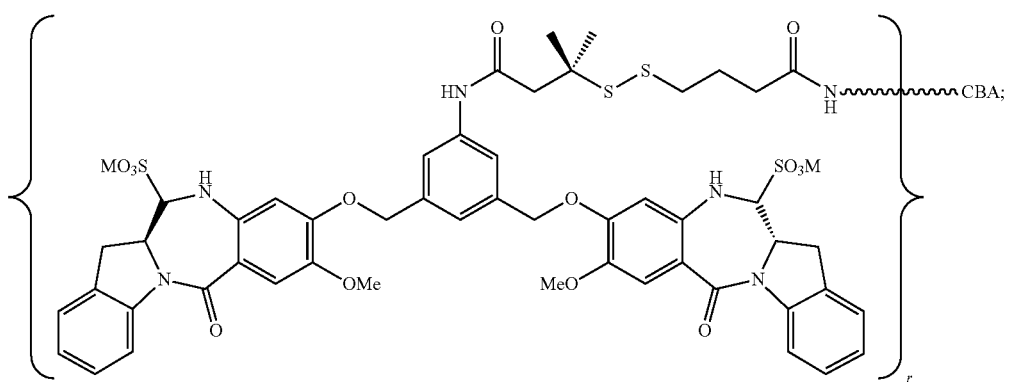
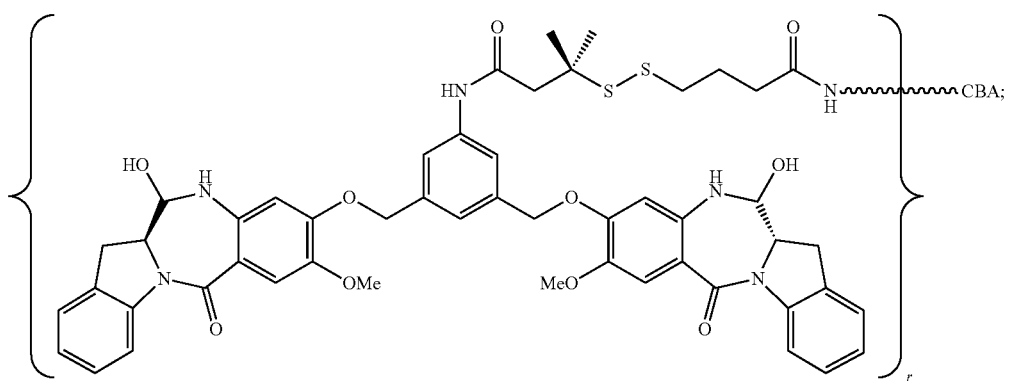

-continued
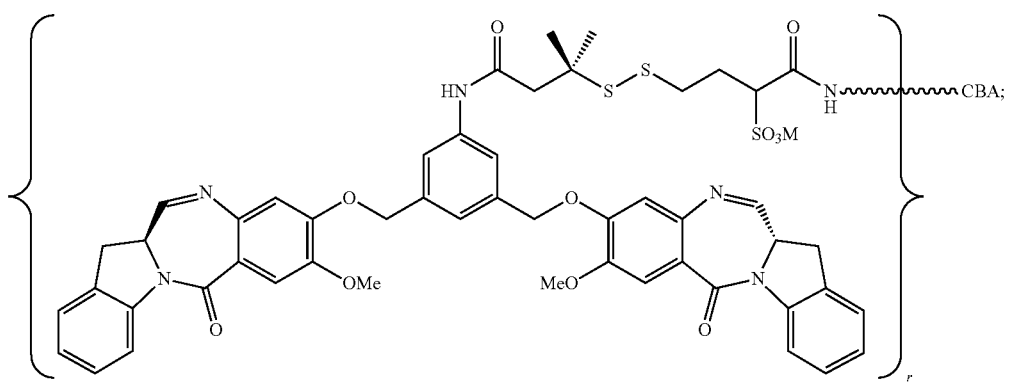
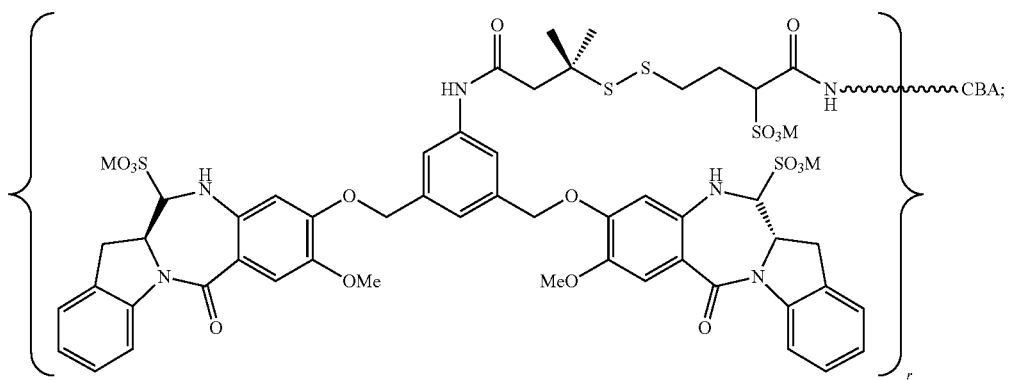
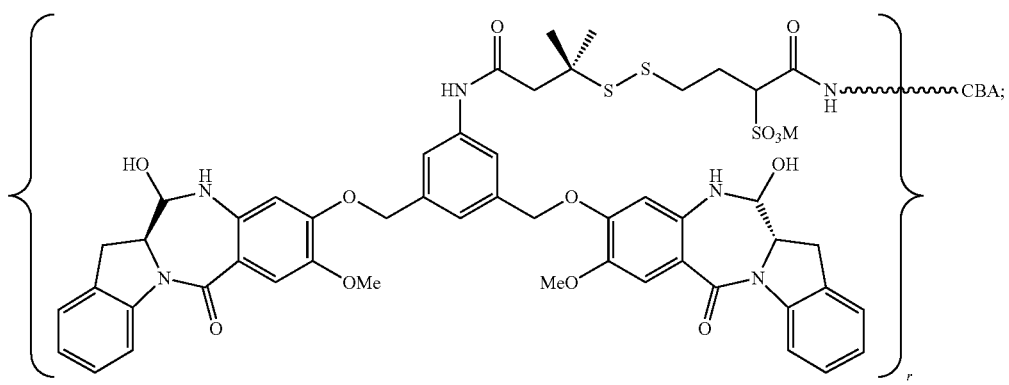
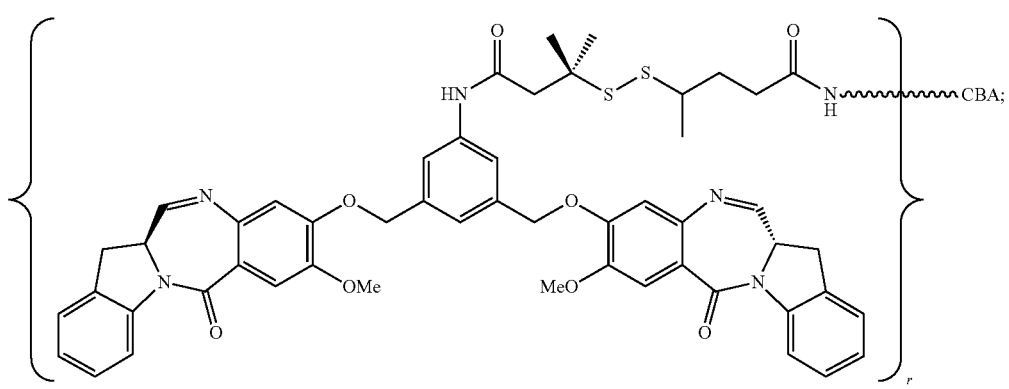

-continued
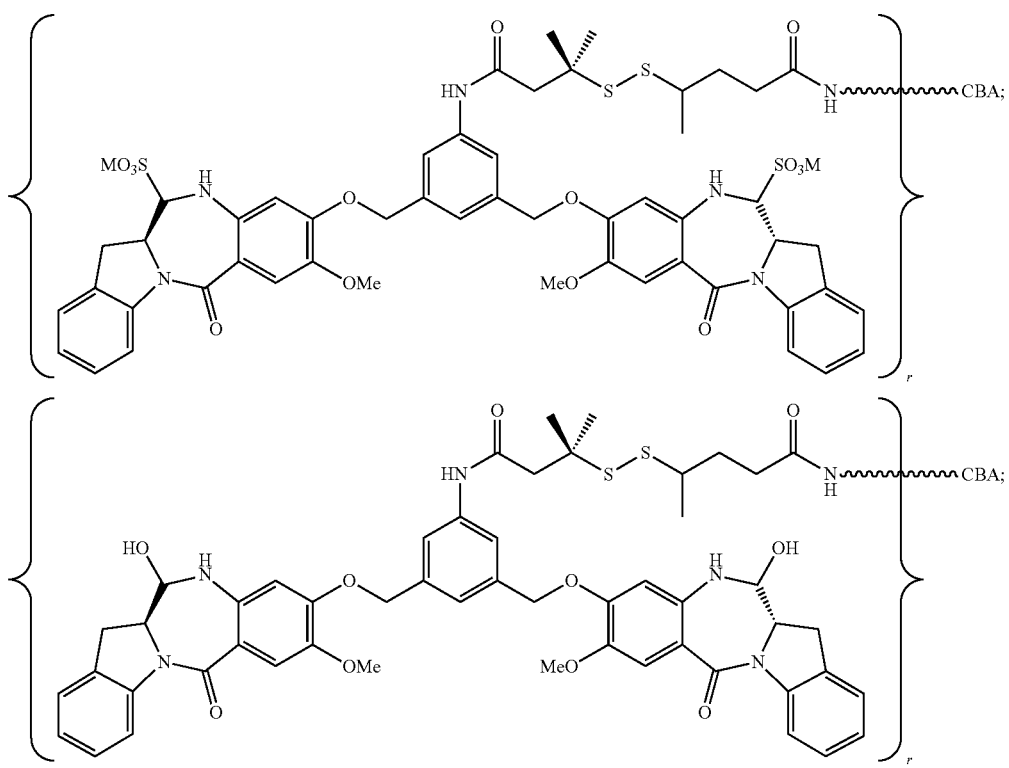
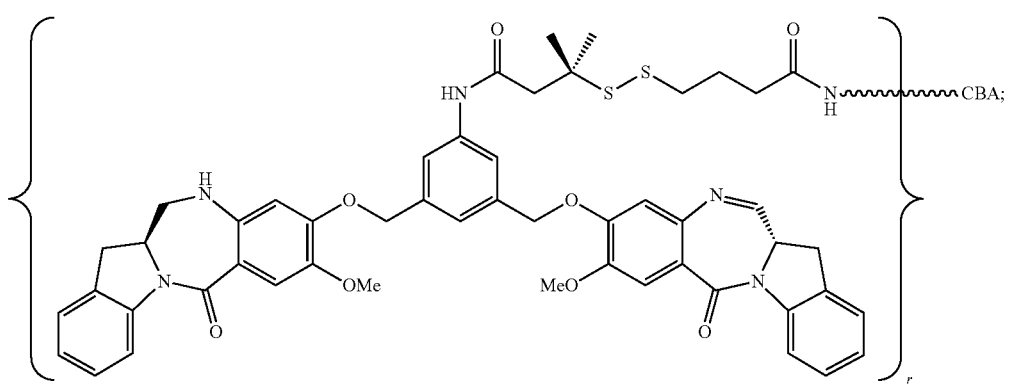
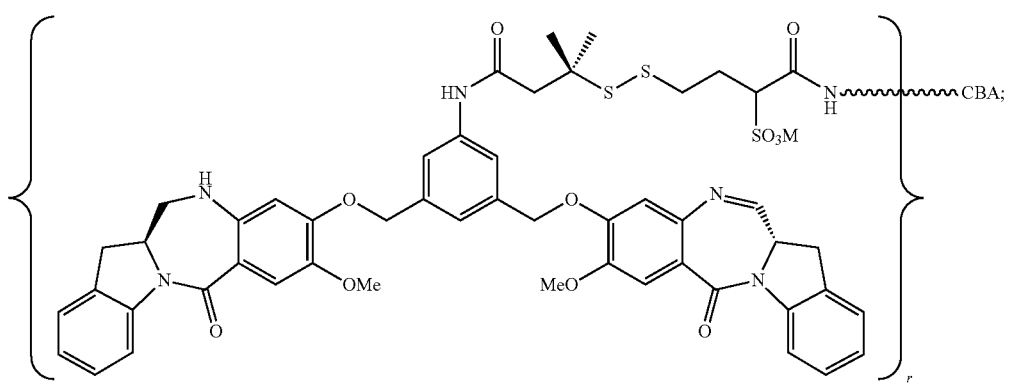

-continued
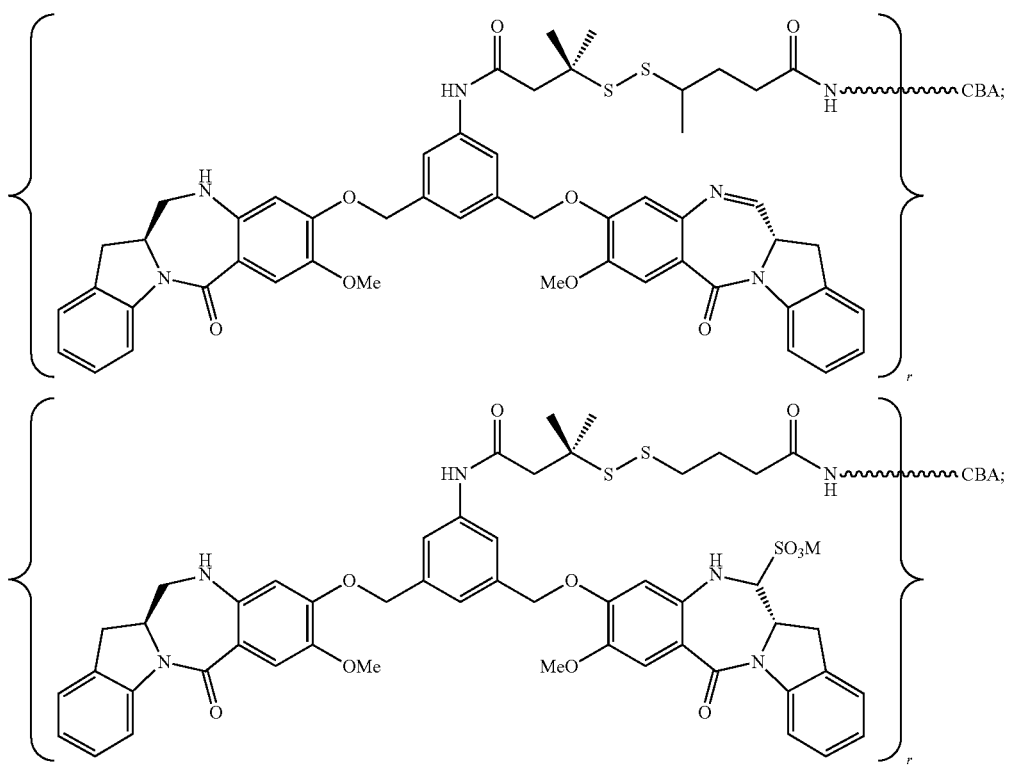
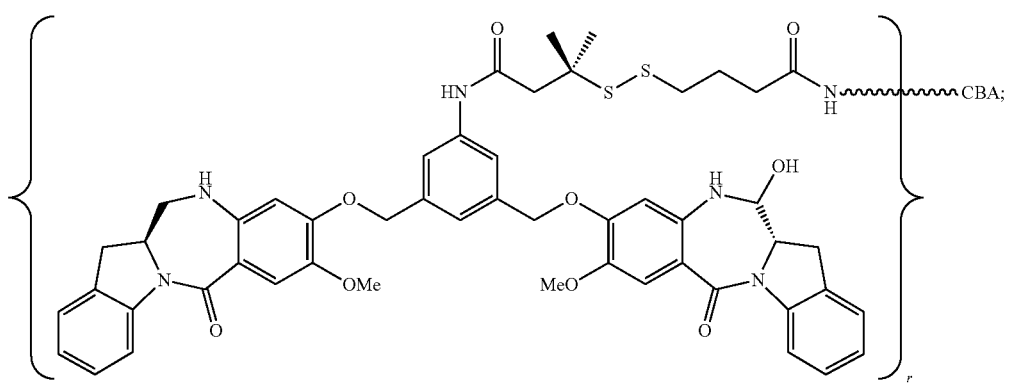
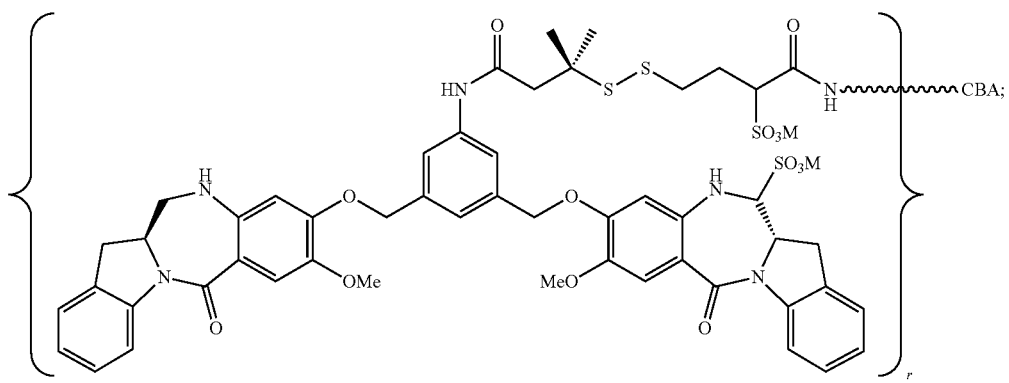

-continued
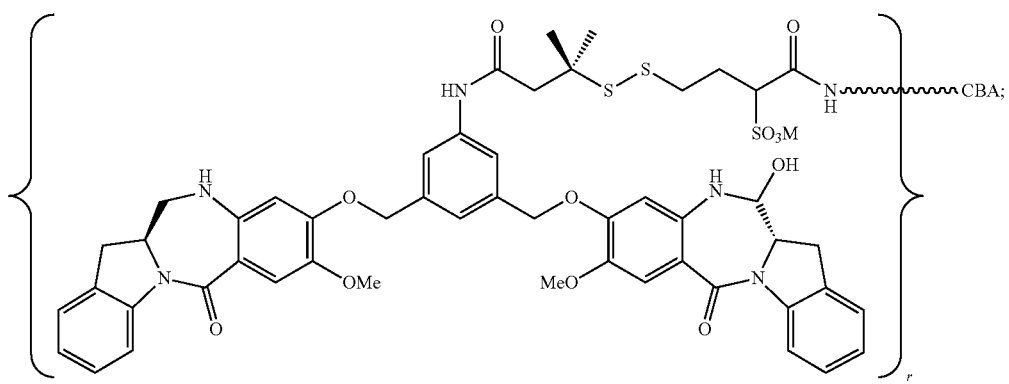
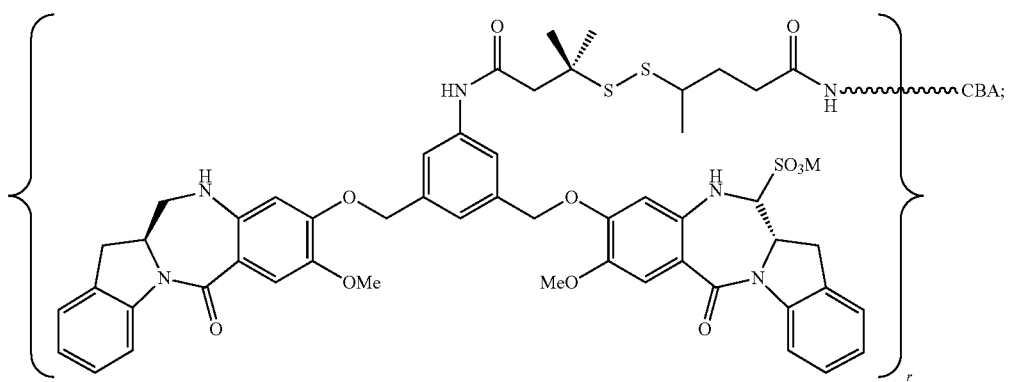
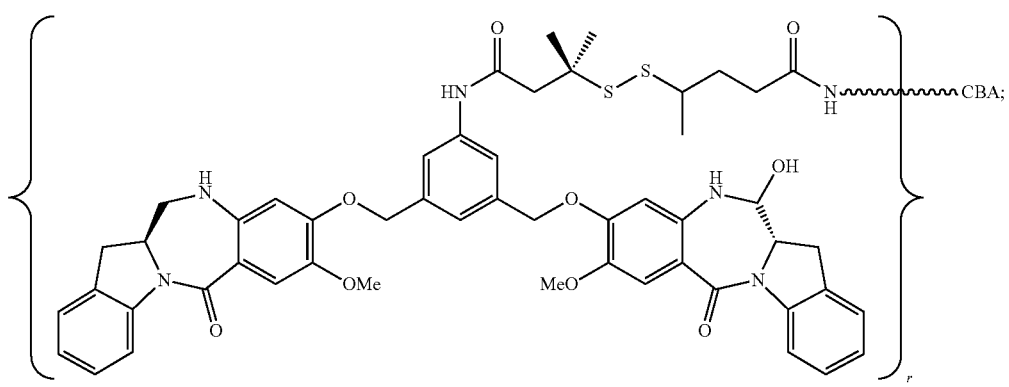
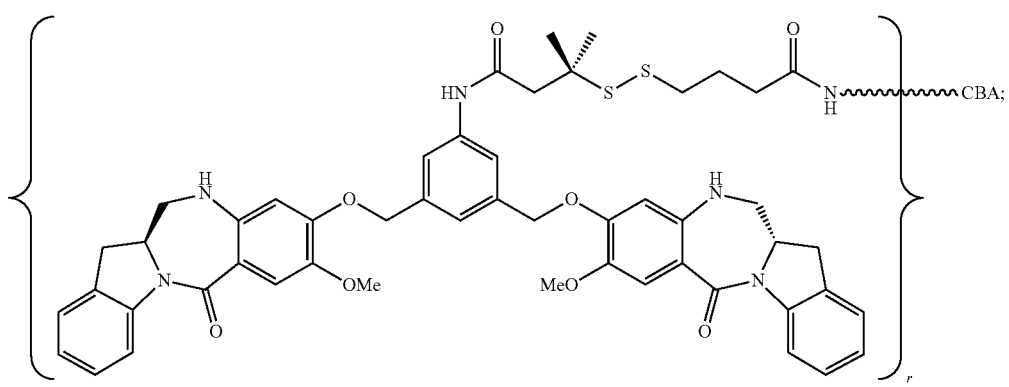

-continued
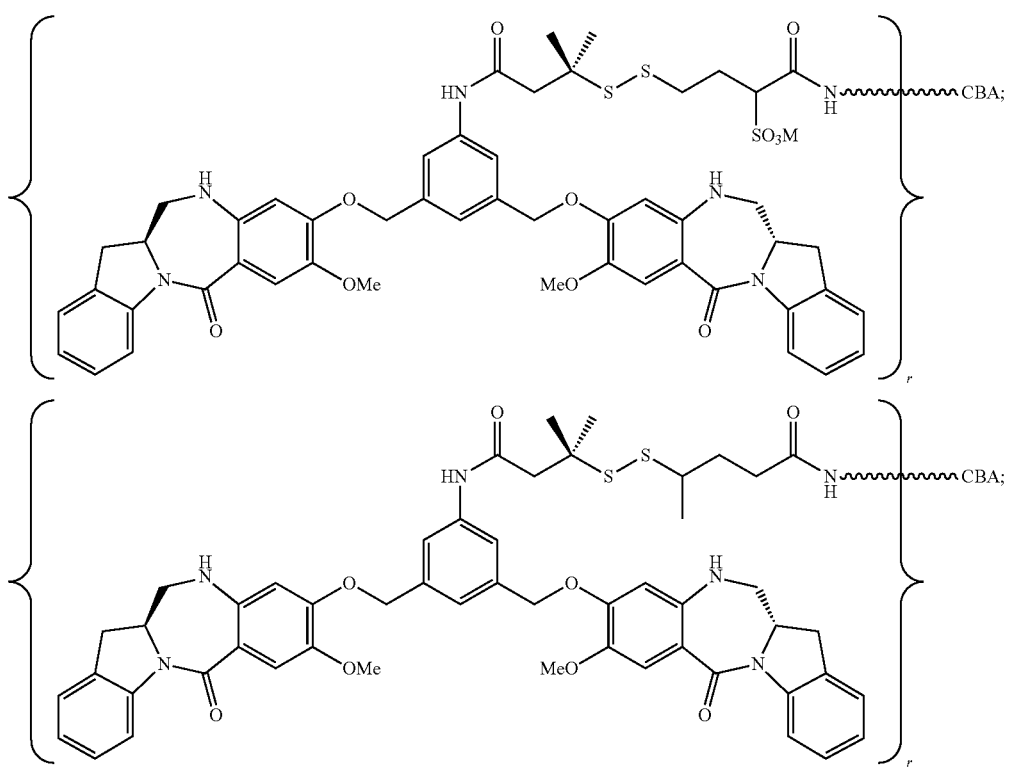
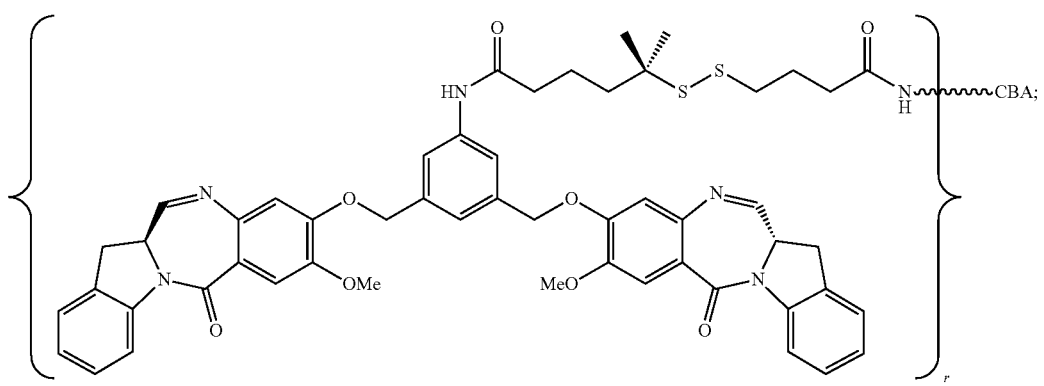
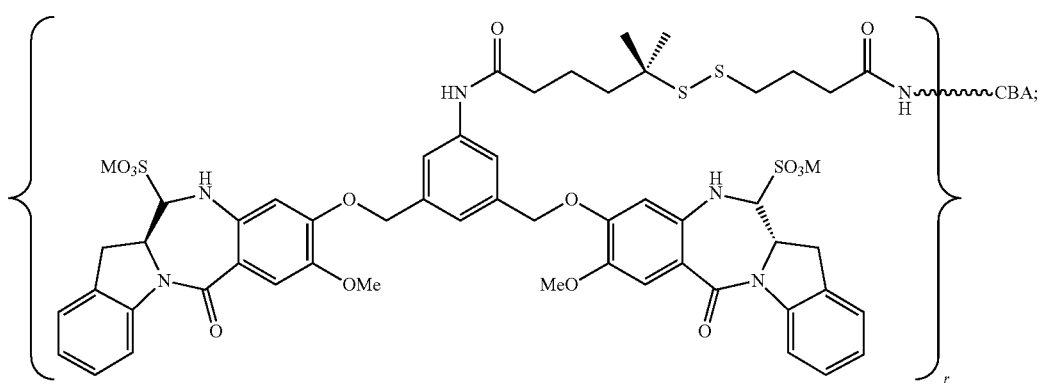

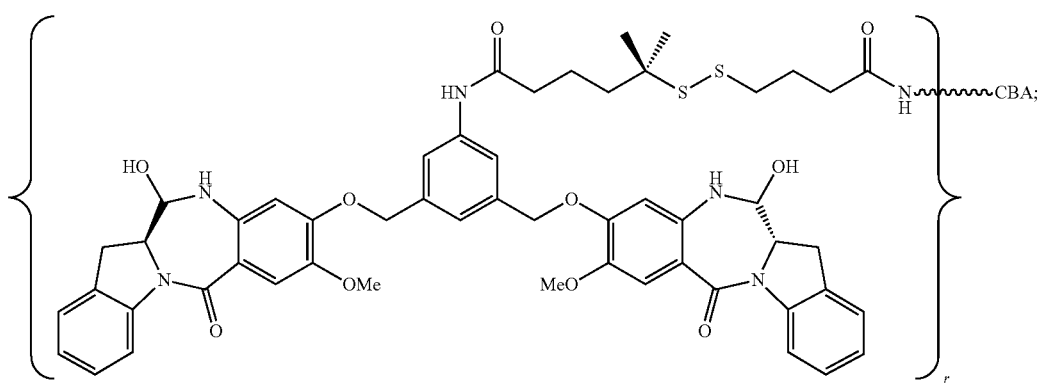
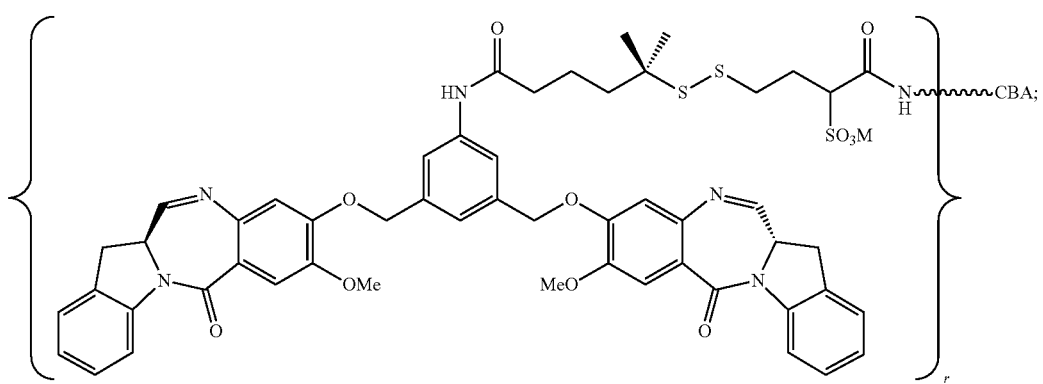
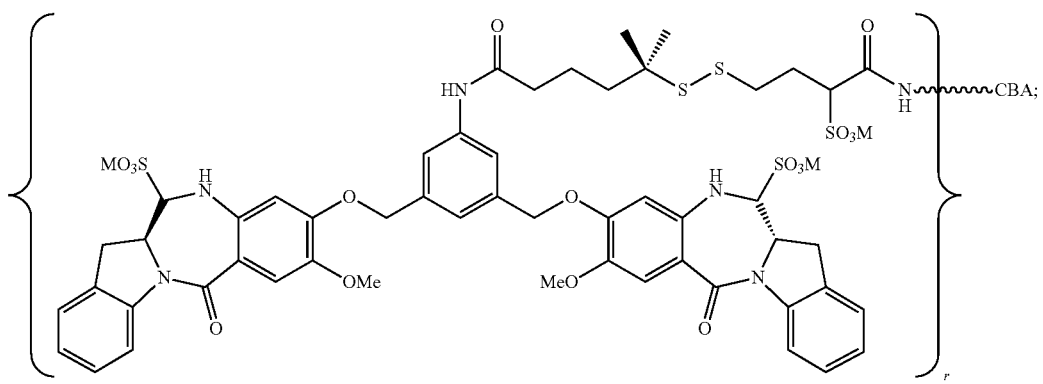
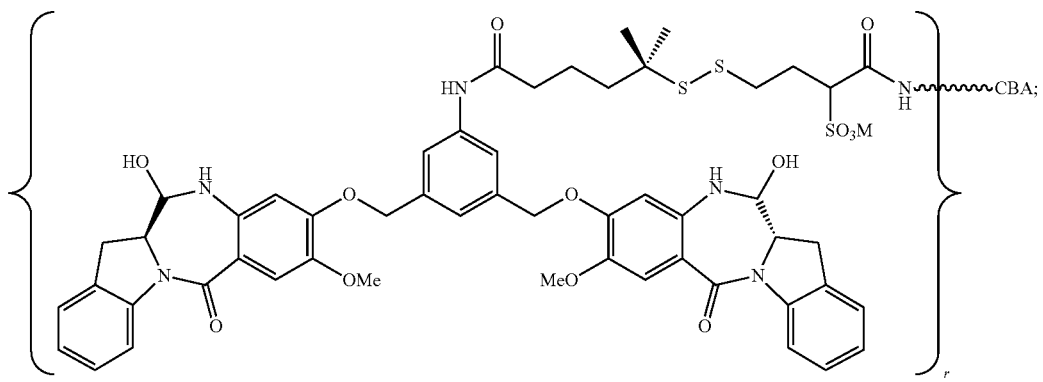

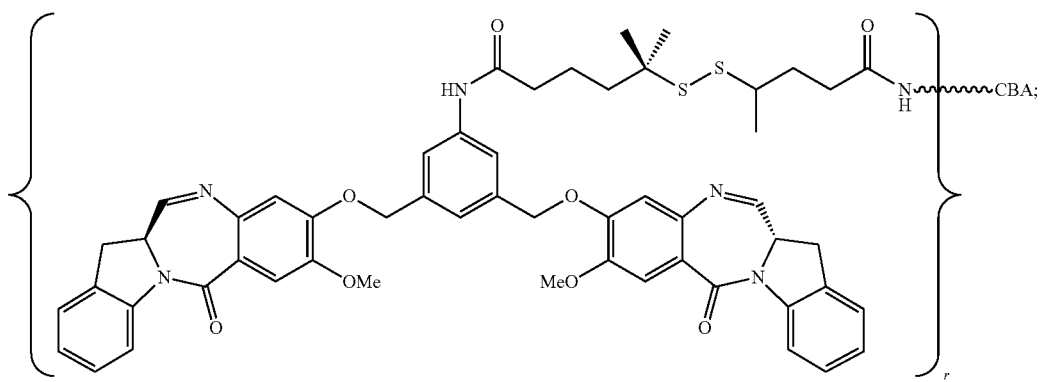
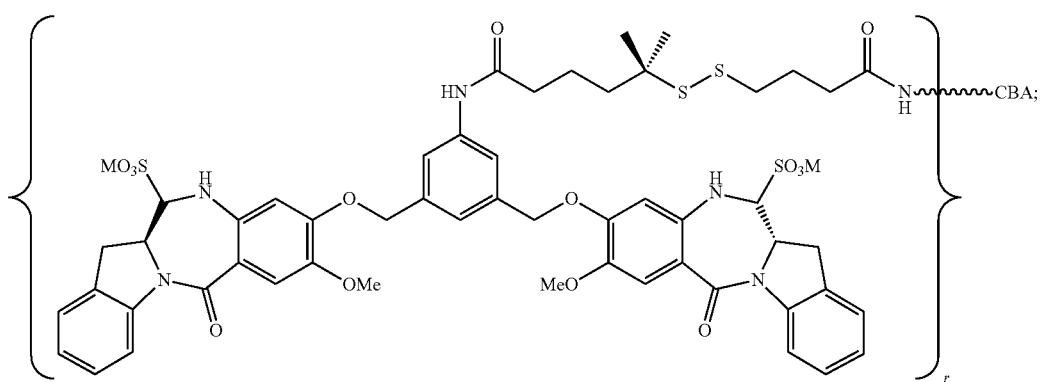
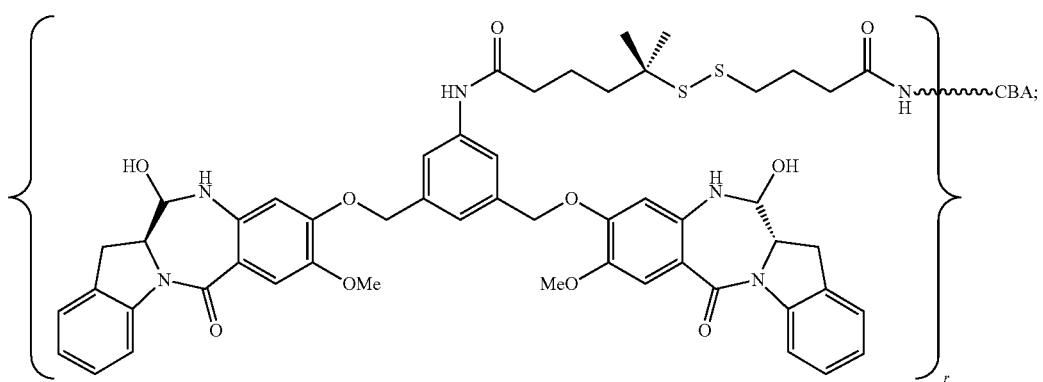
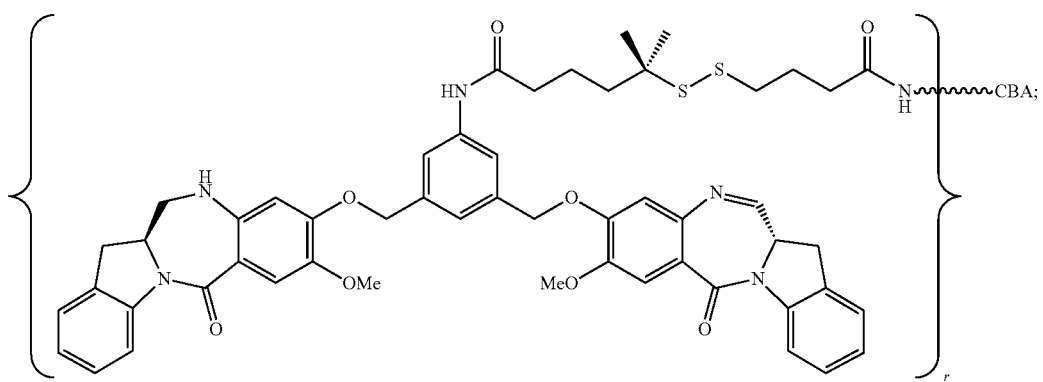

-continued
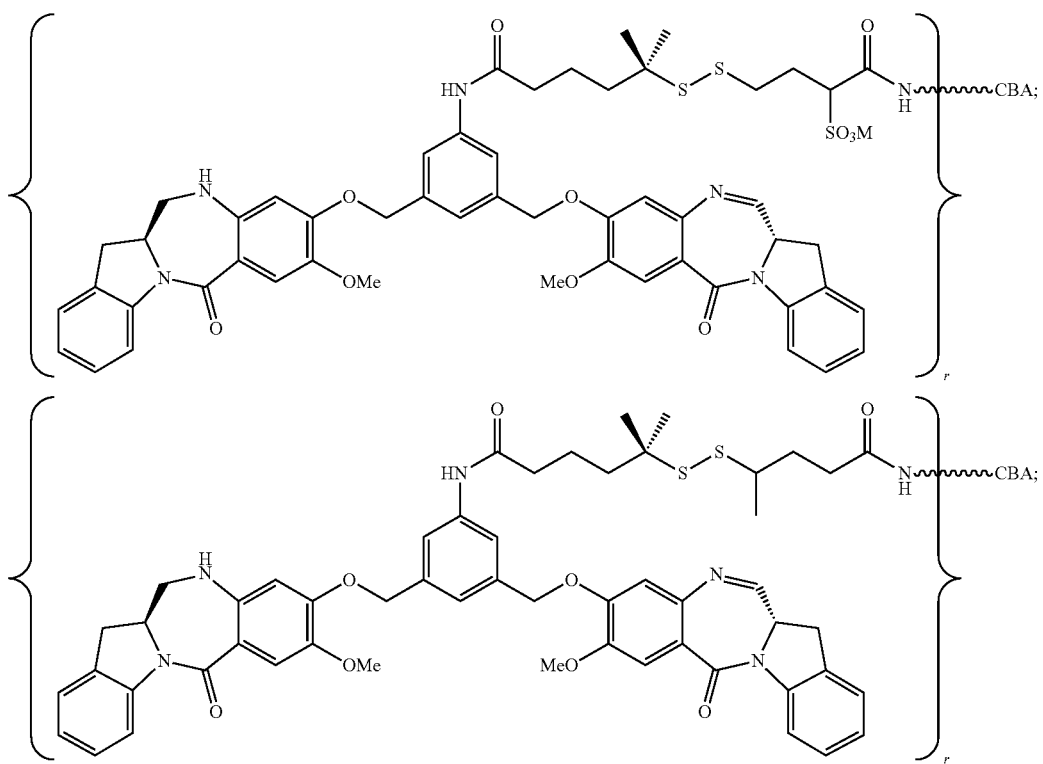
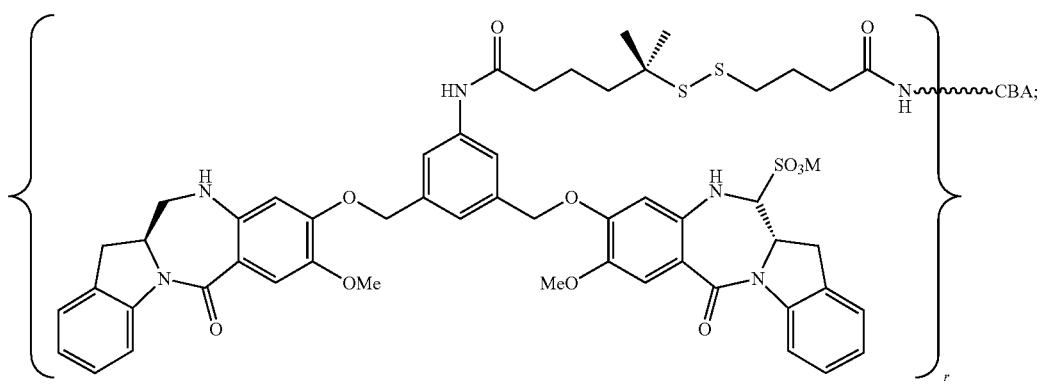
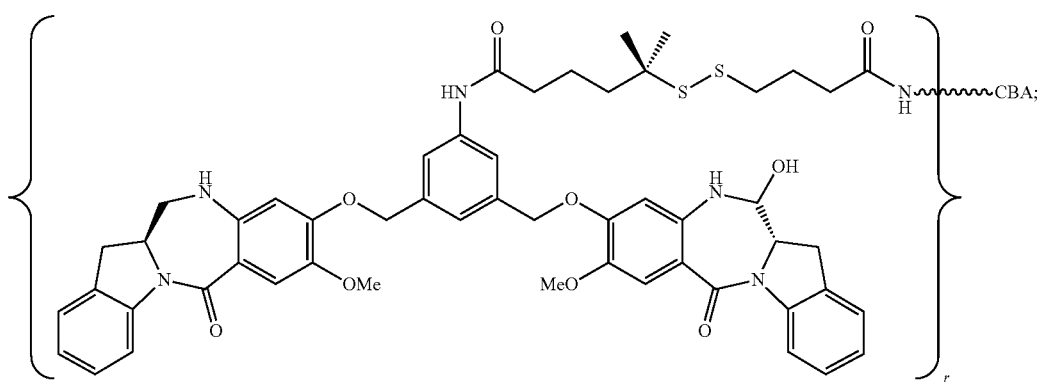

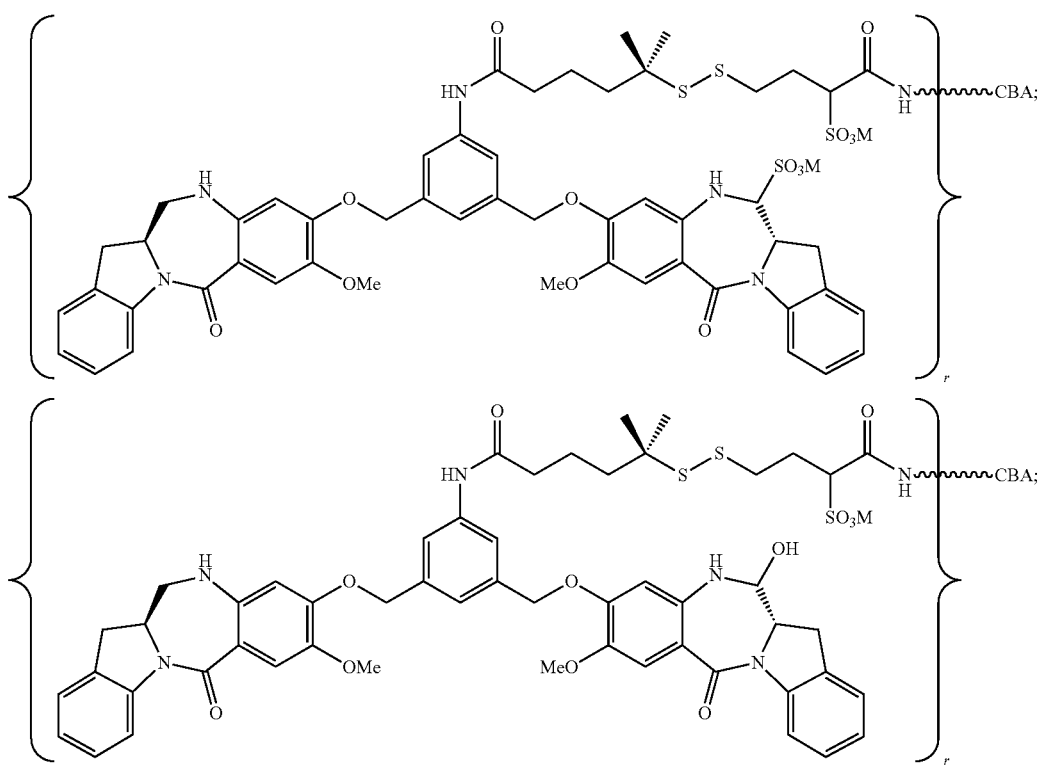
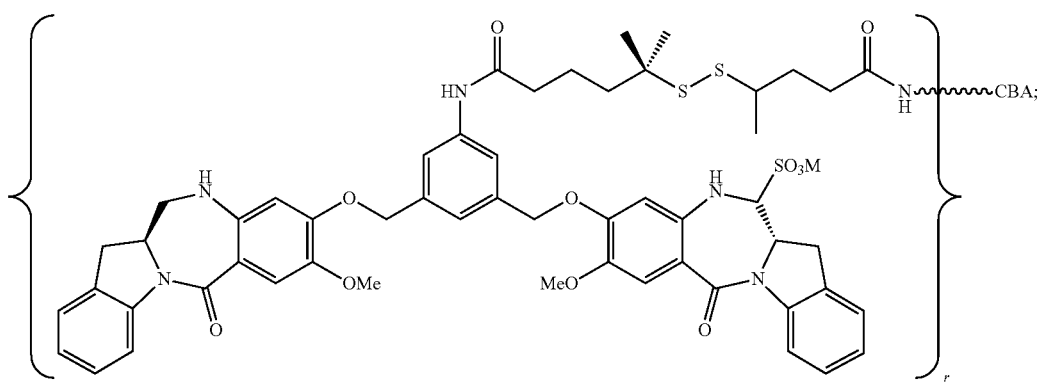
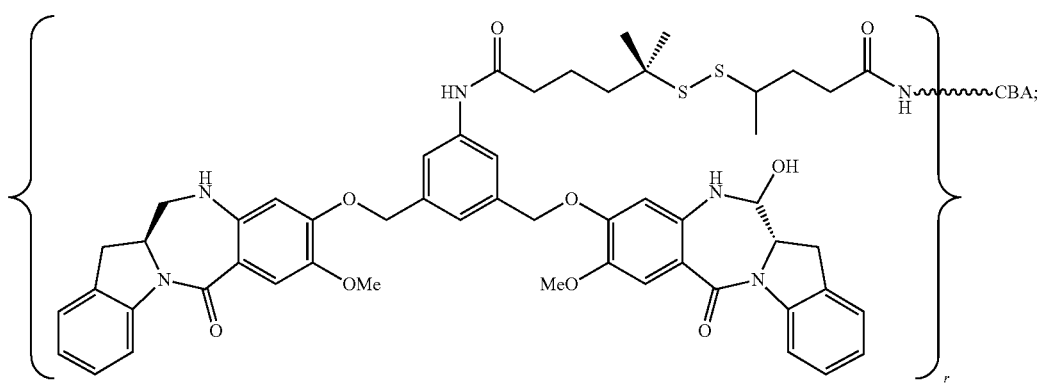

-continued
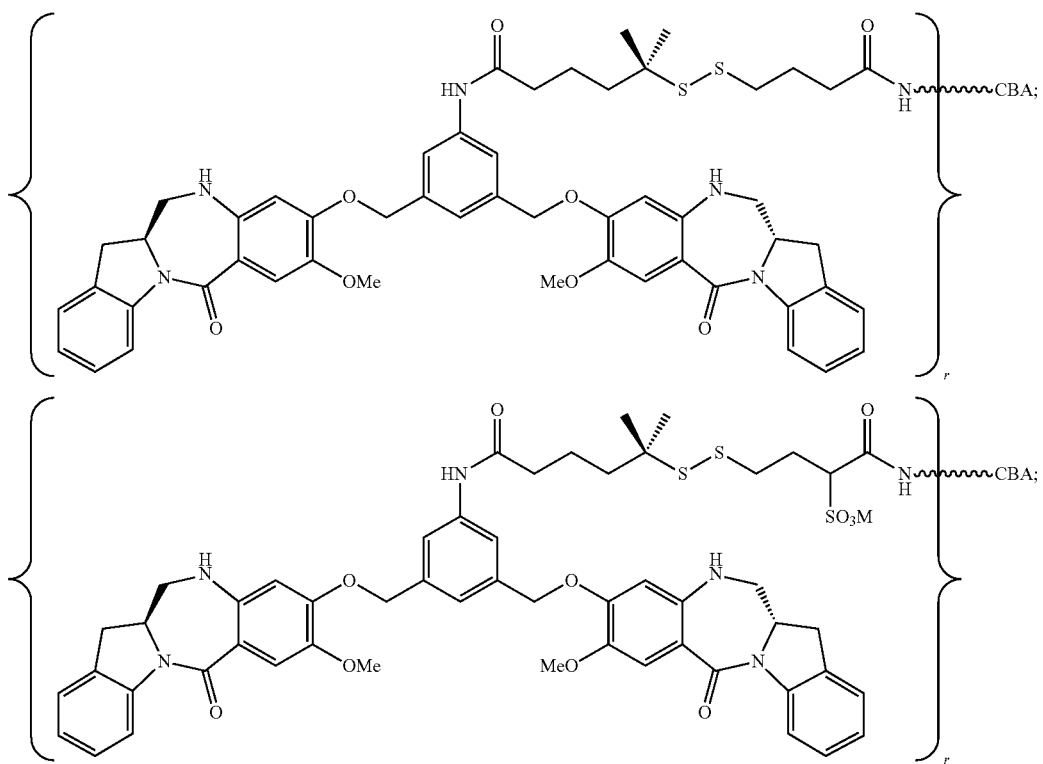
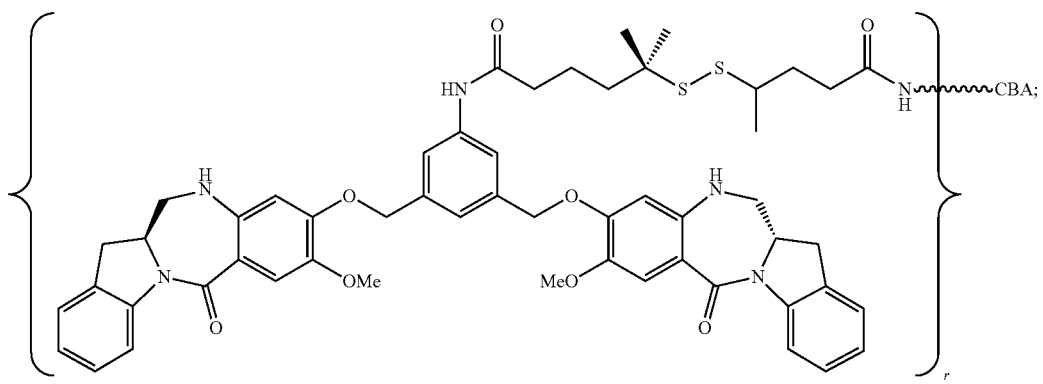
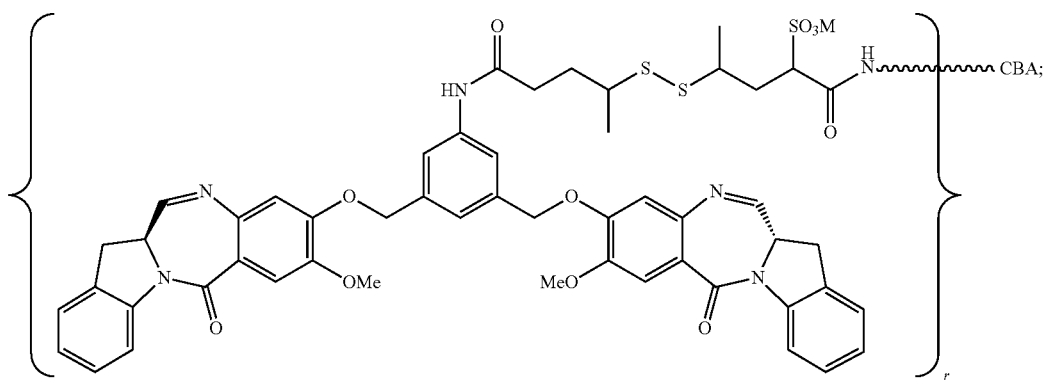

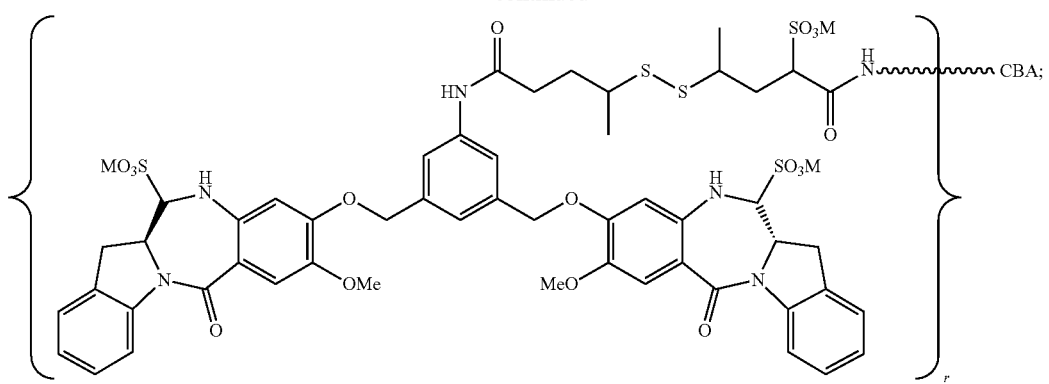
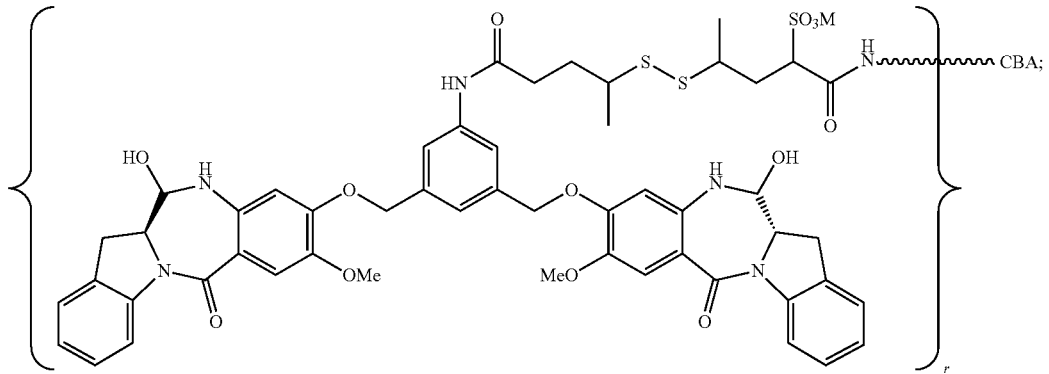
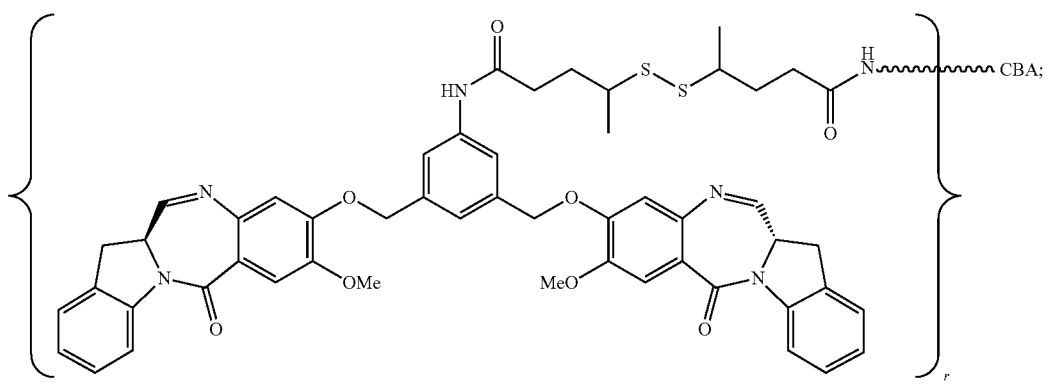
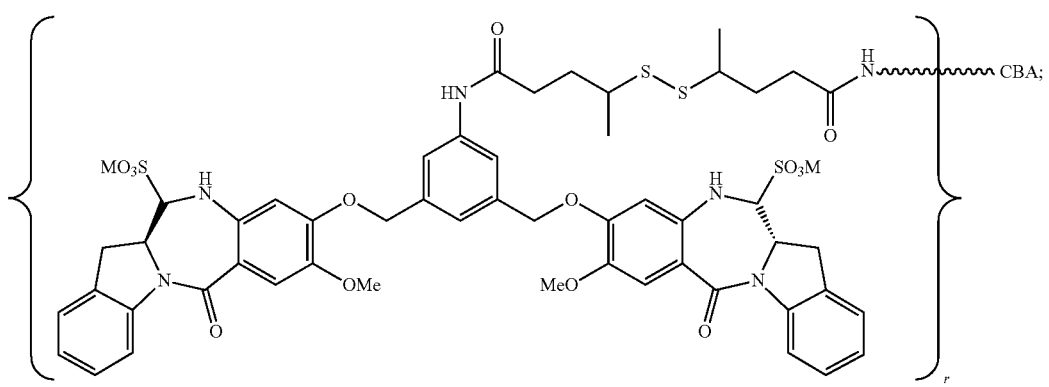

-continued
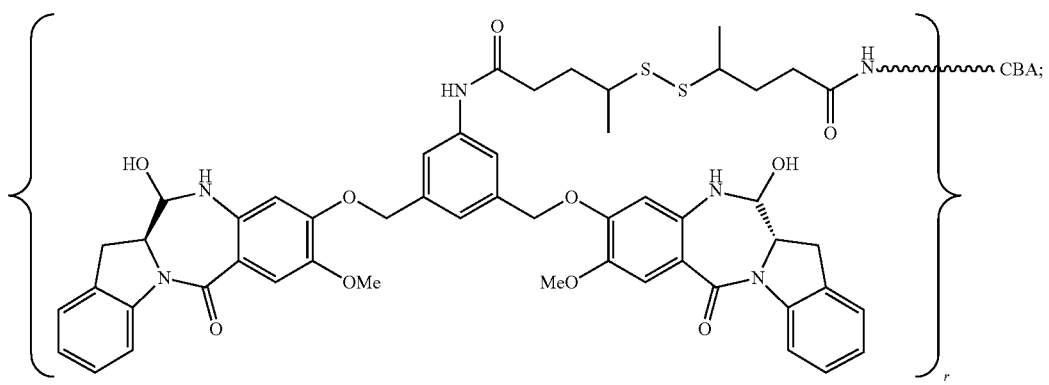
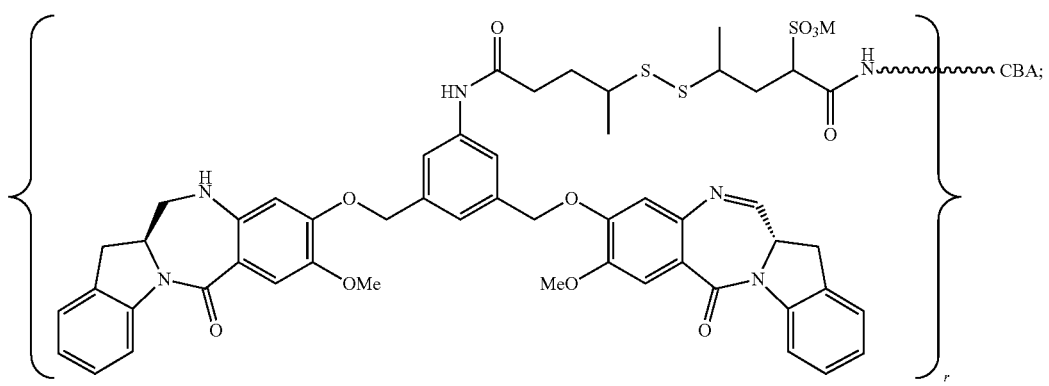
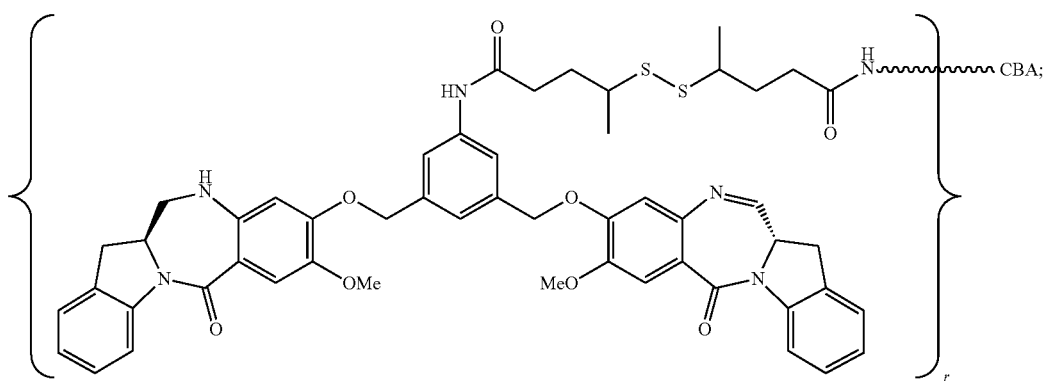
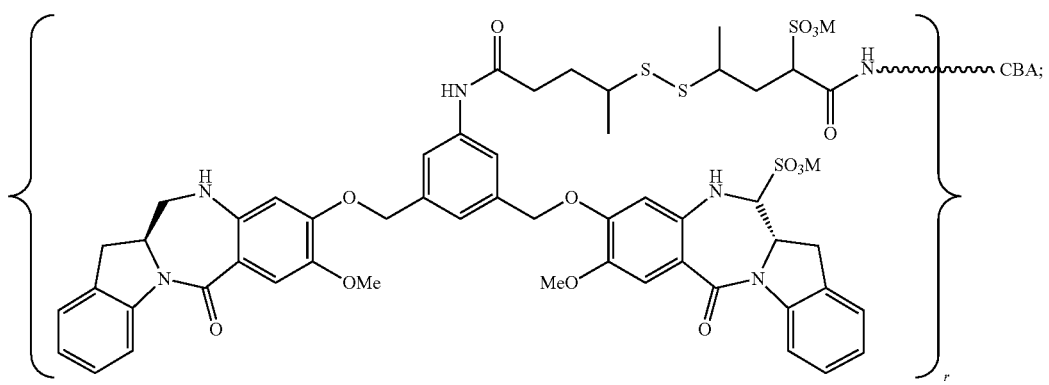

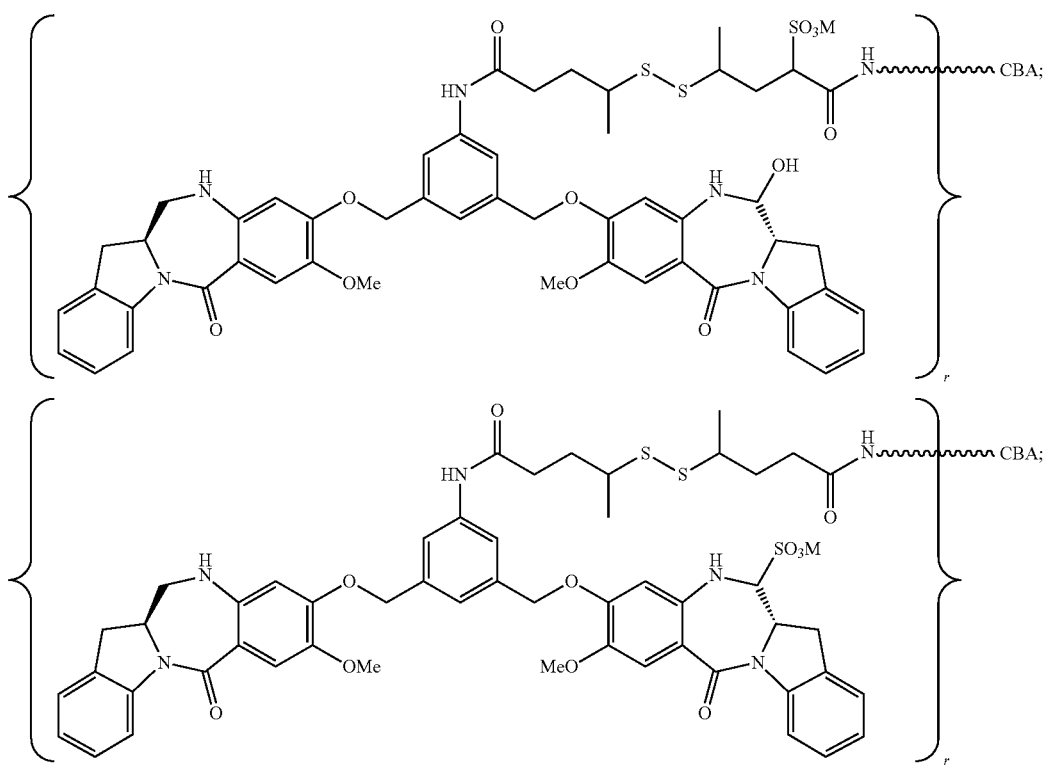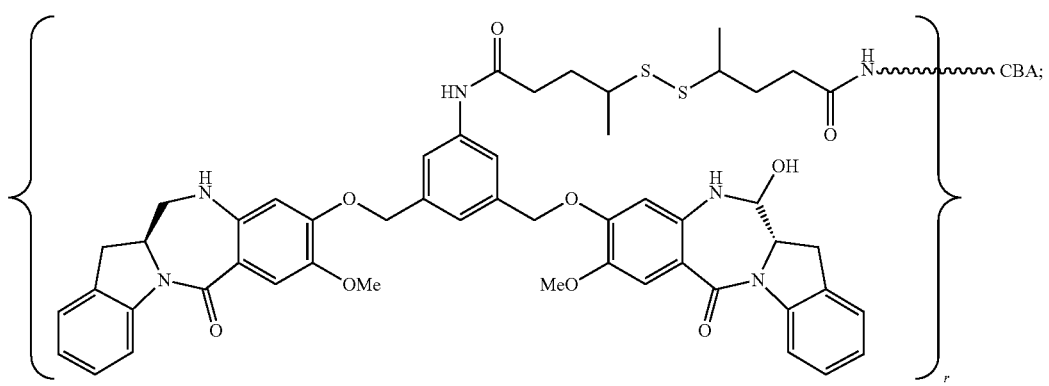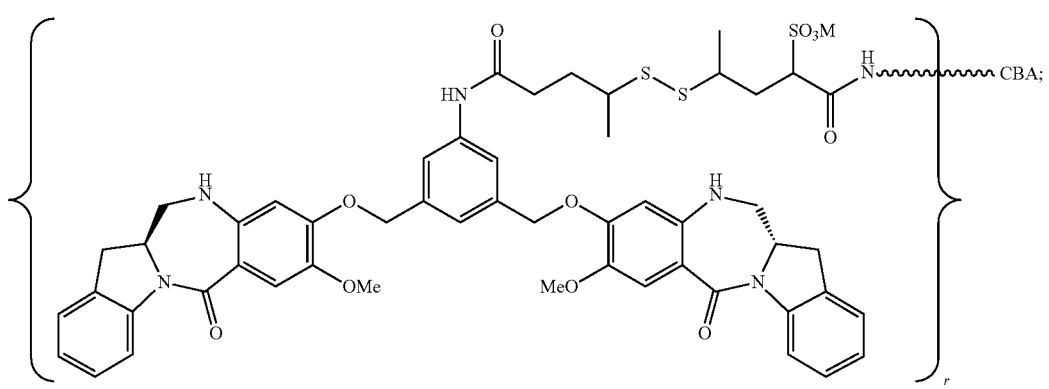

-continued
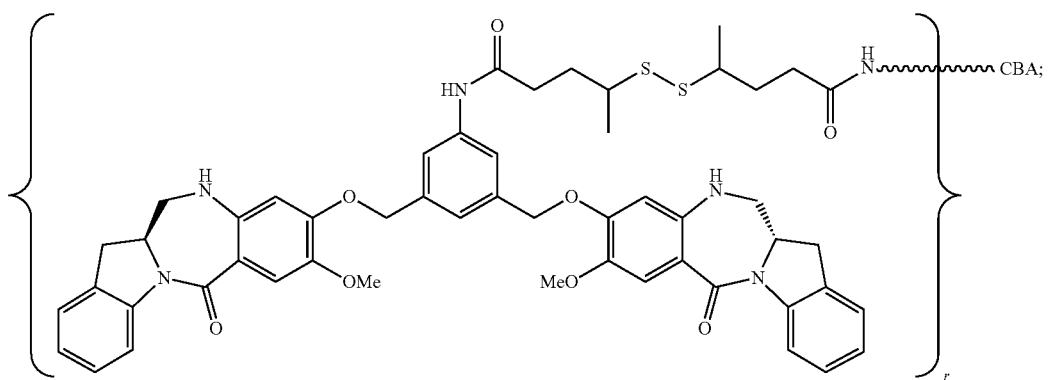
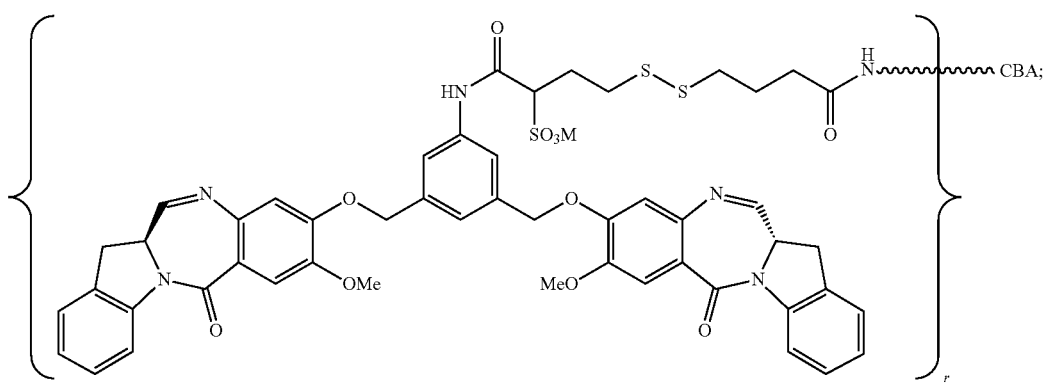
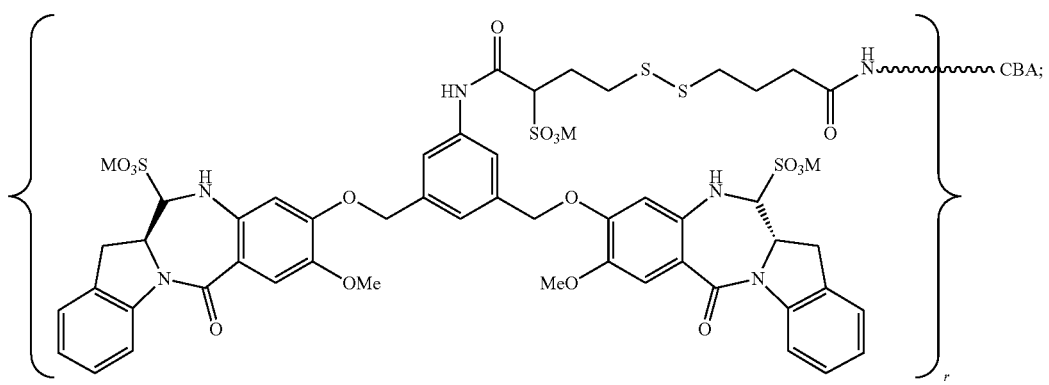
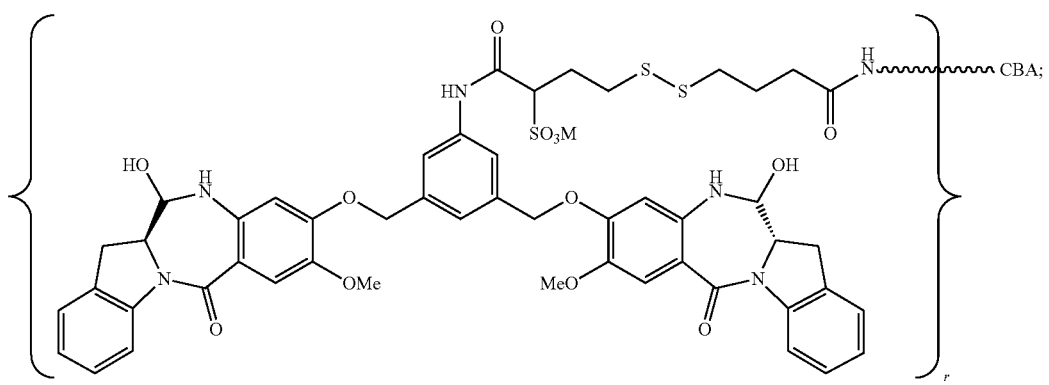

-continued
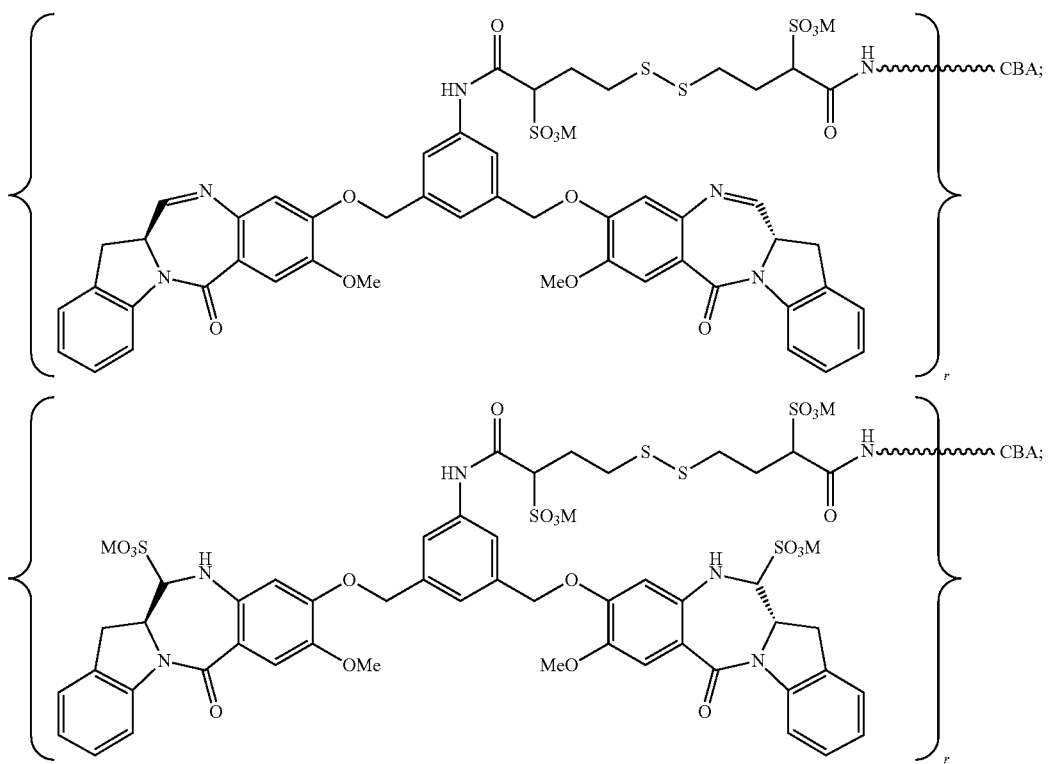
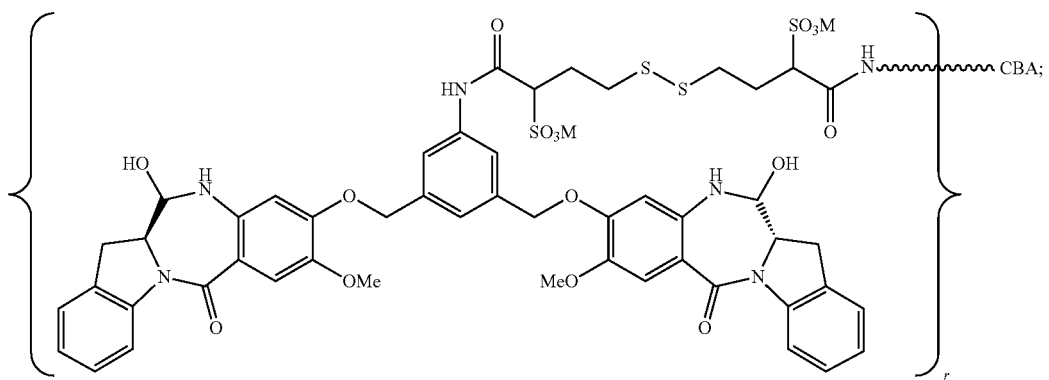
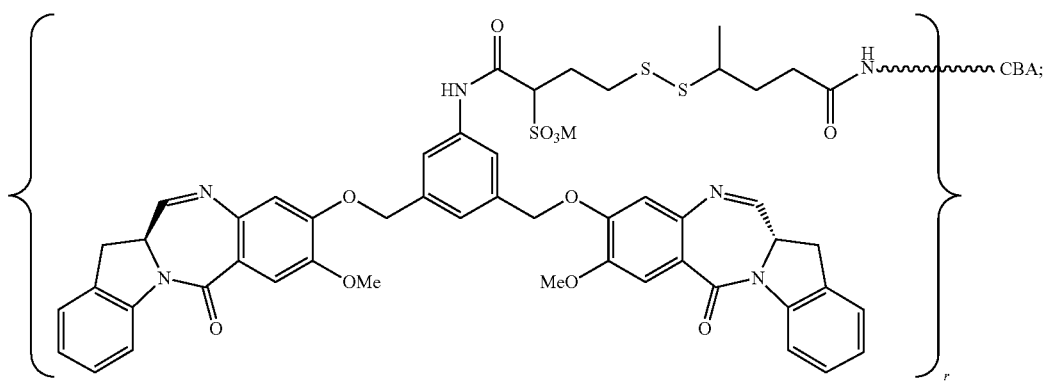

-continued
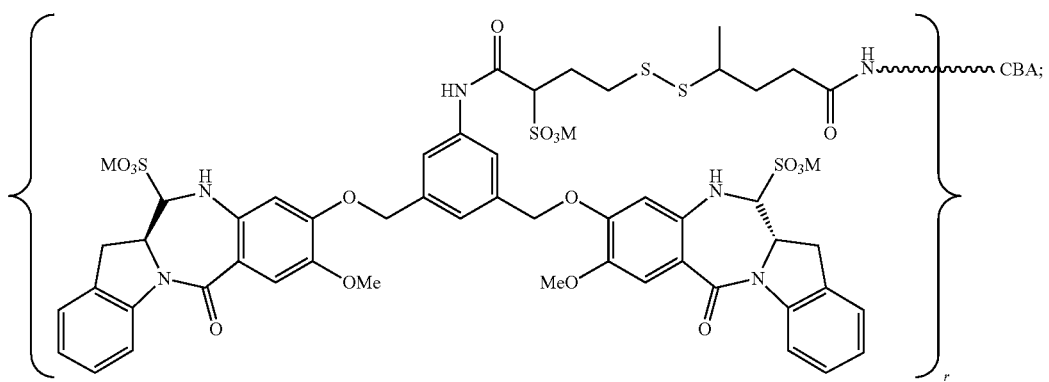
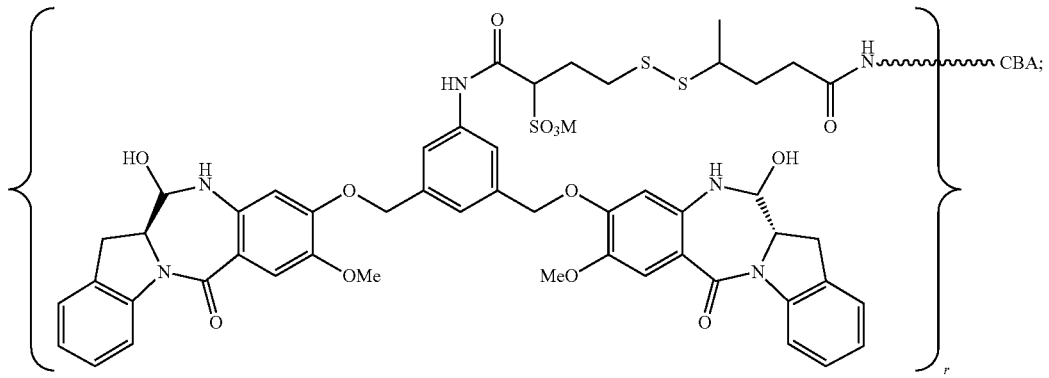
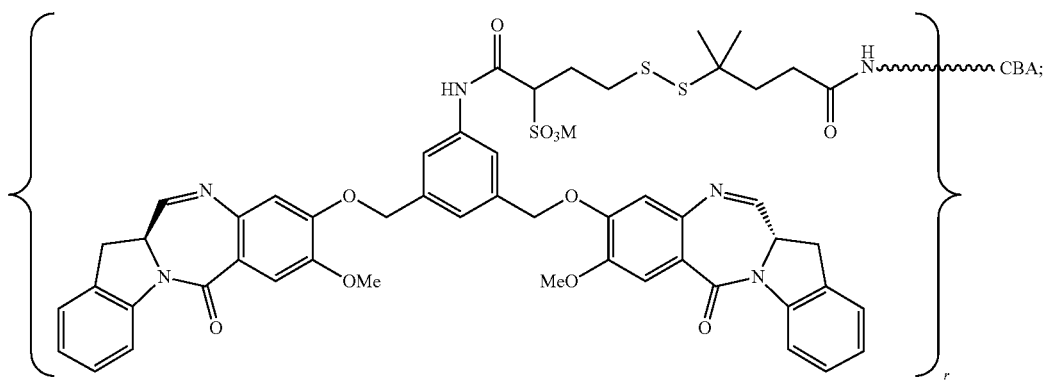
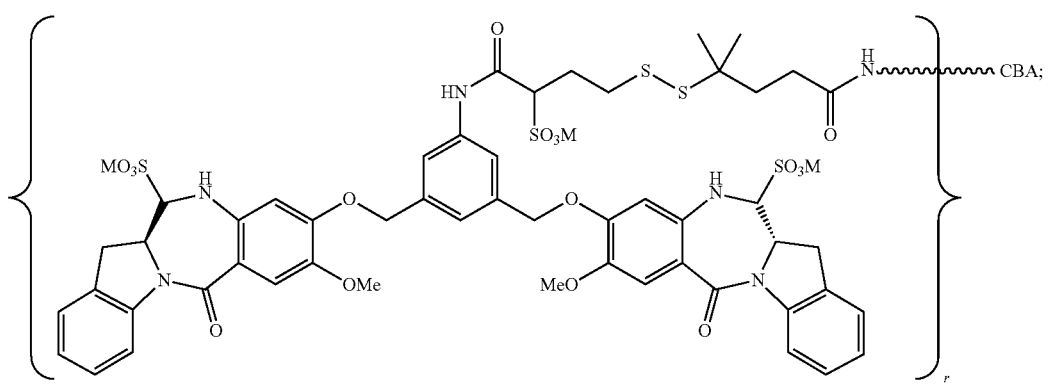

-continued
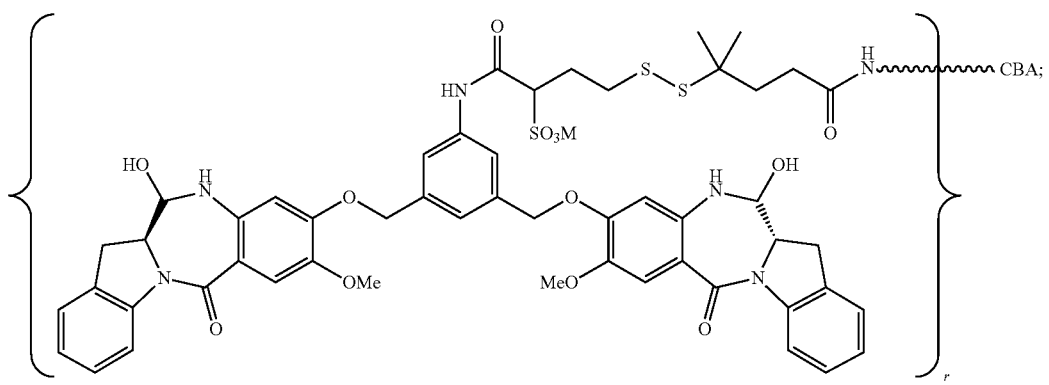
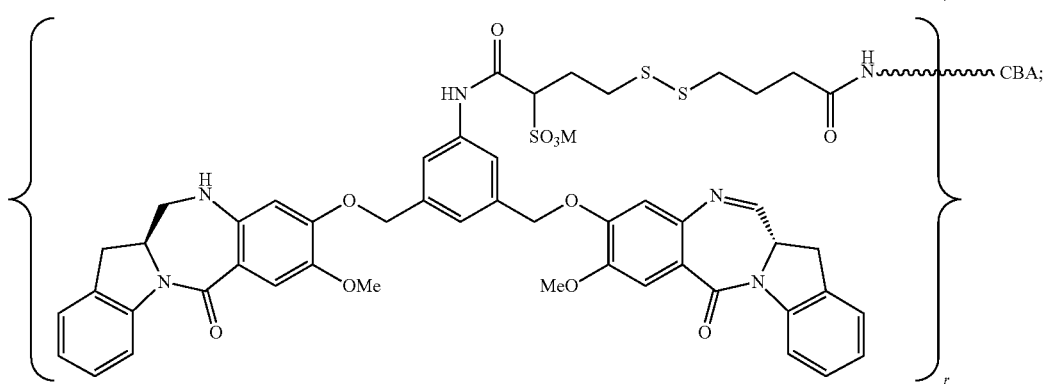
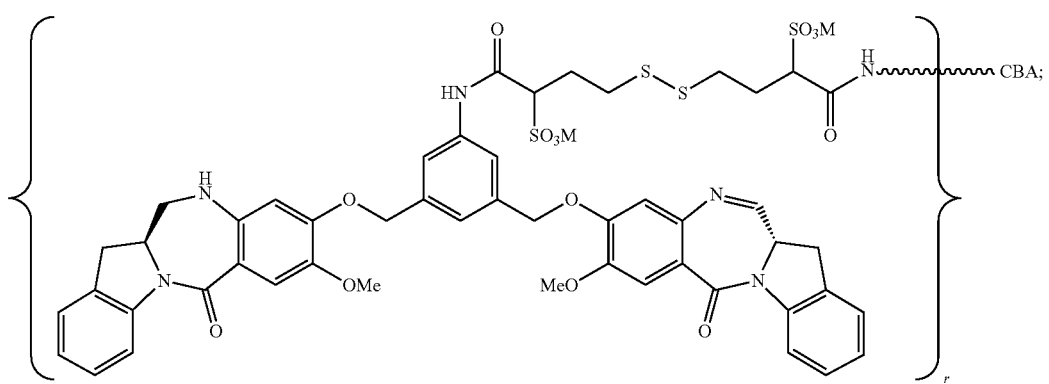
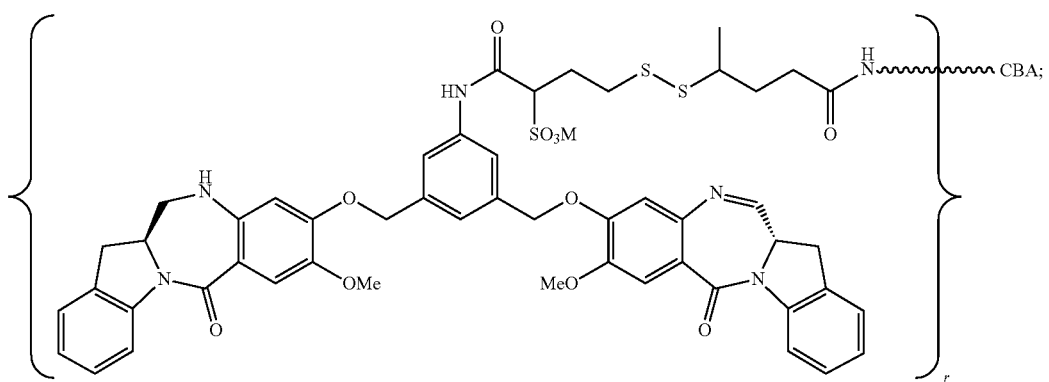

-continued
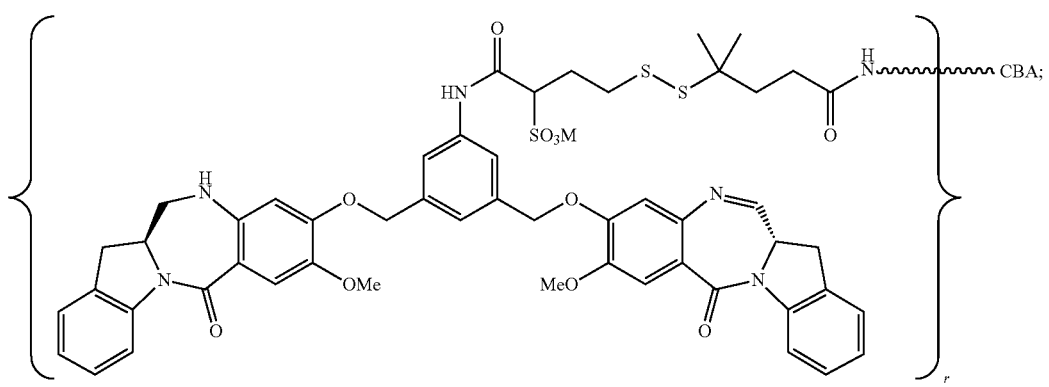
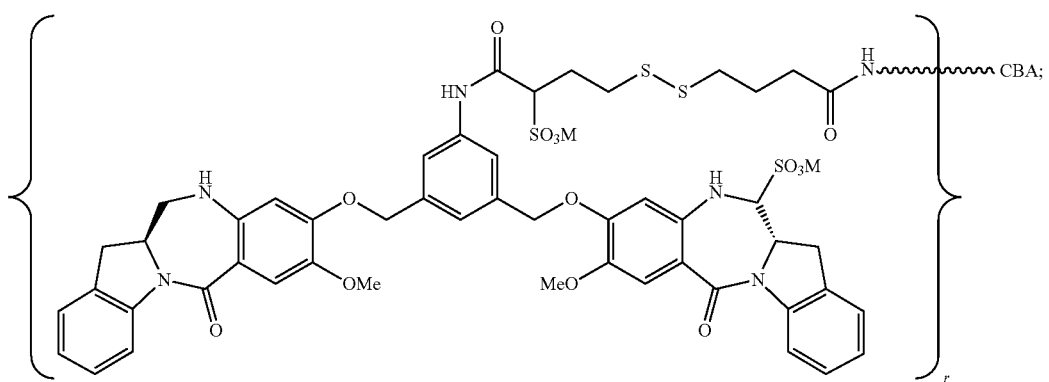
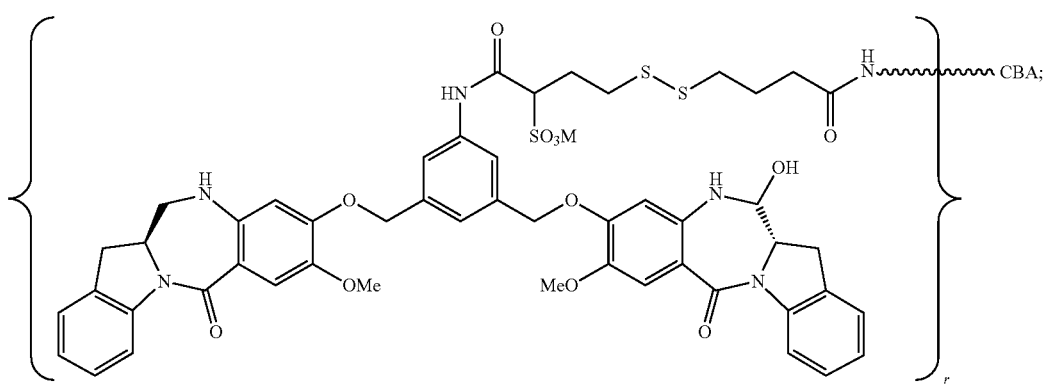
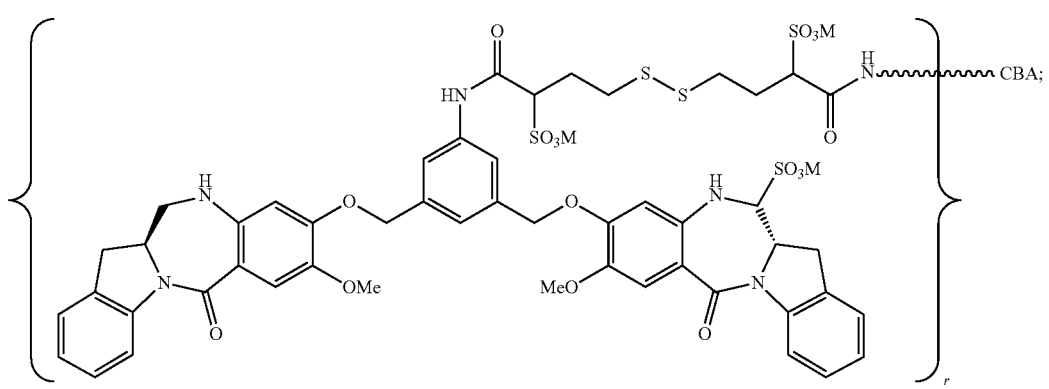

-continued
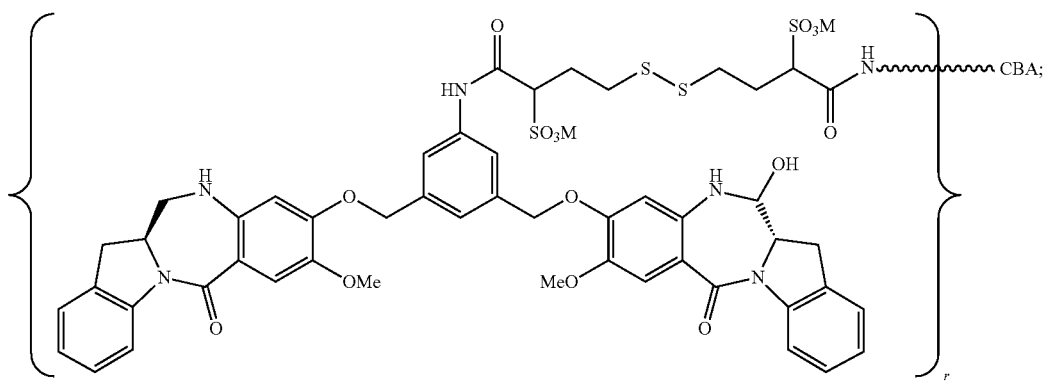
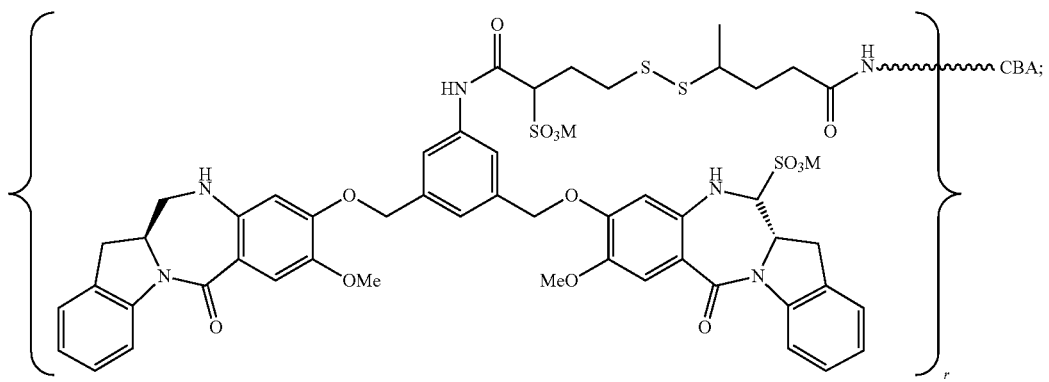
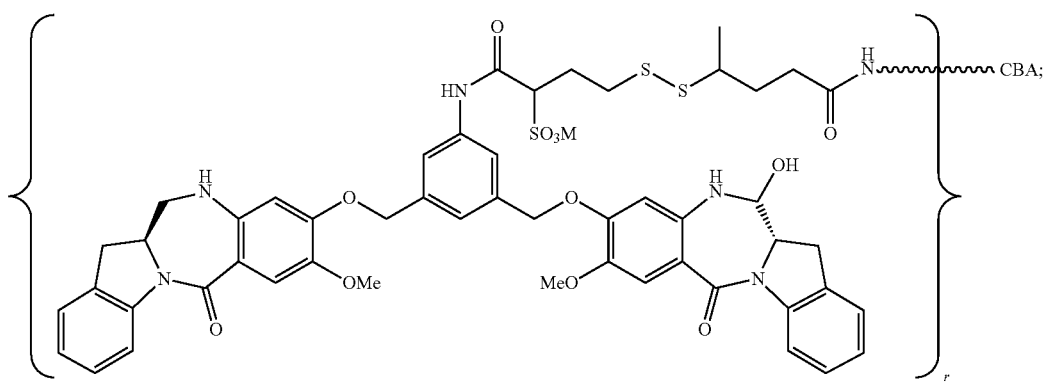
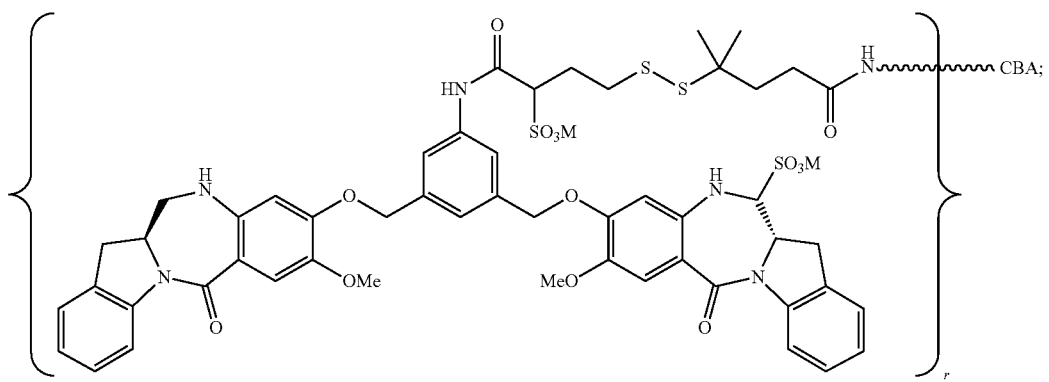

-continued
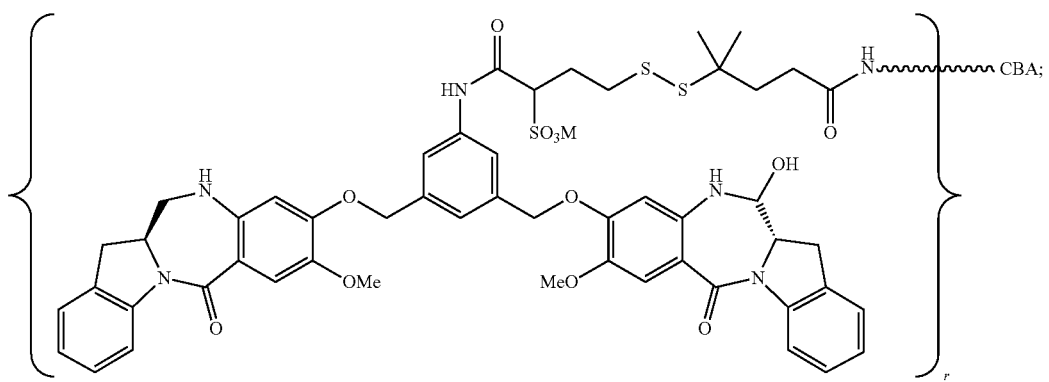
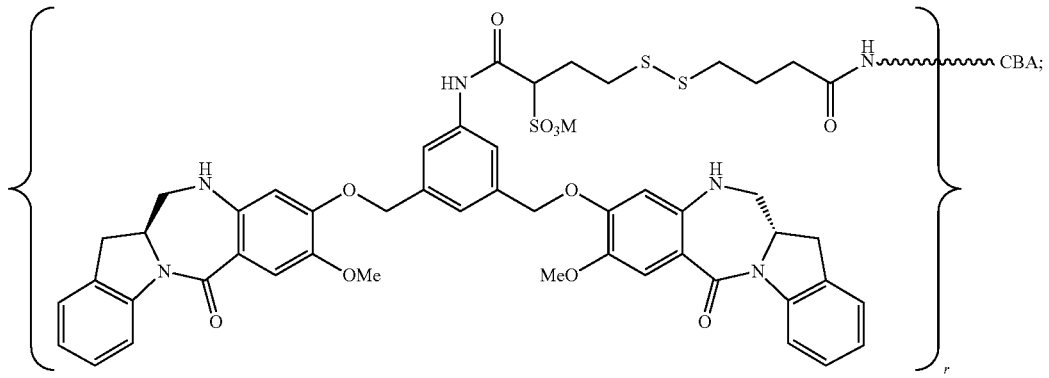
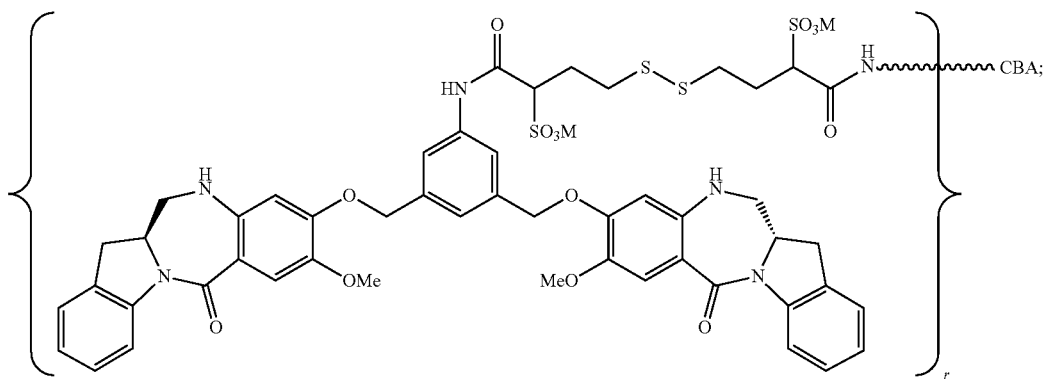
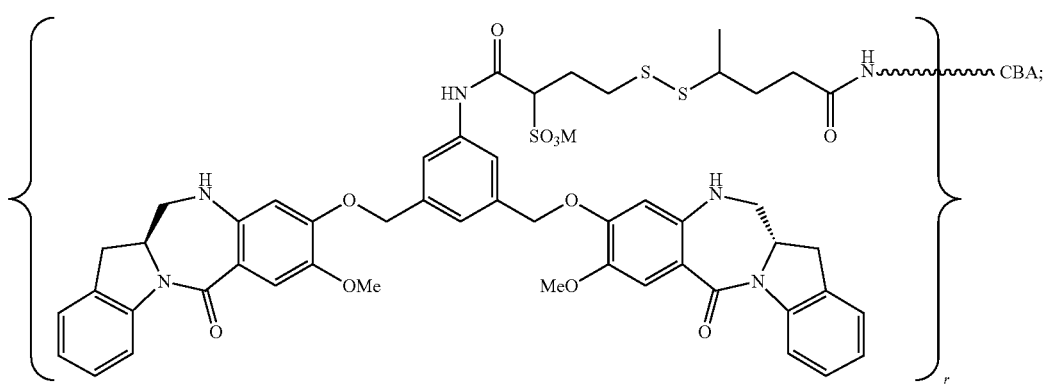

-continued
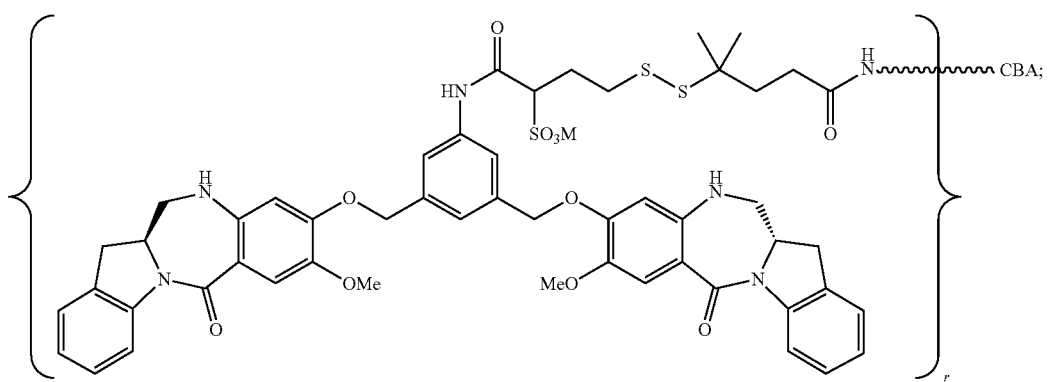
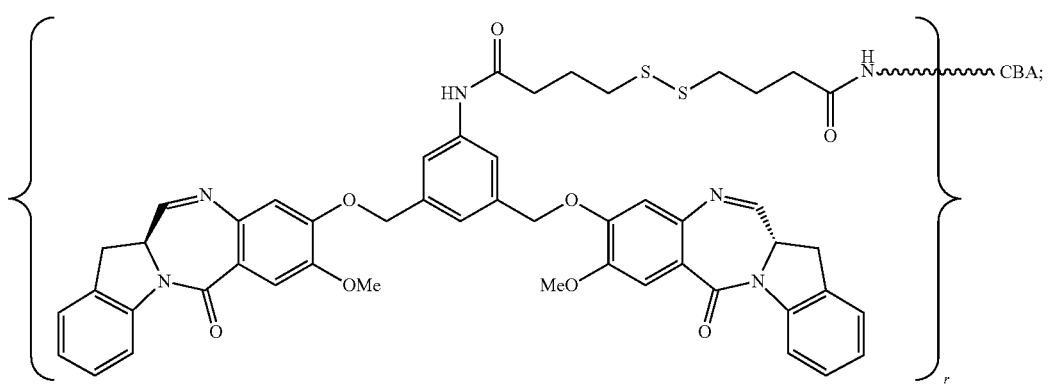
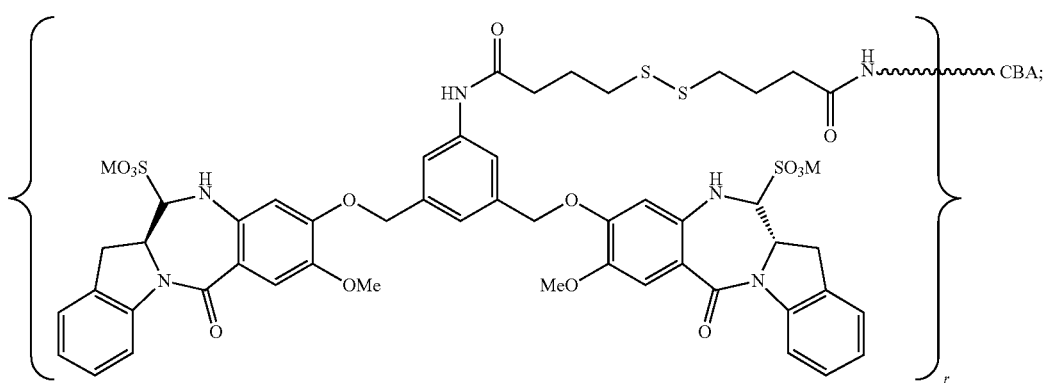
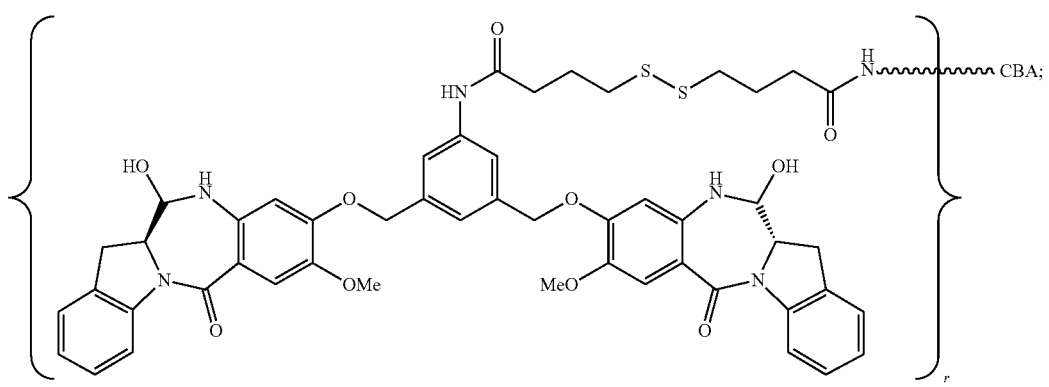

-continued
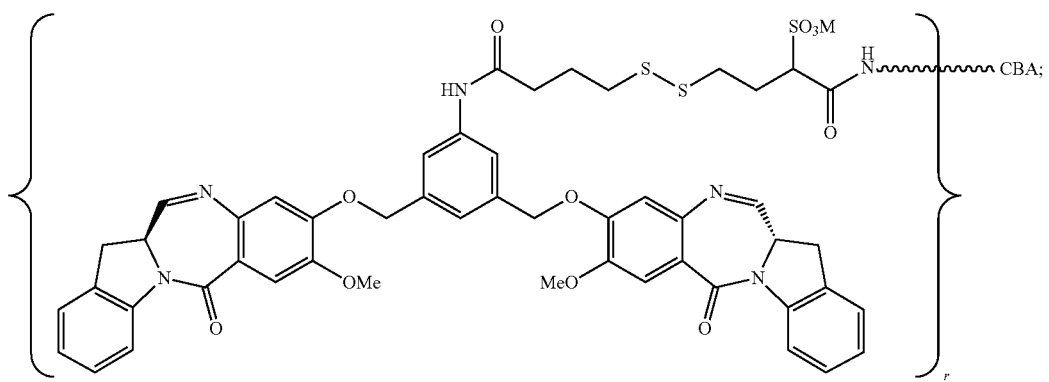
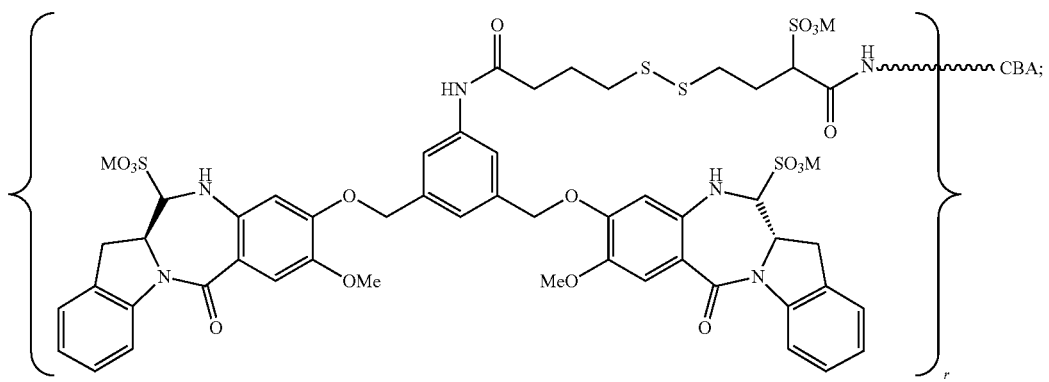
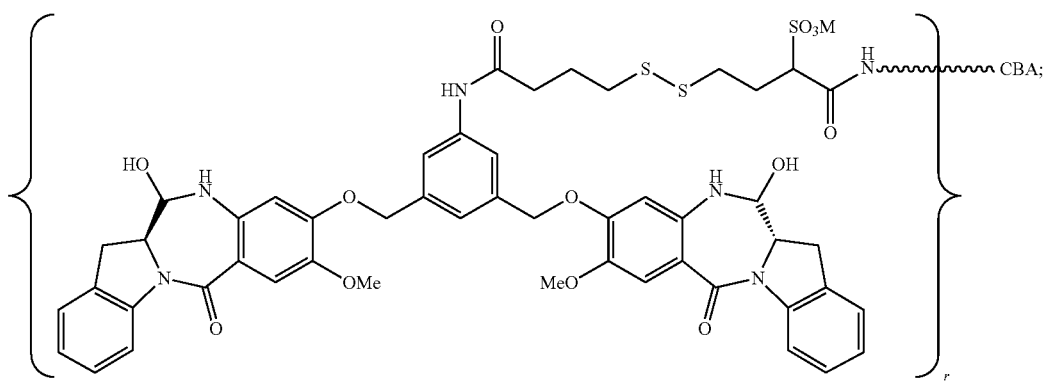
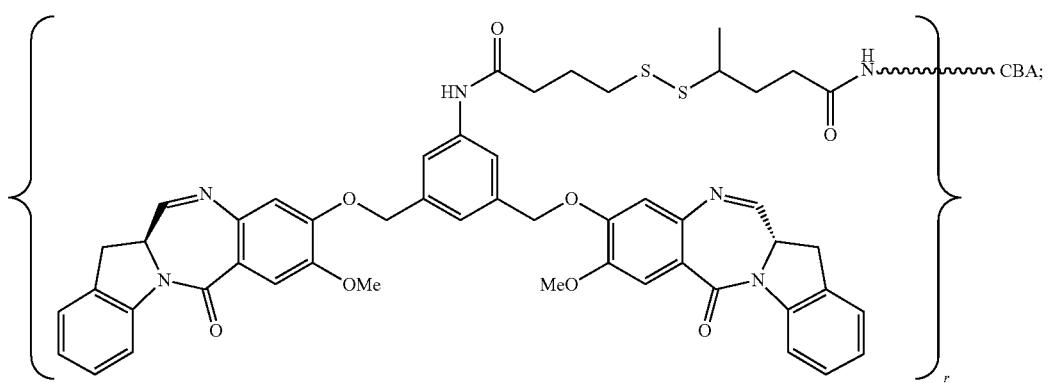

-continued
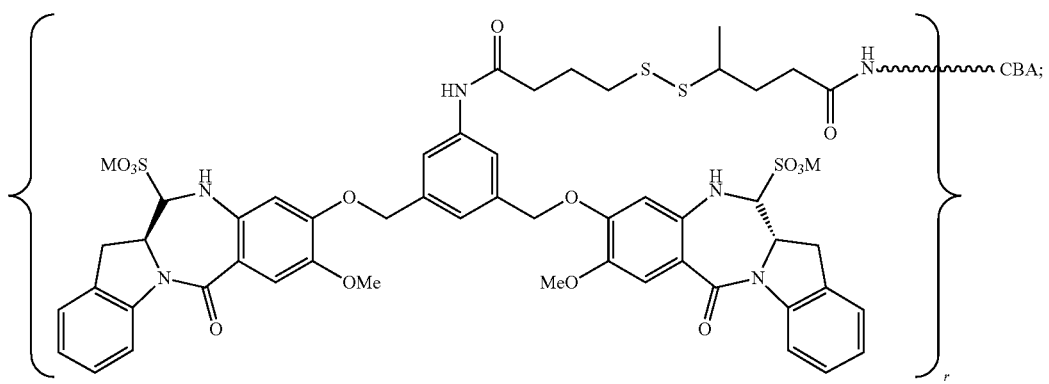
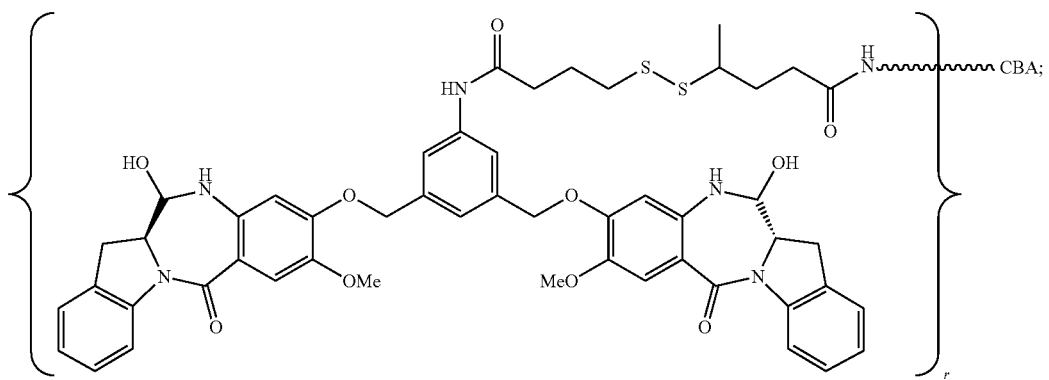
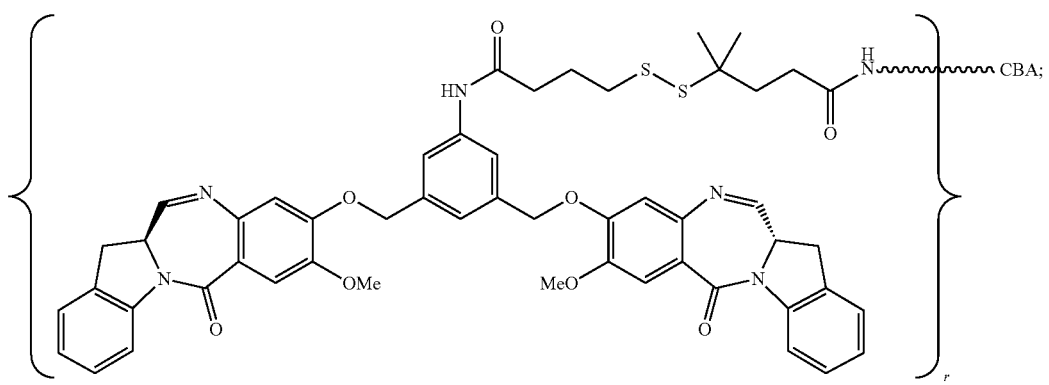
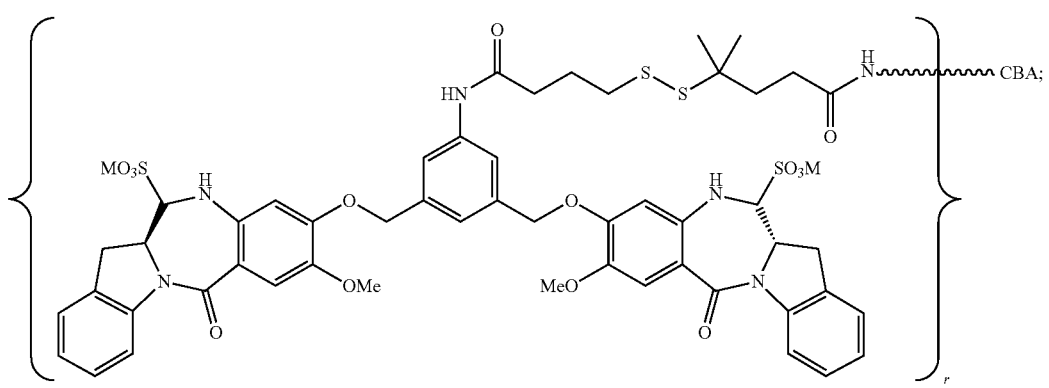

-continued
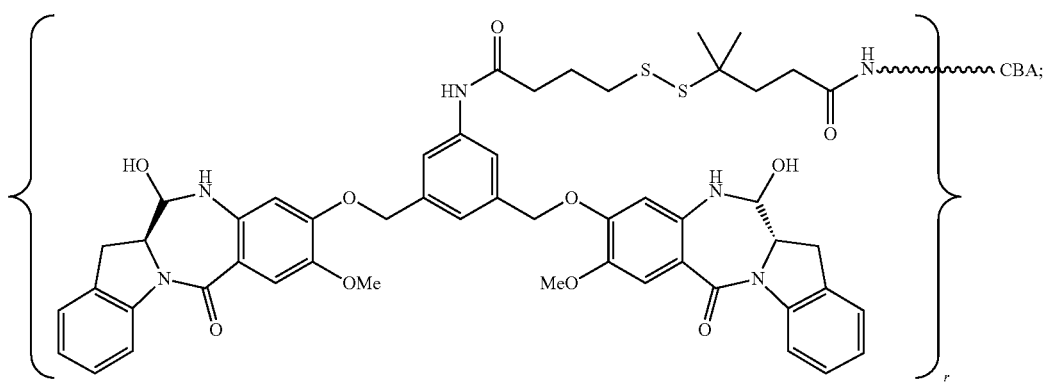
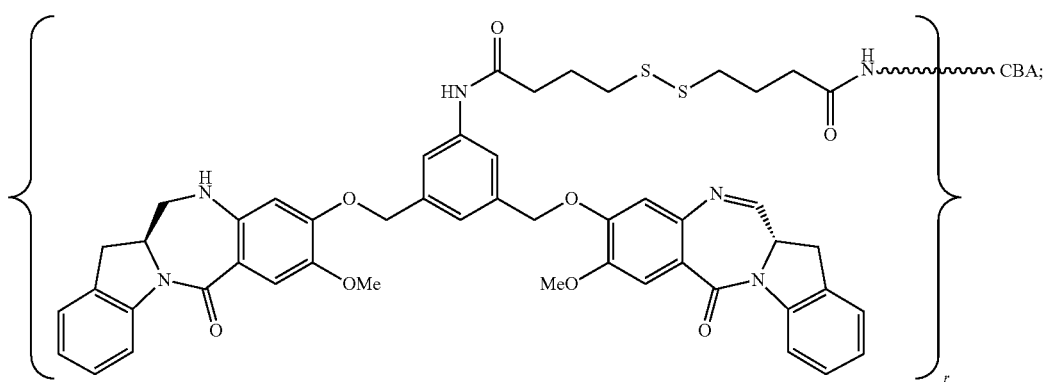
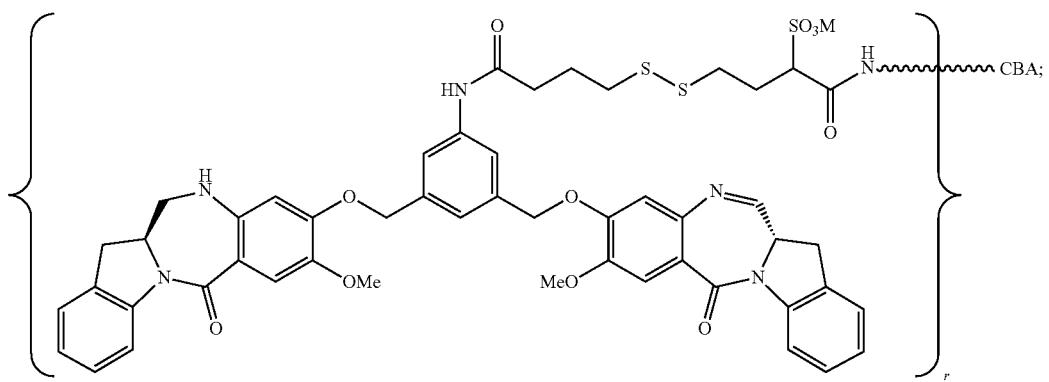
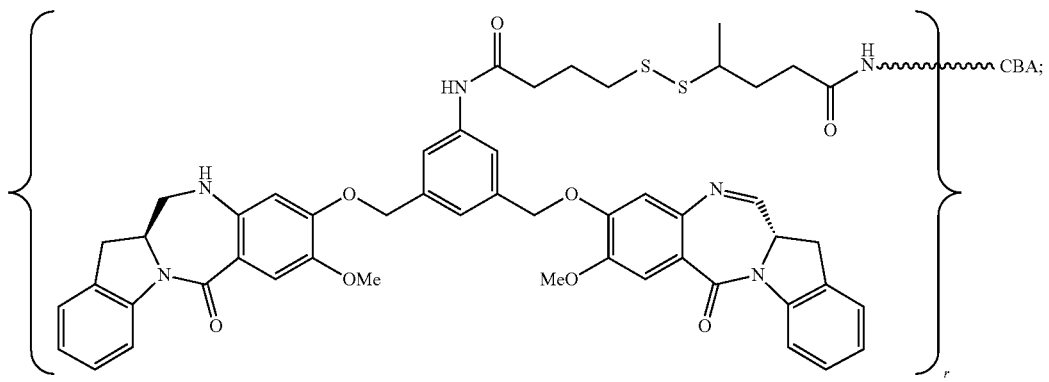

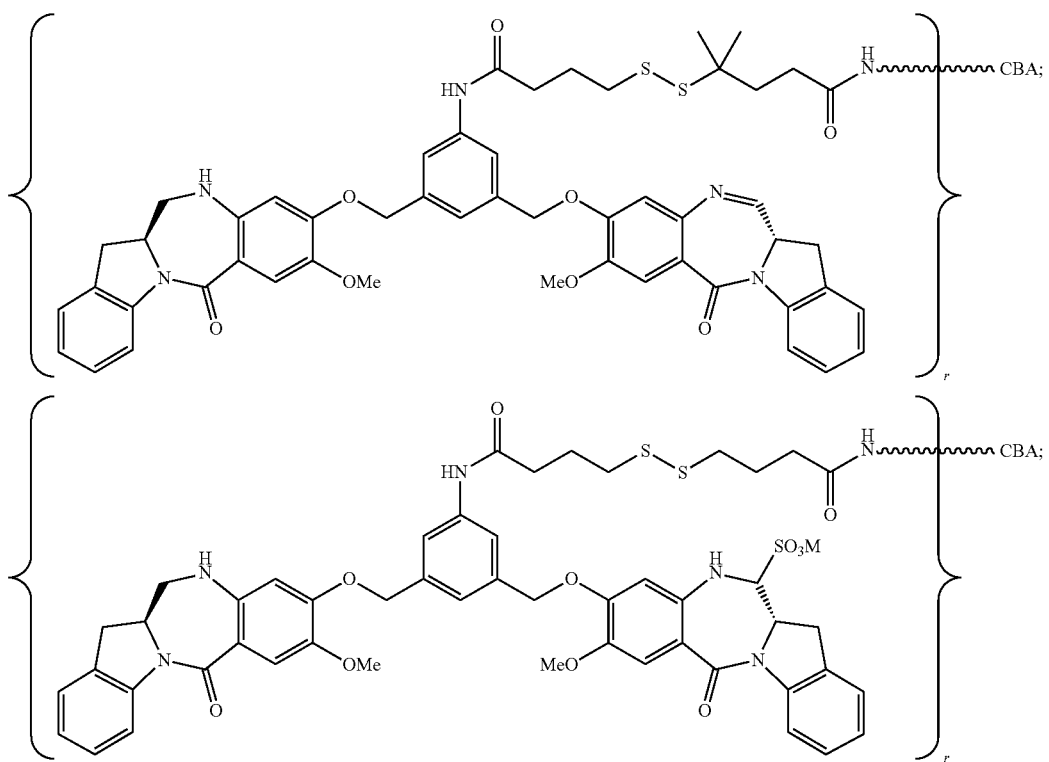
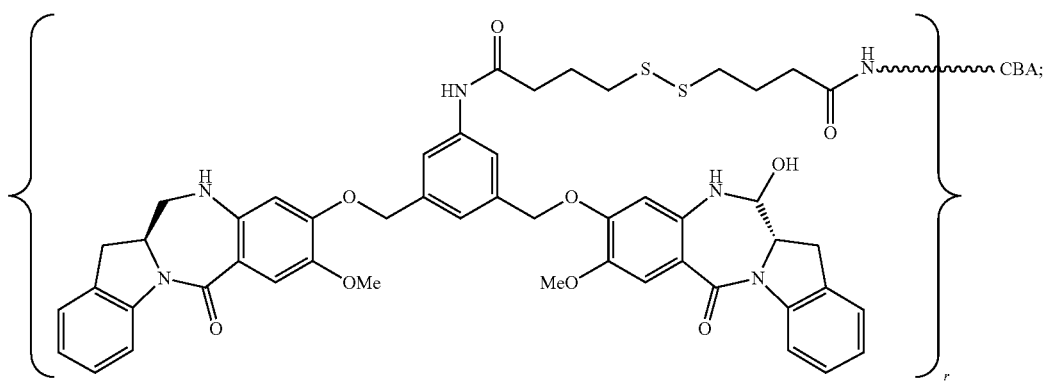
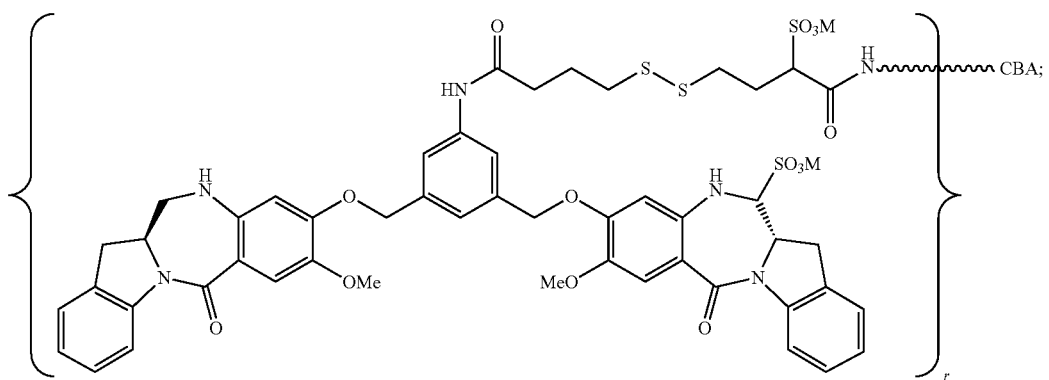

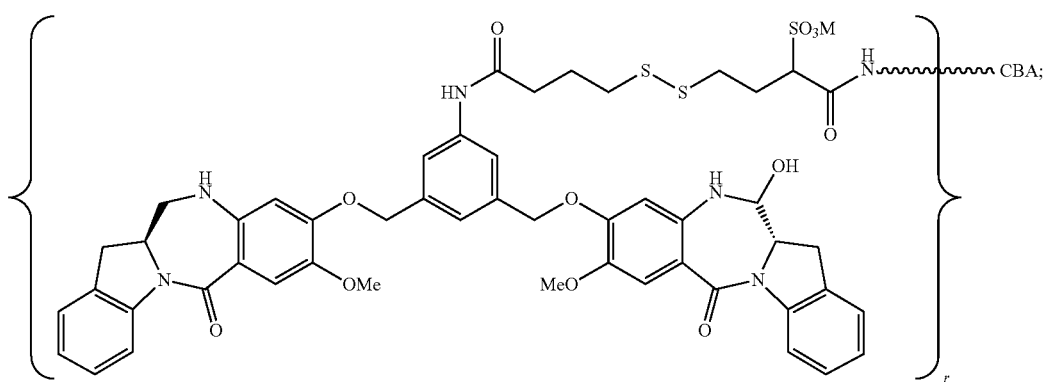
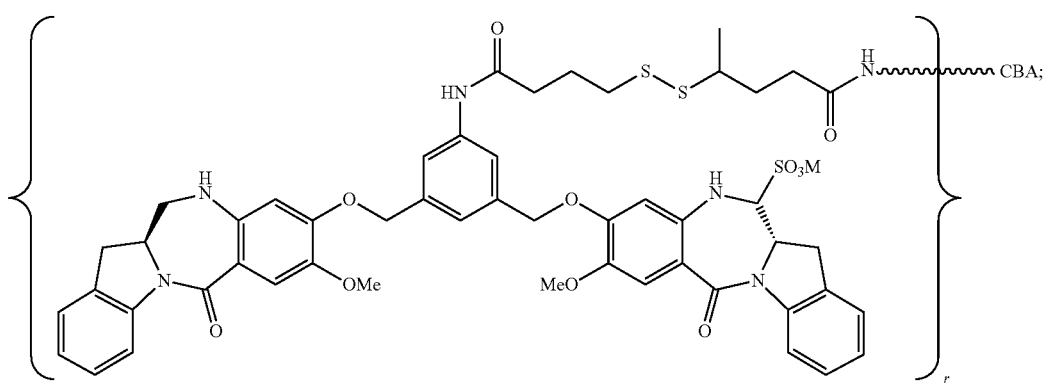
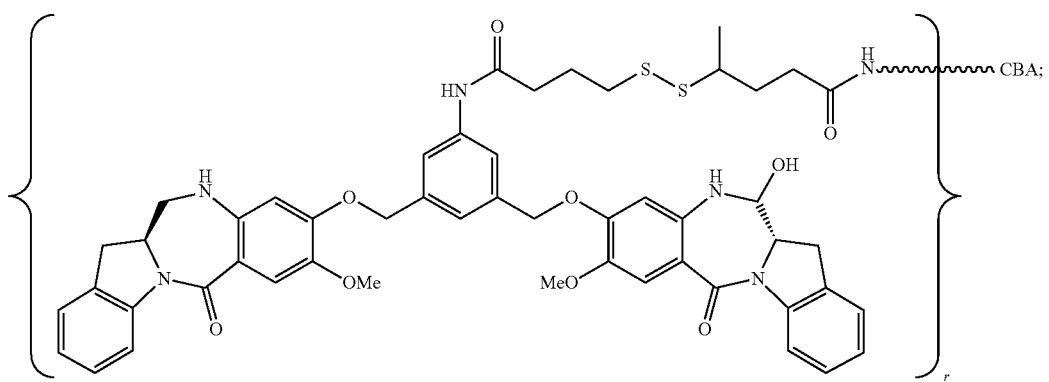
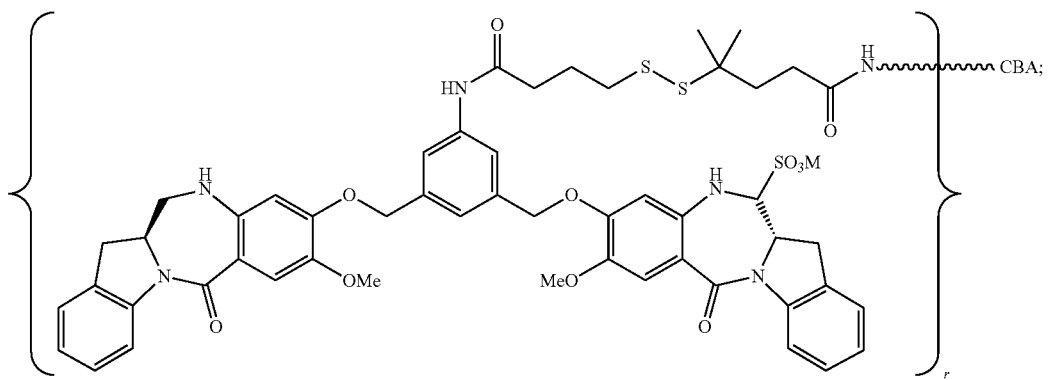

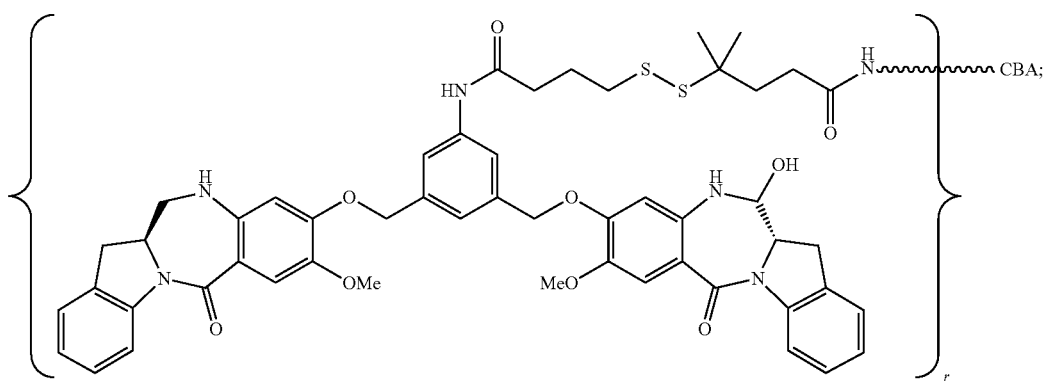
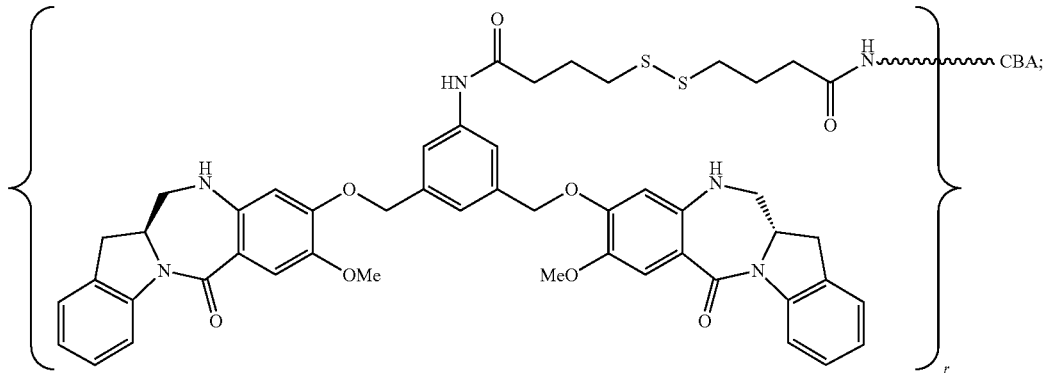
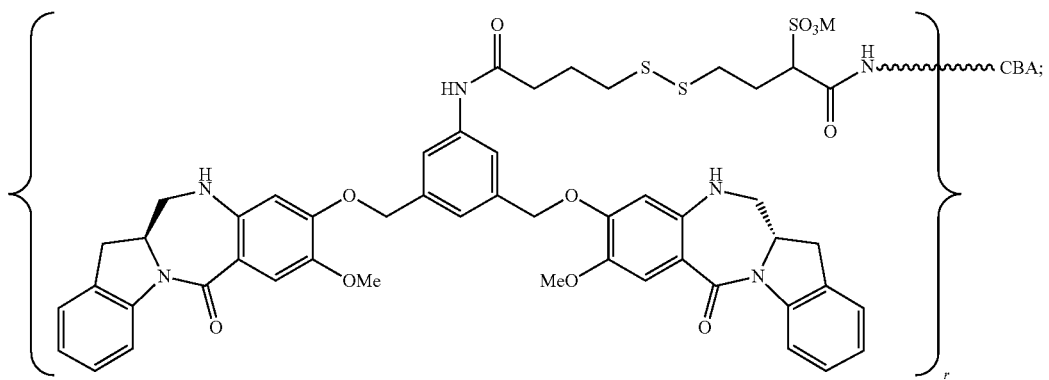
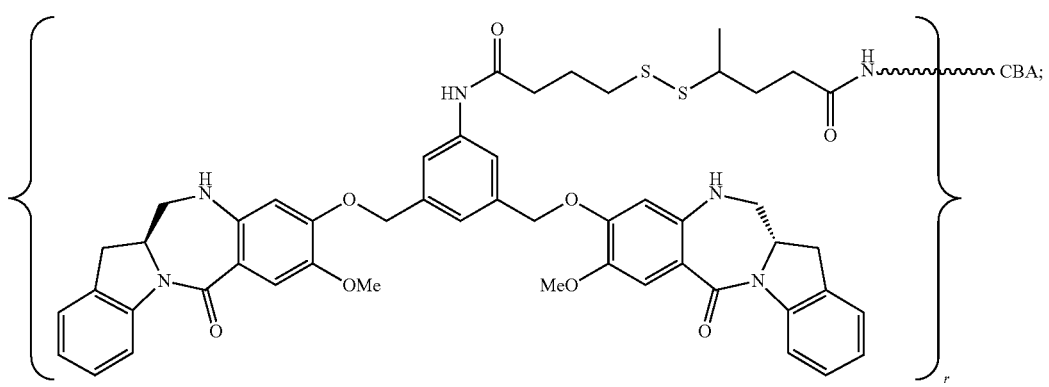

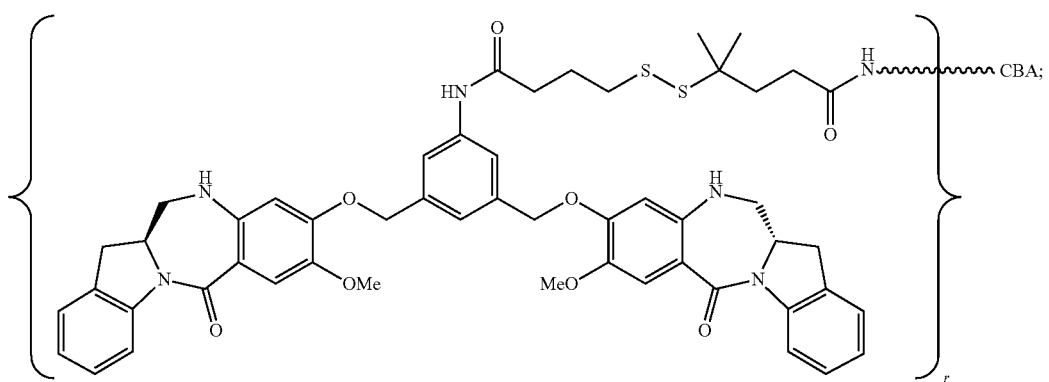
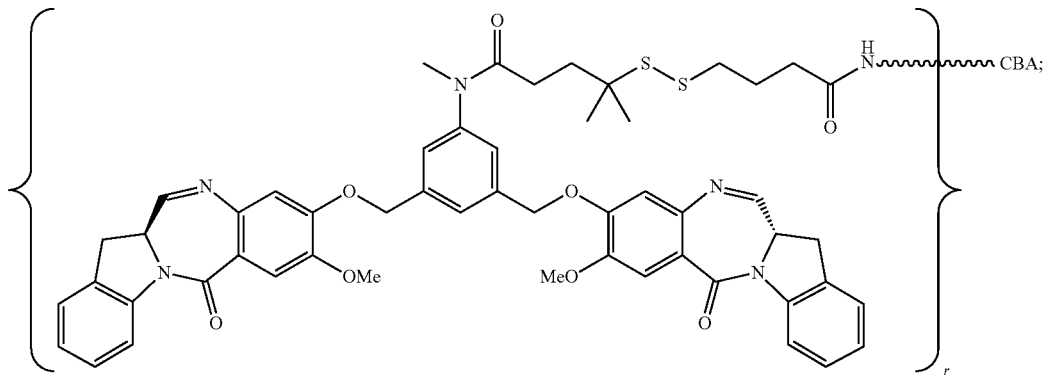
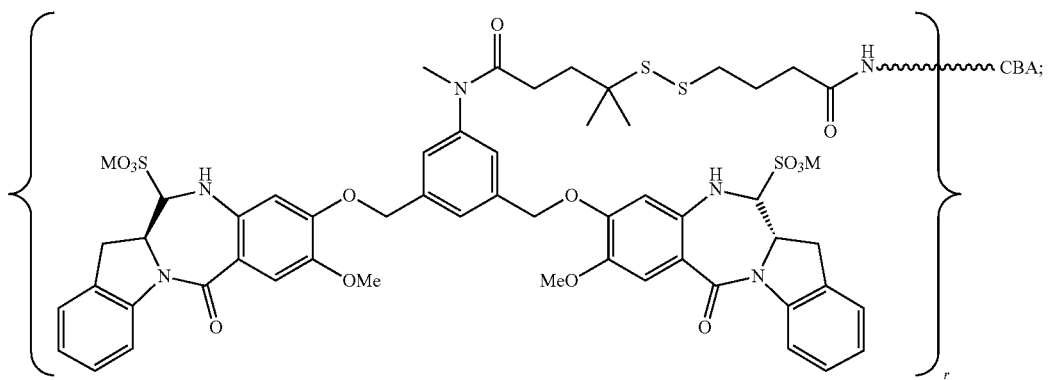
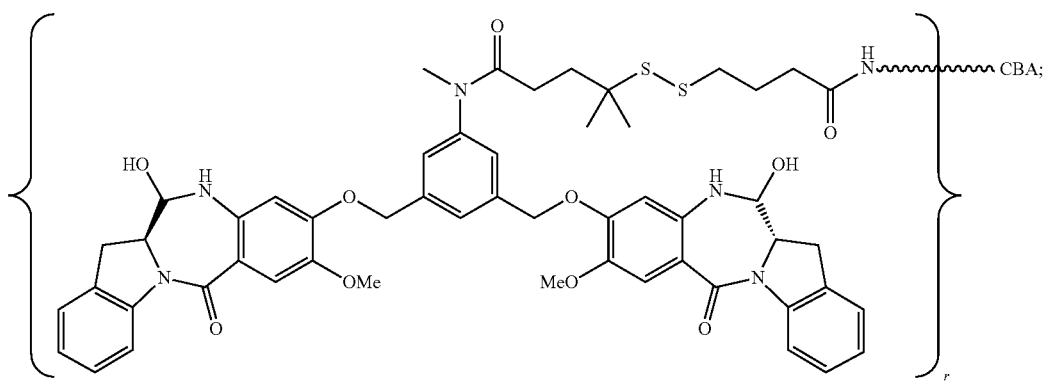

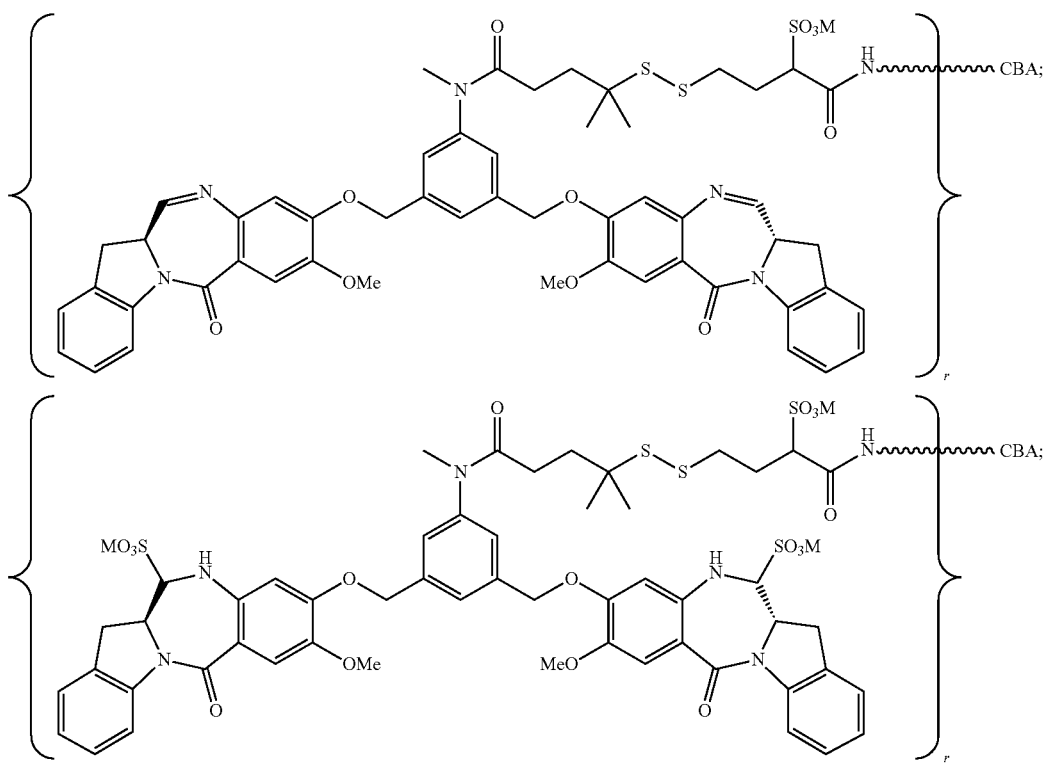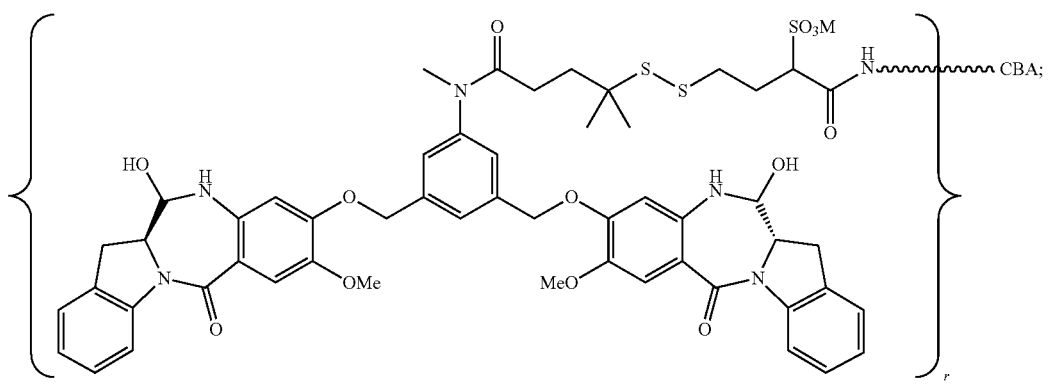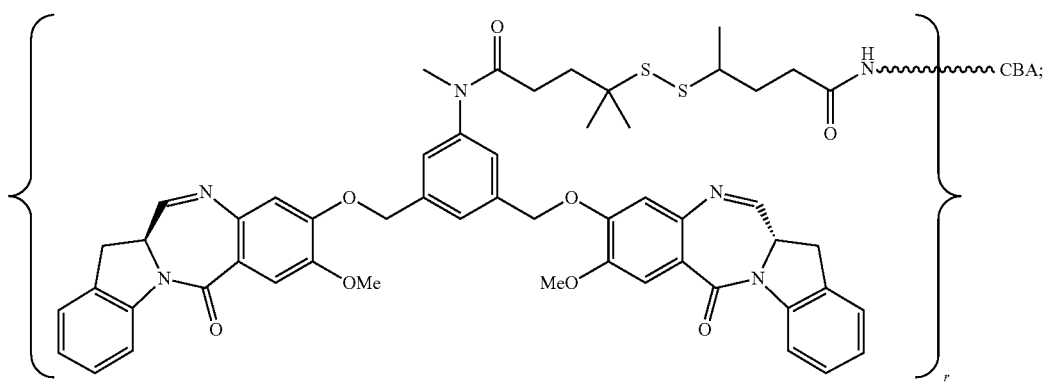

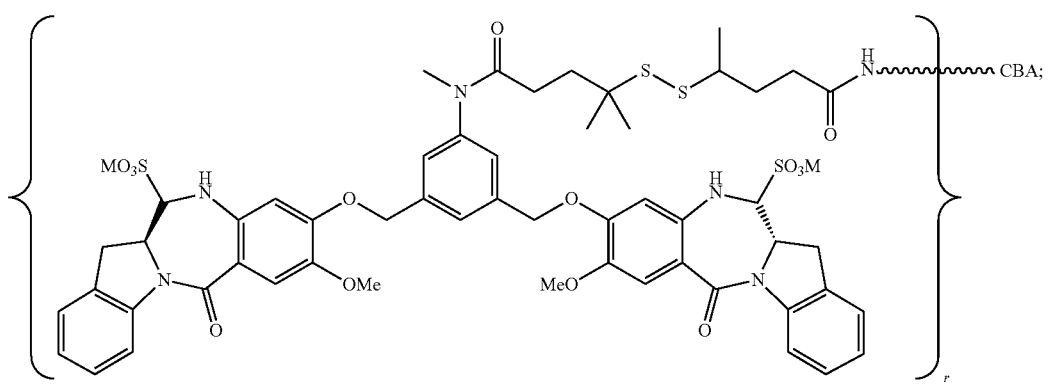
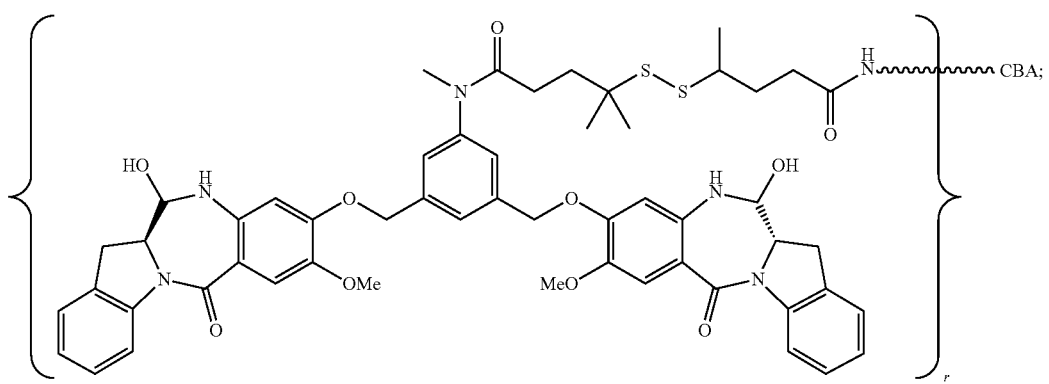
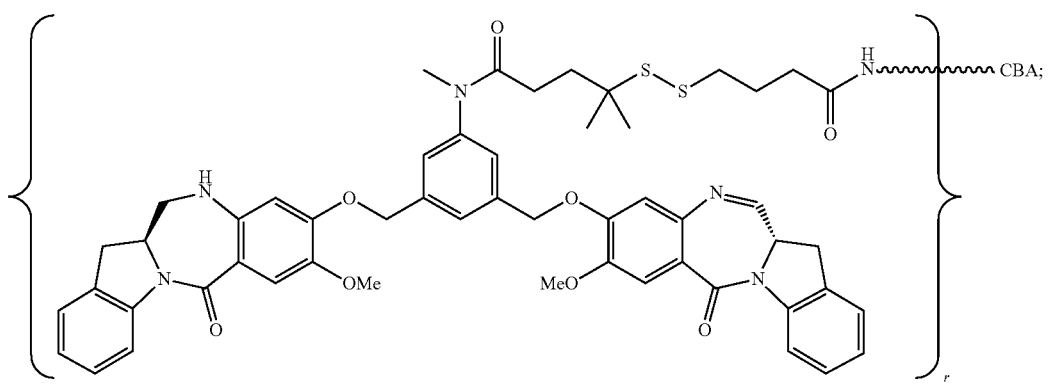
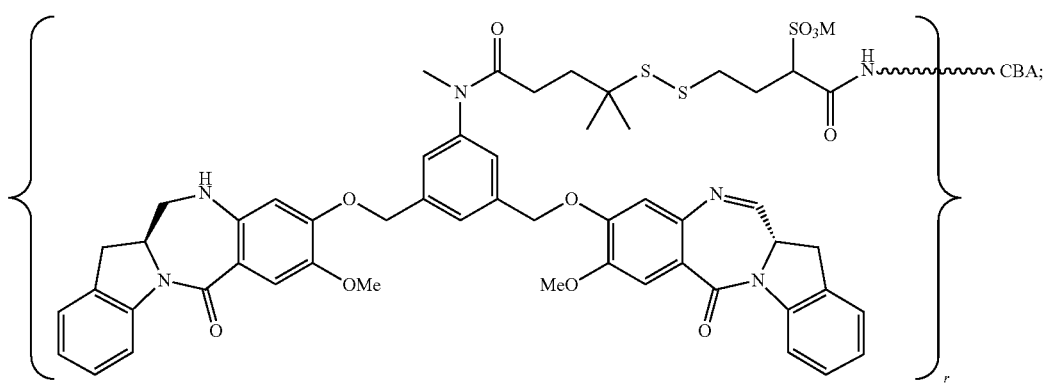

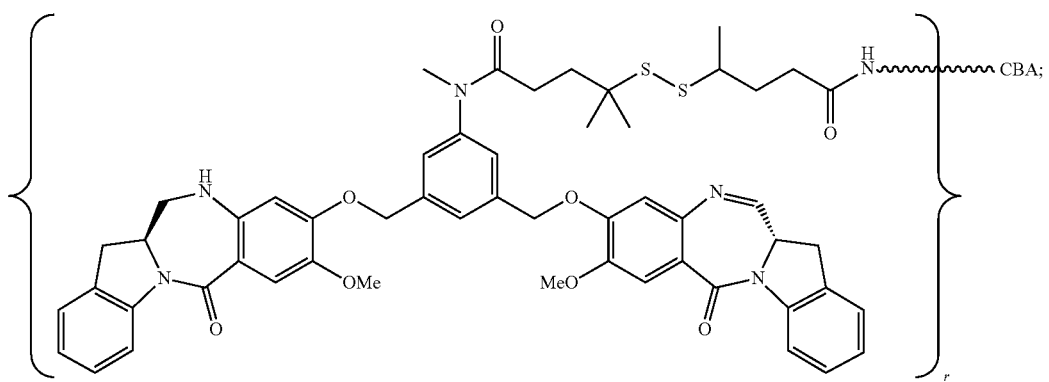
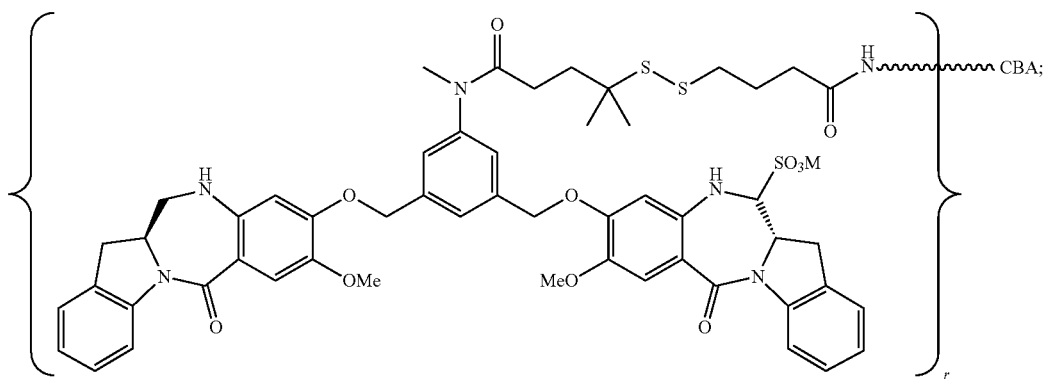
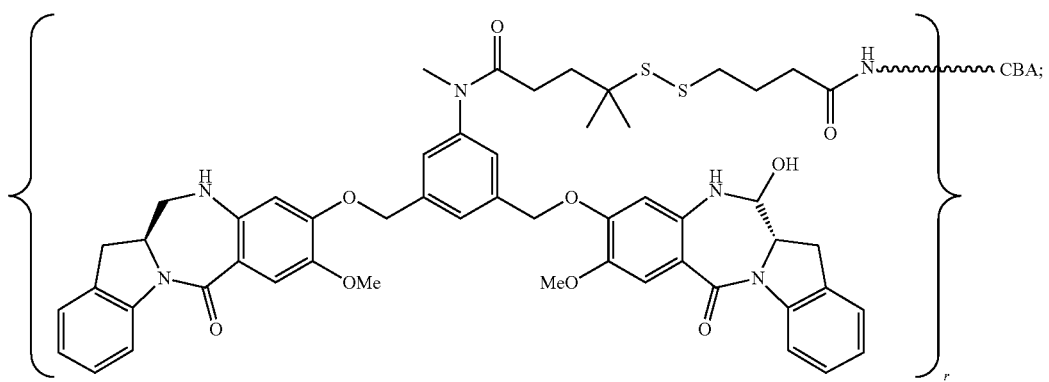
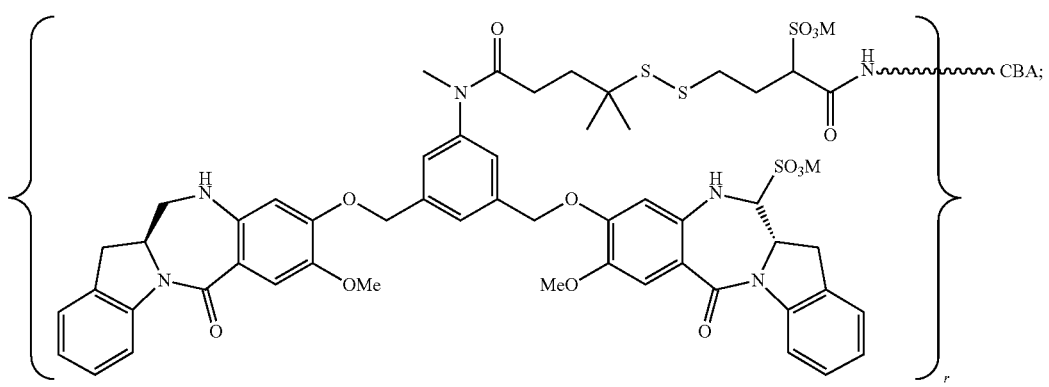

-continued
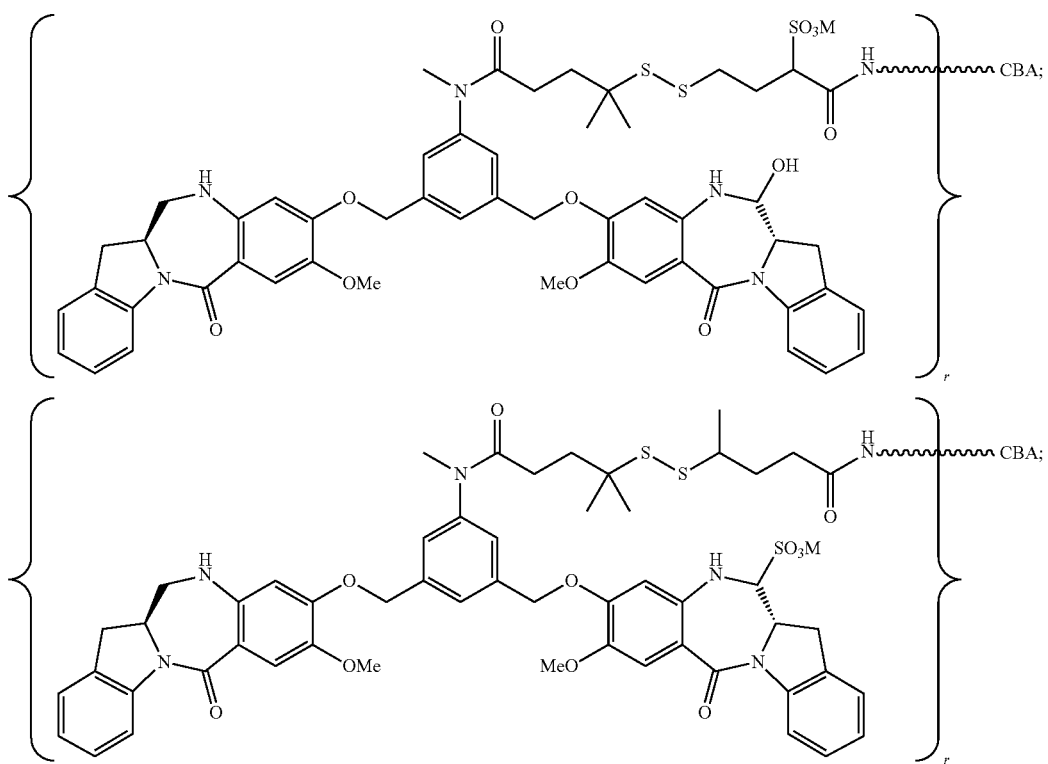
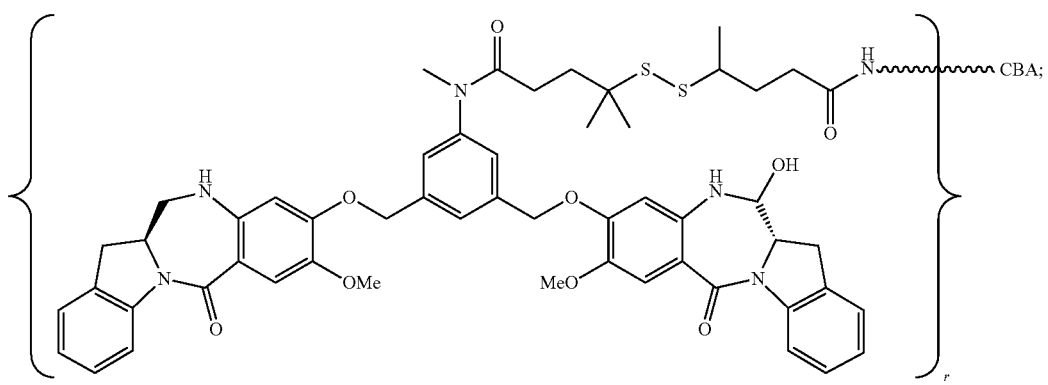
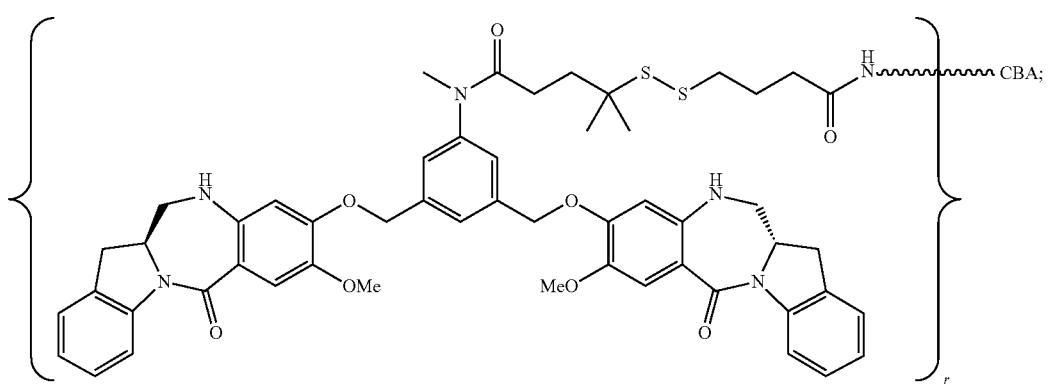

-continued
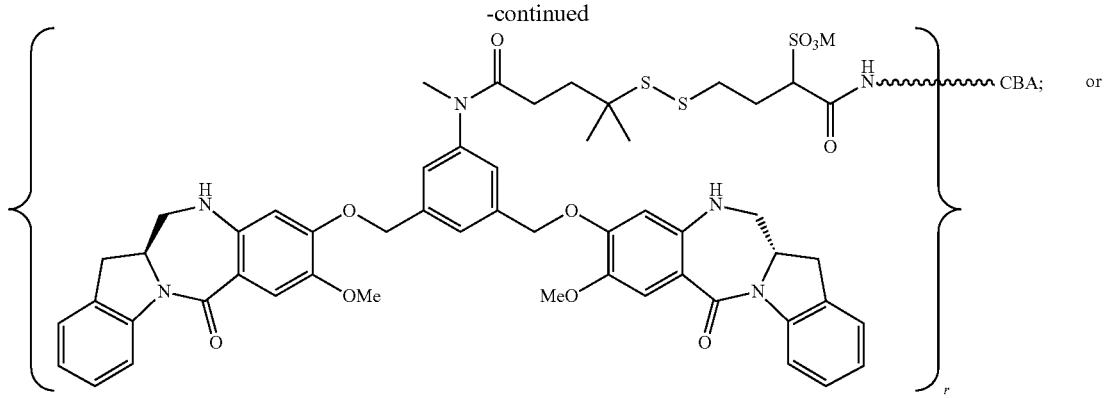
or
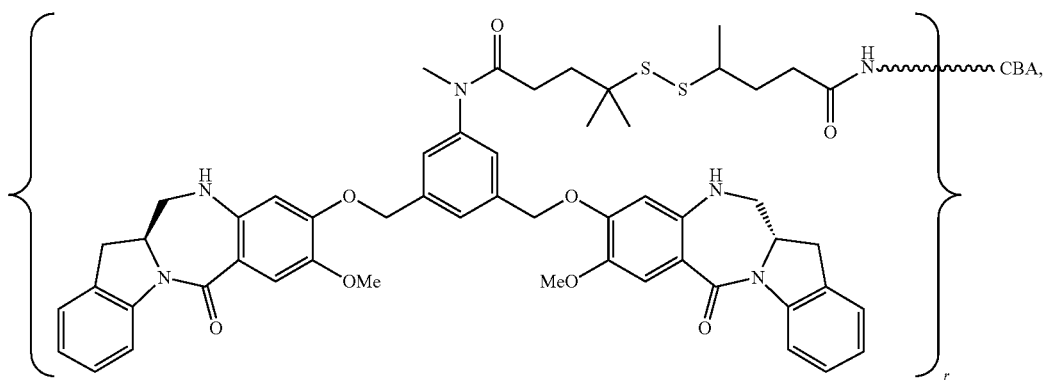
or a pharmaceutically acceptable salt thereof, wherein M is H⁺ or a pharmaceutically acceptable cation; and r is an integer from 1 to 10. More specifically, M is H⁺, Na⁺ or K⁺.
In a 11$^{th}$ specific embodiment, the conjugate is represented by any one of the following formulas:
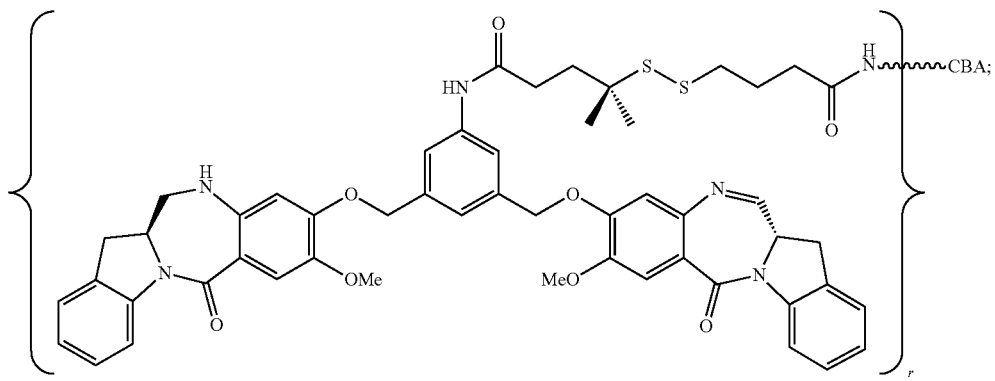

-continued
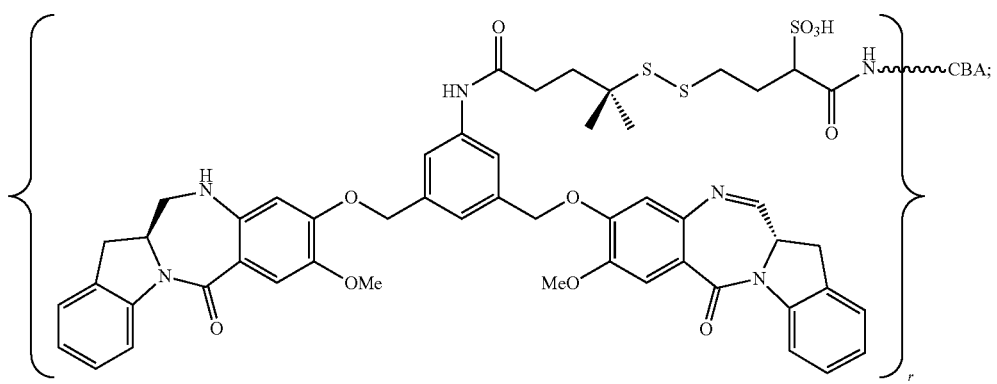
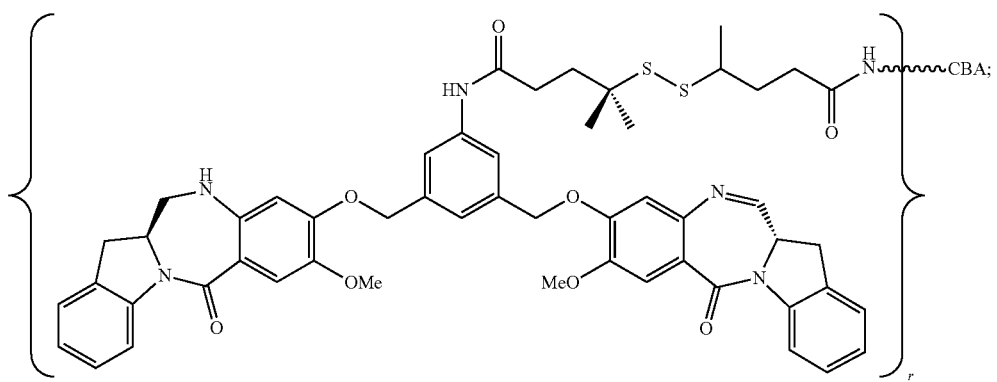
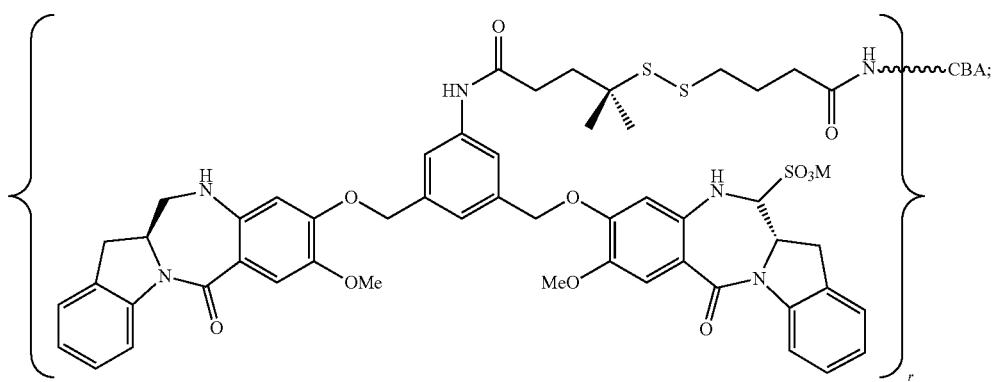
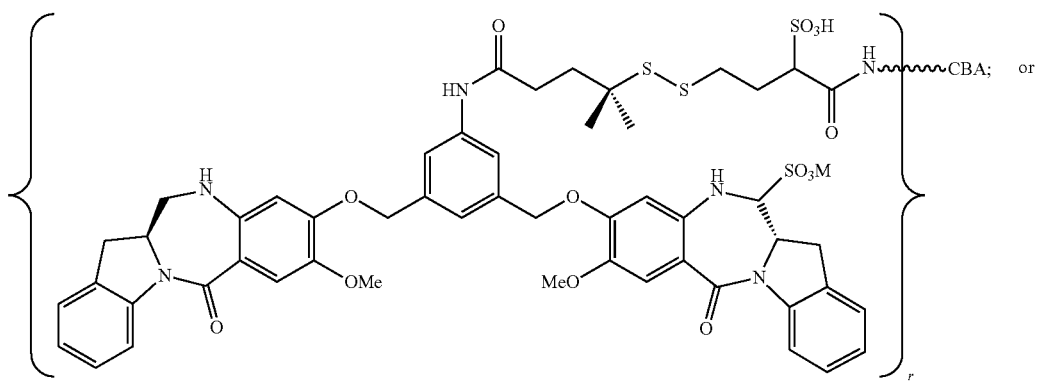 or

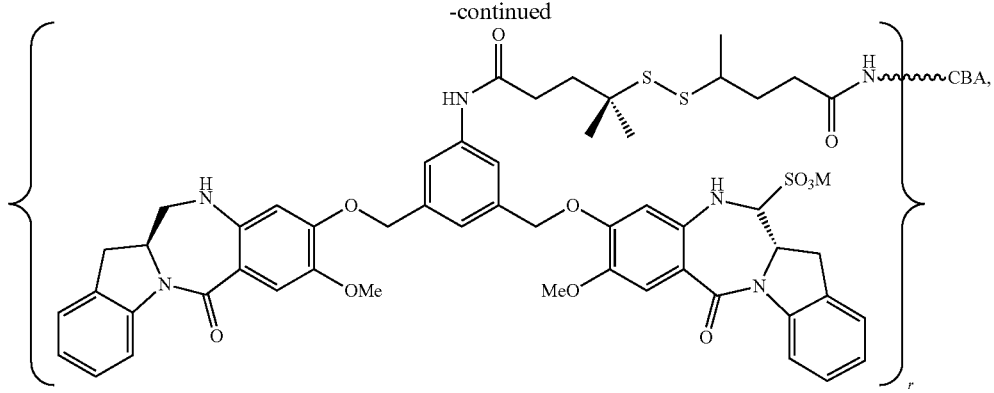
or a pharmaceutically acceptable salt thereof, wherein M is H⁺ or a pharmaceutically acceptable cation; and r is an integer from 1 to 10. More specifically, M is $H^+$, $Na^+$ or $K^+$.
In a 11$^{th}$ specific embodiment, the conjugate is represented by any one of the following formulas:
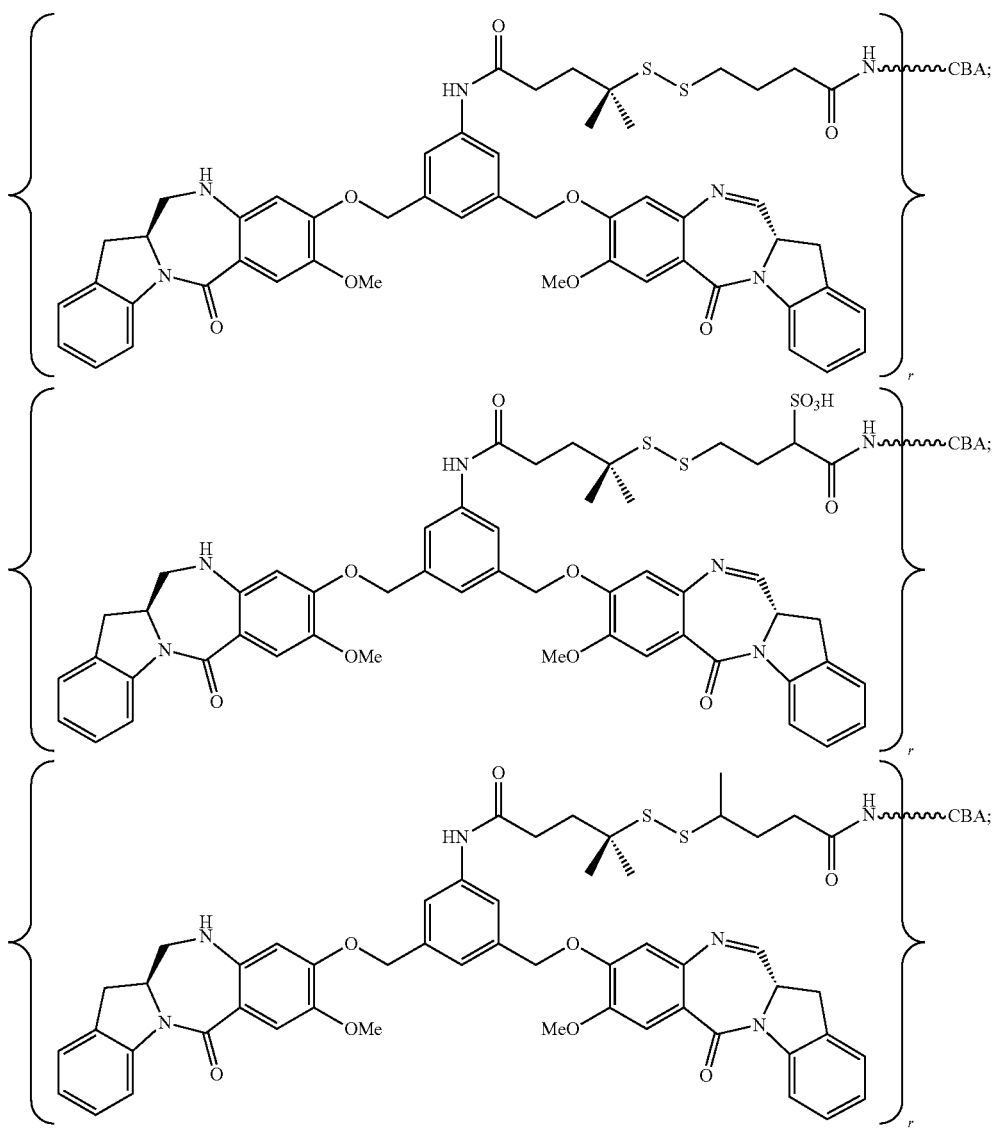

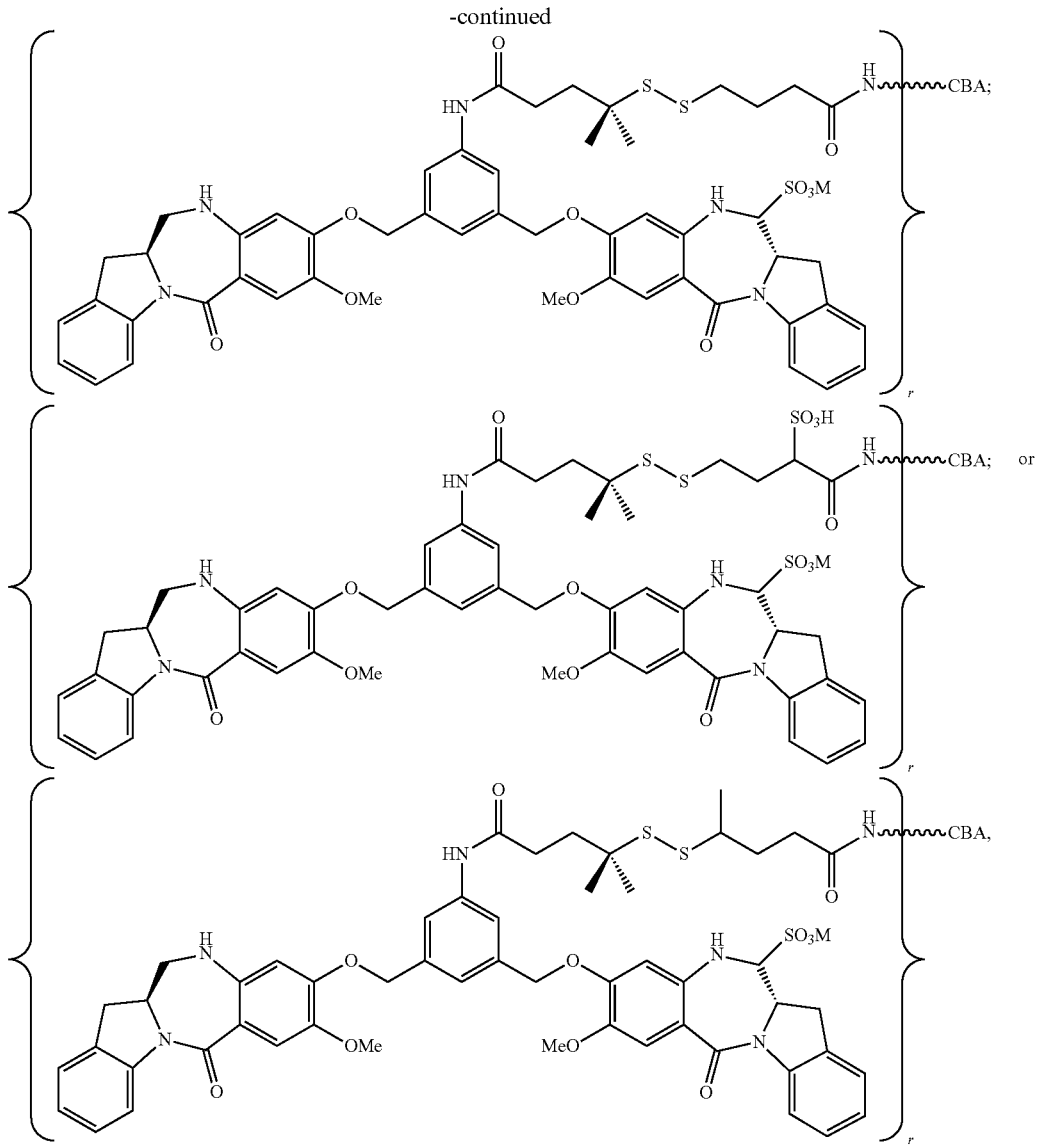

or a pharmaceutically acceptable salt thereof, wherein M is $H^+$, $Na^+$ or $K^+$; and r is an integer from 1 to 10.

In certain embodiments, the conjugate of any one of the described embodiments, such as those described in the second embodiment or the $1^{st}$ to $11^{th}$ specific embodiment, comprises 1-10 cytotoxic compounds, 2-9 cytotoxic compounds, 3-8 cytotoxic compounds, 4-7 cytotoxic compounds, or 5-6 cytotoxic compounds, each cytotoxic compound comprising the linking group linking the cytotoxic compound to the CBA, and each cytotoxic compound on the conjugate is the same.

In any of the above-described embodiments regarding conjugates of the invention, such as those described in the second embodiment or the $1^{st}$ to $11^{th}$ specific embodiment, the cell-binding agent can bind to target cells selected from tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, or Her-2 antigens; Her-3 antigens; or cells expressing insulin growth factor receptor, epidermal growth factor receptor, and folate receptor.

In any of the conjugates embodiments, such as those described in the second embodiment or the $1^{st}$ to $11^{th}$ specific embodiment, the cell-binding agent can be an antibody, a single chain antibody, an antibody fragment that specifically binds to the target cell, a monoclonal antibody, a single chain monoclonal antibody, or a monoclonal antibody fragment that specifically binds to a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule.

The antibody can be a resurfaced antibody, a resurfaced single chain antibody, or a resurfaced antibody fragment.

The antibody can be a monoclonal antibody, a single chain monoclonal antibody, or a monoclonal antibody fragment thereof.

The antibody can be a humanized antibody, a humanized single chain antibody, or a humanized antibody fragment.

In any of the conjugates embodiments, such as those described in the second embodiment or the $1^{st}$ to $11^{th}$ specific embodiment, the cell-binding agent can be anti-folate receptor antibody or an antibody fragment thereof. More specifically, the anti-folate receptor antibody is huMOV19 antibody.

In any of the conjugates embodiments, such as those described in the second embodiment or the $1^{st}$ to $11^{th}$ specific embodiment, the cell-binding agent can be anti-EGFR antibody or an antibody fragment thereof. In one embodiment, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66. More specifically, the anti-EGFR antibody is huML66.

The invention further provides a pharmaceutical composition comprising any of the conjugates described herein, and a pharmaceutically acceptable carrier.

The invention further provides a drug-linker compound comprising any of the subject compound covalently linked to a bifunctional linker.

The invention additional provides a conjugate comprising any of the subject compounds, or the subject drug-linker compounds, linked to a cell-binding agent.

The invention further provides a method of inhibiting abnormal cell growth or treating a proliferative disorder, an autoimmune disorder, destructive bone disorder, infectious disease, viral disease, fibrotic disease, neurodegenerative disorder, pancreatitis or kidney disease in a mammal comprising administering to the mammal a therapeutically effective amount of any of the compounds (with or without any linker group) or conjugates of the invention, and, optionally, a second chemotherapeutic agent.

In certain embodiments, the second chemotherapeutic agent is administered to the mammal sequentially or consecutively.

In certain embodiments, the method is for treating a condition selected from cancer, rheumatoid arthritis, multiple sclerosis, graft versus host disease (GVHD), transplant rejection, lupus, myositis, infection, and immune deficiency.

In certain embodiments, the method or conjugate is for treating a cancer.

In certain embodiments, the cancer is a hematological cancer or a solid tumor. More specifically, the cancer is ovarian cancer, pancreatic cancer, melanoma, lung cancer (e.g., non-small cell lung cancer (NSCLC)), cervical cancer, breast cancer, squamous cell carcinoma of the head and neck, prostate cancer, endometrial cancer, lymphoma (e.g., non-Hodgkin lymphoma), myelodysplastic syndrome (MDS), peritoneal cancer, or leukemia (e.g., acute myeloid leukemia (AML), acute monocytic leukemia, promyelocytic leukemia, eosinophilic leukaemia, acute lymphoblastic leukemia (e.g., B-ALL), chronic lymphocytic leukemia (CLL) and chronic myeloid leukemia (CML)).

Production of Cell-Binding Agent-Drug Conjugates

In order to link the cytotoxic compounds or derivative thereof of the present invention to the cell-binding agent, the cytotoxic compound can comprise a linking moiety with a reactive group bonded thereto. In one embodiment, a bifunctional crosslinking reagent can be first reacted with the cytotoxic compound to provide the compound bearing a linking moiety with one reactive group bonded thereto (i.e., drug-linker compound), which can then react with a cell binding agent. Alternatively, one end of the bifunctional crosslinking reagent can first react with the cell binding agent to provide the cell binding agent bearing a linking moiety with one reactive group bonded thereto, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 2005/0169933, or charged linkers or hydrophilic linkers and are described in US 2009/0274713, US 2010/01293140 and WO 2009/134976, each of which is expressly incorporated herein by reference, each of which is expressly incorporated herein by reference.

In one embodiment, a solution of a cell-binding agent (e.g., an antibody) in aqueous buffer may be incubated with a molar excess of a bifunctional crosslinking agent, such as N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. The modified cell-binding agent (e.g., modified antibody) is then reacted with the thiol-containing cytotoxic compound described herein, such as compound 1d or 2k, to produce a disulfide-linked cell-binding agent-cytotoxic agent conjugate of the present invention.

In another embodiment, the thiol-containing cytotoxic compound described herein, such as compound 1d or 2k can react with a bifunctional crosslinking agent such as N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to form a cytotoxic agent-linker compound, which can then react with a cell-biding agent to produce a disulfide-linked cell-binding agent-cytotoxic agent conjugate of the present invention. The cytotoxic agent-linker compound can be prepared in situ without purification before reacting with the cell-binding agent. A representative process is described in Example 3. Alternatively, the cytotoxic agent-linker compound can be purified prior to reacting with the cell-binding agent.

The cell binding agent-cytotoxic agent conjugate may be purified using any purification methods known in the art, such as those described in U.S. Pat. No. 7,811,572 and US Publication No. 2006/0182750, both of which are incorporated herein by reference. For example, the cell-binding agent-cytotoxic agent conjugate can be purified using tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

Alternatively, the cell-binding agent (e.g., an antibody) may be incubated with a molar excess of an antibody modifying agent such as 2-iminothiolane, L-homocysteine thiolactone (or derivatives), or N-succinimidyl-S-acetylthioacetate (SATA) to introduce sulfhydryl groups. The modified antibody is then reacted with the appropriate disulfide-containing cytotoxic agent, to produce a disulfide-linked antibody-cytotoxic agent conjugate. The antibody-cytotoxic agent conjugate may then be purified by methods described above. The cell binding agent may also be engineered to introduce thiol moieties, such as cysteine-engineered antibodies disclosed in U.S. Pat. Nos. 7,772,485 and 7,855,275.

In another embodiment, a solution of a cell-binding agent (e.g., an antibody) in aqueous buffer may be incubated with a molar excess of an antibody-modifying agent such as N-succinimidyl-4-(N-maleimidomethyl)-cyclohexane-1-carboxylate to introduce maleimido groups, or with N-succinimidyl-4-(iodoacetyl)-aminobenzoate (SIAB) to introduce iodoacetyl groups. The modified cell-binding agent (e.g., modified antibody) is then reacted with the thiol-containing cytotoxic agent to produce a thioether-linked cell-binding agent-cytotoxic agent conjugate. The conjugate may then be purified by methods described above.

The number of cytotoxic molecules bound per antibody molecule can be determined spectrophotometrically by measuring the ratio of the absorbance at 280 nm and 330 nm. An average of 1-10 cytotoxic compounds/antibody molecule(s) can be linked by the methods described herein. The preferred average number of linked cytotoxic compounds per antibody molecule is 2-5, and the most preferred is 2.5-4.0.

Representative processes for preparing the cell-binding agent-drug conjugates of the present invention are described in U.S. Pat. No. 8,765,740 and U.S. Application Publication No. 2012/0238731. The entire teachings of these references are incorporated herein by reference.

Cytotoxicity of Compounds and Conjugates

The cytotoxic compounds and cell-binding agent-drug conjugates of the invention can be evaluated for their ability to suppress proliferation of various cancer cell lines in vitro. Cells to be evaluated can be exposed to the compounds or conjugates for 1-5 days and the surviving fractions of cells measured in direct assays by known methods. $IC_{50}$ values can then be calculated from the results of the assays. Alternatively or in addition, an in vitro cell line sensitivity screen, such as the one described by the U.S. National Cancer Institute (see Voskoglou-Nomikos et al., 2003, Clinical Cancer Res. 9: 42227-4239, incorporated herein by reference) can be used as one of the guides to determine the types of cancers that are sensitive to treatment with the compounds or conjugates of the invention.

In one example, in vivo efficacy of a cell binding agent/cytotoxic agent conjugate was measured. SCID mice bearing NCI-H2110 tumor cells were treated with huMov19-sulfo-SPDB-1d conjugate and significant tumor regression was observed at multiple doses while untreated mice grew tumors rapidly (FIG. 2). Activity was observed at doses as low as 5 µg/kg.

Compositions and Methods of Use

The present invention includes a composition (e.g., a pharmaceutical composition) comprising novel benzodiazepine compounds described herein (e.g., indolinobenzodiazepine or oxazolidinobenzodiazepine), derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel benzodiazepine compounds described herein, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human) The present compositions are also useful for treating depression, anxiety, stress, phobias, panic, dysphoria, psychiatric disorders, pain, and inflammatory diseases in a mammal (e.g., human)

The present invention includes a method of inhibiting abnormal cell growth or treating a proliferative disorder in a mammal (e.g., human) comprising administering to said mammal a therapeutically effective amount of novel benzodiazepine compounds described herein (e.g., indolinobenzodiazepine or oxazolidinobenzodiazepine), derivatives thereof, or conjugates thereof, (and/or solvates and salts thereof) or a composition thereof, alone or in combination with a second therapeutic agent.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the cytotoxic compound-cell-binding agents (e.g., indolinobenzodiazepine or oxazolidinobenzodiazepine dimer linked to a cell binding agent) of the present invention, a salt or solvate thereof. The target cells are cells to which the cell-binding agent can bind.

If desired, other active agents, such as other anti-tumor agents, can be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and can also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T-cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 mL of normal saline to which 5 to 10 mL of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Cancer therapies and their dosages, routes of administration and recommended usage are known in the art and have been described in such literature as the Physicians Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:
Comprehensive index
By Manufacturer
Products (by company's or trademarked drug name)
Category index
Generic/chemical index (non-trademark common drug names)
Color images of medications
Product information, consistent with FDA labeling
Chemical information
Function/action
Indications & Contraindications
Trial research, side effects, warnings
Analogues and Derivatives One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument. Mass spectra were acquired on a Bruker Daltonics Esquire 3000 instrument and LCMS were acquired on an Agilent 1260 Infinity LC with an Agilent 6120 single quadropole MS using electrospray ionization.

Example 1

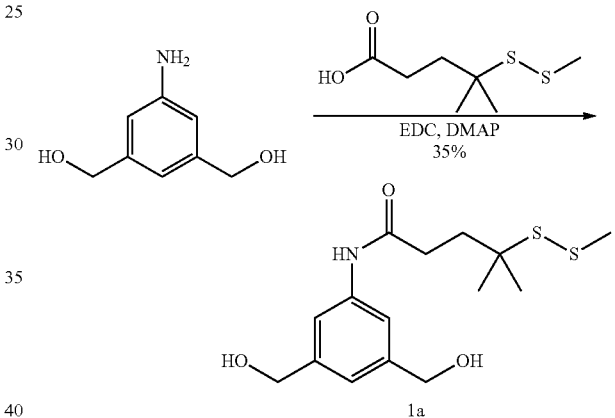

Compound 1a

To a stirred solution of (5-amino-1,3-phenylene)dimethanol (1.01 g, 6.59 mmol) in anhydrous dimethylformamide (16.48 mL) and anhydrous tetrahydrofuran (16.48 ml) was added 4-methyl-4-(methyldisulfanyl)pentanoic acid (1.281 g, 6.59 mmol), N-(3-dimethylaminopropyl)-N'-ethylcarbodiimide hydrochloride (2.53 g, 13.19 mmol), and 4-dimethylaminopyridine (0.081 g, 0.659 mmol). The resulting mixture was stirred for 18 hours at room temperature. The reaction was quenched with saturated ammonium chloride solution and extracted with ethyl acetate (3×50 mL). The organic extracts were washed with water and brine, then dried over anhydrous sodium sulfate. The solution was filtered and concentrated in vacuo and the resulting residue was purified by silica gel chromatography (Ethyl acetate/Hexanes) to obtain compound 1a as a white solid (0.70 g, 32% yield). $^1$H NMR (400 MHz, DMSO-d6: δ 9.90 (s, 1H), 7.43 (s, 2H), 6.93 (s, 1H), 5.16 (t, 2H, J=5.7 Hz), 4.44 (d, 4H, J=5.7 Hz), 2.43 (s, 3H), 2.41-2.38 (m, 2H), 1.92-1.88 (m, 2H), 1.29 (s, 6H). MS (m/z), found 330.0 (M+1)$^+$.

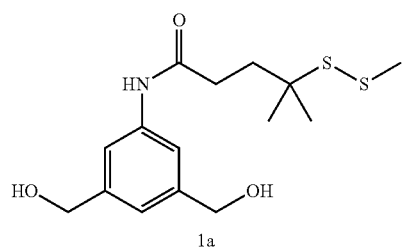

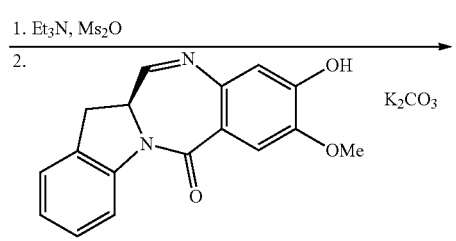

IGN monomer, A

35%

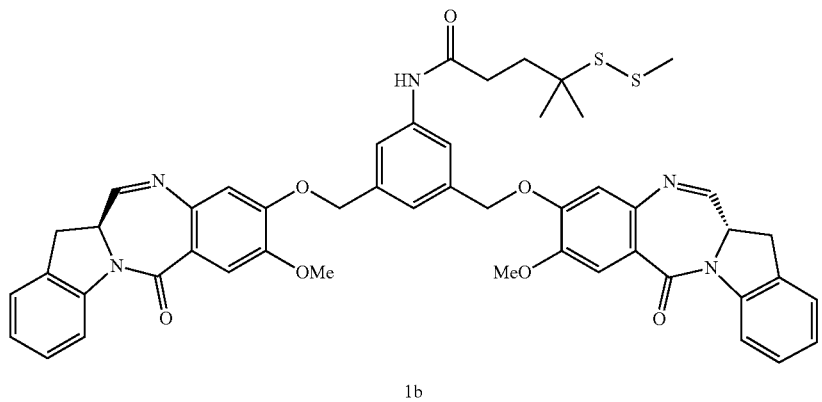

1b

Compound 1b

To a cooled (−10° C.) solution of compound 1a (219 mg, 0.665 mmol) in anhydrous dichloromethane (6.65 mL) was added triethylamine (463 µl, 3.32 mmol) followed by dropwise addition of methanesulfonic anhydride (298 mg, 1.662 mmol). The mixture stirred at −10° C. for 2 hours, then the mixture was quenched with ice water and extracted with cold ethyl acetate (2×30 mL). The organic extracts were washed with ice water, dried with anhydrous sodium sulfate, filtered and concentrated under reduced pressure to obtain the crude dimesylate.

The crude dimesylate (227 mg, 0.467 mmol) and IGN monomer A (303 mg, 1.028 mmol) were dissolved in anhydrous DMF (3.11 mL). Potassium carbonate (161 mg, 1.169 mmol) was added and the mixture stirred for 18 hours at room temperature. Deionized water was added and the resulting precipitate was filtered and rinsed with water. The solid was re-dissolved in dichloromethane and washed with water. The organic layer was dried with anhydrous magnesium sulfate, filtered, and concentrated. The crude residue was purified by silica gel chromatography (Methanol/Dichloromethane) to give compound 1b (227 mg, 36% yield). MS (m/z), found 882.5 (M+1)$^+$.

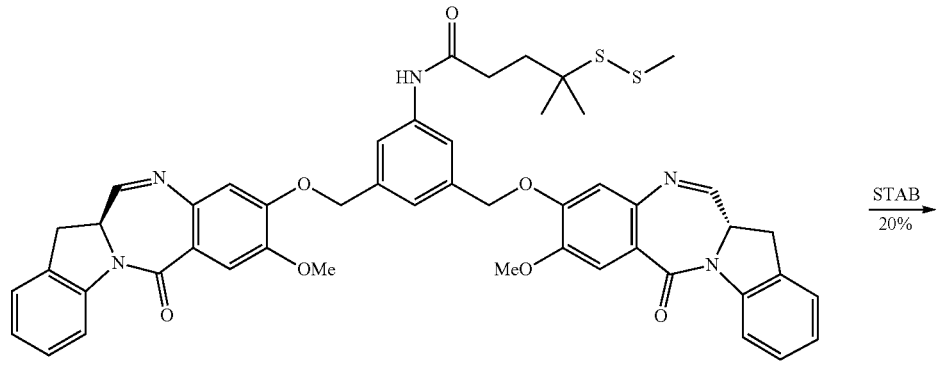

1b

-continued

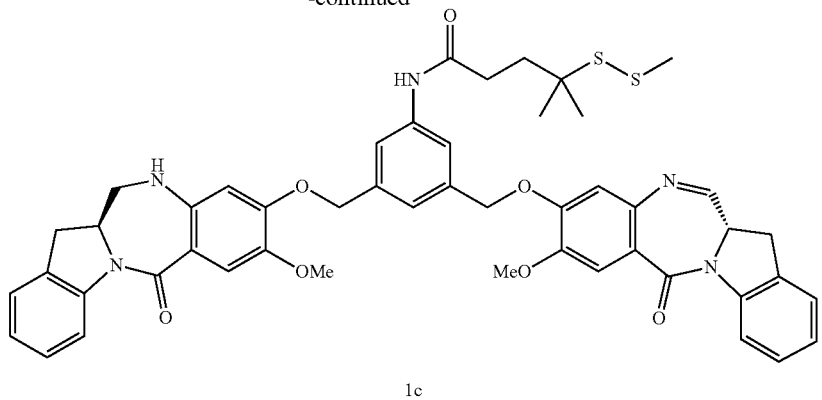

1c

Compound 1c

To a suspension of compound 1b (227 mg, 0.167 mmol) in anhydrous 1,2-dichloroethane (3.346 mL) was added sodium triacetoxyborohydride (37.3 mg, 0.167 mmol). The mixture was stirred at room temp for one hour upon which it was quenched with saturated ammonium chloride solution. The mixture was extracted with dichloromethane and washed with brine. The organic layer was dried with anhydrous magnesium sulfate, filtered and concentrated. The crude residue was purified by RP-HPLC (C18, Water/Acetonitrile). Fractions containing desired product were extracted with dichloromethane, dried with anhydrous magnesium sulfate, filtered and concentrated to give compound 1c (35 mg, 19% yield). MS (m/z), found 884.3 (M+1)$^+$.

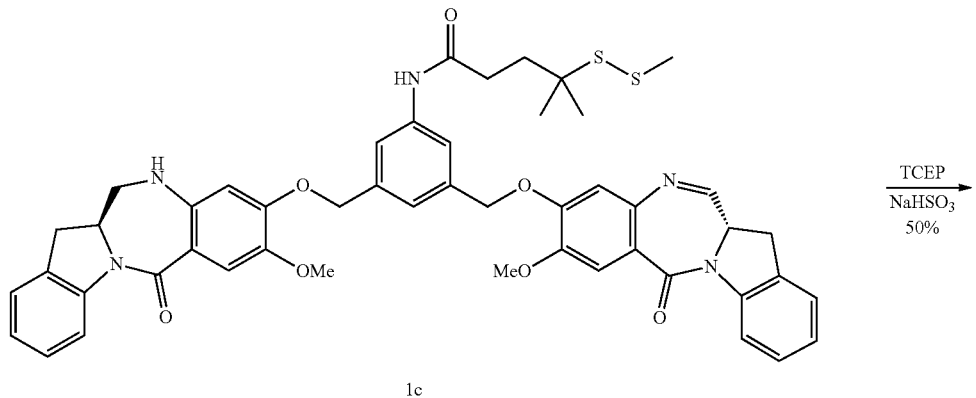

1c

TCEP
NaHSO$_3$
50%

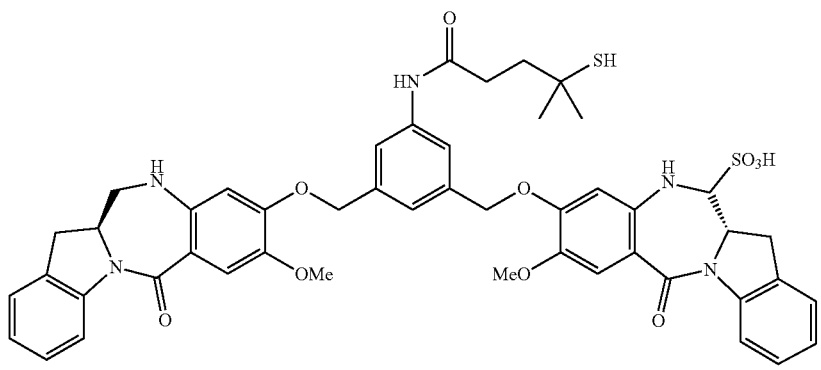

1d

Compound 1d

To a solution of compound 1c (18 mg, 0.017 mmol) in acetonitrile (921 μL) and methanol (658 μL) was added tris(2-carboxyethyl)phosphine hydrochloride (17.51 mg, 0.060 mmol) (neutralized with saturated sodium bicarbonate solution (0.2 mL) in sodium phosphate buffer (132 μL, 0.75 M, pH 6.5). The mixture was stirred at room temperature for 3.5 hours, then diluted with dichloromethane and deionized water. The organic layer was separated, washed with brine, dried with anhydrous sodium sulfate, filtered and concentrated under reduced pressure to obtain the crude thiol. MS (m/z), found 838.3 (M+1)+.

The crude thiol from step 5 (15.5 mg, 0.018 mmol) was dissolved in 2-propanol (1.23 mL). Deionized water (617 μL) and sodium bisulfite (5.77 mg, 0.055 mmol) were added and the mixture stirred for five hours at room temperature. The reaction was frozen in an acetone/dry ice bath, lyophilized, and purified by RP-HPLC (C18, deionized water/acetonitrile). Fractions containing desired product were frozen and lyophilized to give compound (12S,12aS)-9-((3-(4-mercapto-4-methylpentanamido)-5-((((R)-8-methoxy-6-oxo-11,12,12a,13-tetrahydro-6H-benzo[5,6][1,4]diazepino[1,2-a]indol-9-yl)oxy)methyl)benzyl)oxy)-8-methoxy-6-oxo-11,12,12a,13-tetrahydro-6H-benzo[5,6][1,4]diazepino[1,2-a]indole-12-sulfonic acid (compound 1d) (6.6 mg, 39% yield). MS (m/z), found 918.2 (M−1)−.

Example 2

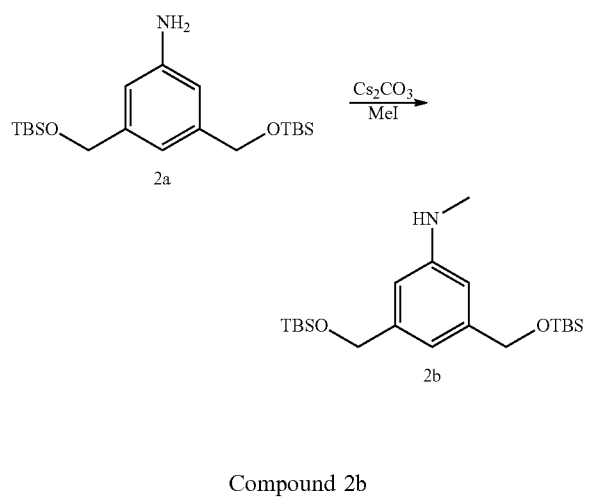

Compound 2b

Cs$_2$CO$_3$ (8.54 g, 26.2 mmol) was added to a stirred solution of aniline 1a (10.0 g, 26.2 mmol) in DMF (52.4 mL). Methyliodide (1.47 mL, 23.58 mmol) was added and the reaction was stirred at rt for 3 h. Water (10 mL) and EtOAc (30 mL) were added to the reaction mixture. The layers were separated and was extracted with EtOAc (2×). The organic layers were washed with water (4×), dried over Na$_2$SO$_4$, filtered and concentrated. The crude residue was purified by silica gel flash chromatography (EtOAc/hexanes, gradient, 0% to 10%) to obtain compound 2b (3.8 g, 37% yield). $^1$H NMR (400 MHz, CDCl$_3$) δ 6.629 (s, 1H), 6.515 (s, 2H), 4.673 (s, 4H), 2.838 (s, 3H), 0.942 (s, 18H), 0.102 (s, 12H).

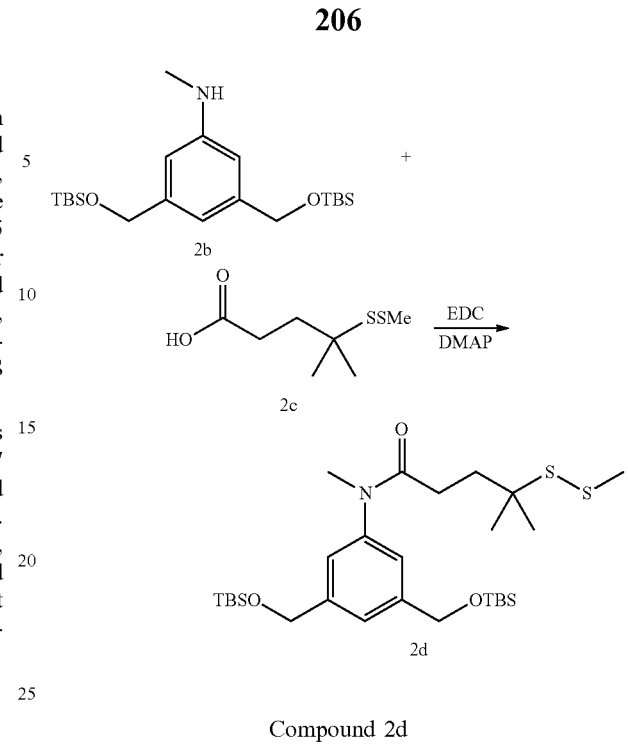

Compound 2d

N-methyl aniline (compound 2b) (500 mg, 1.26 mmol) and compound 2c (258 mg, 1.33 mmol) were dissolved in CH$_2$Cl$_2$ (6.32 ml). EDC (484 mg, 2.53 mmol) and DMAP (77.0 mg, 0.632 mmol) were added and the reaction mixture was stirred overnight at room temperature. The reaction was diluted with dichloromethane and was washed with saturated NH$_4$Cl and brine, dried over Na$_2$SO$_4$, filtered and concentrated. The crude residue was purified by silica gel flash chromatography (EtOAc/hexanes, gradient, 0% to 30% to 100%) to obtain compound 2d a colorless oil (705 mg, 98% yield). $^1$H NMR (400 MHz, CDCl$_3$) δ 7.236 (s, 1H), 7.016 (s, 2H), 4.744 (s, 4H), 3.242 (s, 3H), 2.336 (s, 3H), 2.190-2.153 (m, 2H), 1.924-1.884 (m, 2H), 1.137 (s, 6H), 0.940 (s, 18H), 0.106 (s, 12H).

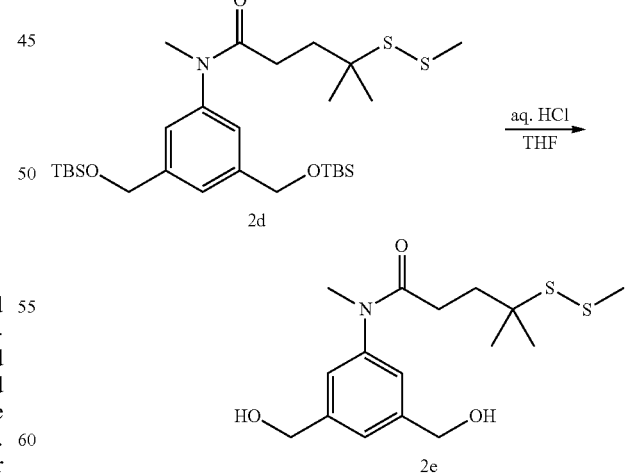

Compound 2e

Compound 2d (700 mg, 1.22 mmol) was dissolved in THF (6.12 mL). 5 M aqueous HCl (4.89 mL, 24.47 mmol) was added at rt and was stirred for a total of 3.5 h. The reaction mixture was diluted with EtOAc and washed with sat'd NaHCO$_3$ and brine, dried over Na$_2$SO$_4$, filtered and concentrated. CH$_3$CN (15 mL) was added to the residue and was concentrated to dryness. This was repeated 3× to obtain compound 2e as a colorless oil (450 mg, 100% yield). LCMS (8 min method)=0.757 min. Mass observed=344.25 (M+H). $^1$H NMR (400 MHz, CDCl$_3$) δ 7.340 (s, 1H), 7.119 (s, 2H), 4.736 (s, 4H), 3.252 (s, 3H), 2.348 (s, 3H), 2.172-2.152 (m, 2H), 1.930-1.890 (m, 2H), 1.165 (s, 6H).

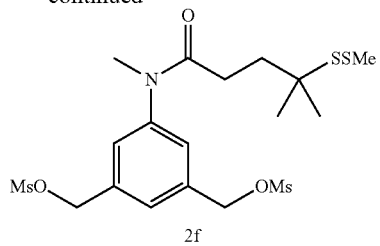

2f

Compound 2f

Compound 2e (370 mg, 1.08 mmol) was dissolved in dichloromethane (7.18 mL). The solution was cooled to −5° C. and triethylamine (0.375 mL, 2.69 mmol) was then added, followed by slow dropwise addition of methanesulfonyl chloride (0.193 mL, 2.48 mmol) under an atmosphere of argon. The reaction mixture was stirred at −5° C. for 2.5 h. The reaction was quenched with ice/water and was diluted with EtOAc (15 mL). The layers were separated and the organic layer was washed with cold water (2×), dried over Na$_2$SO$_4$, filtered and concentrated to give the crude compound 2f as a colorless oil (530 mg, 98% yield) and was taken onto the next step without purification. Mass observed=522.68 (M+Na).

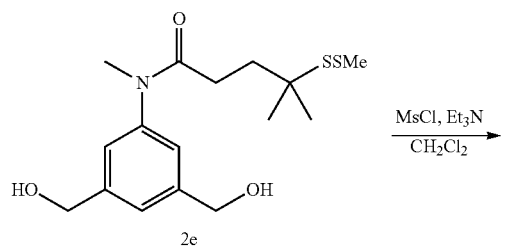

2e

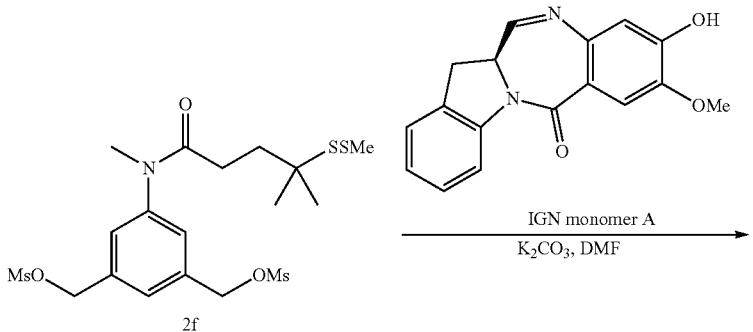

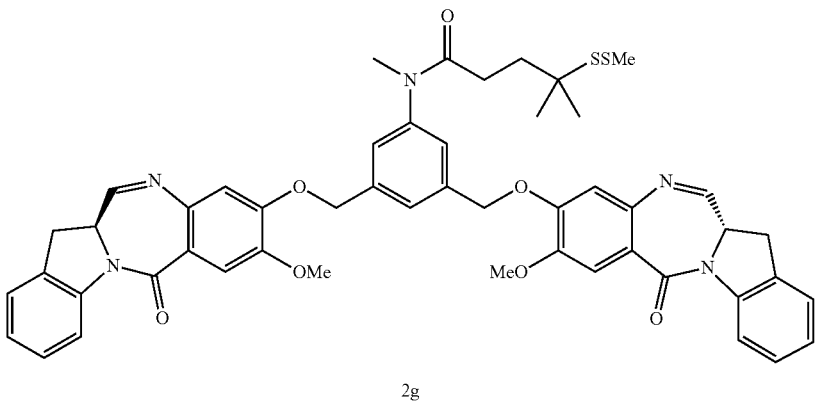

2g

Compound 2g

Dimesylate 2f (530 mg, 1.06 mmol) and IGN monomer A (723 mg, 2.33 mmol) were dissolved in anhydrous dimethylformamide (10.61 mL). Potassium carbonate (586 mg, 4.24 mmol) was added and the reaction was stirred overnight at room temperature. Water (20 mL) was added to precipitate out the product. The slurry was stirred for 5 min, filtered and dried under vacuum/$N_2$ for 1 h. The crude residue was purified by silica gel flash chromatography (EtOAc/hexanes, 50% to 100%, then switched to 5% MeOH/$CH_2Cl_2$) to obtain 2g as a brownish solid (715 mg, 56% yield, 75% purity). LCMS (8 min method)=5.891 min. Mass observed=896.50 (M+H).

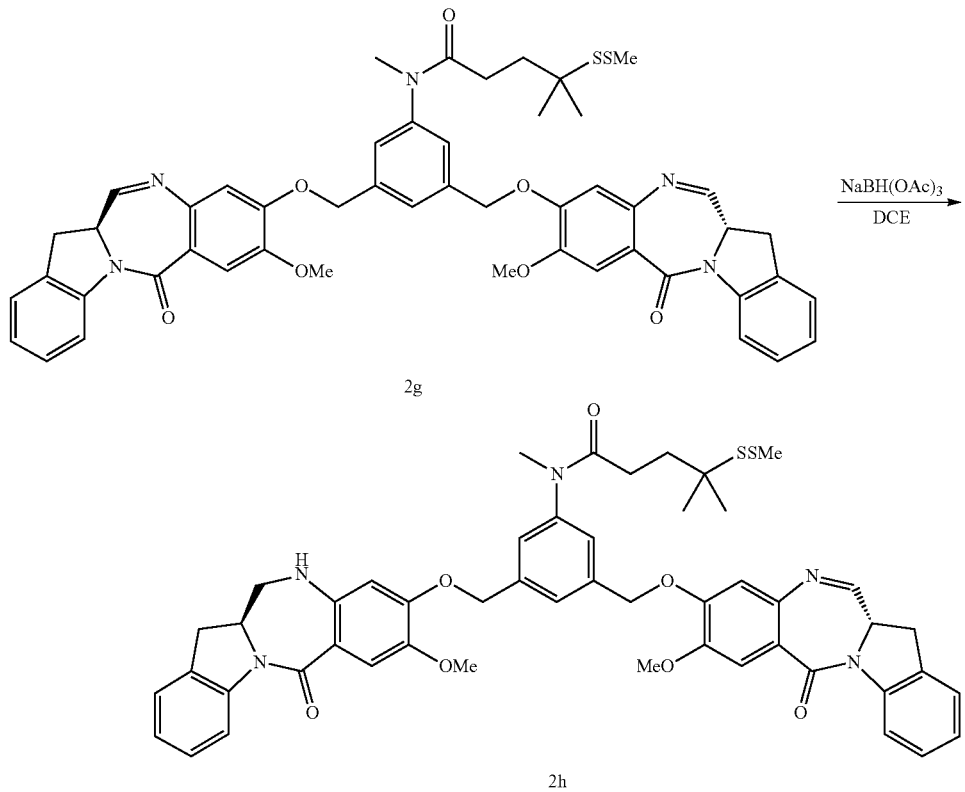

Compound 2h

Compound 2g (440 mg, 0.368 mmol) was dissolved in 1,2-dichloroethane (3.68 mL). Sodium triacetoxyborohydride (78 mg, 0.368 mmol) was added and the reaction was stirred at rt under an atmosphere of argon for 1 h. The reaction mixture was diluted with dichloromethane and was washed with sat'd $NH_4Cl$, brine, dried over $Na_2SO_4$, filtered and concentrated. The crude reside was purified by RPHPLC (C18 column, $CH_3CN/H_2O$, gradient, 55% to 75%) to yield mono imine 2h as a white fluffy solid (125 mg, 34% yield). LCMS (15 min method)=8.847 min. Mass observed=898.6 (M+H).

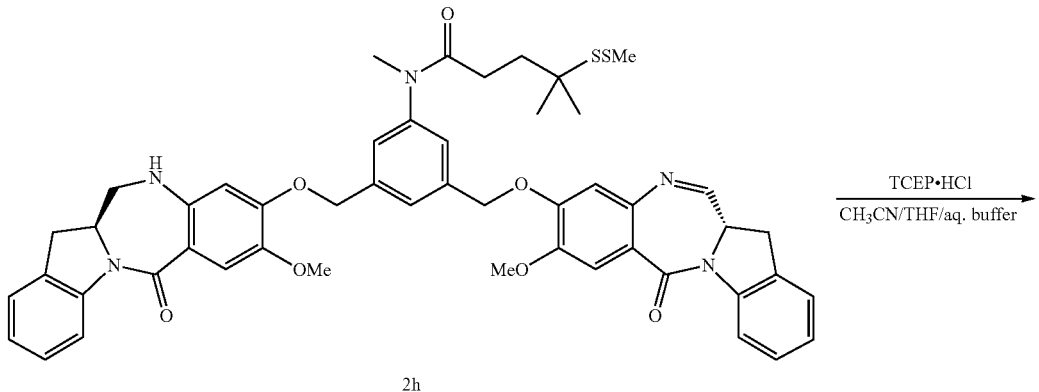

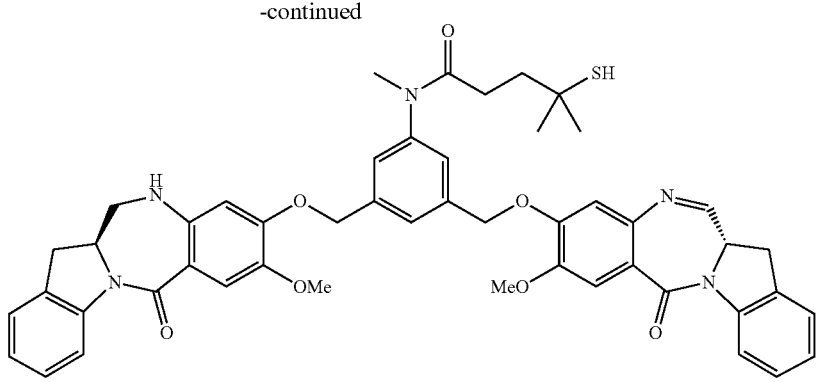

2j

Compound 2j

TCEP.HCl (108 mg, 0.376 mmol) was neutralized with water (~100 μL) and sat'd aq. NaHCO₃ (~925 μL). 0.1 M NaH₂PO₄ buffer pH=6.5 (193 μL) was added to the TCEP solution. In a separate flask, compound 2h (125 mg, 0.125 mmol) was dissolved in acetonitrile (1.35 mL) and tetrahydrofuran (900 μL). The TCEP/buffer mixture (pH=6.5-7) was added to the solution of compound 2h in acetonitrile, followed by the addition of methanol (964 μL). An additional tetrahydrofuran (200 μL) was added to get a clear homogeneous solution. The reaction mixture was stirred at rt for 3 h. The reaction was diluted with dichloromethane and water. The layers were separated and the organic layer was washed with brine, dried over anhydrous Na₂SO₄, filtered and concentrated to give crude compound 2j, which was used in the next step without purification (118 mg, 100% yield). LCMS (8 min method)=5.880 min. Mass observed=852.30 (M+H).

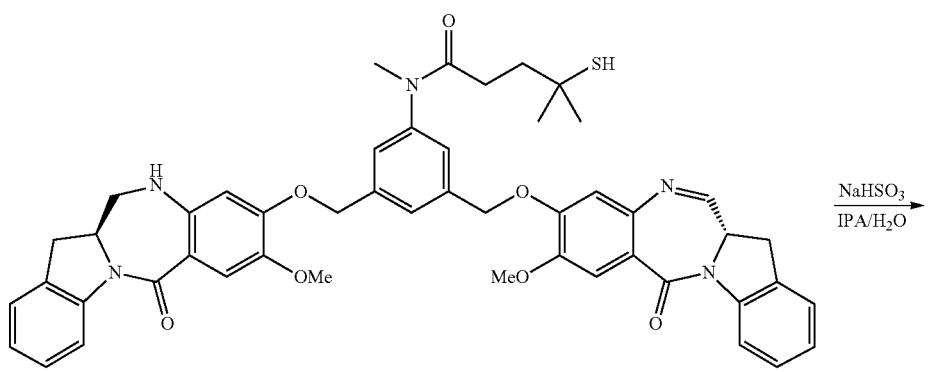

2j

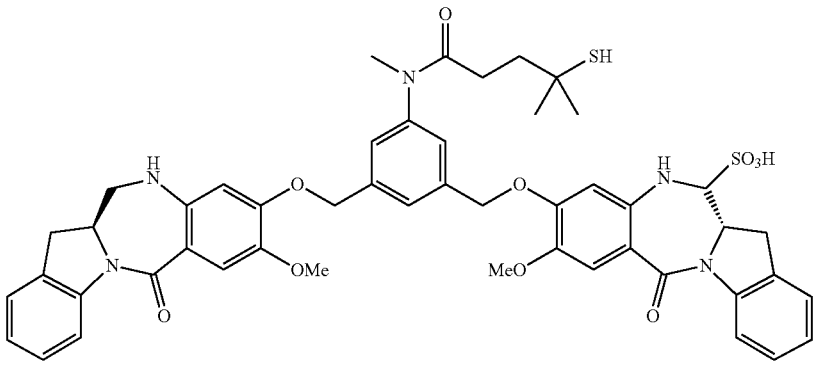

2k

Compound 2k

The crude compound 2j (118 mg, 0.125 mmol) was suspended in 2-propanol (5.54 mL) and water (2.77 mL) and was sonicated for a few minutes. NaHSO₃ (130 mg, 1.25 mmol) was added and the reaction was stirred overnight at room temperature. The clear solution was diluted with CH₃CN/H₂O (1:1, 15 mL) and was frozen and lyophilized. The resulting fluffy white powder was dissolved in CH₃CN/H₂O (1:1) and was purified by RPHPLC (C18 column, CH₃CN/H₂O, gradient, 25% to 45%) to obtain (12S,12aS)-

9-((3-(4-mercapto-N,4-dimethylpentanamido)-5-((((S)-8-methoxy-6-oxo-11,12,12a,13-tetrahydro-6H-benzo[5,6][1,4]diazepino[1,2-a]indol-9-yl)oxy)methyl)benzyl)oxy)-8-methoxy-6-oxo-11,12,12a,13-tetrahydro-6H-benzo[5,6][1,4]diazepino[1,2-a]indole-12-sulfonic acid (compound 2k) as a white powder (65 mg, 56% yield, 98% purity). LCMS (15 min method)=4.841 min. Mass observed=852.6 (ESI$^+$, M-SO$_3$H+H), 932.4 (ESI$^-$, M-H).

Example 3. Preparation of huMOV19-sulfo-SPDB-1d

A reaction containing 2.0 mg/mL huMOV19 antibody and 6 molar equivalents of sulfo-SPDB-1d in situ mixture by linker in 50 mM HEPES (4-(2-hydroxyethyl)-1-piperazine ethanesulfonic acid) pH 8.5 buffer and 15% v/v DMA (N,N-Dimethylacetamide) cosolvent was allowed to conjugate for 6 hours at 25° C. The in situ mixture was prepared by reacting 1.5 mM sulfo-SPDB linker with 1.95 mM of compound 1d in 100% DMA for 4 hours in the presence of 10 mM N,N-Diisopropylethyl amine (DIPEA). Free thiol was then capped by adding a 3-fold excess of maleimidopropionic acid.

Post-reaction, the conjugate was purified and buffer exchanged into 100 mM Arginine, 20 mM Histidine, 2% sucrose, 0.01% Tween-20, 50 µM sodium bisulfite formulation buffer pH 6.1 using NAP desalting columns (Illustra Sephadex G-25 DNA Grade, GE Healthcare). Dialysis was performed in the same buffer for 20 hours at 4° C. utilizing Slide-a-Lyzer dialysis cassettes (ThermoScientific 20,000 MWCO).

The purified conjugate was found to have an average of 2.5 molecules of compound 1d linked per antibody (by UV-Vis using molar extinction coefficients $\epsilon_{330\ nm}$=15,280 cm$^{-1}$ M$^{-1}$ and $\epsilon_{280\ nm}$=30,115 cm$^{-1}$ M$^{-1}$ for compound 1d, and $\epsilon_{280\ nm}$=201,400 cm$^{-1}$ M$^{-1}$ for huMOV19 antibody), 95% monomer (by size exclusion chromatography), <0.1% unconjugated compound 1d (by acetone precipitation, reverse-phase HPLC analysis) and a final protein concentration of 1.8 mg/ml. The conjugated antibody was found to be >80% intact by gel chip analysis.

Example 4. Antitumor Activity of Single-Dose huMOV19-sulfo-SPDB-1d Against NCI-H2110 NSCLC Xenografts in Female SCID Mice Female CB.17 SCID mice, 6 weeks old, were received from Charles River Laboratories. Mice were inoculated with 1×10$^7$ NCI-H2110 tumor cells suspended in 0.1 ml 50% matrigel/serum free medium by subcutaneous injection in the right flank. When tumor volumes reached approximately 100 mm$^3$ (day 7 post inoculation), animals were randomized based on tumor volume into 3 groups of 6 mice each. Mice received a single IV administration of vehicle control (0.2 ml/mouse) or huMOV19-sulfo-SPDB-1d at 5 and 25 µg/kg based on concentration of compound 1d on day 1 (day 8 post inoculation).

Tumor size was measured twice to three times weekly in three dimensions using a caliper. The tumor volume was expressed in mm$^3$ using the formula V=Length×Width×Height×½. A mouse was considered to have a partial regression (PR) when tumor volume was reduced by 50% or greater, complete tumor regression (CR) when no palpable tumor could be detected. Tumor volume was determined by StudyLog software. Tumor growth inhibition (T/C Value) was determined using the following formula:

T/C (%)=Median tumor volume of the treated/Median tumor volume of the control×100.

Tumor volume was determined simultaneously for treated (T) and the vehicle control (C) groups when tumor volume of the vehicle control reached predetermined size of 1000 mm$^3$. The daily median tumor volume of each treated group was determined, including tumor-free mice (0 mm$^3$). According to NCI standards, a T/C≤42% is the minimum level of anti-tumor activity. A T/C<10% is considered a high anti-tumor activity level.

As shown in FIG. 1, the conjugate is highly active at both 5 and 25 µg/kg dose.

Example 5. Preparation of huML66-sulfo-SPDB-1d Conjugate

Sulfo-SPDB-1d was formed in situ by incubating 3.0 mM sulfo-SPDB, 3.9 mM compound 1d, and 20 mM DIPEA (N,N-diisopropylethylamine) in DMA (N,N-dimethylacetamide) for 5 hours at 25° C. A reaction containing 2.0 mg/mL huML66 antibody, an anti-EGFR antibody (see WO 2012/058592), and 5.8 molar equivalents of sulfo-SPDB-1d in 15 mM HEPES (4-(2-hydroxyethyl)-1-piperazine ethanesulfonic acid) pH 8.5 buffer and 15% v/v DMA cosolvent was incubated overnight at 25° C.

Post-reaction, the conjugate was purified into 10 mM histidine, 250 mM glycine, 1% sucrose, 0.01% Tween-20, 50 µM sodium bisulfite pH 6.2 formulation buffer using NAP desalting columns (Illustra Sephadex G-25 DNA Grade, GE Healthcare). Dialysis was performed in the same buffer for 4 hours at room temperature and then overnight at 4° C. using Slide-a-Lyzer dialysis cassettes (ThermoScientific 30,000 MWCO).

Figure 3:
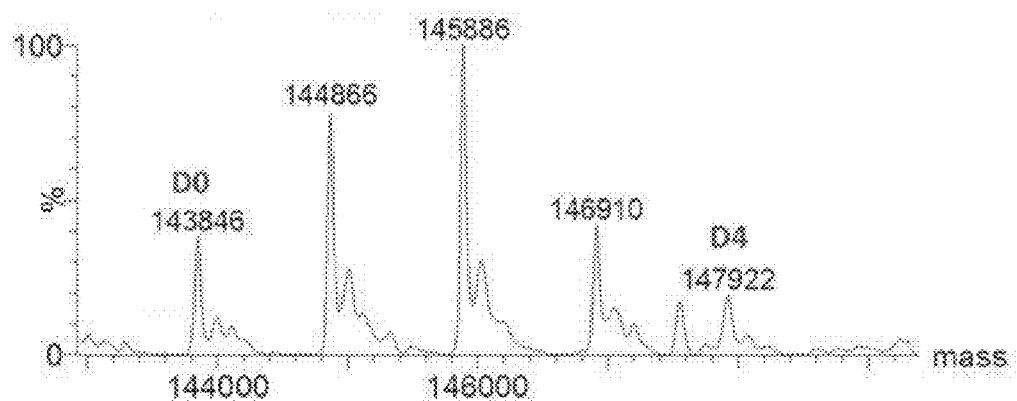
FIG. 3 shows MS spectrometry data for huML66-sulfo-SPDB-1d conjugate.

The purified conjugate was found to have a final protein concentration of 2.9 mg/ml and an average of 3.0 molecules of compound 1d linked per antibody (by UV-Vis using molar extinction coefficients $\epsilon_{330\ nm}$=15,484 cm$^{-1}$ M$^{-1}$ and $\epsilon_{280\ nm}$=30,115 cm$^{-1}$ M$^{-1}$ for compound 1d, and $\epsilon_{280\ nm}$=205,520 cm$^{-1}$ M$^{-1}$ for huML66 antibody); 92.8% monomer (by size exclusion chromatography); and 0.8% unconjugated compound 1d (by acetone precipitation, reverse-phase HPLC analysis). The MS spectrometry data is shown in FIG. 3.

Example 6. In Vitro Cytotoxic Assays for Conjugates

The ability of huML66-sulfo-SPDB-1d conjugate to inhibit cell growth was measured using in vitro cytotoxicity assays. Target cells were plated at 1-2,000 cells per well in 100 µL in complete RPMI media (RPMI-1640, 10% fetal bovine serum, 2 mM glutamine, 1% penicillin-streptomycin, all reagents from Invitrogen). Antibodies were diluted into complete RPMI media using 3-fold dilution series and 100 µL were added per well. The final concentration typically ranged from 3×10$^{-8}$ M to 4.6×10$^{-12}$ M. Cells were incubated at 37° C. in a humidified 5% CO$_2$ incubator for 5-6 days. Viability of remaining cells was determined by colorimetric WST-8 assay (Dojindo Molecular Technologies, Inc., Rockville, Md., US). WST-8 is reduced by dehydrogenases in living cells to an orange formazan product that is soluble in tissue culture medium. The amount of formazan produced is directly proportional to the number of living cells. WST-8 was added to 10% of the final volume and plates were incubated at 37° C. in a humidified 5% CO2 incubator for an additional 2-4 hours. Plates were analyzed by measuring the absorbance at 450 nm (A450) in a multiwell plate reader. Background A450 absorbance of wells with media and WST-8 only was subtracted from all values. The percent viability was calculated by dividing each treated sample value by the average value of wells with untreated cells. Percent viability=100*(A450 treated sample−A450 background)/(A450 untreated sample−A450 background). The percent viability value was plotted against the antibody concentration in a semi-log plot for each treatment. Dose-response curves were generated by non-linear regression and the $EC_{50}$ value of each curve was calculated using GraphPad Prism (GraphPad software, San Diego, Calif.). In vitro cytotoxic activity.

Figure 4:
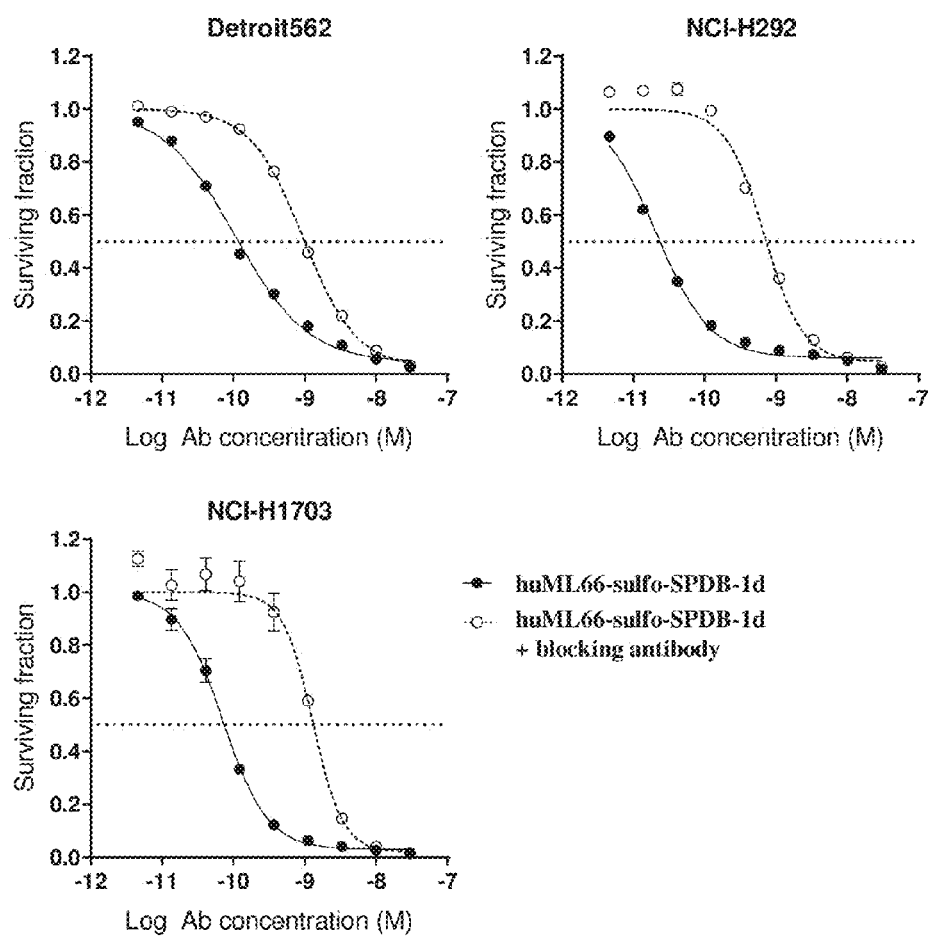
FIG. 4 shows in vitro cytotoxicity of huML66-sulfo-SPDB-1d conjugate against various cancer cell lines.

The in vitro cytotoxicity of huML66-sulfo-SPDB-1d conjugate was evaluated in the presence and absence of excess unconjugated antibody and compared to the activity of a non-specific IgG-sulfo-SPDB-1d conjugate in EGFR-expressing cells and the results from a typical cytotoxicity assay are shown in FIG. 4. The huML66-sulfo-SPDB-1d conjugate resulted in specific cell killing of Detroit-562 SCC-HN cells with an $EC_{50}$ value of 110 pM. The presence of excess unconjugated antibody significantly reduced activity and resulting in an $EC_{50}$ value of approximately 1 nM.

Likewise, the huML66-sulfo-SPDB-1d conjugate resulted in specific cell killing of NCI-H292 NSCLC cells with an $EC_{50}$ value of 20 pM. The presence of excess unconjugated antibody significantly reduced activity and resulting in an $EC_{50}$ value of approximately 0.7 nM. Additionally, the huML66-sulfo-SPDB-1d conjugate resulted in specific cell killing of NCI-H1703 NSCLC cells with an $EC_{50}$ value of 70 pM. The presence of excess unconjugated antibody significantly reduced activity and resulting in an EC50 value of approximately 1 nM.

TABLE 1

| Conjugate | Detroit562 EC50 in pM | NCI-H292 EC50 in pM | NCI-H1703 EC50 in pM |
|---|---|---|---|
| huML66-sulfo-SPDB-1d | 110 | 20 | 70 |
| huML66-sulfo-SPDB-1d + block | 960 | 690 | 1,310 |

Example 7. Cytotoxicity Assay of huMOV19-sulfo-SPDB-1d Conjugate

100 μl/well of huMOV19-sulfo-SPDB-1d conjugate was each diluted in RPMI-1640 (Life Technologies) supplemented with heat-inactivated 10% FBS (Life Technologies) and 0.1 mg/ml gentamycin (Life Technologies) in a 96-well plate (Corning, flat bottom) at starting concentrations of 3.5e-9 M and to 3.5 e-8 M in triplicate and serially diluted 3-fold in media above at ambient temperature. KB cells (buccal epithelial tumor), grown in EMEM (ATCC) supplemented with heat-inactivated 10% FBS (Life Technologies) and 0.1 mg/ml gentamycin (Life Technologies), were washed once in PBS and removed with 0.05% trypsin-EDTA (Life Technologies). Other cells tested were NCI-H2110 (NSCLC) and T47D (breat epthelial) grown in RPMI-1640 (LifeTechnologies) supplemented with heat-inactived 10% FBS (Life Technologies) and 0.1 mg/ml gentamycin (Life Technologies). T47D media also was supplemented with 0.2 IU/ml bovine insulin. All cells were resuspended in growth media (see above) to neutralize trypsin and counted using a hemacytometer. 100 μl/ml of 1000 KB cells/well or 2000 T47D and NCI-H2110 cells/well were added to wells containing ADC or media only and incubated in a 37° C. incubator with 5% $CO_2$ for 5 days with and without 1 μM blocking anti-FOLR1 antibody (M9346A). Total volume is 200 μl/well. The starting concentration of each conjugate on KB cells was 3.5e-9 M and for T47D and NCI-H2110 cells, the starting concentration of each conjugate was 3.5e-8 M. After incubation, cell viability was analyzed by addition of 20 μl/well WST-8 (Dojindo) and allowed to develop for 2 hr. Absorbance was read on a plate reader at 450 and 620 nm. Absorbances at 620 nm were subtracted from absorbances at 450 nm. Background in wells containing media only was further subtracted from corrected absorbances and surviving fraction (SF) of untreated cells was calculated in Excel. An XY graph of ADC concentration (M) vs. SF was created using Graph Pad Prism.

Figure 5:
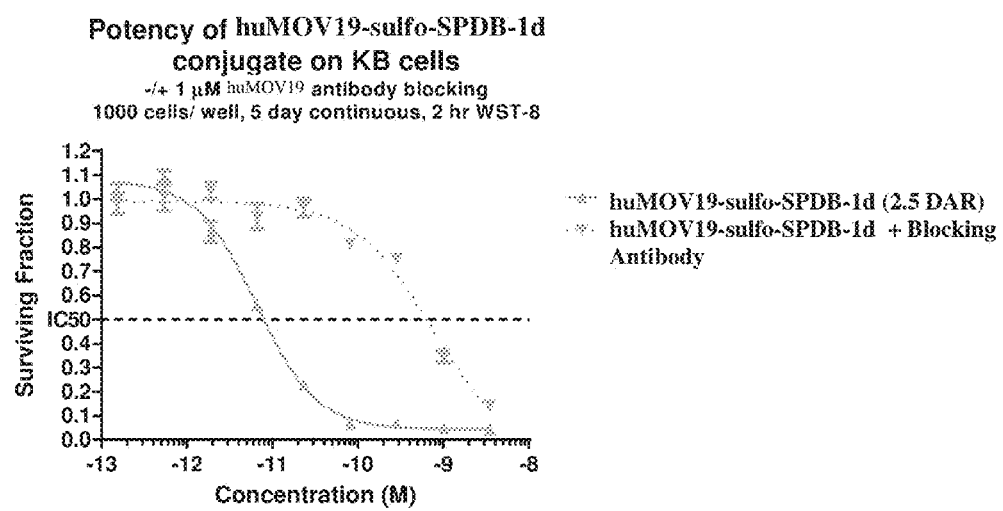
FIGS. 5-7 show in vitro cytotoxicity of huMOV19-sulfo-SPDB-1d conjugate against various cancer cell lines.
Figure 6:
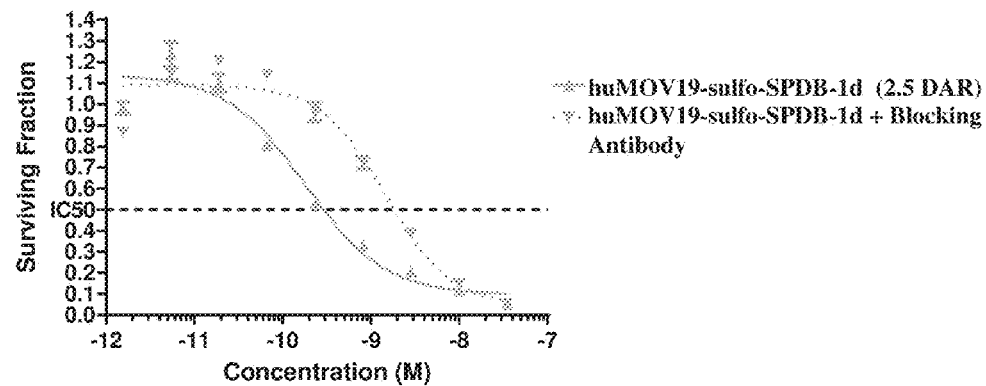
Figure 7:
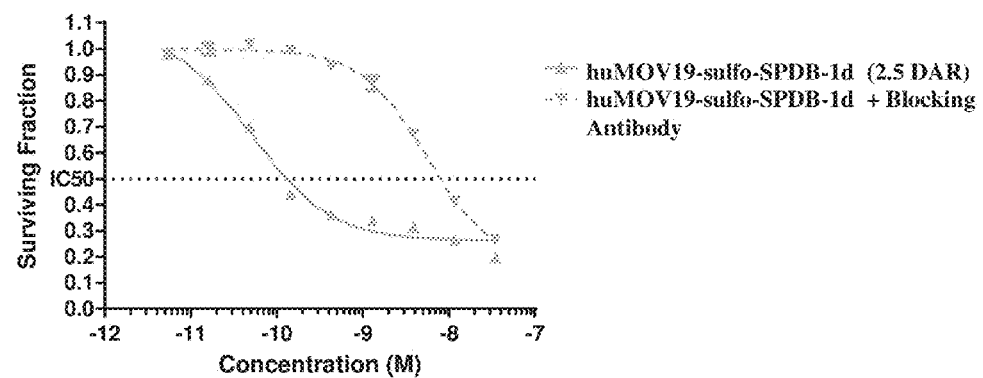

As shown in FIGS. 5-7 and Table 2, the conjugate is highly potent against KB cells, NCI-H2110 cells and T47D cells.

TABLE 2

| | KB | | NCI-H2110 | | T47D | |
|---|---|---|---|---|---|---|
| huMOV19-sulfo-SPDB-1d | −Block | +Block | −Block | +Block | −Block | +Block |
| $IC_{50}$ | 8e-12M | 6e-10M | 3e-10M | 2e-9M | 1e-10M | 9e-9M |

In another experiment, the ability of the conjugate to inhibit cell growth was measured using a WST-8-based in vitro cytotoxicity assay. Cells in 96-well plates (typically, $1 \times 10^3$ per well) were treated with the conjugate at various concentrations in an appropriate cell culture medium with a total volume of 0.2 ml. Control wells containing cells and the medium but lacking test compounds, and wells containing medium only, were included in each assay plate. The plates were incubated for 4 to 6 days at 37° C. in a humidified atmosphere containing 6% $CO_2$. WST-8 reagent (10%, volume/volume; Dojindo Molecular Technologies) was then added to the wells, and the plates were incubated at 37° C. for 2 to 6 hours depending on a cell line. Then, the absorbance was measured on a plate reader spectrophotometer in the dual-wavelength mode 450 nm/620 nm, and the absorbance at the 620 nm (nonspecific light scattering by cells) was subtracted. The resulting $OD_{450}$ values were utilized to calculate apparent surviving fractions of cells using GraphPad Prism v4 (GraphPad software, San Diego, Calif.). The apparent surviving fraction of the cells in each well was calculated by first correcting for the medium background absorbance and then dividing each value by the average of the values in the control wells (non-treated cells). Dose response curves were generated by non-linear regression using a sigmoidal curve fit with variable slope in Graph Pad Prism. $IC_{50}$ (inhibitory concentration 50%) was generated by the software.

The conjugate is active against the tested cell lines Ishikawa (endometrial cancer), KB (cervical cancer) and NCI-H2110 (non-small cell lung carcinoma) and T47D (breast cancer) as shown in FIG. 14. The cell-killing activity was FOLR1-dependent, since an excess of unmodified huMOV19 antibody (1 μM) markedly decreased potency of the conjugate (from 10 to 100-fold), Table 3, FIG. 14.

TABLE 3

| | IC50, nM | |
|---|---|---|
| Cell line | huMOV19-sulfo-SPDB-1d | huMOV19-sulfo-SPDB-1d + unmodified huMOV19 |
| Ishikawa | 0.04 | 0.4 |
| KB | 0.01 | 1.0 |

TABLE 3-continued

| | IC50, nM | |
|---|---|---|
| Cell line | huMOV19-sulfo-SPDB-1d | huMOV19-sulfo-SPDB-1d + unmodified huMOV19 |
| NCI-H2110 | 0.1 | 1.0 |
| T47D | 0.1 | 7.0 |

Example 8. Bystander Killing Activity

100 μl/well of huMOV19-sulfo-SPDB-1d conjugate were each diluted in RPMI-1640 (Life Technologies) supplemented with heat-inactivated 10% FBS (Life Technologies), 0.1 mg/ml gentamycin (Life Technologies) and βME (Life Technologies) in a 96-well plate (Falcon, round bottom) at concentrations of 1 e-10 M and 4 e-10 M in sextuplicate. Both 300.19 cells (mouse) expressing recombinant FOLR1 (FR1#14) or no expression vector (parental) were counted on a hemacytometer. 50 μl/ml of 1000 FR1#14 cells/well were added to wells containing the conjugate or media only, 50 μl/ml of 2000 parental cells/well were added to wells containing the conjugate or media only and both FR1#14 and parental cells were added together to wells containing ADC or media only. All plates were incubated in a 37° C. incubator with 5% $CO_2$ for 4 days. Total volume was 150 μl/well. After incubation, cell viability was analyzed by addition of 75 μl/well Cell Titer Glo (Promega) and allowed to develop for 45 min Luminescence was read on a luminometer and background in wells containing media only was subtracted from all values. A bar graph of the average of each cell treatment was graphed using Graph Pad Prism.

Figure 8:
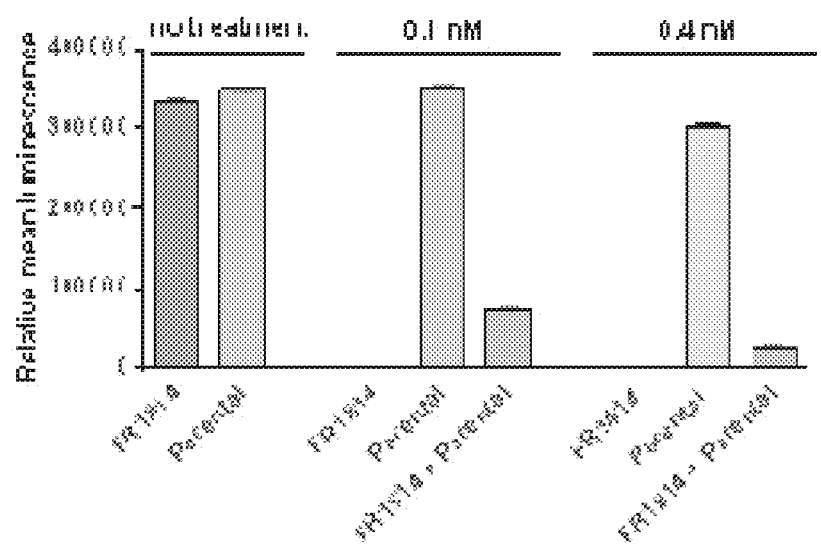
FIG. 8 shows that huMOV19-sulfo-SPDB-1d conjugate exhibits strong cytotoxic effect on the neighboring antigen-negative cells.

As shown in FIG. 8, huMov19-sulfo-SPDB-1d exhibits strong bystander killing activity.

Example 9. Flow Cytometry Assay for Binding Affinity of huMOV19-sSPBD-1d Conjugate 100 μl/well of the conjugate huMOV19-sulfo-SPDB-1d or the antibody huMOV19 were diluted in FACS buffer (1% BSA, 1×PBS) in a 96-well plate (Falcon, round bottom) at a starting concentration of 3×10-8 M in duplicate and serially diluted 3-fold in FACS buffer at 4° C. T47D cells (human breast tumor) grown in RPMI-1640 (Life Technologies) supplemented with heat-inactivated 10% FBS (Life Technologies), 0.1 mg/ml gentamycin (Life Technologies) and 0.2 IU bovine insulin/ml (Sigma) were washed once in PBS and removed with versene (Life Technologies). T47D cells were resuspended in growth media (see above) to neutralize versene and counted on a Coulter counter. Cells were then washed twice in cold FACS buffer, centrifuging in between washes at 1200 rpm for 5 min. 100 μl/ml of 2×10$^4$ cells/well were added to wells containing the conjugate, antibody or FACS buffer only and incubated at 4° C. for 2 hr. After incubation, cells were centrifuged as before and washed once in 200 μl/well cold FACS buffer. Cells were then stained with 200 μl/well FITC-conjugated Goat Anti-Human-IgG-Fcγ secondary antibody (controls included were unstained cells and those stained with secondary antibody only) for 40 min at 4° C., centrifuged and washed once in 200 μl/well cold PBS. Cells were fixed in 200 μl/well 1% formaldehyde/PBS and stored at 4° C. After storage, cellular surface staining of conjugate or antibody was detected using flow cytometry on a FACS Calibur (BD Biosciences). The geometric means were plotted against the log concentration of the conjugate or antibody using Graph-Pad Prism and the $EC_{50}$ was calculated via non-linear 4-parameter logistic regression analysis.

Figure 9A:
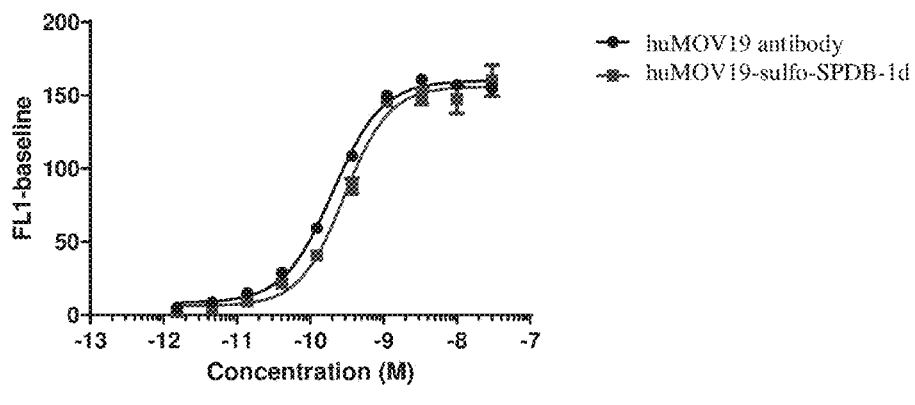
FIGS. 9A and 9B show binding affinity of huMOV19-sulfo-SPDB-1d conjugate as compared to unconjugated antibody huMOV19 on T47D cells.
Figure 9B:
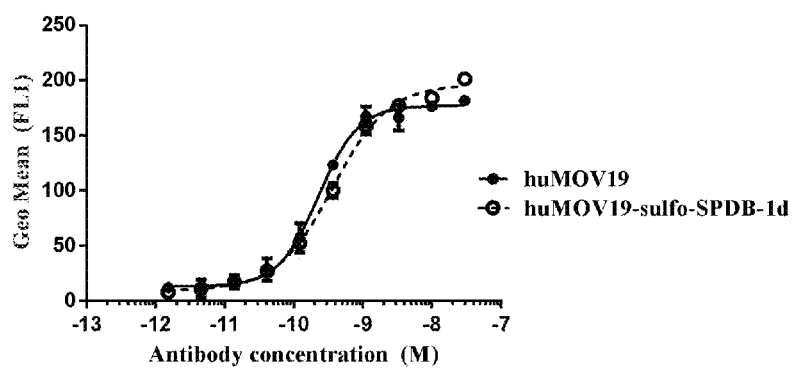

As shown in FIG. 9A, the conjugate binds similarly to the surface of T47D cells expressing the target antigen as the unconjugated antibody in flow cytometry, thereby demonstrating that binding is not affected by the conjugation process. The binding assay was repeated and similar results are observed (see FIG. 9B).

Example 10. Antitumor Activity of Single-Dose huMOV19-Sulfo-SPDB-1d Against NCI-H2110 NSCLC Xenografts in Female SCID Mice Female CB.17 SCID mice, 6 weeks old, were received from Charles River Laboratories. Mice were inoculated with 1×107 NCI-H2110 tumor cells suspended in 0.1 ml 50% matrigel/serum free medium by subcutaneous injection in the right flank. When tumor volumes reached approximately 100 mm3 (day 7 post inoculation), animals were randomized based on tumor volume into 4 groups of 6 mice each. Mice received a single IV administration of vehicle control (0.2 ml/mouse) or huMOV19-sulfo-SPDB-1d at 1, 3 or 5 μg/kg based on concentration of compound 1d on day 1 (day 8 post inoculation).

Tumor size was measured twice to three times weekly in three dimensions using a caliper. The tumor volume was expressed in mm3 using the formula V=Length×Width×Height×½. A mouse was considered to have a partial regression (PR) when tumor volume was reduced by 50% or greater, complete tumor regression (CR) when no palpable tumor could be detected. Tumor volume was determined by StudyLog software.

Tumor growth inhibition (T/C Value) was determined using the following formula:

$$T/C\ (\%) = \text{Median tumor volume of the treated/Median tumor volume of the control} \times 100.$$

Tumor volume was determined simultaneously for treated (T) and the vehicle control (C) groups when tumor volume of the vehicle control reached predetermined size of 1000 mm3 The daily median tumor volume of each treated group was determined, including tumor-free mice (0 mm3) According to NCI standards, a T/C≤42% is the minimum level of anti-tumor activity. A T/C<10% is considered a high anti-tumor activity level.

Figure 10:
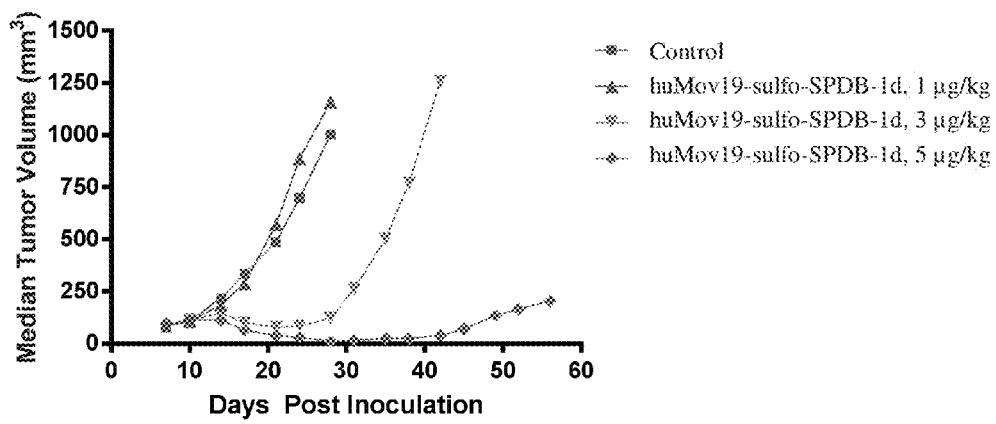
FIG. 10 shows in vivo efficacy of huMOV19-sulfo-SPDB-1d conjugate in NCI-H2110 tumor bearing SCID mice at 1, 3 and 5 µg/kg doses.

As shown in FIG. 10, the conjugate is highly active at 5 μg/kg dose and active at 3 μg/kg dose.

Example 11. Antitumor Activity of Single-Dose huML66-sulfo-SPDB-1d Against NCI-H1703 NSCLC Xenografts in Female SCID Mice Female CB.17 SCID mice, 6 weeks old, were received from Charles River Laboratories. Mice were inoculated with 5×10$^6$ NCI-H1703 tumor cells suspended in 0.2 ml 50% matrigel/serum free medium by subcutaneous injection in the right flank. When tumor volumes reached approximately 100 mm$^3$ (day 16 post inoculation), animals were randomized based on tumor volume into 4 groups of 6 mice each. Mice received a single IV administration of vehicle control (0.1 ml/mouse) or huML66-sulfo-SPDB-1d at 5, 20, or 50 μg/kg based on compound 1d concentration on day 1 (day 17 post inoculation).

Tumor size was measured twice to three times weekly in three dimensions using a caliper. The tumor volume was expressed in mm$^3$ using the formula V=Length×Width×Height×½. A mouse was considered to have a partial regression (PR) when tumor volume was reduced by 50% or greater, complete tumor regression (CR) when no palpable tumor could be detected. Tumor volume was determined by StudyLog software. Tumor growth inhibition (T/C Value) was determined using the following formula:

T/C (%)=Median tumor volume of the treated/Median tumor volume of the control×100.

Tumor volume was determined simultaneously for treated (T) and the vehicle control (C) groups when tumor volume of the vehicle control reached predetermined size of 1000 mm$^3$. The daily median tumor volume of each treated group was determined, including tumor-free mice (0 mm$^3$). According to NCI standards, a T/C≤42% is the minimum level of anti-tumor activity. A T/C<10% is considered a high anti-tumor activity level.

Figure 11:
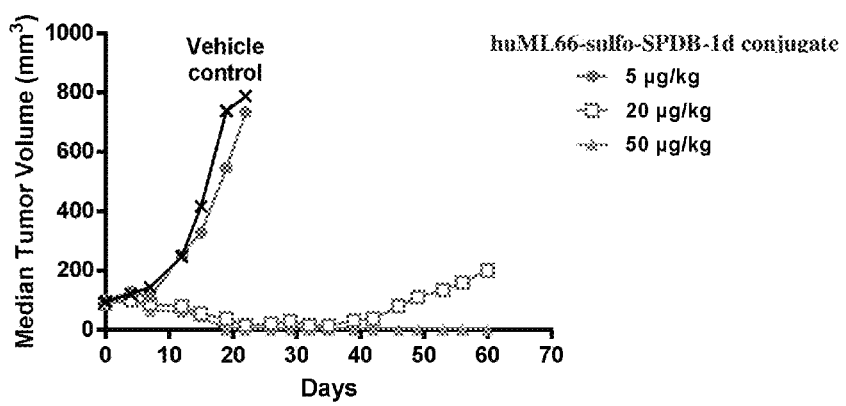
FIG. 11 shows in vivo efficacy of huML66-sulfo-SPDB-1d conjugate in NCI-H1703 tumor bearing SCID mice at 5, 20 and 50 µg/kg doses.

As shown in FIG. 11, the huML66-sulfo-SPDB-1d conjugate is highly active at 20 μg/kg and 50 μg/kg doses, with 20 μg/kg as the minimal effective dose (MED).

Example 12. Pharmacokinetics of Single-Dose huMov19-sulfo-SPDB-1d in Female CD-1 Mice Female CD-1 mice, 7 weeks old, were received from Charles River Laboratories. Mice received a single IV administration of huMov19-sulfo-SPDB-1d conjugate as a single intravenous bolus injection via a lateral tail vein. Each mouse received a dose of 2.5 mg/kg based on Ab. The dose and injected volume were individualized on the basis of the body weight of each mouse. Injections were carried out using a 1.0 mL syringe fitted with a 27 gauge, ½ inch needle. At 2 and 30 min, and at 2, 4 and 8 hours, and at 1, 2, 3, 5, 7, 10, 14, 21 and 28 days after administration of huMov19-sulfo-SPDB-1d conjugate, mice were anesthetized by isoflurane inhalation, and approximately 150 μL of blood was collected from mice via the right retro-orbital blood sinus into a heparinized capillary tube. At each time point (from 0 to 21 days), blood was collected from all three mice in one group. Groups were bled in turn; so that the mice in the set were not bled more than two times in a 24-hour period. At the final time point, 28 days post-administration, all mice were included for sample collection. Blood samples were centrifuged to separate the plasma. 30 μl plasma was transferred to individual labeled microcentrifuge tubes for each sample and time point, and then stored frozen at −80° C. to allow subsequent analysis by ELISA to determine concentrations of total Ab (both unconjugated Ab and intact ADC) and intact conjugate.

Figure 12:
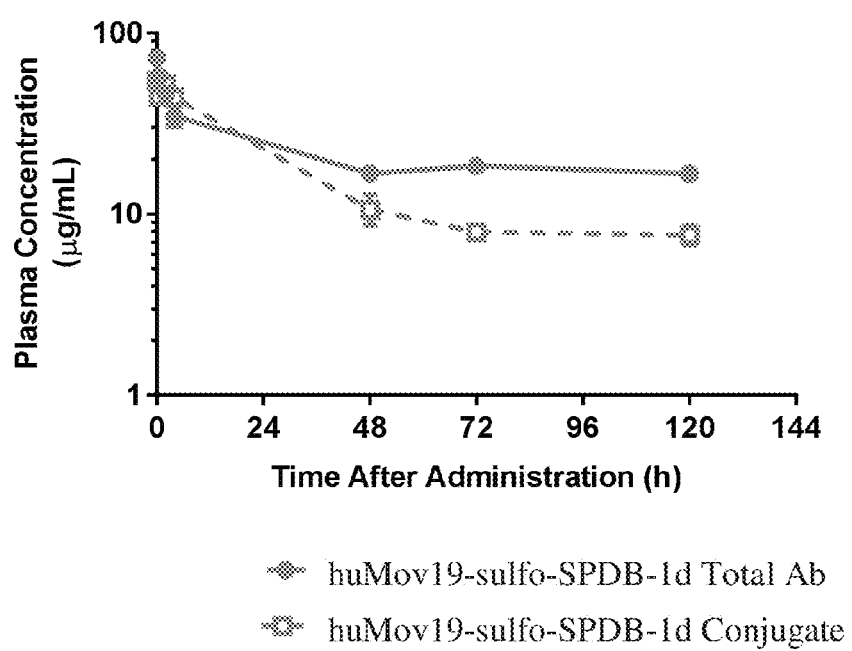
FIG. 12 shows pharmacokinetics of huMOV19-sulfo-SPDB-1d conjugate in CD-1 Mice.

As shown in FIG. 12, the huMov19-sulfo-SPDB-1d conjugate shows slow time-dependent release of benzodiazepine compound.

Example 13. Catabolite Enrichment by Affinity Capture with Protein a Resin

KB cells expressing folate receptor α (FRα) were cultured in 5×T150 tissue culture plates. Saturating amount of FRα-targeting huMov19-sulfo-SPDB-1d conjugate was incubated with KB cells for 24 hours at 37° C. in a humidified incubator buffered with 5% CO2. After 24 hours, the media containing cell-effluxed catabolites were harvested and pooled for the following assay.

Saturating amount of anti-indolinobenzodiazepine antibody was bound to a slurry of protein A resins by overnight incubation at 4° C. 1 mL of pre-bound protein A/anti-indolinobenzodiazepine antibody complex was incubated with 25 mL of media on an end-to-end rotator for several hours. The resins were centrifuged gently at 1,000 rpm, and the supernatant was decanted. The protein-A/anti-indolinobenzodiazepine antibody resins bound to the catabolites were washed with PBS. The catabolites were released into organic phase by acetone extraction. The catabolites were vacuum-dried overnight until the organic solution was completely evaporated. The catabolites were reconstituted with 20% acetonitrile in water, and analyzed by LC/MS.

MS Analysis

Figure 13:
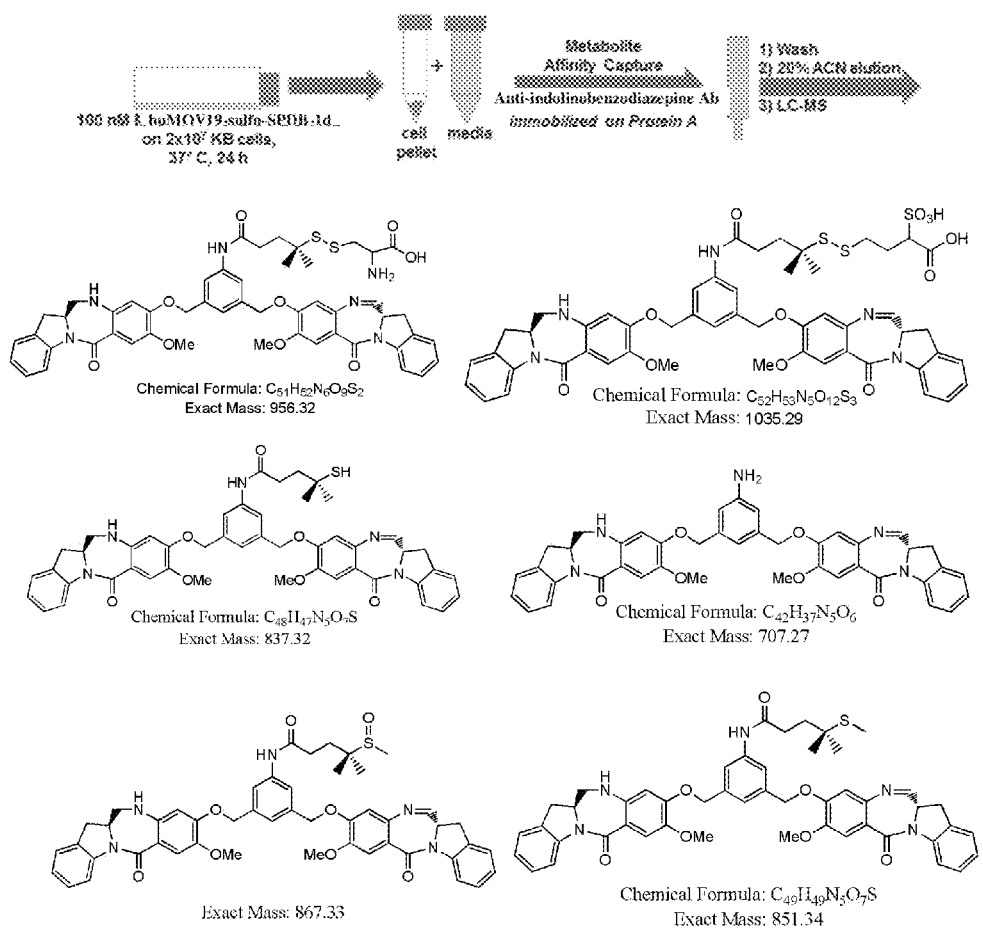
FIG. 13 shows the scheme for incubation, purification, and isolation of catabolites from huMOV19-sulfo-SPDB-1d conjugate formed in KB cervical cancer cells in vitro. The six catabolites identified by LC-MS are shown along with the calculated mass.

Cell catabolites were identified by UHPLC/MS/MS using Q-Exactive high resolution mass spec (Thermo). Extracted ion-chromatograms (XIC) were used to identify and characterize the target cell catabolites. All catabolite species containing the characteristic indolinobenzodiazepine (286 m/z) mass signatures were identified (see FIG. 13).

Example 14. Antitumor Activity of Single-Dose huMov19-Sulfo-SPDB-1d Against NCI-H2110 NSCLC Xenografts, Hec-1b Endometrial Xenografts and Ishikawa Endometrial Xenografts in Female CB.17 SCID Mice Female CB.17 SCID mice, 6 weeks old, were received from Charles River Laboratories. One cohort of mice were inoculated with 1×10$^7$ NCI-H2110 tumor cells suspended in 0.1 ml 50% matrigel/serum free medium by subcutaneous injection in the right flank. The second cohort of mice were inoculated with 1×10$^7$ Hec-1b tumor cells suspended in 0.1 ml serum free medium by subcutaneous injection in the right flank. The third cohort of mice were inoculated with 1×10$^7$ Ishikawa tumor cells suspended in 0.1 ml 50% matrigel/serum free medium by subcutaneous injection in the right flank. When tumor volumes reached approximately 100 mm$^3$ (NCI-H2110 on day 7, Hec-1b on day 7, and Ishikawa on day 17 post inoculation), animals were randomized based on tumor volume into groups of 6 mice each.

Mice in the NCI-H2110 xenograft experiment received a single IV administration of vehicle control (0.2 ml/mouse) or huMov19-sulfo-SPDB-1d at 1, 3, or 5 μg/kg based on drug concentration on day 1 (day 8 post inoculation). Mice in the Hec-1b xenograft experiment received a single IV administration of vehicle control (0.2 ml/mouse) or huMov19-sulfo-SPDB-1d at 10 or 30 μg/kg or the non-targeting control conjugate chKTI-sulfo-SPDB-1d at 30 μg/kg based on drug concentration on day 1 (day 8 post inoculation). Mice in the Ishikawa xenograft experiment received a single IV administration of vehicle control (0.2 ml/mouse) or huMov19-sulfo-SPDB-1d at 10 or 30 μg/kg or the non-targeting control conjugate chKTI-sulfo-SPDB-1d at 30 μg/kg based on drug concentration on day 1 (day 18 post inoculation).

For all experiments, tumor size was measured twice to three times weekly in three dimensions using a caliper. The tumor volume was expressed in mm$^3$ using the formula V=Length×Width×Height×½. A mouse was considered to have a partial regression (PR) when tumor volume was reduced by 50% or greater, complete tumor regression (CR) when no palpable tumor could be detected. Tumor volume was determined by StudyLog software.

Tumor growth inhibition (T/C Value) was determined using the following formula:

T/C (%)=Median tumor volume of the treated/Median tumor volume of the control×100.

Tumor volume was determined simultaneously for treated (T) and the vehicle control (C) groups when tumor volume of the vehicle control reached predetermined size of 1000 mm³. The daily median tumor volume of each treated group was determined, including tumor-free mice (0 mm³). According to NCI standards, a T/C≤42% is the minimum level of anti-tumor activity. A T/C<10% is considered a high anti-tumor activity level.

Figure 15:
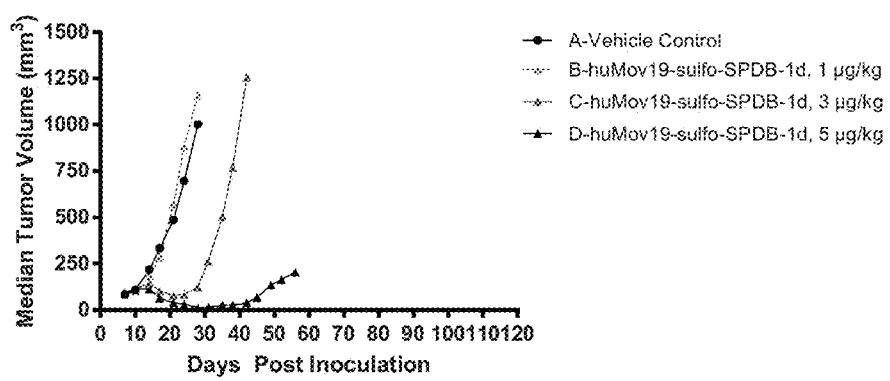
FIG. 15 shows in vivo efficacy of huMov19-sulfo-SPDB-1d in SCID mice bearing NCI-H2110 NSCLC xenografts.

As shown in FIG. 15, the huMov19-sulfo-SPDB-1d conjugate was inactive in the NCI-H2110 xenograft model at a dose of 1 µg/kg, active at a dose of 3 µg/kg with a T/C of 12% and highly active at a dose of 5 µg/kg with a T/C of 4%, 6/6 PRs and ⅜ CRs.

Figure 16:
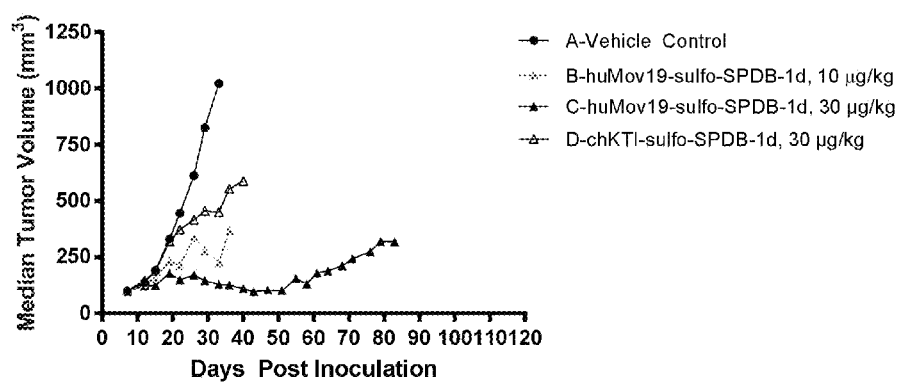
FIG. 16 shows in vivo efficacy of huMov19-sulfo-SPDB-1d in SCID mice bearing Hec-1b endometrial xenografts.

As shown in FIG. 16, the huMov19-sulfo-SPDB-1d conjugate was active in Hec-1b xenograft model at both 10 µg/kg and 30 µg/kg doses. As shown in FIG. 2, the huMov19-sulfo-SPDB-1d conjugate was active in the Hec-1b xenograft model at a dose of 10 µg/kg with a T/C of 22% and active at a dose of 30 µg/kg with a T/C of 13%, ⅙ PRs and ⅙ CRs. The non-targeting control conjugate chKTI-sulfo-SPDB-1d was inactive at a dose of 30 µg/kg.

Figure 17:
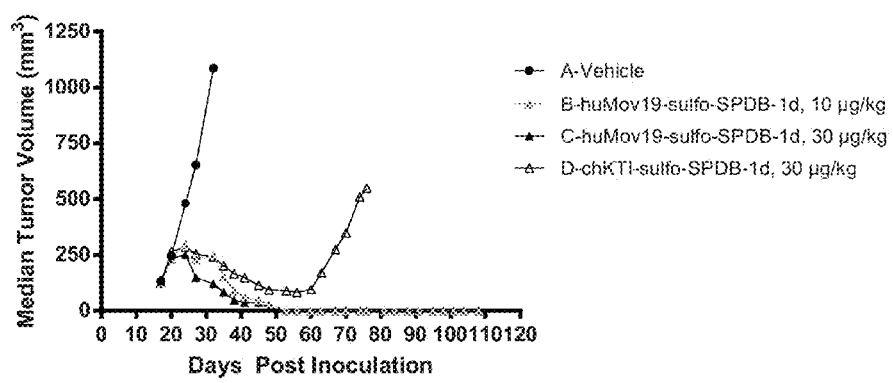
FIG. 17 shows in vivo efficacy of huMov19-sulfo-SPDB-1d in SCID mice bearing Ishikawa endometrial xenografts.

As shown in FIG. 17, the huMov19-sulfo-SPDB-1d conjugate was active in the Ishikawa xenograft model at a dose of 10 µg/kg with a T/C of 23%, 6/6 PRs and 6/6 CRs and active at a dose of 30 µg/kg with a T/C of 11%, 6/6 PRs and 6/6 CRs. The non-targeting control conjugate chKTI-sulfo-SPDB-1d was active at a dose of 30 µg/kg with a T/C of 22% and ⅜ PRs.

Example 15. Binding Affinity of CD123-Sulfo-SPDB-1d Conjugate

Binding affinity of the ADC conjugate of an exemplary humanized anti-CD123 antibody, huCD123-6Gv4.7S3 antibody, was assayed and compared to the corresponding unconjugated antibody by flow cytometry using HNT-34 cells. HNT-34 cells ($5\times10^4$ cells per sample) were incubated with varying concentrations of the ADC and the unconjugated huCD123-6Gv4.7S3 antibody in 200 µL FACS buffer (DMEM medium supplemented with 2% normal goat serum). The cells were then pelleted, washed twice, and incubated for 1 hr with 100 µL of phycoerythrin (PE)-conjugated goat anti-human IgG-antibody (Jackson Laboratory). The cells were pelleted again, washed with FACS buffer and resuspended in 200 µL of PBS containing 1% formaldehyde. Samples were acquired using a FACSCalibur flow cytometer with the HTS multiwell sampler, or a FACS array flow cytometer, and analyzed using CellQuest Pro (all from BD Biosciences, San Diego, US). For each sample the geomean fluorescence intensity for FL2 was calculated and plotted against the antibody concentration in a semi-log plot. A dose-response curve was generated by non-linear regression and the EC50 value of each curve, which corresponds to the apparent dissociation constant (Kd) of each antibody, was calculated using GraphPad Prism v4 (GraphPad software, San Diego, Calif.).

Figure 18:
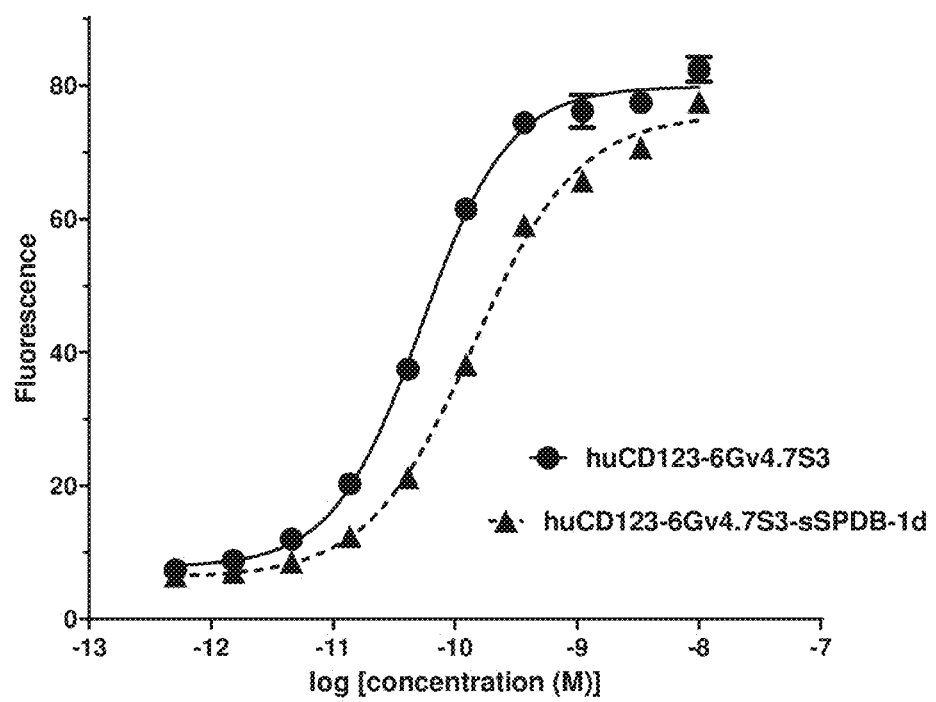
FIG. 18 shows binding affinity of huCD123-6Gv4.7S3-sSPDB-1d conjugate as compared to the unconjugated antibody on HNT-34 cells.

As shown in FIG. 18, conjugation only moderately affected the binding affinity of the exemplary anti-CD123 antibody.

Example 16. In Vitro Cytotoxic Activity for huCD123-sulfo-SPDB-1d Conjugate

The ability of antibody-drug conjugates (ADC) of huCD123-6, an anti-CD123 antibody, to kill cells that express CD123 on their cell surface was measured using in vitro cytotoxicity assays. The cell lines were cultured in culture medium as recommended by the cell supplier (ATCC or DSMZ). The cells, 2,000 to 10,000 in 100 µL of the culture medium, were added to each well of flat bottom 96-well plates. To block Fc receptors on the cell surface, the culture medium was supplemented with 100 nM chKTI antibody (an antibody of the same isotype). Conjugates were diluted into the culture medium using 3-fold dilution series and 100 µL were added per well. To determine the contribution of CD123-independent cytotoxicity, CD123 block (e.g., 100 nM of chCD123-6 antibody) was added to some wells prior to the conjugates. Control wells containing cells and the medium but lacking the conjugates, as well as wells contained medium only, were included in each assay plate. Assays were performed in triplicate for each data point. The plates were incubated at 37° C. in a humidified 6% $CO_2$ incubator for 4 to 7 days. Then the relative number of viable cells in each well was determined using the WST-8 based Cell Counting Kit-8 (Dojindo Molecular Technologies, Inc., Rockville, Md.). The apparent surviving fraction of cells in each well was calculated by first correcting for the medium background absorbance, and then dividing each value by the average of the values in the control wells (non-treated cells). The surviving fraction of cells was plotted against conjugate concentration in semi-log plots.

Fifteen CD123-positive cell lines of different origin (AML, B-ALL, CML and NHL) were used in the study (Table 4). The majority of the cell lines were derived from patients carrying a malignancy with at least one negative prognostic factor (e.g., overexpression of P-glycoprotein, overexpression of EVIL p53 alterations, DNMT3A mutation, FLT3 internal tandem duplication). The conjugates demonstrated high potency on these cell lines with $IC_{50}$ values ranging from sub-pM to low nM (Table 4).

TABLE 4

In vitro cytotoxicity of huCD123-6-90 conjugate against CD123-positive cell lines of different origin

| Cell Line | Origin | Negative Prognostic Factor | $IC_{50}$ (M) |
|---|---|---|---|
| THP1 | AML | p53 deletion | 5.8E−11 |
| SHI-1 | AML | p53 gene alterations | 3.2E−11 |
| KO52 | AML | p53 mutant, Pgp overexpression | 4.1E−10 |
| KASUMI-3 | AML | EVI1 and Pgp overexpression | 1.4E−10 |
| KG-1 | AML | p53 mutant, Pgp overexpression | 4.1E−09 |
| OCI-AML2 | AML | DNMT3A mutation | 2.1E−10 |
| HNT-34 | AML | MECOM (EVI1) overexpression | 5.9E−12 |
| MV4-11 | AML | FLT3 internal tadem duplication | 1.3E−12 |
| MOLM-13 | AML | FLT3 internal tadem duplication | 1.2E−12 |
| EOL-1 | AML | | 4.7E−12 |
| MOLM-1 | CML | EVI1 and Pgp overexpression | 2.1E−10 |
| KOPN8 | B-ALL | | 3.0E−11 |
| JM-1 | B-ALL | | 4.1E−10 |
| KCL-22 | CML | | 2.9E−10 |

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

We claim:

1. A compound represented by the following formula:

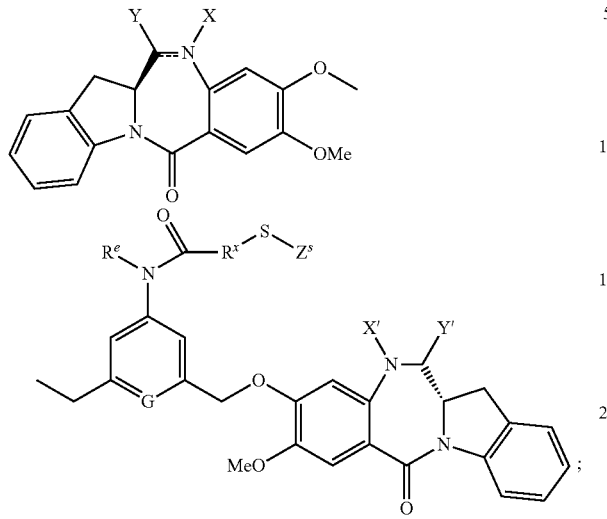

or a pharmaceutically acceptable salt thereof, wherein:

the double line == between N and C represents a single bond or a double bond, provided that when it is a double bond, X is absent and Y is —H, and when it is a single bond, X is selected from —H, or an amine protecting group;

Y is —H, —SO$_3$M, or —OH;

X' is —H;

Y' is —H;

R$^x$ is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3;

R$^e$ is —H or a linear or branched alkyl having 1 to 6 carbon atoms;

G is —CH—;

Z$^s$ is —H, —SR$^d$, or is selected from any one of the following formulas:

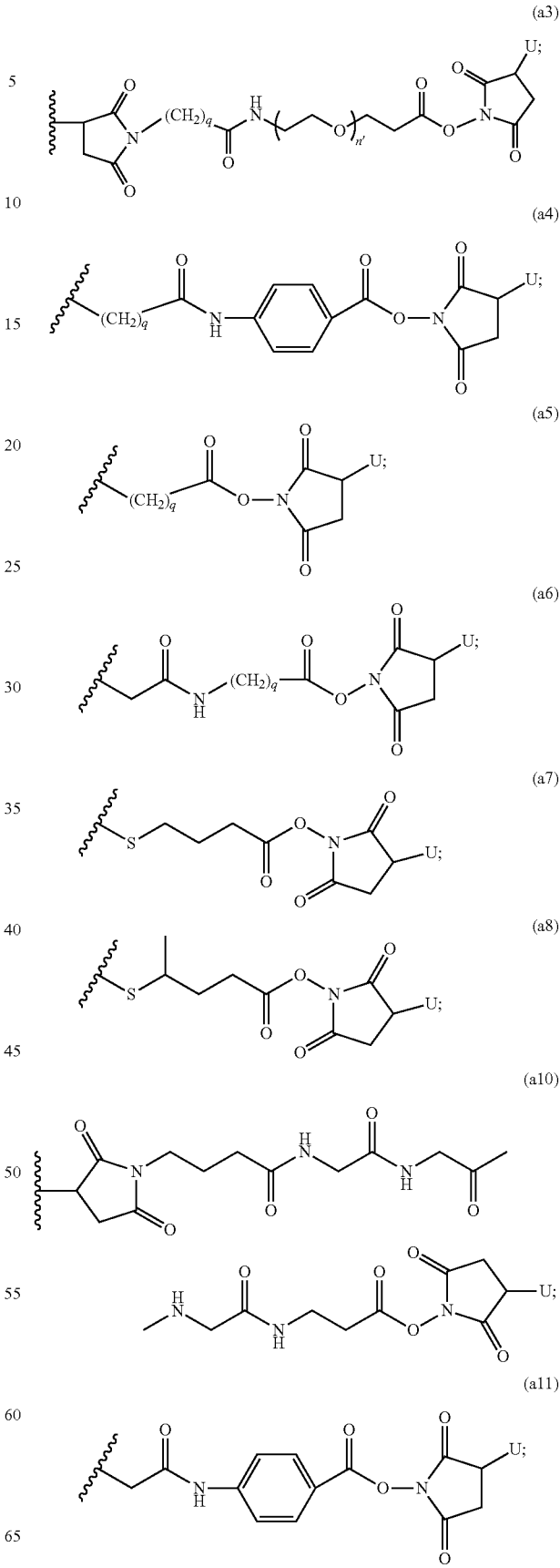

(a12) 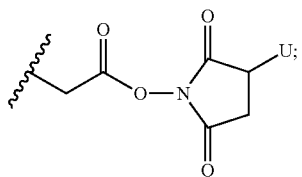

(a13) 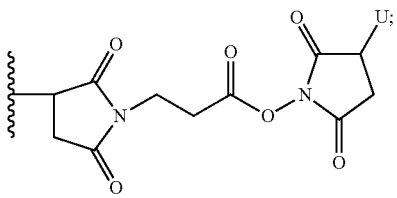

(a14) 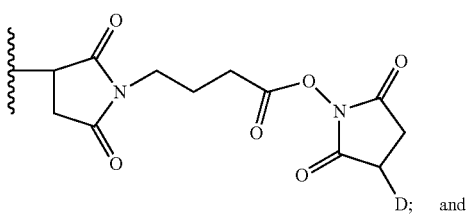
D; and (a15) 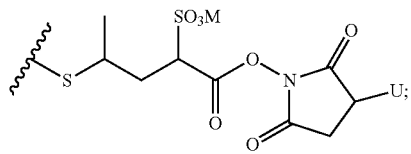

wherein:
q is an integer from 1 to 5;
$R^d$ is a linear or branched alkyl having 1 to 6 carbon atoms or is selected from phenyl, nitrophenyl, dinitrophenyl, carboxynitrophenyl, pyridyl and nitropyridyl;
n' is an integer from 2 to 6;
U is —H or —$SO_3M$; and
M is —H or a cation.

2. The compound of claim 1, wherein $Z^s$ is —H or —$SR^d$, wherein $R^d$ is -Me or pyridyl.

3. The compound of claim 1, wherein $Z^s$ is —H.

4. The compound of claim 1, wherein $R^e$ is —H or -Me.

5. The compound of claim 1, wherein $R^f$ and $R^g$ are the same or different, and are selected from —H and -Me.

6. The compound of claim 1, wherein M is —H, $Na^+$ or $K^+$.

7. The compound of claim 1, wherein the compound is represented by one of the following formulas:

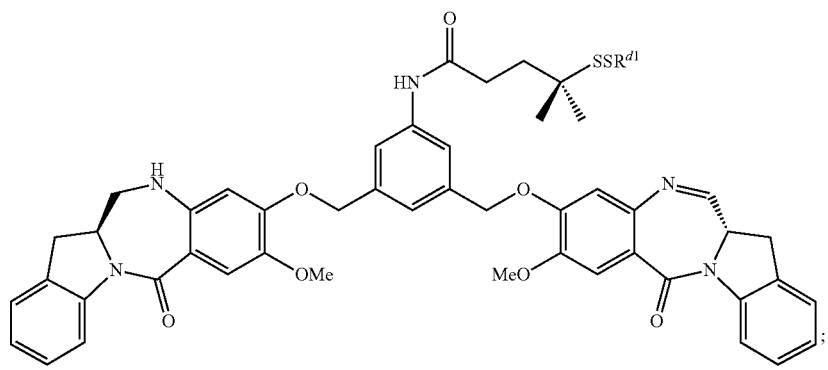

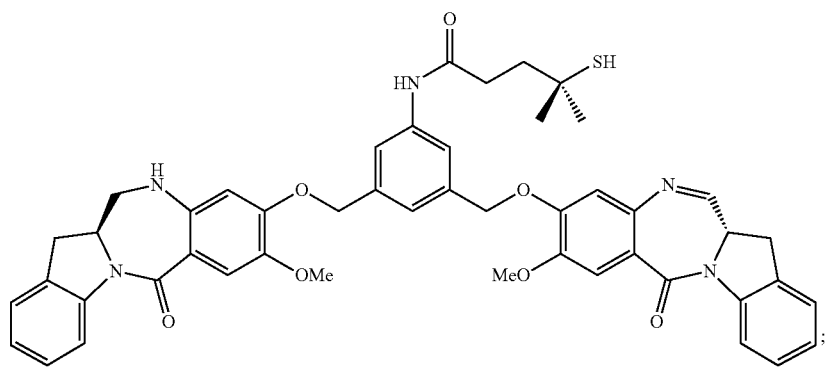

-continued
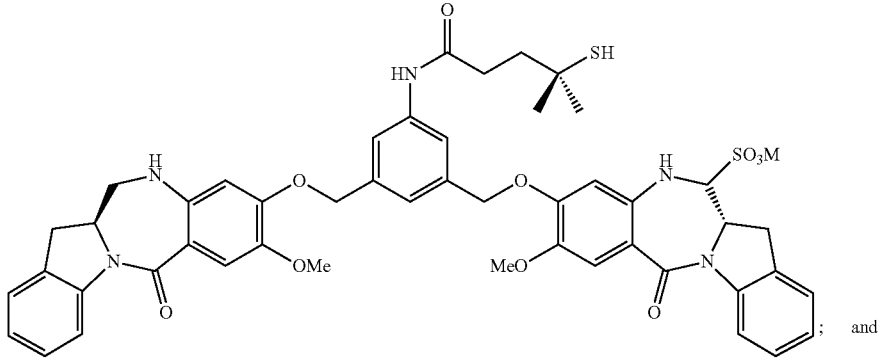
; and
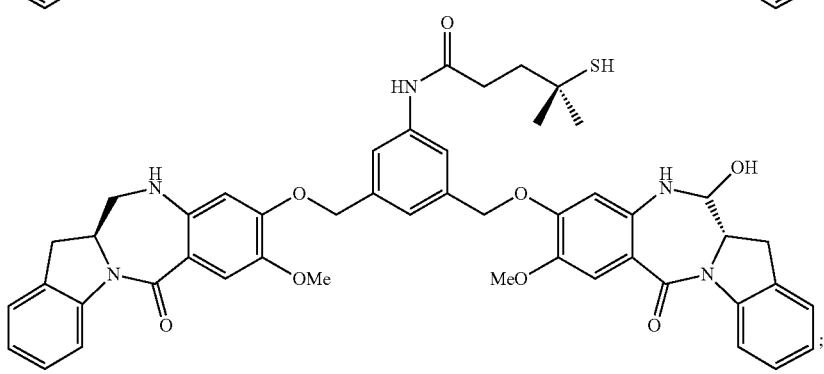
;
or a pharmaceutically acceptable salt thereof, wherein M is —H, Na⁺ or K⁺; and $R^{d1}$ is Me or pyridyl.
8. The compound of claim 1, wherein the compound is represented by one of the following formulas:
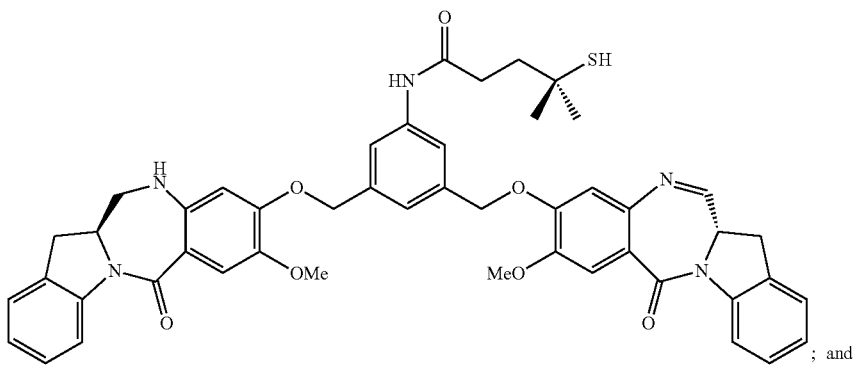
; and
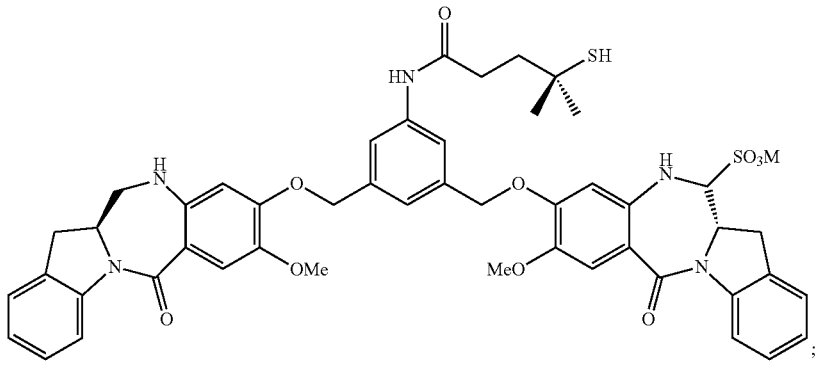
;
or a pharmaceutically acceptable salt thereof, wherein CBA is an antibody; and M is —H, Na⁺ or K⁺.

9. A conjugate comprising a cytotoxic compound and a cell-binding agent (CBA), wherein the cytotoxic compound is covalently linked to the CBA, and wherein said cytotoxic compound is represented by the following formula:

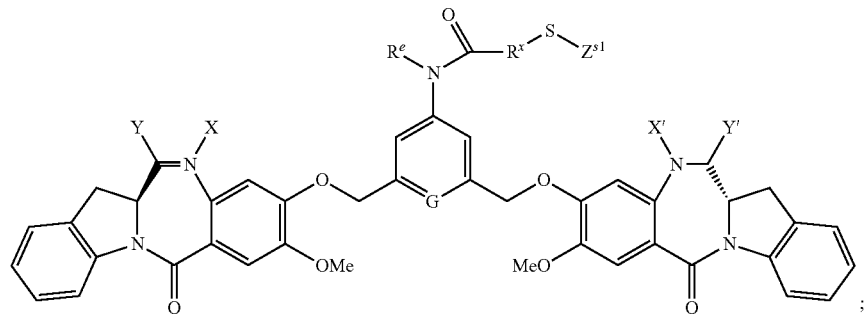

or a pharmaceutically acceptable salt thereof, wherein:
- CBA is an antibody or an antibody fragment that specifically binds to a target cell;
- the double line == between N and C represents a single bond or a double bond, provided that when it is a double bond, X is absent and Y is —H, and when it is a single bond, X is —H;
- Y is —H, —SO$_3$M or —OH;
- X' is —H;
- Y' is —H;
- R' is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3;
- R$^e$ is —H or a linear or branched alkyl having 1 to 6 carbon atoms;
- G is —CH—;
- Z$^{s1}$ is selected from any one of the following formulas:

(b1) 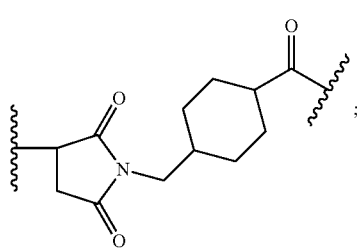

(b2) 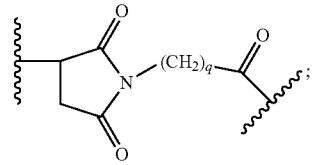

(b3) 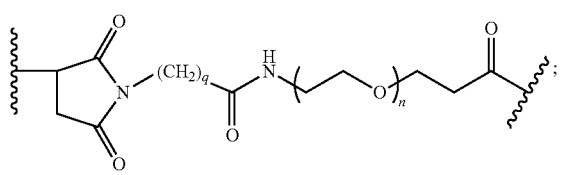

(b4) 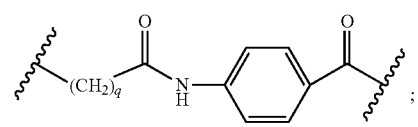

(b5) 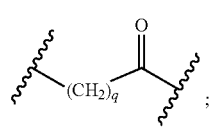

(b6) 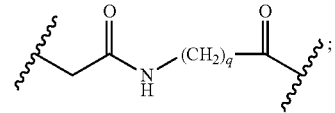

(b7) 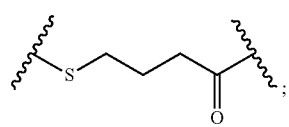

(b8) 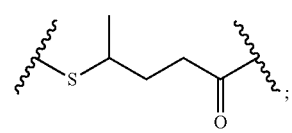

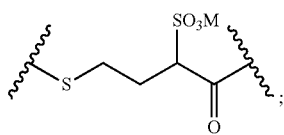
(b9)
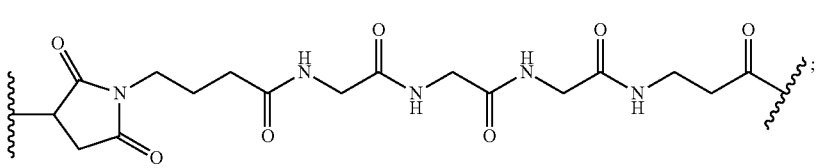
(b10)
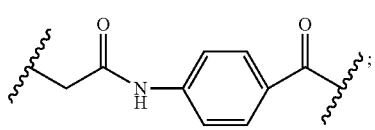
(b11)
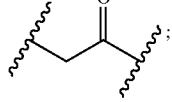
(b12)
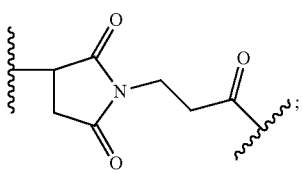
(b13)
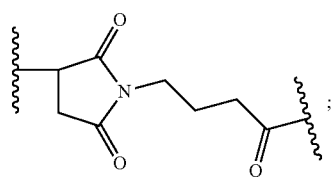
(b14)
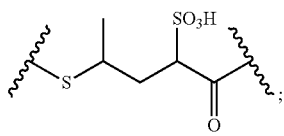
(b15)
wherein:
q is an integer from 1 to 5;
n is an integer from 2 to 6; and
M is —H⁺ or a cation.
10. The conjugate of claim 9, wherein $Z^{s1}$ is represented by one of the following formulas:
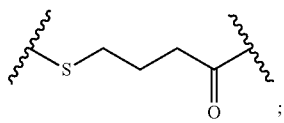
(b7)
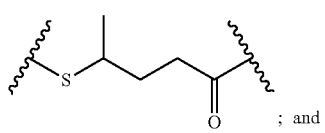
(b8)
; and
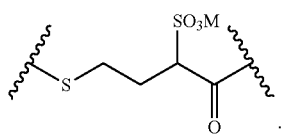
(b9)
11. The conjugate of claim 9, wherein $R^e$ is —H or -Me.
12. The conjugate of claim 9, wherein $R^f$ and $R^g$ are the same or different, and are selected from —H and -Me.

13. The conjugate of claim 9, wherein the conjugate is represented by any one of the following formulas:
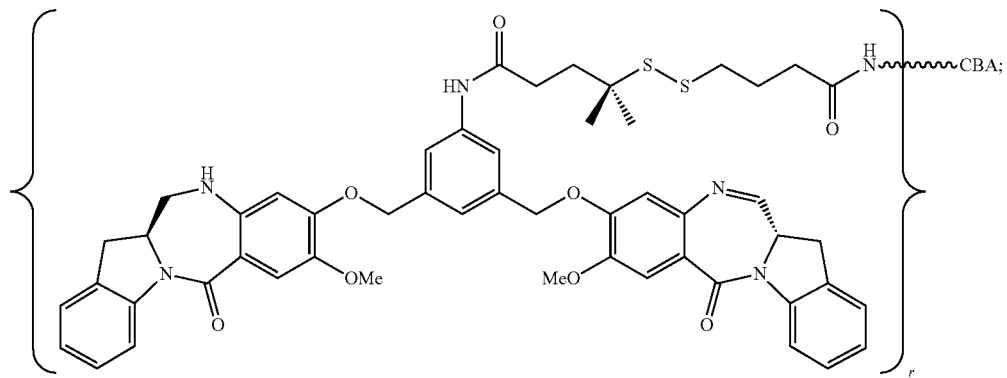
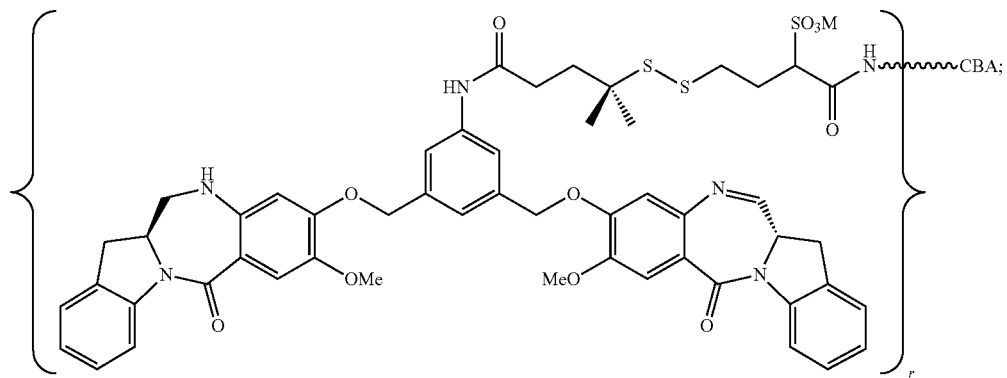
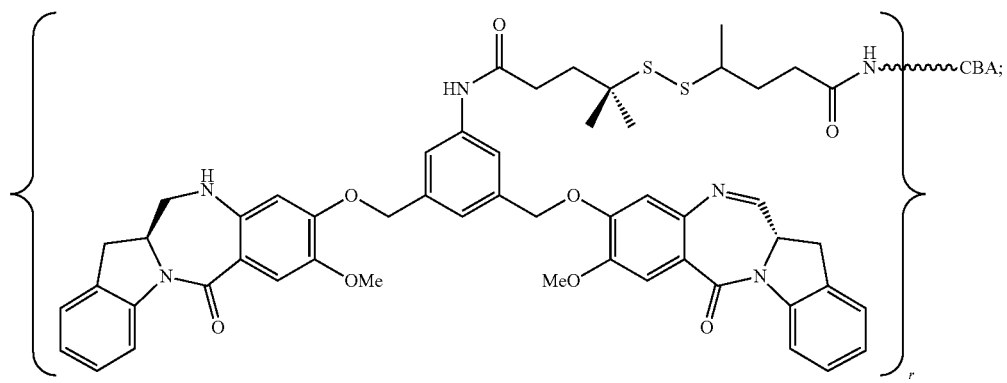
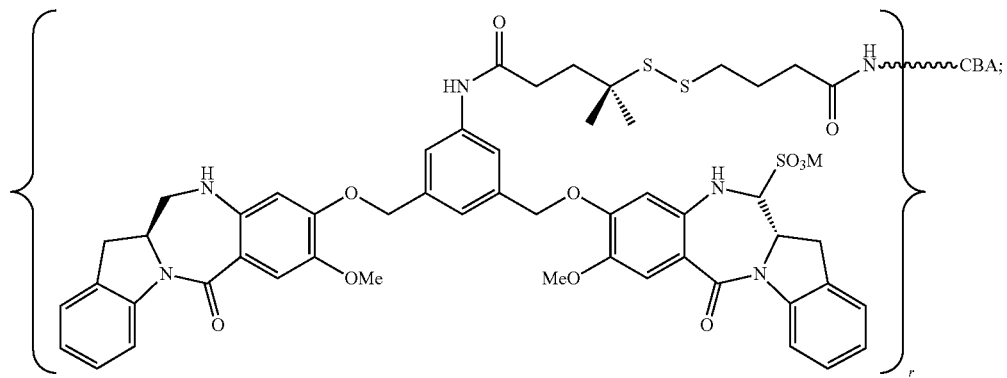

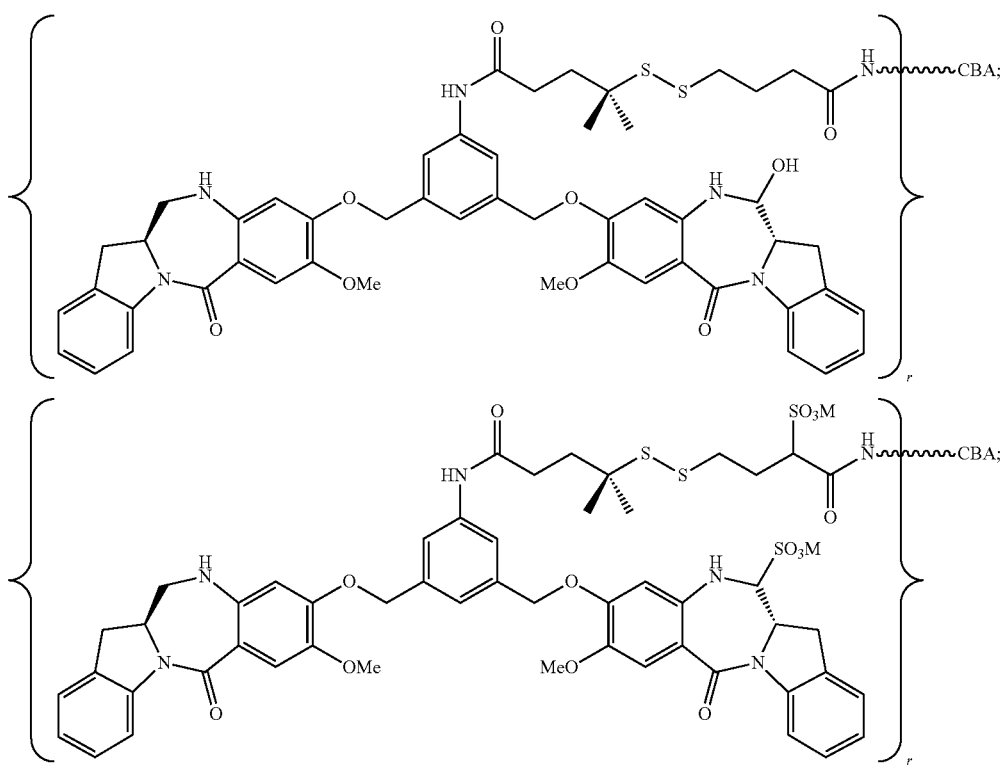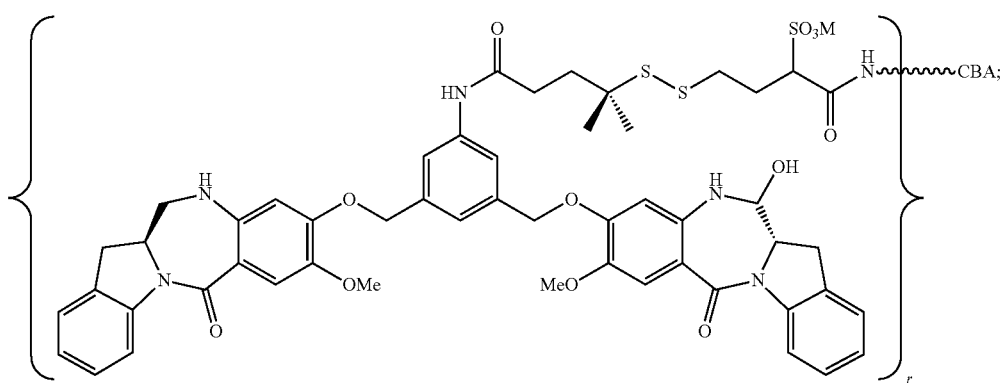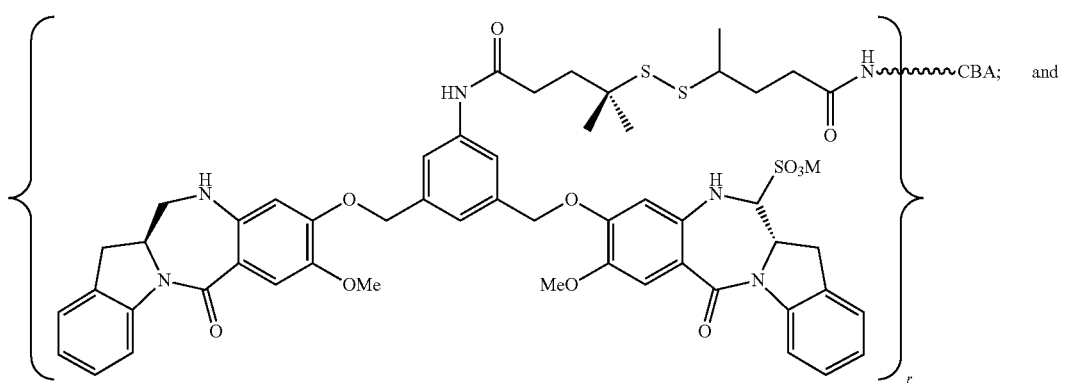

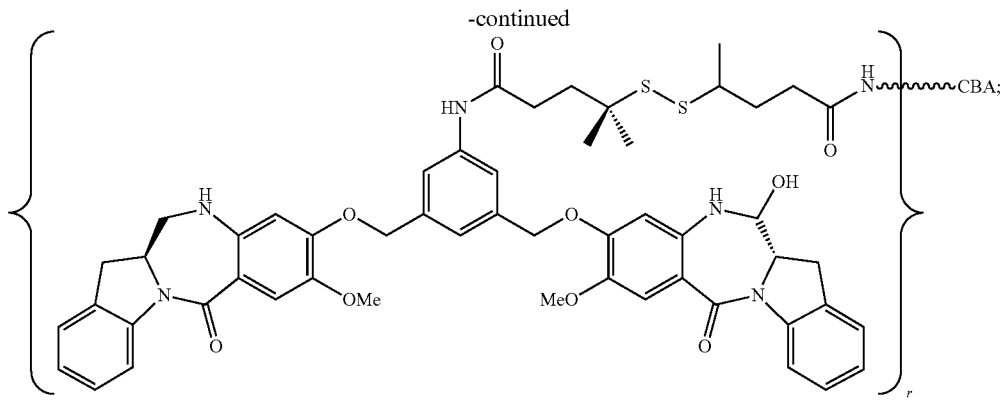

or a pharmaceutically acceptable salt thereof, wherein M is —H, Na+ or K+.

14. The conjugate of claim 9, wherein the cell-binding agent is an anti-folate receptor antibody or an antibody fragment thereof, an anti-EGFR antibody or an antibody fragment thereof, an anti-CD33 antibody or an antibody fragment thereof, an anti-CD19 antibody or an antibody fragment thereof, an anti-Muc1 antibody or an antibody fragment thereof, or an anti-CD37 antibody or an antibody fragment thereof.

15. The conjugate of claim 9, wherein the antibody is huMOV19, huML66, huMy9-6, huB4, huDS6 or huCD37-3 antibody.

16. A method of treating a cancer in a mammal, comprising administering to said mammal a therapeutically effective amount of the conjugate of claim 8, and optionally, a chemotherapeutic agent.

17. The method of claim 16, wherein the cancer is ovarian cancer, pancreatic cancer, melanoma, lung cancer, cervical cancer, breast cancer, squamous cell carcinoma of the head and neck, prostate cancer, endometrial cancer, lymphoma, myelodysplastic syndrome (MDS), peritoneal cancer, leukemia.

18. The method of claim 17, wherein the cancer is acute myeloid leukemia (AML), non-small cell lung cancer or ovarian cancer.

19. The method of claim 16, wherein the conjugate is represented by one of the following formulas:

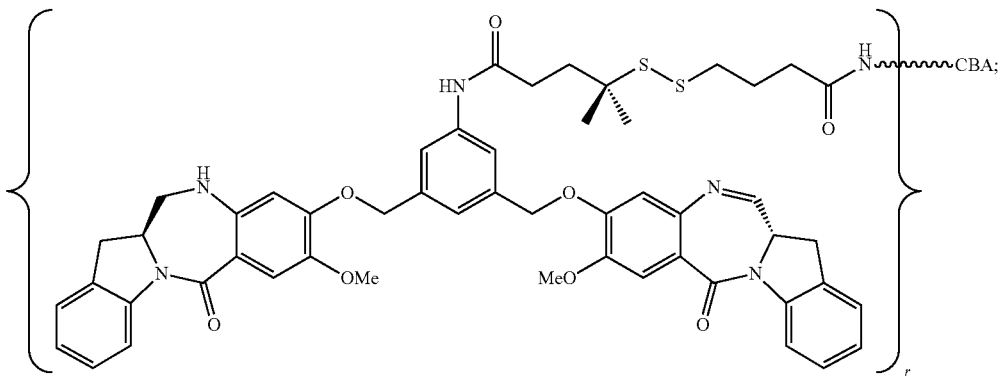

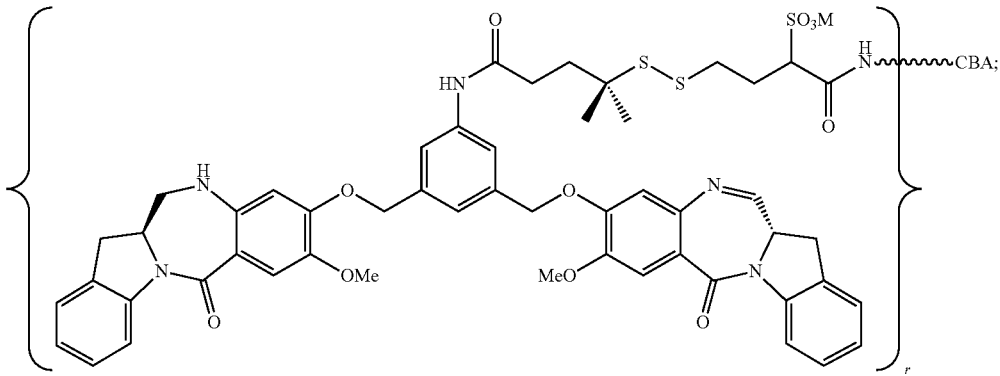

-continued
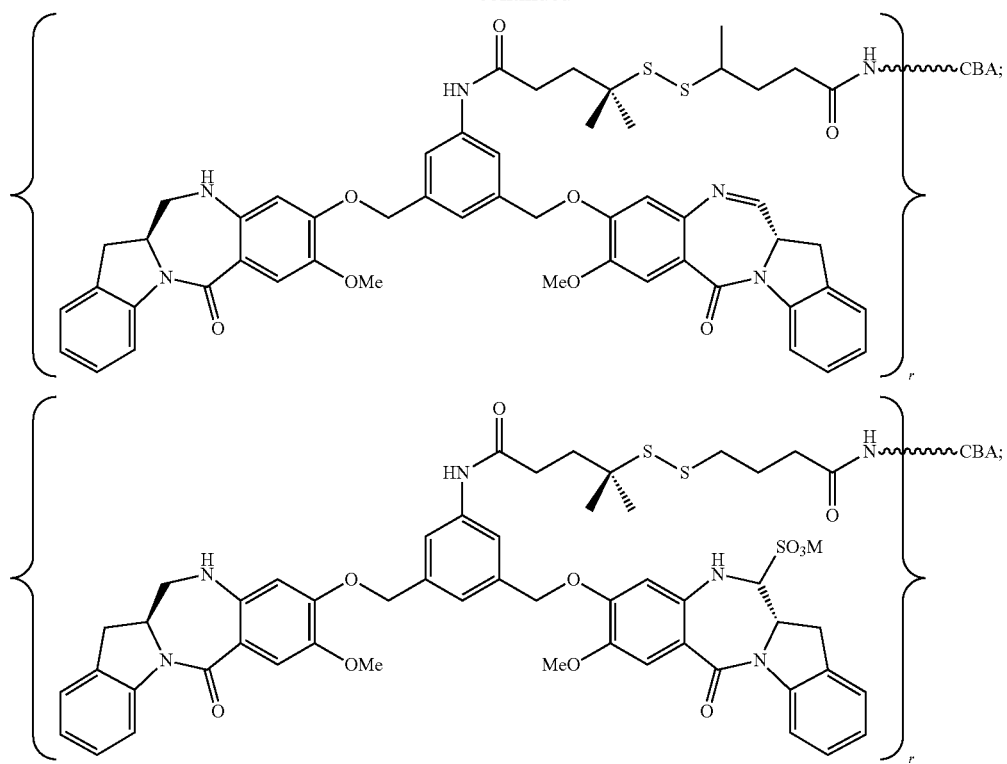
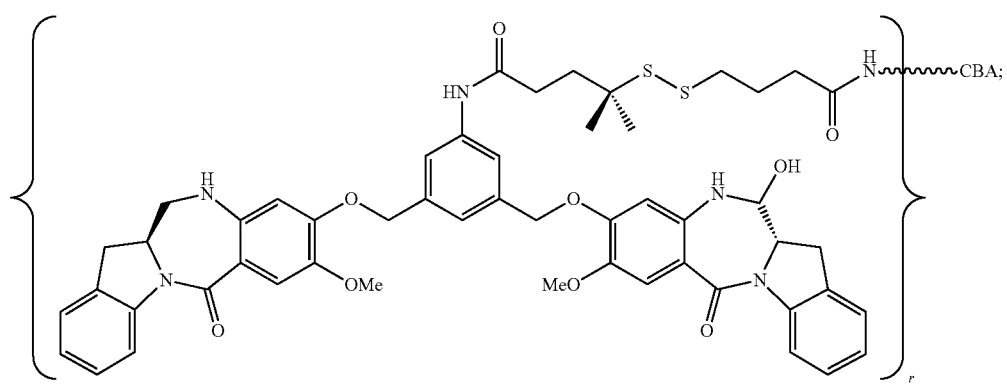
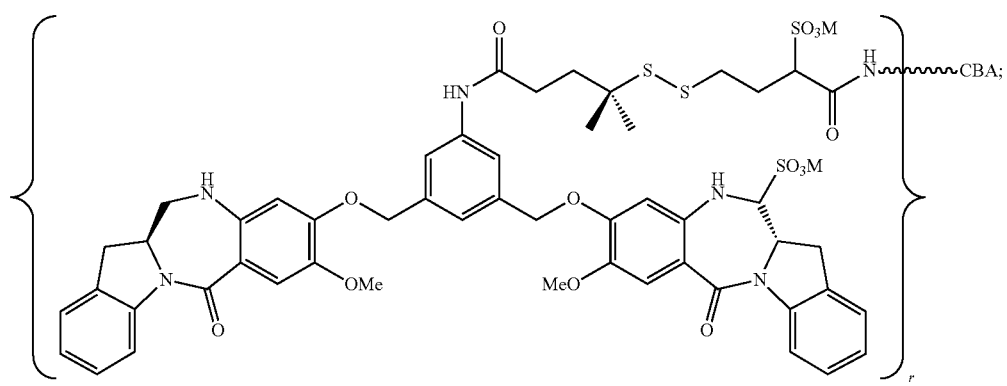

-continued
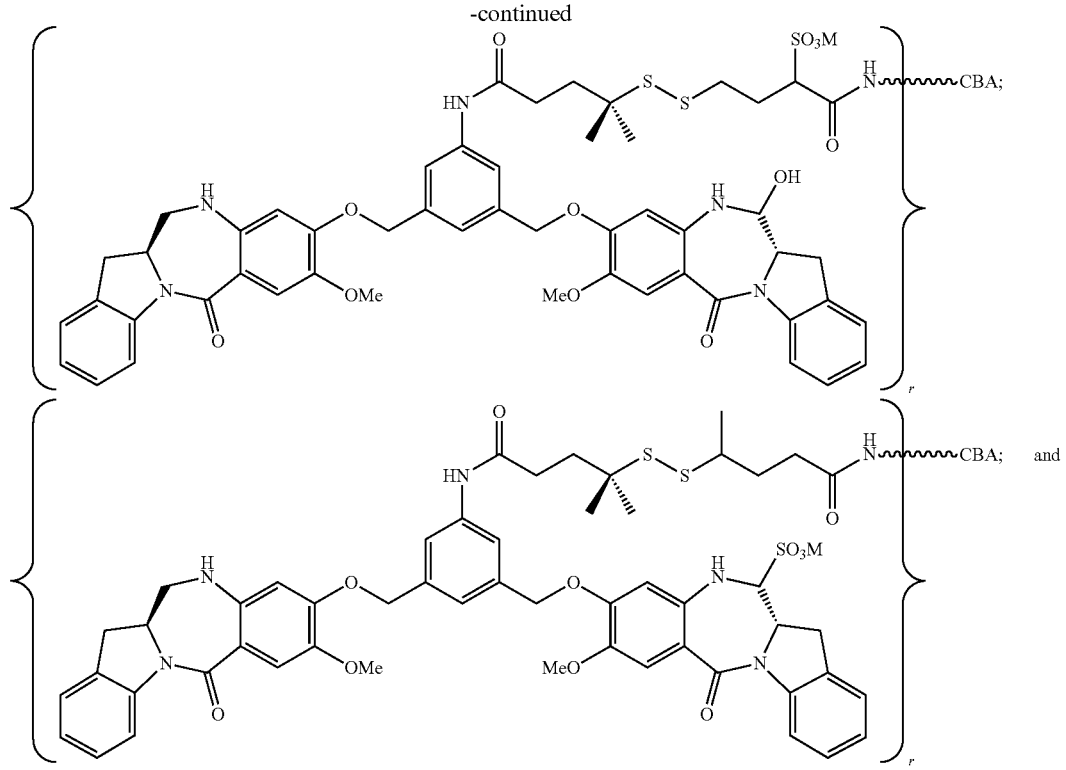
or a pharmaceutically acceptable salt thereof, wherein M is —H, Na⁺ or K⁺.
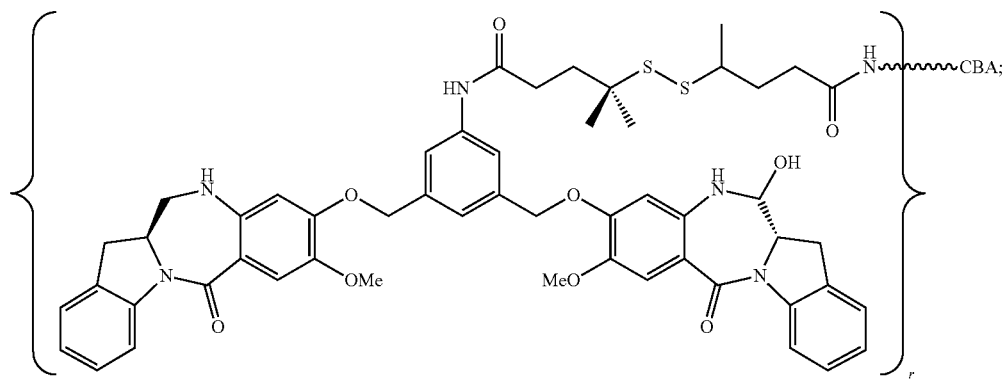
20. The method of claim 16, wherein the conjugate is represented by one of the following formulas:
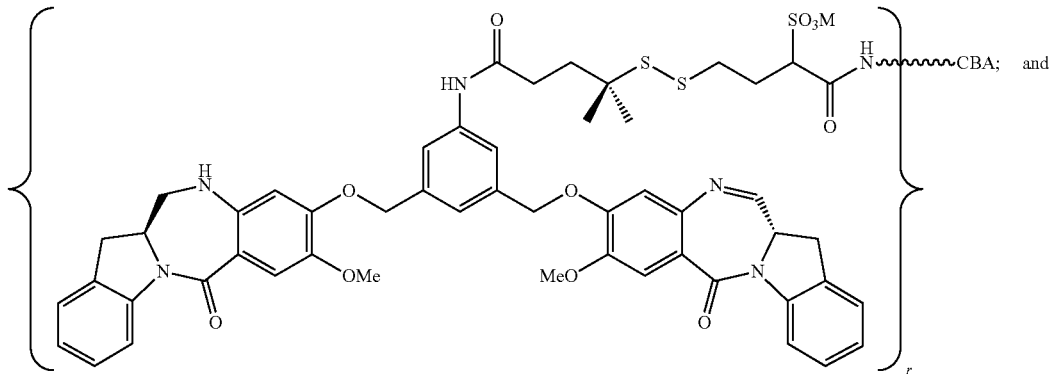

-continued
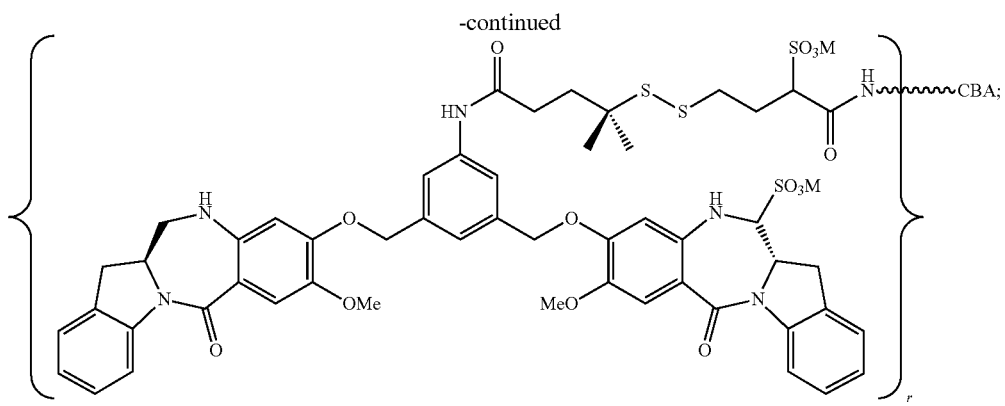
or a pharmaceutically acceptable salt thereof, wherein CBA is an antibody; and M is —H, Na$^+$ or K$^+$.
* * * * *

SEQUENCE LISTING

<160> NUMBER OF SEQ ID NOS: 29

<210> SEQ ID NO 1
<211> LENGTH: 5
<212> TYPE: PRT
<213> ORGANISM: Artificial
<220> FEATURE:
<223> OTHER INFORMATION: FOLR1 antibody heavy chain CDR1

<400> SEQUENCE: 1

Gly Tyr Phe Met Asn
1               5

<210> SEQ ID NO 2
<211> LENGTH: 17
<212> TYPE: PRT
<213> ORGANISM: Artificial
<220> FEATURE:
<223> OTHER INFORMATION: FOLR1 antibody heavy chain CDR2
<220> FEATURE:
<221> NAME/KEY: X
<222> LOCATION: (14)..(14)
<223> OTHER INFORMATION: Lys, Gln, His, or Arg
<220> FEATURE:
<221> NAME/KEY: X
<222> LOCATION: (16)..(16)
<223> OTHER INFORMATION: Gln, His, Asn, or Arg
<220> FEATURE:
<221> NAME/KEY: X
<222> LOCATION: (17)..(17)
<223> OTHER INFORMATION: Gly, GLu, Thr, Ser, Ala, or Val
<220> FEATURE:
<221> NAME/KEY: X
<222> LOCATION: (17)..(17)
<223> OTHER INFORMATION: Gly, Glu, Thr, Ser, Ala, or Val

<400> SEQUENCE: 2

Arg Ile His Pro Tyr Asp Gly Asp Thr Phe Tyr Asn Gln Xaa Phe Xaa
1               5                   10                  15

Xaa

<210> SEQ ID NO 3
<211> LENGTH: 9
<212> TYPE: PRT
<213> ORGANISM: Artificial
<220> FEATURE:
<223> OTHER INFORMATION: FOLR1 antibody heavy chain CDR3

<400> SEQUENCE: 3

Tyr Asp Gly Ser Arg Ala Met Asp Tyr
1               5

<210> SEQ ID NO 4
<211> LENGTH: 15
<212> TYPE: PRT
<213> ORGANISM: Artificial
<220> FEATURE:
<223> OTHER INFORMATION: FOLR1 antibody light chain CDR1

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial
<220> FEATURE:
<223> OTHER INFORMATION: FOLR1 antibody light chain CDR2

-continued

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial
<220> FEATURE:
<223> OTHER INFORMATION: FOLR1 antibody light chain CDR3

<400> SEQUENCE: 6

Gln Gln Ser Arg Glu Tyr Pro Tyr Thr
1               5

<210> SEQ ID NO 7
<211> LENGTH: 17
<212> TYPE: PRT
<213> ORGANISM: Artificial
<220> FEATURE:
<223> OTHER INFORMATION: FOLR1 antibody heavy chain CDR2

<400> SEQUENCE: 7

Arg Ile His Pro Tyr Asp Gly Asp Thr Phe Tyr Asn Gln Lys Phe Gln
1               5                   10                  15

Gly

<210> SEQ ID NO 8
<211> LENGTH: 448
<212> TYPE: PRT
<213> ORGANISM: Artificial
<220> FEATURE:
<223> OTHER INFORMATION: FOLR1 antibody heavy chain

<400> SEQUENCE: 8

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

```
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 9
<211> LENGTH: 218
<212> TYPE: PRT
<213> ORGANISM: Artificial
<220> FEATURE:
<223> OTHER INFORMATION: FOLR1 antibody light chain

<400> SEQUENCE: 9

Asp Ile Val Leu Thr Gln Ser Pro Leu Ser Leu Ala Val Ser Leu Gly
1               5                   10                  15
Gln Pro Ala Ile Ile Ser Cys Lys Ala Ser Gln Ser Val Ser Phe Ala
            20                  25                  30
Gly Thr Ser Leu Met His Trp Tyr His Gln Lys Pro Gly Gln Gln Pro
        35                  40                  45
Arg Leu Leu Ile Tyr Arg Ala Ser Asn Leu Glu Ala Gly Val Pro Asp
    50                  55                  60
Arg Phe Ser Gly Ser Gly Ser Lys Thr Asp Phe Thr Leu Asn Ile Ser
65                  70                  75                  80
Pro Val Glu Ala Glu Asp Ala Ala Thr Tyr Tyr Cys Gln Gln Ser Arg
                85                  90                  95
Glu Tyr Pro Tyr Thr Phe Gly Gly Gly Thr Lys Leu Glu Ile Lys Arg
                100                 105                 110
```

```
Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 10
<211> LENGTH: 218
<212> TYPE: PRT
<213> ORGANISM: Artificial
<220> FEATURE:
<223> OTHER INFORMATION: FOLR1 antibody light chain

<400> SEQUENCE: 10

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 11
<211> LENGTH: 118
<212> TYPE: PRT
<213> ORGANISM: Artificial
```

```
<220> FEATURE:
<223> OTHER INFORMATION: FOLR1 antibody heavy chain variable domain

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
                100                 105                 110

Thr Val Thr Val Ser Ser
            115

<210> SEQ ID NO 12
<211> LENGTH: 112
<212> TYPE: PRT
<213> ORGANISM: Artificial
<220> FEATURE:
<223> OTHER INFORMATION: FOLR1 antibody light chain variable domain

<400> SEQUENCE: 12

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
                100                 105                 110

<210> SEQ ID NO 13
<211> LENGTH: 112
<212> TYPE: PRT
<213> ORGANISM: Artificial
<220> FEATURE:
<223> OTHER INFORMATION: FOLR1 antibody light chain variable domain

<400> SEQUENCE: 13

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45
```

```
Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
                 85                  90                  95

Glu Tyr Pro Tyr Thr Phe Gly Gly Gly Thr Lys Leu Glu Ile Lys Arg
                100                 105                 110

<210> SEQ ID NO 14
<211> LENGTH: 445
<212> TYPE: PRT
<213> ORGANISM: Artificial
<220> FEATURE:
<223> OTHER INFORMATION: huML66HC Full-Length Heavy Chain

<400> SEQUENCE: 14

Gln Val Gln Leu Gln Glu Ser Gly Pro Gly Leu Val Lys Pro Ser Glu
 1               5                  10                  15

Thr Leu Ser Leu Thr Cys Thr Val Ser Gly Leu Ser Leu Ala Ser Asn
             20                  25                  30

Ser Val Ser Trp Ile Arg Gln Pro Pro Gly Lys Gly Leu Glu Trp Met
         35                  40                  45

Gly Val Ile Trp Asn His Gly Gly Thr Asp Tyr Asn Pro Ser Ile Lys
 50                  55                  60

Ser Arg Leu Ser Ile Ser Arg Asp Thr Ser Lys Ser Gln Val Phe Leu
 65                  70                  75                  80

Lys Met Asn Ser Leu Thr Ala Ala Asp Thr Ala Met Tyr Phe Cys Val
                 85                  90                  95

Arg Lys Gly Gly Ile Tyr Phe Asp Tyr Trp Gly Gln Gly Val Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 15
<211> LENGTH: 213
<212> TYPE: PRT
<213> ORGANISM: Artificial
<220> FEATURE:
<223> OTHER INFORMATION: huML66LC Full-Length Light Chain

<400> SEQUENCE: 15

Asp Thr Val Leu Thr Gln Ser Pro Ser Leu Ala Val Ser Pro Gly Glu
1               5                   10                  15

Arg Ala Thr Ile Ser Cys Arg Ala Ser Glu Ser Val Ser Thr Leu Met
                20                  25                  30

His Trp Tyr Gln Gln Lys Pro Gly Gln Gln Pro Lys Leu Leu Ile Tyr
            35                  40                  45

Leu Ala Ser His Arg Glu Ser Gly Val Pro Ala Arg Phe Ser Gly Ser
        50                  55                  60

Gly Ser Gly Thr Asp Phe Thr Leu Thr Ile Asp Pro Met Glu Ala Glu
65                  70                  75                  80

Asp Thr Ala Thr Tyr Tyr Cys Gln Gln Ser Arg Asn Asp Pro Trp Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 16
<211> LENGTH: 448
<212> TYPE: PRT
<213> ORGANISM: Artificial
<220> FEATURE:
<223> OTHER INFORMATION: anti-EGFR antibody immunoglobulin heavy chain

<400> SEQUENCE: 16

```
Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 17
<211> LENGTH: 214
<212> TYPE: PRT
<213> ORGANISM: Artificial
<220> FEATURE:
<223> OTHER INFORMATION: anti-EGFR antibody immunoglobulin light chain

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
                20                  25                  30

Leu Ala Trp Tyr Gln His Lys Pro Gly Lys Gly Pro Lys Leu Leu Ile
            35                  40                  45

His Tyr Thr Ser Thr Leu His Pro Gly Ile Pro Ser Arg Phe Ser Gly
        50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 214
<212> TYPE: PRT
<213> ORGANISM: Artificial
<220> FEATURE:
<223> OTHER INFORMATION: anti-EGFR antibody immunoglobulin light chain

<400> SEQUENCE: 18

Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asp Ile Asn Asn Tyr
            20                  25                  30

Leu Ala Trp Tyr Gln His Lys Pro Gly Lys Gly Pro Lys Leu Leu Ile
            35                  40                  45

His Tyr Thr Ser Thr Leu His Pro Gly Ile Pro Ser Arg Phe Ser Gly
 50                  55                  60

Ser Gly Ser Gly Arg Asp Tyr Ser Phe Ser Ile Ser Ser Leu Glu Pro
 65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 450
<212> TYPE: PRT
<213> ORGANISM: Artificial
<220> FEATURE:
<223> OTHER INFORMATION: anti-CD19 antibody heavy chain

<400> SEQUENCE: 19

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
        35                  40                  45

Gly Glu Ile Asp Pro Ser Asp Ser Tyr Thr Asn Tyr Asn Gln Asn Phe
 50                  55                  60

Gln Gly Lys Ala Lys Leu Thr Val Asp Lys Ser Thr Ser Thr Ala Tyr
 65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 20
<211> LENGTH: 211
<212> TYPE: PRT
<213> ORGANISM: Artificial
<220> FEATURE:
<223> OTHER INFORMATION: anti-CD19 antibody light chain

<400> SEQUENCE: 20

Glu Ile Val Leu Thr Gln Ser Pro Ala Ile Met Ser Ala Ser Pro Gly
1               5                   10                  15
Glu Arg Val Thr Met Thr Cys Ser Ala Ser Ser Gly Val Asn Tyr Met
            20                  25                  30
His Trp Tyr Gln Gln Lys Pro Gly Thr Ser Pro Arg Arg Trp Ile Tyr
        35                  40                  45
Asp Thr Ser Lys Leu Ala Ser Gly Val Pro Ala Arg Phe Ser Gly Ser
    50                  55                  60
```

```
Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 21
<211> LENGTH: 447
<212> TYPE: PRT
<213> ORGANISM: Artificial
<220> FEATURE:
<223> OTHER INFORMATION: anti-Muc1 antibody heavy chain

<400> SEQUENCE: 21

Gln Ala Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Tyr Ile Tyr Pro Gly Asn Gly Ala Thr Asn Tyr Asn Gln Lys Phe
50                  55                  60

Gln Gly Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Asp Ser Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 22
<211> LENGTH: 213
<212> TYPE: PRT
<213> ORGANISM: Artificial
<220> FEATURE:
<223> OTHER INFORMATION: anti-Muc1 antibody light chain

<400> SEQUENCE: 22

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
        35                  40                  45

Ser Thr Ser Ser Leu Ala Ser Gly Val Pro Ala Arg Phe Gly Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
            85                  90                  95

Phe Gly Ala Gly Thr Lys Leu Glu Leu Lys Arg Thr Val Ala Ala Pro
        100                 105                 110

Ser Val Phe Ile Phe Pro Pro Ser Asp Glu Gln Leu Lys Ser Gly Thr
    115                 120                 125

```
Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 23
<211> LENGTH: 447
<212> TYPE: PRT
<213> ORGANISM: Artificial
<220> FEATURE:
<223> OTHER INFORMATION: anti-CD33 antibody immunoglobulin heavy chain

<400> SEQUENCE: 23

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 24
<211> LENGTH: 219
<212> TYPE: PRT
<213> ORGANISM: Artificial
<220> FEATURE:
<223> OTHER INFORMATION: anti-CD33 antibody immunoglobulin light chain

<400> SEQUENCE: 24

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

<210> SEQ ID NO 25
<211> LENGTH: 214
<212> TYPE: PRT
<213> ORGANISM: Artificial
<220> FEATURE:
<223> OTHER INFORMATION: anti-CD37 antibody immunoglobulin light chain

<400> SEQUENCE: 25

```
Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 444
<212> TYPE: PRT
<213> ORGANISM: artificial
<220> FEATURE:
<223> OTHER INFORMATION: anti-CD37 antibody immunoglobulin heavy chain

<400> SEQUENCE: 26

```
Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
```

```
            50                  55                  60
Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 27
<211> LENGTH: 444
<212> TYPE: PRT
<213> ORGANISM: artificial
```

<220> FEATURE:
<223> OTHER INFORMATION: anti-CD37 antibody immunoglobulin heavy chain

<400> SEQUENCE: 27

```
Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
        435                 440

<210> SEQ ID NO 28
<211> LENGTH: 213
<212> TYPE: PRT
<213> ORGANISM: artificial
<220> FEATURE:
<223> OTHER INFORMATION: anti-CD37 antibody immunoglobulin light chain

<400> SEQUENCE: 28

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Asn Leu Pro Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
            85                  90                  95

Phe Gly Gln Gly Thr Lys Leu Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 29
<211> LENGTH: 449
<212> TYPE: PRT
<213> ORGANISM: artificial
<220> FEATURE:
<223> OTHER INFORMATION: anti-CD37 antibody immunoglobulin heavy chain

<400> SEQUENCE: 29

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln His Pro Gly Asn Lys Leu Glu Trp

```
                35                  40                  45
Met Gly Tyr Ile Leu Tyr Ser Gly Ser Thr Val Tyr Ser Pro Ser Leu
            50                  55                  60
Lys Ser Arg Ile Ser Ile Thr Arg Asp Thr Ser Lys Asn His Phe Phe
 65                  70                  75                  80
Leu Gln Leu Asn Ser Val Thr Ala Ala Asp Thr Ala Thr Tyr Tyr Cys
                85                  90                  95
Ala Arg Gly Tyr Tyr Gly Tyr Gly Ala Trp Phe Ala Tyr Trp Gly Gln
            100                 105                 110
Gly Thr Leu Val Thr Val Ser Ala Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Gln Thr Tyr Ile Cys Asn Val Asn His Lys
    195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Asp Glu Leu Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly
```